(12) United States Patent
Ding et al.

(10) Patent No.: US 11,879,144 B2
(45) Date of Patent: Jan. 23, 2024

(54) MODIFIED BACTERIA FOR PRODUCTION OF NITROAROMATICS

(71) Applicant: University of Florida Research Foundation, Incorporated, Gainesville, FL (US)

(72) Inventors: Yousong Ding, Gainesville, FL (US); Ran Zuo, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 0 days.

(21) Appl. No.: 18/152,329

(22) Filed: Jan. 10, 2023

(65) Prior Publication Data
US 2023/0287466 A1 Sep. 14, 2023

Related U.S. Application Data

(62) Division of application No. 16/982,087, filed as application No. PCT/US2019/023370 on Mar. 21, 2019, now Pat. No. 11,591,627.

(60) Provisional application No. 62/818,024, filed on Mar. 13, 2019, provisional application No. 62/645,873, filed on Mar. 21, 2018.

(51) Int. Cl.
| | |
|---|---|
| *C12P 13/22* | (2006.01) |
| *C12N 9/04* | (2006.01) |
| *C12N 9/02* | (2006.01) |
| *C12N 15/62* | (2006.01) |

(52) U.S. Cl.
CPC .......... *C12P 13/227* (2013.01); *C12N 9/0006* (2013.01); *C12N 9/0042* (2013.01); *C12N 9/0075* (2013.01); *C12N 15/62* (2013.01); *C12Y 101/9901* (2013.01); *C12Y 106/02004* (2013.01); *C12Y 114/13039* (2013.01)

(58) Field of Classification Search
None
See application file for complete search history.

(56) References Cited

U.S. PATENT DOCUMENTS

| | | |
|---|---|---|
| 5,126,256 A | 6/1992 | Ebeling et al. |
| 7,208,303 B2 | 4/2007 | Loria et al. |
| 10,138,205 B2 | 11/2018 | Ding |
| 11,591,627 B2 | 2/2023 | Ding et al. |
| 2011/0262988 A1 | 10/2011 | Morag |
| 2017/0009213 A1 | 1/2017 | Osborne et al. |
| 2018/0044291 A1 | 2/2018 | Ding |

OTHER PUBLICATIONS

Invitation to Pay Additional Fees dated Aug. 8, 2019 in connection with PCT/US2019/023370.
International Search Report and Written Opinion dated Oct. 22, 2019 in connection with PCT/US2019/023370.
[No Author Listed], National Center for Biotechnology Information. Cytochrome P450 [Bacillus megaterium]. Genbank entry. Dec. 13, 2017 [Retrieved on Sep. 17, 2019]. Retrieved from the internet: htttps://www.ncbi.nlm.nih.gov/protein/WP_097822791. 2 pages.
Keefe et al., Functional proteins from a random-sequence library. Nature. Apr. 5, 2001;410(6829):715-8. Genbank supplemental pages included. 3 pages.

*Primary Examiner* — Christian L Fronda
(74) *Attorney, Agent, or Firm* — Wolf, Greenfield & Sacks, P.C.

(57) ABSTRACT

The disclosure relates, in some aspects, to compositions and methods useful for production of nitrated aromatic molecules. The disclosure is based, in part, on whole cell systems expressing artificial fusion proteins comprising cytochrome P450 enzymes linked to reductase enzymes. In some aspects, the disclosure relates to methods of producing nitrated aromatic molecules in whole cell systems having artificial fusion proteins comprising cytochrome P450 enzymes linked to reductase enzymes.

17 Claims, 12 Drawing Sheets

Specification includes a Sequence Listing.

MODIFIED BACTERIA FOR PRODUCTION OF NITROAROMATICS

RELATED APPLICATIONS

This Application is a Division of U.S. application Ser. No. 16/982,087, filed Sep. 18, 2020, which is a national stage filing under 35 U.S.C. § 371 of international PCT application, PCT/US2019/023370, filed Mar. 21, 2019, which claims priority under 35 U.S.C. § 119(e) to U.S. provisional patent application Ser. No. 62/818,024, filed Mar. 13, 2019, and 62/645,873, filed Mar. 21, 2018, the entire contents of each of which are incorporated herein by reference.

GOVERNMENT SUPPORT

This invention was made with government support under FA9550-16-1-0186 awarded by the United States Air Force. The government has certain rights in the invention.

REFERENCE TO AN ELECTRONIC SEQUENCE LISTING

The contents of the electronic sequence listing (U119570123US03-SEQ-KZM.xml; Size: 118,348 bytes; and Date of Creation: Jan. 9, 2023) is herein incorporated by reference in its entirety.

BACKGROUND

The nitro (—$NO_2$) group acts as an essential unit in a number of pharmaceuticals, exemplified by anticancer drug nilutamine, anti-Parkinson agent tolcapone, and anti-infective agents chloramphenicol and the recently approved delamanid and nifurtimox-eflornithine combination. Drug candidates bearing the —$NO_2$ group also commonly appear in drug pipelines for treating a variety of existing and emerging diseases. Additionally, the nitro group in particular is a versatile synthetic handle present in numerous building blocks in the synthesis of complex drug molecules. The fundamental importance of the nitro group in pharmaceutical industry has driven the development of chemical nitration methods. Classical electrophilic nitration methods with nitric acid as the nitrating reagent dominate current industrial processes. The limitations of the electrophilic method, however, is that it is generally non-selective, poorly tolerates other functional groups, potentially raises safety concerns, and generates large quantities of acidic waste.

SUMMARY

The disclosure relates, in some aspects, to compositions and methods useful for production of nitrated aromatic molecules. The disclosure is based, in part, on whole cell systems expressing artificial fusion proteins comprising cytochrome P450 enzymes linked to reductase enzymes. In some aspects, the disclosure relates to methods of producing nitrated aromatic molecules in whole cell systems having artificial fusion proteins comprising cytochrome P450 enzymes linked to reductase enzymes. In some aspects, the disclosure relates to methods of producing nitrated tryptophan molecules in whole cell systems having artificial fusion proteins comprising cytochrome P450 enzymes linked to reductase enzymes.

One significant advantage of whole cell nitration systems described by the disclosure compared to in vitro nitration reactions is the in situ production of NO from L-Arg. Typically, expensive NO donors are a major barrier for industrial application of nitration biocatalysts (e.g., TxtE fusion proteins, for example TB14). With the help of functional helper genes, such as *Bacillus subtilis* nitric oxide synthase (BsNOS) in whole cell nitration systems described herein, recombinant bacterial cells produce NO from L-Arg, which is synthesized by the *E. coli* cell from cheap carbon and nitrogen sources, and hence greatly lower the cost of biocatalytic nitration processes.

Accordingly, in some aspects, the disclosure relates to a recombinant bacterial cell comprising one or more isolated nucleic acids engineered to express: a fusion protein comprising a TxtE enzyme linked to a catalytic domain of a CYP102A1 (P450BM3) reductase enzyme via an amino acid linker sequence that can be varied in terms of identities and length, e.g., between 14 and 27 amino acids in length; and a nitric oxide synthase (NOS) enzyme.

In some embodiments, a recombinant bacterial cell is a Gram-negative bacterial cell. In some embodiments, a recombinant bacterial cell is an *E. coli* bacterial cell.

In some embodiments, a fusion protein is a TB14 fusion protein having the sequence set forth in SEQ ID NO: 1. In some embodiments, a fusion protein is a TB14 fusion protein encoded by the sequence set forth in SEQ ID NO: 2.

In some embodiments, a NOS enzyme is a bacterial NOS enzyme. In some embodiments, a NOS enzyme is a *Bacillus subtilis* NOS enzyme. In some embodiments, a *Bacillus subtilis* NOS enzyme is encoded by the sequence set forth in SEQ ID NO: 3. In some embodiments, a *Bacillus subtilis* NOS enzyme comprises the amino acid sequence set forth in SEQ ID NO: 5.

In some embodiments, a recombinant bacterial cell further comprises an isolated nucleic acid engineered to express an enzyme that is able to regenerate reducing agent, e.g., NADH and/or NADPH. In some embodiments, this enzyme is a glucose 1-dehydrogenase (GDH) enzyme. In some embodiments, a GDH enzyme is a bacterial GDH enzyme. In some embodiments, a bacterial GDH enzyme is a *Bacillus megaterium* GDH enzyme. In some embodiments, a *Bacillus megaterium* GDH enzyme comprises the sequence set forth in SEQ ID NO: 6. In some embodiments, a *Bacillus megaterium* GDH enzyme is encoded by the sequence set forth in SEQ ID NO: 7.

In some aspects, one or more isolated nucleic acids are located (e.g., situated) on a plasmid, for example a bacterial plasmid. In some embodiments, a bacterial cell comprises one or more plasmids comprising the one or more isolated nucleic acids. In some embodiments, an isolated nucleic acid engineered to express the NOS enzyme and an isolated nucleic acid engineered to express the GDH enzyme are located on the same plasmid. In some embodiments, an isolated nucleic acid engineered to express the fusion protein is located on a plasmid that does not contain an isolated nucleic acid engineered to express the NOS enzyme and/or an isolated nucleic acid engineered to express the GDH enzyme.

In some embodiments, one or more isolated nucleic acids (e.g., one or more isolated nucleic acids encoding a fusion protein, a NOS enzyme, and/or a GDH enzyme) are integrated into a chromosome of a bacterial cell.

In some embodiments, one or more isolated nucleic acid is operably linked to a promoter sequence. In some embodiments, an isolated nucleic acid engineered to express a fusion protein is operably linked to a first promoter, an isolated nucleic acid engineered to express a NOS enzyme is operably linked to a second promoter, and an isolated nucleic acid engineered to express a GDH enzyme is operably linked to a third promoter. In some embodiments, a first promoter, a second promoter, and/or a third promoter is a T7 promoter. In some embodiments, a promoter is an inducible promoter.

In some embodiments, a bacterial cell is genetically modified to lack expression of one or more of the following genes: traA (tryptophanase), trpR (tryptophan repressor), tyrA (T protein), and pheA (P protein). In some embodiments, a bacterial cell comprises the genotype ΔtrpRΔtyrAΔpheA (e.g., is a triple deletion mutant for trpR, tyrA, and pheA).

In some aspects, the disclosure relates to an isolated nucleic acid comprising the sequence set forth in any one of SEQ ID NOs: 8-13.

In some aspects, the disclosure relates to a composition comprising one or more of a recombinant bacterial cell as described by the disclosure, and a bacterial culture media. In some embodiments, a composition comprises a plurality of recombinant bacterial cells as described herein.

In some embodiments, a bacterial culture media is selected from the group consisting of M9, Lysogeny Broth (LB), SOC media, and Terrific Broth (TB).

In some embodiments, a composition further comprises one or more antibiotic agents. In some embodiments, one or more antibiotic agent is ampicillin or kanamycin.

In some embodiments, a composition further comprises a tryptophan or tryptophan analogue. In some embodiments, a composition further comprises one or more of the following:
L-tryptophan (L-Trp), L-arginine (L-Arg), or an analogue of L-tryptophan. In some embodiments, an analogue of L-tryptophan is selected from the group consisting of α-Me-Trp, 4-F-Trp, 4-Me-Trp, 5-MeO-Trp, 5-Me-Trp, 5-F-Trp, 6-F-Trp, and 7-Me-Trp. In some embodiments, the tryptophan or tryptophan analogue is a compound of Formula Ia:

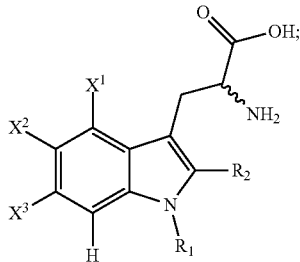

Formula Ia wherein:
each $X^1$ is independently halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$;
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or —$SR^{A1a}$;
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;
$R_1$ is H or optionally substituted alkyl; and
$R_2$ is H, optionally substituted alkyl, optionally substituted alkenyl, optionally substituted alkynyl, optionally substituted aryl, or optionally substituted heteroaryl. In another aspect, $R_1$ is H or alkyl. In another aspect, $R_1$ is H. In another aspect, $R_1$ is alkyl. In another aspect, $R_1$ is H methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In some embodiments, the tryptophan or tryptophan analogue is a compound of Formula IVa:

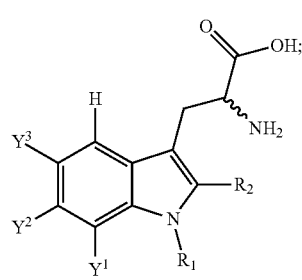

Formula IVa wherein:
each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, $N(R^{A1a})_2$, or $SR^{A1a}$; and
wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

$R_1$ is H or optionally substituted alkyl; and $R_2$ is H, optionally substituted alkyl, optionally substituted alkenyl, optionally substituted alkynyl, optionally substituted aryl, or optionally substituted heteroaryl. In another aspect, $R_1$ is H or alkyl. In another aspect, $R_1$ is H. In another aspect, $R_1$ is alkyl. In another aspect, $R_1$ is H or methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In some embodiments, a composition further comprises one or more of a nitrated tryptophan or a nitrated tryptophan analogue. In some embodiments, a composition further comprises one or more of the following: 4-NO$_2$-L-Trp, nitrated 4-NO$_2$-α-Me-Trp, 4-F-7-NO$_2$-Trp, 4-Me-7-NO$_2$-Trp, 5-MeO-4-NO$_2$-Trp, 5-Me-4-NO$_2$-Trp, nitrated 5-F-4-NO$_2$-Trp, 6-F-4-NO$_2$-Trp, or 7-Me-4-NO$_2$-Trp.

In some embodiments, the nitrated tryptophan or nitrated tryptophan analogue is a compound of Formula I, or a pharmaceutically acceptable salt, prodrug, hydrate, or solvate thereof:

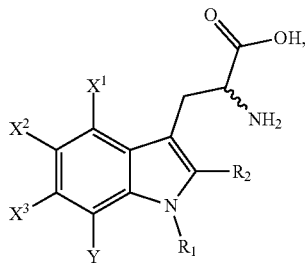

(Formula I)

wherein:

$X^1$ is halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, $NR^{A1a})_2$, or —$SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

each of $X^2$ and $X^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, $N(R^{A1a})_2$, or —$SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl; and Y is NO$_2$. In another aspect, $R_1$ is H or alkyl. In another aspect, $R_1$ is H. In another aspect, $R_1$ is alkyl. In another aspect, $R_1$ is H or methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In some aspects, the compound disclosure relates to a compound of Formula I, wherein at least one of $X^1$, $X^2$, or $X^3$ is a "weakly deactivating group", a "weakly activating group", a "moderately activating group", or a "strongly activating group", as known in the art and as defined herein. In other aspects, at least one of $X^1$, $X^2$, or $X^3$ is H, halogen (e.g., F, Cl, Br, I), substituted or unsubstituted $C_{1-6}$ alkyl (e.g., methyl, CH$_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, $NR^{A1a})_2$, or —$SR^{A1a}$.

In another aspect, $X^1$ is halogen (e.g., F, Cl, Br, I), substituted or unsubstituted $C_{1-6}$ alkyl (e.g., methyl, CH$_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, —$N(R^{A1a})_2$, or $SR^{A1a}$; and $X^2$ and $X^3$ are each independently H, halogen (e.g., F, Cl, Br, I), substituted or unsubstituted $C_{1-6}$ alkyl (e.g., methyl, CH$_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$), —$N(R^{A1a})_2$, or —$SR^{A1a}$. In another aspect, $X^1$ is halogen or $C_{1-6}$ alkyl (e.g., methyl, CH$_3$). In another aspect, $X^1$ is halogen. In another aspect, $X^1$ is $C_{1-6}$ alkyl (e.g., methyl, CH$_3$). In another aspect, $X^1$ is halogen or $C_{1-6}$ alkyl (e.g., methyl, CH$_3$) and at least one of $X^2$ and $X^3$ is hydrogen. In another aspect, $X^1$ is halogen and each of $X^2$ and $X^3$ is hydrogen. In another aspect, $X^1$ if fluorine and each of $X^2$ and $X^3$ is hydrogen. In another aspect, $X^1$ is $C_{1-6}$ alkyl and each of $X^2$ and $X^3$ is hydrogen. In another aspect, $X^1$ is methyl and each of $X^2$ and $X^3$ is hydrogen.

In some embodiments, the compound of Formula I is a compound of Formula II:

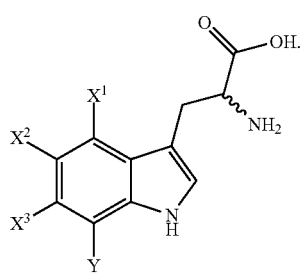

(Formula II)

In certain embodiments, the compound of Formula I is a compound of Formula III:

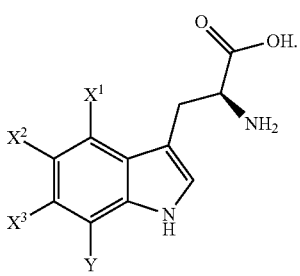

(Formula III)

In some embodiments, the nitrated tryptophan or nitrated tryptophan analogue is a compound of Formula IV, or a pharmaceutically acceptable salt, prodrug, hydrate, or solvate thereof:

wherein:

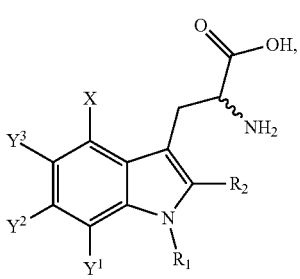

(Formula IV)

each of $Y^1$, $Y^2$, and $Y^3$ is, independently, hydrogen, halogen, substituted or unsubstituted $C_{1-6}$ alkyl, substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, $N(R^{A1a})_2$, or $SR^{A1a}$, wherein each $R^{A1a}$ is independently hydrogen, substituted or unsubstituted acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two instances of $R^{A1a}$ are joined to form a substituted or unsubstituted, heterocyclic ring, or substituted or unsubstituted, heteroaryl ring;

$R_1$ is H or optionally substituted alkyl;

$R_2$ is H, optionally substituted alkyl, optionally substituted alkenyl, optionally substituted alkynyl, optionally substituted aryl, or optionally substituted heteroaryl; and X is $NO_2$. In another aspect, $R_1$ is H or alkyl. In another aspect, $R_1$ is H. In another aspect, $R_1$ is alkyl. In another aspect, $R_1$ is H or methyl. In another aspect, $R_2$ is H. In another aspect, $R_1$ and $R_2$ are each H. In another aspect, $R_1$ is alkyl and $R_2$ is H. In another aspect, $R_1$ is methyl and $R_2$ is H.

In some aspects, the compound disclosure relates to a compound of Formula IV, wherein at least one of $Y^1$, $Y^2$, or $Y^3$ is a "weakly deactivating group", a "weakly activating group", a "moderately activating group", or a "strongly activating group", as known in the art and as defined herein. In other aspects, at least one of $Y^1$, $Y^2$, or $Y^3$ is H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, $N(R^{A1a})_2$, or —$SR^{A1a}$.

In embodiments, $Y^1$, $Y^2$, or $Y^3$ is halogen and the halogen is fluorine. In embodiments, $Y^1$, $Y^2$, or $Y^3$ is unsubstituted $C_1$-$C_6$ alkyl. In embodiments, the unsubstituted $C_1$-$C_6$ alkyl is methyl (—$CH_3$). In embodiments, two of $Y^1$, $Y^2$ and $Y^3$ are hydrogen. In embodiments, $Y^2$ and $Y^3$ are hydrogen. In embodiments, $Y^1$ and $Y^3$ are hydrogen. In embodiments, $Y^1$ and $Y^2$ are hydrogen.

In some aspects, the disclosure relates to a compound of Formula IV, wherein at least one of $Y^1$, $Y^2$ or $Y^3$ is halogen or $C_{1-6}$ alkyl (e.g. methyl, $CH_3$). In another aspect, $Y^3$ is halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, $N(R^{A1a})_2$, or —$SR^{A1a}$; and $Y^1$ and $Y^2$ are each independently H, halogen (e.g. F, Cl, Br, I), substituted or unsubstituted $C_{1-6}$ alkyl (e.g. methyl, $CH_3$), substituted or unsubstituted $C_{2-6}$ alkenyl, substituted or unsubstituted $C_{2-6}$ alkynyl, substituted or unsubstituted, monocyclic, 3- to 6-membered carbocyclyl, substituted or unsubstituted, monocyclic, 3- to 6-membered heterocyclyl, substituted or unsubstituted phenyl, substituted or unsubstituted, monocyclic, 5- to 6-membered heteroaryl, —$OR^{A1a}$, $N(R^{A1a})_2$, or —$SR^{A1a}$. In another aspect, $Y^3$ is halogen or $C_{1-6}$ alkyl (e.g. methyl, $CH_3$). In another aspect, $Y^3$ is halogen or $C_{1-6}$ alkyl (e.g. methyl, $CH_3$) and at least one of $Y^1$ and $Y^2$ is hydrogen. In another aspect, $Y^3$ is halogen or $C_{1-6}$ alkyl (e.g. methyl, $CH_3$) and $Y^1$ and $Y^2$ are each hydrogen. In another aspect, $Y^3$ is halogen. In another aspect, $Y^3$ is halogen and at least one of $Y^1$ and $Y^2$ is hydrogen. In another aspect, $Y^3$ is halogen and $Y^1$ and $Y^2$ are each hydrogen. In certain embodiments, $Y^3$ is fluorine and at least one of $Y^1$ and $Y^2$ is hydrogen. In another aspect, $Y^3$ is fluorine and $Y^1$ and $Y^2$ are each hydrogen. In another aspect, $Y^3$ is $C_{1-6}$ alkyl. In another aspect, $Y^3$ is $C_{1-6}$ alkyl and at least one of $Y^1$ and $Y^2$ is hydrogen. In another aspect, $Y^3$ is $C_{1-6}$ alkyl and $Y^1$ and $Y^2$ are each hydrogen. In certain embodiments, $Y^3$ is methyl and at least one of $Y^1$ and $Y^2$ is hydrogen. In another aspect, $Y^3$ is methyl and $Y^1$ and $Y^2$ are each hydrogen.

In certain embodiments, the compound of Formula IV is a compound of Formula V:

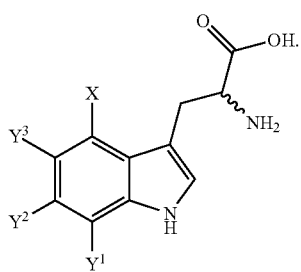

(Formula V)

In certain embodiments, the compound of Formula IV is a compound of Formula VI:

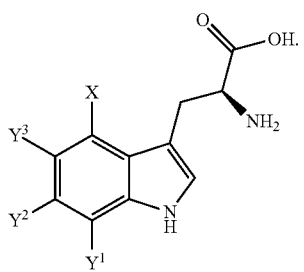

(Formula VI)

In another aspect, the invention is directed to a compound of Formulae I-VI, wherein the compound is:

(S)-2-amino-3-(4-methyl-5-nitro-1H-indol-3-yl)propanoic acid;
(S)-2-amino-3-(5-methyl-4-nitro-1H-indol-3-yl)propanoic acid;
(S)-2-amino-3-(6-methyl-4-nitro-1H-indol-3-yl)propanoic acid;
(S)-2-amino-3-(7-methyl-4-nitro-1H-indol-3-yl)propanoic acid;
(S)-2-amino-3-(4-methyl-7-nitro-1H-indol-3-yl)propanoic acid;
(S)-2-amino-3-(5-fluoro-4-nitro-1H-indol-3-yl)propanoic acid;
(S)-2-amino-3-(6-fluoro-4-nitro-1H-indol-3-yl)propanoic acid;
(S)-2-amino-3-(7-fluoro-4-nitro-1H-indol-3-yl)propanoic acid;
(S)-2-amino-3-(4-fluoro-7-nitro-1H-indol-3-yl)propanoic acid;
(S)-2-amino-3-(5-chloro-4-nitro-1H-indol-3-yl)propanoic acid;
(S)-2-amino-3-(6-chloro-4-nitro-1H-indol-3-yl)propanoic acid;
(S)-2-amino-3-(7-chloro-4-nitro-1H-indol-3-yl)propanoic acid;
(S)-2-amino-3-(4-chloro-7-nitro-1H-indol-3-yl)propanoic acid;
(S)-2-amino-3-(5-bromo-4-nitro-1H-indol-3-yl)propanoic acid;
(S)-2-amino-3-(6-bromo-4-nitro-1H-indol-3-yl)propanoic acid;
(S)-2-amino-3-(7-bromo-4-nitro-1H-indol-3-yl)propanoic acid;
(S)-2-amino-3-(4-bromo-7-nitro-1H-indol-3-yl)propanoic acid;
(S)-2-amino-3-(5-methoxy-4-nitro-1H-indol-3-yl)propanoic acid;
(S)-2-amino-3-(6-methoxy-4-nitro-1H-indol-3-yl)propanoic acid;
(S)-2-amino-3-(7-methoxy-4-nitro-1H-indol-3-yl)propanoic acid;
(S)-2-amino-3-(4-methoxy-7-nitro-1H-indol-3-yl)propanoic acid;
(S)-2-amino-3-(5-amino-4-nitro-1H-indol-3-yl)propanoic acid;
(S)-2-amino-3-(6-amino-4-nitro-1H-indol-3-yl)propanoic acid;
(S)-2-amino-3-(7-amino-4-nitro-1H-indol-3-yl)propanoic acid;
(S)-2-amino-3-(4-amino-7-nitro-1H-indol-3-yl)propanoic acid;
(S)-2-amino-3-(5-hydroxy-4-nitro-1H-indol-3-yl)propanoic acid;
(S)-2-amino-3-(6-hydroxy-4-nitro-1H-indol-3-yl)propanoic acid;
(S)-2-amino-3-(7-hydroxy-4-nitro-1H-indol-3-yl)propanoic acid;
(S)-2-amino-3-(4-hydroxy-7-nitro-1H-indol-3-yl)propanoic acid;
(S)-2-amino-3-(4-nitro-5-phenyl-1H-indol-3-yl)propanoic acid;
(S)-2-amino-3-(4-nitro-6-phenyl-1H-indol-3-yl)propanoic acid;
(S)-2-amino-3-(4-nitro-7-phenyl-1H-indol-3-yl)propanoic acid;
(S)-2-amino-3-(7-nitro-4-phenyl-1H-indol-3-yl)propanoic acid;
(S)-2-amino-3-(5-cyclopropyl-4-nitro-1H-indol-3-yl)propanoic acid;
(S)-2-amino-3-(6-cyclopropyl-4-nitro-1H-indol-3-yl)propanoic acid;
(S)-2-amino-3-(7-cyclopropyl-4-nitro-1H-indol-3-yl)propanoic acid;
(S)-2-amino-3-(4-cyclopropyl-7-nitro-1H-indol-3-yl)propanoic acid;
(S)-2-amino-3-(4-nitro-5-vinyl-1H-indol-3-yl)propanoic acid;
(S)-2-amino-3-(4-nitro-6-vinyl-1H-indol-3-yl)propanoic acid;
(S)-2-amino-3-(4-nitro-7-vinyl-1H-indol-3-yl)propanoic acid;
(S)-2-amino-3-(7-nitro-4-vinyl-1H-indol-3-yl)propanoic acid;
(S)-2-amino-3-(5-ethynyl-4-nitro-1H-indol-3-yl)propanoic acid;

(S)-2-amino-3-(6-ethynyl-4-nitro-1H-indol-3-yl)propanoic acid;
(S)-2-amino-3-(7-ethynyl-4-nitro-1H-indol-3-yl)propanoic acid;
(S)-2-amino-3-(4-ethynyl-7-nitro-1H-indol-3-yl)propanoic acid;
(S)-2-amino-3-(5-morpholino-4-nitro-1H-indol-3-yl)propanoic acid;
(S)-2-amino-3-(6-morpholino-4-nitro-1H-indol-3-yl)propanoic acid;
(S)-2-amino-3-(7-morpholino-4-nitro-1H-indol-3-yl)propanoic acid;
(S)-2-amino-3-(4-morpholino-7-nitro-1H-indol-3-yl)propanoic acid;
(S)-2-amino-3-(5-(methylthio)-4-nitro-1H-indol-3-yl)propanoic acid;
(S)-2-amino-3-(6-(methylthio)-4-nitro-1H-indol-3-yl)propanoic acid;
(S)-2-amino-3-(7-(methylthio)-4-nitro-1H-indol-3-yl)propanoic acid;
(S)-2-amino-3-(4-(methylthio)-7-nitro-1H-indol-3-yl)propanoic acid;
(S)-2-amino-3-(4-nitro-5-(pyridin-4-yl)-1H-indol-3-yl)propanoic acid;
(S)-2-amino-3-(4-nitro-6-(pyridin-4-yl)-1H-indol-3-yl)propanoic acid;
(S)-2-amino-3-(4-nitro-7-(pyridin-4-yl)-1H-indol-3-yl)propanoic acid;
(S)-2-amino-3-(7-nitro-4-(pyridin-4-yl)-1H-indol-3-yl)propanoic acid;
2-amino-3-(4-methyl-5-nitro-1H-indol-3-yl)propanoic acid;
2-amino-3-(5-methyl-4-nitro-1H-indol-3-yl)propanoic acid;
2-amino-3-(6-methyl-4-nitro-1H-indol-3-yl)propanoic acid;
2-amino-3-(7-methyl-4-nitro-1H-indol-3-yl)propanoic acid;
2-amino-3-(4-methyl-7-nitro-1H-indol-3-yl)propanoic acid;
2-amino-3-(6-fluoro-4-nitro-1H-indol-3-yl)propanoic acid;
2-amino-3-(7-fluoro-4-nitro-1H-indol-3-yl)propanoic acid;
2-amino-3-(4-fluoro-7-nitro-1H-indol-3-yl)propanoic acid;
2-amino-3-(5-chloro-4-nitro-1H-indol-3-yl)propanoic acid;
2-amino-3-(6-chloro-4-nitro-1H-indol-3-yl)propanoic acid;
2-amino-3-(7-chloro-4-nitro-1H-indol-3-yl)propanoic acid;
2-amino-3-(4-chloro-7-nitro-1H-indol-3-yl)propanoic acid;
2-amino-3-(5-bromo-4-nitro-1H-indol-3-yl)propanoic acid;
2-amino-3-(6-bromo-4-nitro-1H-indol-3-yl)propanoic acid;
2-amino-3-(7-bromo-4-nitro-1H-indol-3-yl)propanoic acid;
2-amino-3-(4-bromo-7-nitro-1H-indol-3-yl)propanoic acid;
2-amino-3-(5-methoxy-4-nitro-1H-indol-3-yl)propanoic acid;
2-amino-3-(6-methoxy-4-nitro-1H-indol-3-yl)propanoic acid;
2-amino-3-(7-methoxy-4-nitro-1H-indol-3-yl)propanoic acid;
2-amino-3-(4-methoxy-7-nitro-1H-indol-3-yl)propanoic acid;
2-amino-3-(5-amino-4-nitro-1H-indol-3-yl)propanoic acid;
2-amino-3-(6-amino-4-nitro-1H-indol-3-yl)propanoic acid;
2-amino-3-(7-amino-4-nitro-1H-indol-3-yl)propanoic acid;
2-amino-3-(4-amino-7-nitro-1H-indol-3-yl)propanoic acid;
2-amino-3-(5-hydroxy-4-nitro-1H-indol-3-yl)propanoic acid;
2-amino-3-(6-hydroxy-4-nitro-1H-indol-3-yl)propanoic acid;
2-amino-3-(7-hydroxy-4-nitro-1H-indol-3-yl)propanoic acid;
2-amino-3-(4-hydroxy-7-nitro-1H-indol-3-yl)propanoic acid;
2-amino-3-(4-nitro-5-phenyl-1H-indol-3-yl)propanoic acid;
2-amino-3-(4-nitro-6-phenyl-1H-indol-3-yl)propanoic acid;
2-amino-3-(4-nitro-7-phenyl-1H-indol-3-yl)propanoic acid;
2-amino-3-(7-nitro-4-phenyl-1H-indol-3-yl)propanoic acid;
2-amino-3-(5-cyclopropyl-4-nitro-1H-indol-3-yl)propanoic acid;
2-amino-3-(6-cyclopropyl-4-nitro-1H-indol-3-yl)propanoic acid;
2-amino-3-(7-cyclopropyl-4-nitro-1H-indol-3-yl)propanoic acid;
2-amino-3-(4-cyclopropyl-7-nitro-1H-indol-3-yl)propanoic acid;
2-amino-3-(4-nitro-5-vinyl-1H-indol-3-yl)propanoic acid;
2-amino-3-(4-nitro-6-vinyl-1H-indol-3-yl)propanoic acid;
2-amino-3-(4-nitro-7-vinyl-1H-indol-3-yl)propanoic acid;
2-amino-3-(7-nitro-4-vinyl-1H-indol-3-yl)propanoic acid;
2-amino-3-(5-ethynyl-4-nitro-1H-indol-3-yl)propanoic acid;
2-amino-3-(6-ethynyl-4-nitro-1H-indol-3-yl)propanoic acid;
2-amino-3-(7-ethynyl-4-nitro-1H-indol-3-yl)propanoic acid;
2-amino-3-(4-ethynyl-7-nitro-1H-indol-3-yl)propanoic acid;
2-amino-3-(5-morpholino-4-nitro-1H-indol-3-yl)propanoic acid;
2-amino-3-(6-morpholino-4-nitro-1H-indol-3-yl)propanoic acid;
2-amino-3-(7-morpholino-4-nitro-1H-indol-3-yl)propanoic acid;
2-amino-3-(4-morpholino-7-nitro-1H-indol-3-yl)propanoic acid;
2-amino-3-(5-(methylthio)-4-nitro-1H-indol-3-yl)propanoic acid;
2-amino-3-(6-(methylthio)-4-nitro-1H-indol-3-yl)propanoic acid;
2-amino-3-(7-(methylthio)-4-nitro-1H-indol-3-yl)propanoic acid;
2-amino-3-(4-(methylthio)-7-nitro-1H-indol-3-yl)propanoic acid;
2-amino-3-(4-nitro-5-(pyridin-4-yl)-1H-indol-3-yl)propanoic acid;
2-amino-3-(4-nitro-6-(pyridin-4-yl)-1H-indol-3-yl)propanoic acid;
2-amino-3-(4-nitro-7-(pyridin-4-yl)-1H-indol-3-yl)propanoic acid;
2-amino-3-(7-nitro-4-(pyridin-4-yl)-1H-indol-3-yl)propanoic acid;
2-amino-3-(1,5-dimethyl-4-nitro-1H-indol-3-yl)propanoic acid;
2-amino-3-(1,6-dimethyl-4-nitro-1H-indol-3-yl)propanoic acid;
2-amino-3-(1,7-dimethyl-4-nitro-1H-indol-3-yl)propanoic acid;
2-amino-3-(1,4-dimethyl-7-nitro-1H-indol-3-yl)propanoic acid;
2-amino-3-(6-fluoro-1-methyl-4-nitro-1H-indol-3-yl)propanoic acid;
2-amino-3-(7-fluoro-1-methyl-4-nitro-1H-indol-3-yl)propanoic acid;
2-amino-3-(4-fluoro-1-methyl-7-nitro-1H-indol-3-yl)propanoic acid;
2-amino-3-(5-chloro-1-methyl-4-nitro-1H-indol-3-yl)propanoic acid;
2-amino-3-(6-chloro-1-methyl-4-nitro-1H-indol-3-yl)propanoic acid;
2-amino-3-(7-chloro-1-methyl-4-nitro-1H-indol-3-yl)propanoic acid;

2-amino-3-(4-chloro-1-methyl-7-nitro-1H-indol-3-yl)propanoic acid;
2-amino-3-(5-bromo-1-methyl-4-nitro-1H-indol-3-yl)propanoic acid;
2-amino-3-(6-bromo-1-methyl-4-nitro-1H-indol-3-yl)propanoic acid;
2-amino-3-(7-bromo-1-methyl-4-nitro-1H-indol-3-yl)propanoic acid;
2-amino-3-(4-bromo-1-methyl-7-nitro-1H-indol-3-yl)propanoic acid;
2-amino-3-(5-methoxy-1-methyl-4-nitro-1H-indol-3-yl)propanoic acid;
2-amino-3-(6-methoxy-1-methyl-4-nitro-1H-indol-3-yl)propanoic acid;
2-amino-3-(7-methoxy-1-methyl-4-nitro-1H-indol-3-yl)propanoic acid;
2-amino-3-(4-methoxy-1-methyl-7-nitro-1H-indol-3-yl)propanoic acid;
2-amino-3-(5-amino-1-methyl-4-nitro-1H-indol-3-yl)propanoic acid;
2-amino-3-(6-amino-1-methyl-4-nitro-1H-indol-3-yl)propanoic acid;
2-amino-3-(7-amino-1-methyl-4-nitro-1H-indol-3-yl)propanoic acid;
2-amino-3-(4-amino-1-methyl-7-nitro-1H-indol-3-yl)propanoic acid;
2-amino-3-(5-hydroxy-1-methyl-4-nitro-1H-indol-3-yl)propanoic acid;
2-amino-3-(6-hydroxy-1-methyl-4-nitro-1H-indol-3-yl)propanoic acid;
2-amino-3-(7-hydroxy-1-methyl-4-nitro-1H-indol-3-yl)propanoic acid;
2-amino-3-(4-hydroxy-1-methyl-7-nitro-1H-indol-3-yl)propanoic acid;
2-amino-3-(1-methyl-4-nitro-5-phenyl-1H-indol-3-yl)propanoic acid;
2-amino-3-(1-methyl-4-nitro-6-phenyl-1H-indol-3-yl)propanoic acid;
2-amino-3-(1-methyl-4-nitro-7-phenyl-1H-indol-3-yl)propanoic acid;
2-amino-3-(1-methyl-7-nitro-4-phenyl-1H-indol-3-yl)propanoic acid;
2-amino-3-(5-cyclopropyl-1-methyl-4-nitro-1H-indol-3-yl)propanoic acid;
2-amino-3-(6-cyclopropyl-1-methyl-4-nitro-1H-indol-3-yl)propanoic acid;
2-amino-3-(7-cyclopropyl-1-methyl-4-nitro-1H-indol-3-yl)propanoic acid;
2-amino-3-(4-cyclopropyl-1-methyl-7-nitro-1H-indol-3-yl)propanoic acid;
2-amino-3-(1-methyl-4-nitro-5-vinyl-1H-indol-3-yl)propanoic acid;
2-amino-3-(1-methyl-4-nitro-6-vinyl-1H-indol-3-yl)propanoic acid;
2-amino-3-(1-methyl-4-nitro-7-vinyl-1H-indol-3-yl)propanoic acid;
2-amino-3-(1-methyl-7-nitro-4-vinyl-1H-indol-3-yl)propanoic acid;
2-amino-3-(5-ethynyl-1-methyl-4-nitro-1H-indol-3-yl)propanoic acid;
2-amino-3-(6-ethynyl-1-methyl-4-nitro-1H-indol-3-yl)propanoic acid;
2-amino-3-(7-ethynyl-1-methyl-4-nitro-1H-indol-3-yl)propanoic acid;
2-amino-3-(4-ethynyl-1-methyl-7-nitro-1H-indol-3-yl)propanoic acid;
2-amino-3-(1-methyl-5-morpholino-4-nitro-1H-indol-3-yl)propanoic acid;
2-amino-3-(1-methyl-6-morpholino-4-nitro-1H-indol-3-yl)propanoic acid;
2-amino-3-(1-methyl-7-morpholino-4-nitro-1H-indol-3-yl)propanoic acid;
2-amino-3-(1-methyl-4-morpholino-7-nitro-1H-indol-3-yl)propanoic acid;
2-amino-3-(1-methyl-5-(methylthio)-4-nitro-1H-indol-3-yl)propanoic acid;
2-amino-3-(1-methyl-6-(methylthio)-4-nitro-1H-indol-3-yl)propanoic acid;
2-amino-3-(1-methyl-7-(methylthio)-4-nitro-1H-indol-3-yl)propanoic acid;
2-amino-3-(1-methyl-4-(methylthio)-7-nitro-1H-indol-3-yl)propanoic acid;
2-amino-3-(1-methyl-4-nitro-5-(pyridin-4-yl)-1H-indol-3-yl)propanoic acid;
2-amino-3-(1-methyl-4-nitro-6-(pyridin-4-yl)-1H-indol-3-yl)propanoic acid;
2-amino-3-(1-methyl-4-nitro-7-(pyridin-4-yl)-1H-indol-3-yl)propanoic acid;
2-amino-3-(1-methyl-7-nitro-4-(pyridin-4-yl)-1H-indol-3-yl)propanoic acid;
2-amino-3-(2,5-dimethyl-4-nitro-1H-indol-3-yl)propanoic acid;
2-amino-3-(2,6-dimethyl-4-nitro-1H-indol-3-yl)propanoic acid;
2-amino-3-(2,7-dimethyl-4-nitro-1H-indol-3-yl)propanoic acid;
2-amino-3-(2,4-dimethyl-7-nitro-1H-indol-3-yl)propanoic acid;
2-amino-3-(6-fluoro-2-methyl-4-nitro-1H-indol-3-yl)propanoic acid;
2-amino-3-(7-fluoro-2-methyl-4-nitro-1H-indol-3-yl)propanoic acid;
2-amino-3-(4-fluoro-2-methyl-7-nitro-1H-indol-3-yl)propanoic acid;
2-amino-3-(5-chloro-2-methyl-4-nitro-1H-indol-3-yl)propanoic acid;
2-amino-3-(6-chloro-2-methyl-4-nitro-1H-indol-3-yl)propanoic acid;
2-amino-3-(7-chloro-2-methyl-4-nitro-1H-indol-3-yl)propanoic acid;
2-amino-3-(4-chloro-2-methyl-7-nitro-1H-indol-3-yl)propanoic acid;
2-amino-3-(5-bromo-2-methyl-4-nitro-1H-indol-3-yl)propanoic acid;
2-amino-3-(6-bromo-2-methyl-4-nitro-1H-indol-3-yl)propanoic acid;
2-amino-3-(7-bromo-2-methyl-4-nitro-1H-indol-3-yl)propanoic acid;
2-amino-3-(4-bromo-2-methyl-7-nitro-1H-indol-3-yl)propanoic acid;
2-amino-3-(5-methoxy-2-methyl-4-nitro-1H-indol-3-yl)propanoic acid;
2-amino-3-(6-methoxy-2-methyl-4-nitro-1H-indol-3-yl)propanoic acid;
2-amino-3-(7-methoxy-2-methyl-4-nitro-1H-indol-3-yl)propanoic acid;
2-amino-3-(4-methoxy-2-methyl-7-nitro-1H-indol-3-yl)propanoic acid;
2-amino-3-(5-amino-2-methyl-4-nitro-1H-indol-3-yl)propanoic acid;
2-amino-3-(6-amino-2-methyl-4-nitro-1H-indol-3-yl)propanoic acid;

2-amino-3-(7-amino-2-methyl-4-nitro-1H-indol-3-yl)propanoic acid;
2-amino-3-(4-amino-2-methyl-7-nitro-1H-indol-3-yl)propanoic acid;
2-amino-3-(5-hydroxy-2-methyl-4-nitro-1H-indol-3-yl)propanoic acid;
2-amino-3-(6-hydroxy-2-methyl-4-nitro-1H-indol-3-yl)propanoic acid;
2-amino-3-(7-hydroxy-2-methyl-4-nitro-1H-indol-3-yl)propanoic acid;
2-amino-3-(4-hydroxy-2-methyl-7-nitro-1H-indol-3-yl)propanoic acid;
2-amino-3-(2-methyl-4-nitro-5-phenyl-1H-indol-3-yl)propanoic acid;
2-amino-3-(2-methyl-4-nitro-6-phenyl-1H-indol-3-yl)propanoic acid;
2-amino-3-(2-methyl-4-nitro-7-phenyl-1H-indol-3-yl)propanoic acid;
2-amino-3-(2-methyl-7-nitro-4-phenyl-1H-indol-3-yl)propanoic acid;
2-amino-3-(5-cyclopropyl-2-methyl-4-nitro-1H-indol-3-yl)propanoic acid;
2-amino-3-(6-cyclopropyl-2-methyl-4-nitro-1H-indol-3-yl)propanoic acid;
2-amino-3-(7-cyclopropyl-2-methyl-4-nitro-1H-indol-3-yl)propanoic acid;
2-amino-3-(4-cyclopropyl-2-methyl-7-nitro-1H-indol-3-yl)propanoic acid;
2-amino-3-(2-methyl-4-nitro-5-vinyl-1H-indol-3-yl)propanoic acid;
2-amino-3-(2-methyl-4-nitro-6-vinyl-1H-indol-3-yl)propanoic acid;
2-amino-3-(2-methyl-4-nitro-7-vinyl-1H-indol-3-yl)propanoic acid;
2-amino-3-(2-methyl-7-nitro-4-vinyl-1H-indol-3-yl)propanoic acid;
2-amino-3-(5-ethynyl-2-methyl-4-nitro-1H-indol-3-yl)propanoic acid;
2-amino-3-(6-ethynyl-2-methyl-4-nitro-1H-indol-3-yl)propanoic acid;
2-amino-3-(7-ethynyl-2-methyl-4-nitro-1H-indol-3-yl)propanoic acid;
2-amino-3-(4-ethynyl-2-methyl-7-nitro-1H-indol-3-yl)propanoic acid;
2-amino-3-(2-methyl-5-morpholino-4-nitro-1H-indol-3-yl)propanoic acid;
2-amino-3-(2-methyl-6-morpholino-4-nitro-1H-indol-3-yl)propanoic acid;
2-amino-3-(2-methyl-7-morpholino-4-nitro-1H-indol-3-yl)propanoic acid;
2-amino-3-(2-methyl-4-morpholino-7-nitro-1H-indol-3-yl)propanoic acid;
2-amino-3-(2-methyl-5-(methylthio)-4-nitro-1H-indol-3-yl)propanoic acid;
2-amino-3-(2-methyl-6-(methylthio)-4-nitro-1H-indol-3-yl)propanoic acid;
2-amino-3-(2-methyl-7-(methylthio)-4-nitro-1H-indol-3-yl)propanoic acid;
2-amino-3-(2-methyl-4-(methylthio)-7-nitro-1H-indol-3-yl)propanoic acid;
2-amino-3-(2-methyl-4-nitro-5-(pyridin-4-yl)-1H-indol-3-yl)propanoic acid;
2-amino-3-(2-methyl-4-nitro-6-(pyridin-4-yl)-1H-indol-3-yl)propanoic acid;
2-amino-3-(2-methyl-4-nitro-7-(pyridin-4-yl)-1H-indol-3-yl)propanoic acid;
2-amino-3-(2-methyl-7-nitro-4-(pyridin-4-yl)-1H-indol-3-yl)propanoic acid;
2-amino-3-(1,2,5-trimethyl-4-nitro-1H-indol-3-yl)propanoic acid;
2-amino-3-(1,2,6-trimethyl-4-nitro-1H-indol-3-yl)propanoic acid;
2-amino-3-(1,2,7-trimethyl-4-nitro-1H-indol-3-yl)propanoic acid;
2-amino-3-(1,2,4-trimethyl-7-nitro-1H-indol-3-yl)propanoic acid;
2-amino-3-(6-fluoro-1,2-dimethyl-4-nitro-1H-indol-3-yl)propanoic acid;
2-amino-3-(7-fluoro-1,2-dimethyl-4-nitro-1H-indol-3-yl)propanoic acid;
2-amino-3-(4-fluoro-1,2-dimethyl-7-nitro-1H-indol-3-yl)propanoic acid;
2-amino-3-(5-chloro-1,2-dimethyl-4-nitro-1H-indol-3-yl)propanoic acid;
2-amino-3-(6-chloro-1,2-dimethyl-4-nitro-1H-indol-3-yl)propanoic acid;
2-amino-3-(7-chloro-1,2-dimethyl-4-nitro-1H-indol-3-yl)propanoic acid;
2-amino-3-(4-chloro-1,2-dimethyl-7-nitro-1H-indol-3-yl)propanoic acid;
2-amino-3-(5-bromo-1,2-dimethyl-4-nitro-1H-indol-3-yl)propanoic acid;
2-amino-3-(6-bromo-1,2-dimethyl-4-nitro-1H-indol-3-yl)propanoic acid;
2-amino-3-(7-bromo-1,2-dimethyl-4-nitro-1H-indol-3-yl)propanoic acid;
2-amino-3-(4-bromo-1,2-dimethyl-7-nitro-1H-indol-3-yl)propanoic acid;
2-amino-3-(5-methoxy-1,2-dimethyl-4-nitro-1H-indol-3-yl)propanoic acid;
2-amino-3-(6-methoxy-1,2-dimethyl-4-nitro-1H-indol-3-yl)propanoic acid;
2-amino-3-(7-methoxy-1,2-dimethyl-4-nitro-1H-indol-3-yl)propanoic acid;
2-amino-3-(4-methoxy-1,2-dimethyl-7-nitro-1H-indol-3-yl)propanoic acid;
2-amino-3-(5-amino-1,2-dimethyl-4-nitro-1H-indol-3-yl)propanoic acid;
2-amino-3-(6-amino-1,2-dimethyl-4-nitro-1H-indol-3-yl)propanoic acid;
2-amino-3-(7-amino-1,2-dimethyl-4-nitro-1H-indol-3-yl)propanoic acid;
2-amino-3-(4-amino-1,2-dimethyl-7-nitro-1H-indol-3-yl)propanoic acid;
2-amino-3-(5-hydroxy-1,2-dimethyl-4-nitro-1H-indol-3-yl)propanoic acid;
2-amino-3-(6-hydroxy-1,2-dimethyl-4-nitro-1H-indol-3-yl)propanoic acid;
2-amino-3-(7-hydroxy-1,2-dimethyl-4-nitro-1H-indol-3-yl)propanoic acid;
2-amino-3-(4-hydroxy-1,2-dimethyl-7-nitro-1H-indol-3-yl)propanoic acid;
2-amino-3-(1,2-dimethyl-4-nitro-5-phenyl-1H-indol-3-yl)propanoic acid;
2-amino-3-(1,2-dimethyl-4-nitro-6-phenyl-1H-indol-3-yl)propanoic acid;
2-amino-3-(1,2-dimethyl-4-nitro-7-phenyl-1H-indol-3-yl)propanoic acid;
2-amino-3-(1,2-dimethyl-7-nitro-4-phenyl-1H-indol-3-yl)propanoic acid;
2-amino-3-(5-cyclopropyl-1,2-dimethyl-4-nitro-1H-indol-3-yl)propanoic acid;

2-amino-3-(6-cyclopropyl-1,2-dimethyl-4-nitro-1H-indol-3-yl)propanoic acid;
2-amino-3-(7-cyclopropyl-1,2-dimethyl-4-nitro-1H-indol-3-yl)propanoic acid;
2-amino-3-(4-cyclopropyl-1,2-dimethyl-7-nitro-1H-indol-3-yl)propanoic acid;
2-amino-3-(1,2-dimethyl-4-nitro-5-vinyl-1H-indol-3-yl)propanoic acid;
2-amino-3-(1,2-dimethyl-4-nitro-6-vinyl-1H-indol-3-yl)propanoic acid;
2-amino-3-(1,2-dimethyl-4-nitro-7-vinyl-1H-indol-3-yl)propanoic acid;
2-amino-3-(1,2-dimethyl-7-nitro-4-vinyl-1H-indol-3-yl)propanoic acid;
2-amino-3-(5-ethynyl-1,2-dimethyl-4-nitro-1H-indol-3-yl)propanoic acid;
2-amino-3-(6-ethynyl-1,2-dimethyl-4-nitro-1H-indol-3-yl)propanoic acid;
2-amino-3-(7-ethynyl-1,2-dimethyl-4-nitro-1H-indol-3-yl)propanoic acid;
2-amino-3-(4-ethynyl-1,2-dimethyl-7-nitro-1H-indol-3-yl)propanoic acid;
2-amino-3-(1,2-dimethyl-5-morpholino-4-nitro-1H-indol-3-yl)propanoic acid;
2-amino-3-(1,2-dimethyl-6-morpholino-4-nitro-1H-indol-3-yl)propanoic acid;
2-amino-3-(1,2-dimethyl-7-morpholino-4-nitro-1H-indol-3-yl)propanoic acid;
2-amino-3-(1,2-dimethyl-4-morpholino-7-nitro-1H-indol-3-yl)propanoic acid;
2-amino-3-(1,2-dimethyl-5-(methylthio)-4-nitro-1H-indol-3-yl)propanoic acid;
2-amino-3-(1,2-dimethyl-6-(methylthio)-4-nitro-1H-indol-3-yl)propanoic acid;
2-amino-3-(1,2-dimethyl-7-(methylthio)-4-nitro-1H-indol-3-yl)propanoic acid;
2-amino-3-(1,2-dimethyl-4-(methylthio)-7-nitro-1H-indol-3-yl)propanoic acid;
2-amino-3-(1,2-dimethyl-4-nitro-5-(pyridin-4-yl)-1H-indol-3-yl)propanoic acid;
2-amino-3-(1,2-dimethyl-4-nitro-6-(pyridin-4-yl)-1H-indol-3-yl)propanoic acid;
2-amino-3-(1,2-dimethyl-4-nitro-7-(pyridin-4-yl)-1H-indol-3-yl)propanoic acid; or
2-amino-3-(1,2-dimethyl-7-nitro-4-(pyridin-4-yl)-1H-indol-3-yl)propanoic acid;
and a pharmaceutically acceptable salt, prodrug, hydrate, or solvate thereof.

In some embodiments, a composition has a temperature below 37° C. (e.g., the temperature of the bacterial culture media of a composition is below 37° C.). In some embodiments, a composition has a temperature between 10 to 30° C. (e.g., the temperature of the bacterial culture media of a composition is between 10 to 30° C.). In some embodiments, a composition at a temperature of 28° C. (e.g., the temperature of the bacterial culture media of a composition is 28° C.).

In some embodiments, the disclosure relates to methods of producing a recombinant bacterial cell as described by the disclosure, the comprising the steps of: transforming a bacterial cell with an isolated nucleic acid engineered to express a fusion protein comprising a TxtE enzyme linked to a catalytic domain of a CYP102A1 (P450BM3) reductase enzyme via an amino acid linker sequence that can be varied in terms of identities and length, e.g., that is between 14 and 27 amino acids in length; and an isolated nucleic acid engineered to express a nitric oxide synthase (NOS) enzyme; and culturing (e.g., growing) the bacterial cell.

In some embodiments of methods described by the disclosure a bacterial cell is transformed with an isolated nucleic acid engineered to express a glucose-1 dehydrogenase (GHD) enzyme.

In some embodiments of methods described by the disclosure, a bacterial cell is transformed with one or more an isolated nucleic acids comprising the sequence set forth in any one of SEQ ID NOs: 8-13.

In some aspects, the disclosure relates to methods for producing a composition as described by the disclosure, comprising the step of inoculating a bacterial culture medium with a recombinant bacterial cell as described by the disclosure.

In some aspects, the disclosure relates to methods for producing a nitrated L-tryptophan or nitrated L-tryptophan analogue, comprising the steps of: introducing into a bacterial cell culture comprising a one or more of a recombinant bacterial cell as described by the disclosure one or more L-Trp molecules and/or one or more L-Trp analogue molecules; and growing the bacterial cell culture under conditions under which a fusion protein expressed by the recombinant bacterial cell catalyzes a nitration reaction which produces one or more nitrated L-Trp molecules and/or one or more nitrated L-Trp analog molecules. In some embodiments, methods further comprise the step of isolating nitrated L-Trp molecules and/or nitrated L-Trp analog molecules from the bacterial cell culture. In some embodiments, the nitrated tryptophan or nitrated tryptophane analogue is a compound of Formulae I-VI. In some embodiments, the nitrated tryptophan or nitrated tryptophane analogue is:

(S)-2-amino-3-(4-methyl-5-nitro-1H-indol-3-yl)propanoic acid;
(S)-2-amino-3-(5-methyl-4-nitro-1H-indol-3-yl)propanoic acid;
(S)-2-amino-3-(6-methyl-4-nitro-1H-indol-3-yl)propanoic acid;
(S)-2-amino-3-(7-methyl-4-nitro-1H-indol-3-yl)propanoic acid;
(S)-2-amino-3-(4-methyl-7-nitro-1H-indol-3-yl)propanoic acid;
(S)-2-amino-3-(5-fluoro-4-nitro-1H-indol-3-yl)propanoic acid;
(S)-2-amino-3-(6-fluoro-4-nitro-1H-indol-3-yl)propanoic acid;
(S)-2-amino-3-(7-fluoro-4-nitro-1H-indol-3-yl)propanoic acid;
(S)-2-amino-3-(4-fluoro-7-nitro-1H-indol-3-yl)propanoic acid;
(S)-2-amino-3-(5-chloro-4-nitro-1H-indol-3-yl)propanoic acid;
(S)-2-amino-3-(6-chloro-4-nitro-1H-indol-3-yl)propanoic acid;
(S)-2-amino-3-(7-chloro-4-nitro-1H-indol-3-yl)propanoic acid;
(S)-2-amino-3-(4-chloro-7-nitro-1H-indol-3-yl)propanoic acid;
(S)-2-amino-3-(5-bromo-4-nitro-1H-indol-3-yl)propanoic acid;
(S)-2-amino-3-(6-bromo-4-nitro-1H-indol-3-yl)propanoic acid;
(S)-2-amino-3-(7-bromo-4-nitro-1H-indol-3-yl)propanoic acid;
(S)-2-amino-3-(4-bromo-7-nitro-1H-indol-3-yl)propanoic acid;

(S)-2-amino-3-(5-methoxy-4-nitro-1H-indol-3-yl)propanoic acid;
(S)-2-amino-3-(6-methoxy-4-nitro-1H-indol-3-yl)propanoic acid;
(S)-2-amino-3-(7-methoxy-4-nitro-1H-indol-3-yl)propanoic acid;
(S)-2-amino-3-(4-methoxy-7-nitro-1H-indol-3-yl)propanoic acid;
(S)-2-amino-3-(5-amino-4-nitro-1H-indol-3-yl)propanoic acid;
(S)-2-amino-3-(6-amino-4-nitro-1H-indol-3-yl)propanoic acid;
(S)-2-amino-3-(7-amino-4-nitro-1H-indol-3-yl)propanoic acid;
(S)-2-amino-3-(4-amino-7-nitro-1H-indol-3-yl)propanoic acid;
(S)-2-amino-3-(5-hydroxy-4-nitro-1H-indol-3-yl)propanoic acid;
(S)-2-amino-3-(6-hydroxy-4-nitro-1H-indol-3-yl)propanoic acid;
(S)-2-amino-3-(7-hydroxy-4-nitro-1H-indol-3-yl)propanoic acid;
(S)-2-amino-3-(4-hydroxy-7-nitro-1H-indol-3-yl)propanoic acid;
(S)-2-amino-3-(4-nitro-5-phenyl-1H-indol-3-yl)propanoic acid;
(S)-2-amino-3-(4-nitro-6-phenyl-1H-indol-3-yl)propanoic acid;
(S)-2-amino-3-(4-nitro-7-phenyl-1H-indol-3-yl)propanoic acid;
(S)-2-amino-3-(7-nitro-4-phenyl-1H-indol-3-yl)propanoic acid;
(S)-2-amino-3-(5-cyclopropyl-4-nitro-1H-indol-3-yl)propanoic acid;
(S)-2-amino-3-(6-cyclopropyl-4-nitro-1H-indol-3-yl)propanoic acid;
(S)-2-amino-3-(7-cyclopropyl-4-nitro-1H-indol-3-yl)propanoic acid;
(S)-2-amino-3-(4-cyclopropyl-7-nitro-1H-indol-3-yl)propanoic acid;
(S)-2-amino-3-(4-nitro-5-vinyl-1H-indol-3-yl)propanoic acid;
(S)-2-amino-3-(4-nitro-6-vinyl-1H-indol-3-yl)propanoic acid;
(S)-2-amino-3-(4-nitro-7-vinyl-1H-indol-3-yl)propanoic acid;
(S)-2-amino-3-(7-nitro-4-vinyl-1H-indol-3-yl)propanoic acid;
(S)-2-amino-3-(5-ethynyl-4-nitro-1H-indol-3-yl)propanoic acid;
(S)-2-amino-3-(6-ethynyl-4-nitro-1H-indol-3-yl)propanoic acid;
(S)-2-amino-3-(7-ethynyl-4-nitro-1H-indol-3-yl)propanoic acid;
(S)-2-amino-3-(4-ethynyl-7-nitro-1H-indol-3-yl)propanoic acid;
(S)-2-amino-3-(5-morpholino-4-nitro-1H-indol-3-yl)propanoic acid;
(S)-2-amino-3-(6-morpholino-4-nitro-1H-indol-3-yl)propanoic acid;
(S)-2-amino-3-(7-morpholino-4-nitro-1H-indol-3-yl)propanoic acid;
(S)-2-amino-3-(4-morpholino-7-nitro-1H-indol-3-yl)propanoic acid;
(S)-2-amino-3-(5-(methylthio)-4-nitro-1H-indol-3-yl)propanoic acid;
(S)-2-amino-3-(6-(methylthio)-4-nitro-1H-indol-3-yl)propanoic acid;
(S)-2-amino-3-(7-(methylthio)-4-nitro-1H-indol-3-yl)propanoic acid;
(S)-2-amino-3-(4-(methylthio)-7-nitro-1H-indol-3-yl)propanoic acid;
(S)-2-amino-3-(4-nitro-5-(pyridin-4-yl)-1H-indol-3-yl)propanoic acid;
(S)-2-amino-3-(4-nitro-6-(pyridin-4-yl)-1H-indol-3-yl)propanoic acid;
(S)-2-amino-3-(4-nitro-7-(pyridin-4-yl)-1H-indol-3-yl)propanoic acid;
(S)-2-amino-3-(7-nitro-4-(pyridin-4-yl)-1H-indol-3-yl)propanoic acid;
2-amino-3-(4-methyl-5-nitro-1H-indol-3-yl)propanoic acid;
2-amino-3-(5-methyl-4-nitro-1H-indol-3-yl)propanoic acid;
2-amino-3-(6-methyl-4-nitro-1H-indol-3-yl)propanoic acid;
2-amino-3-(7-methyl-4-nitro-1H-indol-3-yl)propanoic acid;
2-amino-3-(4-methyl-7-nitro-1H-indol-3-yl)propanoic acid;
2-amino-3-(6-fluoro-4-nitro-1H-indol-3-yl)propanoic acid;
2-amino-3-(7-fluoro-4-nitro-1H-indol-3-yl)propanoic acid;
2-amino-3-(4-fluoro-7-nitro-1H-indol-3-yl)propanoic acid;
2-amino-3-(5-chloro-4-nitro-1H-indol-3-yl)propanoic acid;
2-amino-3-(6-chloro-4-nitro-1H-indol-3-yl)propanoic acid;
2-amino-3-(7-chloro-4-nitro-1H-indol-3-yl)propanoic acid;
2-amino-3-(4-chloro-7-nitro-1H-indol-3-yl)propanoic acid;
2-amino-3-(5-bromo-4-nitro-1H-indol-3-yl)propanoic acid;
2-amino-3-(6-bromo-4-nitro-1H-indol-3-yl)propanoic acid;
2-amino-3-(7-bromo-4-nitro-1H-indol-3-yl)propanoic acid;
2-amino-3-(4-bromo-7-nitro-1H-indol-3-yl)propanoic acid;
2-amino-3-(5-methoxy-4-nitro-1H-indol-3-yl)propanoic acid;
2-amino-3-(6-methoxy-4-nitro-1H-indol-3-yl)propanoic acid;
2-amino-3-(7-methoxy-4-nitro-1H-indol-3-yl)propanoic acid;
2-amino-3-(4-methoxy-7-nitro-1H-indol-3-yl)propanoic acid;
2-amino-3-(5-amino-4-nitro-1H-indol-3-yl)propanoic acid;
2-amino-3-(6-amino-4-nitro-1H-indol-3-yl)propanoic acid;
2-amino-3-(7-amino-4-nitro-1H-indol-3-yl)propanoic acid;
2-amino-3-(4-amino-7-nitro-1H-indol-3-yl)propanoic acid;
2-amino-3-(5-hydroxy-4-nitro-1H-indol-3-yl)propanoic acid;
2-amino-3-(6-hydroxy-4-nitro-1H-indol-3-yl)propanoic acid;
2-amino-3-(7-hydroxy-4-nitro-1H-indol-3-yl)propanoic acid;
2-amino-3-(4-hydroxy-7-nitro-1H-indol-3-yl)propanoic acid;
2-amino-3-(4-nitro-5-phenyl-1H-indol-3-yl)propanoic acid;
2-amino-3-(4-nitro-6-phenyl-1H-indol-3-yl)propanoic acid;
2-amino-3-(4-nitro-7-phenyl-1H-indol-3-yl)propanoic acid;
2-amino-3-(7-nitro-4-phenyl-1H-indol-3-yl)propanoic acid;
2-amino-3-(5-cyclopropyl-4-nitro-1H-indol-3-yl)propanoic acid;
2-amino-3-(6-cyclopropyl-4-nitro-1H-indol-3-yl)propanoic acid;
2-amino-3-(7-cyclopropyl-4-nitro-1H-indol-3-yl)propanoic acid;
2-amino-3-(4-cyclopropyl-7-nitro-1H-indol-3-yl)propanoic acid;
2-amino-3-(4-nitro-5-vinyl-1H-indol-3-yl)propanoic acid;
2-amino-3-(4-nitro-6-vinyl-1H-indol-3-yl)propanoic acid;
2-amino-3-(4-nitro-7-vinyl-1H-indol-3-yl)propanoic acid;
2-amino-3-(7-nitro-4-vinyl-1H-indol-3-yl)propanoic acid;

2-amino-3-(5-ethynyl-4-nitro-1H-indol-3-yl)propanoic acid;
2-amino-3-(6-ethynyl-4-nitro-1H-indol-3-yl)propanoic acid;
2-amino-3-(7-ethynyl-4-nitro-1H-indol-3-yl)propanoic acid;
2-amino-3-(4-ethynyl-7-nitro-1H-indol-3-yl)propanoic acid;
2-amino-3-(5-morpholino-4-nitro-1H-indol-3-yl)propanoic acid;
2-amino-3-(6-morpholino-4-nitro-1H-indol-3-yl)propanoic acid;
2-amino-3-(7-morpholino-4-nitro-1H-indol-3-yl)propanoic acid;
2-amino-3-(4-morpholino-7-nitro-1H-indol-3-yl)propanoic acid;
2-amino-3-(5-(methylthio)-4-nitro-1H-indol-3-yl)propanoic acid;
2-amino-3-(6-(methylthio)-4-nitro-1H-indol-3-yl)propanoic acid;
2-amino-3-(7-(methylthio)-4-nitro-1H-indol-3-yl)propanoic acid;
2-amino-3-(4-(methylthio)-7-nitro-1H-indol-3-yl)propanoic acid;
2-amino-3-(4-nitro-5-(pyridin-4-yl)-1H-indol-3-yl)propanoic acid;
2-amino-3-(4-nitro-6-(pyridin-4-yl)-1H-indol-3-yl)propanoic acid;
2-amino-3-(4-nitro-7-(pyridin-4-yl)-1H-indol-3-yl)propanoic acid;
2-amino-3-(7-nitro-4-(pyridin-4-yl)-1H-indol-3-yl)propanoic acid;
2-amino-3-(1,5-dimethyl-4-nitro-1H-indol-3-yl)propanoic acid;
2-amino-3-(1,6-dimethyl-4-nitro-1H-indol-3-yl)propanoic acid;
2-amino-3-(1,7-dimethyl-4-nitro-1H-indol-3-yl)propanoic acid;
2-amino-3-(1,4-dimethyl-7-nitro-1H-indol-3-yl)propanoic acid;
2-amino-3-(6-fluoro-1-methyl-4-nitro-1H-indol-3-yl)propanoic acid;
2-amino-3-(7-fluoro-1-methyl-4-nitro-1H-indol-3-yl)propanoic acid;
2-amino-3-(4-fluoro-1-methyl-7-nitro-1H-indol-3-yl)propanoic acid;
2-amino-3-(5-chloro-1-methyl-4-nitro-1H-indol-3-yl)propanoic acid;
2-amino-3-(6-chloro-1-methyl-4-nitro-1H-indol-3-yl)propanoic acid;
2-amino-3-(7-chloro-1-methyl-4-nitro-1H-indol-3-yl)propanoic acid;
2-amino-3-(4-chloro-1-methyl-7-nitro-1H-indol-3-yl)propanoic acid;
2-amino-3-(5-bromo-1-methyl-4-nitro-1H-indol-3-yl)propanoic acid;
2-amino-3-(6-bromo-1-methyl-4-nitro-1H-indol-3-yl)propanoic acid;
2-amino-3-(7-bromo-1-methyl-4-nitro-1H-indol-3-yl)propanoic acid;
2-amino-3-(4-bromo-1-methyl-7-nitro-1H-indol-3-yl)propanoic acid;
2-amino-3-(5-methoxy-1-methyl-4-nitro-1H-indol-3-yl)propanoic acid;
2-amino-3-(6-methoxy-1-methyl-4-nitro-1H-indol-3-yl)propanoic acid;
2-amino-3-(7-methoxy-1-methyl-4-nitro-1H-indol-3-yl)propanoic acid;
2-amino-3-(4-methoxy-1-methyl-7-nitro-1H-indol-3-yl)propanoic acid;
2-amino-3-(5-amino-1-methyl-4-nitro-1H-indol-3-yl)propanoic acid;
2-amino-3-(6-amino-1-methyl-4-nitro-1H-indol-3-yl)propanoic acid;
2-amino-3-(7-amino-1-methyl-4-nitro-1H-indol-3-yl)propanoic acid;
2-amino-3-(4-amino-1-methyl-7-nitro-1H-indol-3-yl)propanoic acid;
2-amino-3-(5-hydroxy-1-methyl-4-nitro-1H-indol-3-yl)propanoic acid;
2-amino-3-(6-hydroxy-1-methyl-4-nitro-1H-indol-3-yl)propanoic acid;
2-amino-3-(7-hydroxy-1-methyl-4-nitro-1H-indol-3-yl)propanoic acid;
2-amino-3-(4-hydroxy-1-methyl-7-nitro-1H-indol-3-yl)propanoic acid;
2-amino-3-(1-methyl-4-nitro-5-phenyl-1H-indol-3-yl)propanoic acid;
2-amino-3-(1-methyl-4-nitro-6-phenyl-1H-indol-3-yl)propanoic acid;
2-amino-3-(1-methyl-4-nitro-7-phenyl-1H-indol-3-yl)propanoic acid;
2-amino-3-(1-methyl-7-nitro-4-phenyl-1H-indol-3-yl)propanoic acid;
2-amino-3-(5-cyclopropyl-1-methyl-4-nitro-1H-indol-3-yl)propanoic acid;
2-amino-3-(6-cyclopropyl-1-methyl-4-nitro-1H-indol-3-yl)propanoic acid;
2-amino-3-(7-cyclopropyl-1-methyl-4-nitro-1H-indol-3-yl)propanoic acid;
2-amino-3-(4-cyclopropyl-1-methyl-7-nitro-1H-indol-3-yl)propanoic acid;
2-amino-3-(1-methyl-4-nitro-5-vinyl-1H-indol-3-yl)propanoic acid;
2-amino-3-(1-methyl-4-nitro-6-vinyl-1H-indol-3-yl)propanoic acid;
2-amino-3-(1-methyl-4-nitro-7-vinyl-1H-indol-3-yl)propanoic acid;
2-amino-3-(1-methyl-7-nitro-4-vinyl-1H-indol-3-yl)propanoic acid;
2-amino-3-(5-ethynyl-1-methyl-4-nitro-1H-indol-3-yl)propanoic acid;
2-amino-3-(6-ethynyl-1-methyl-4-nitro-1H-indol-3-yl)propanoic acid;
2-amino-3-(7-ethynyl-1-methyl-4-nitro-1H-indol-3-yl)propanoic acid;
2-amino-3-(4-ethynyl-1-methyl-7-nitro-1H-indol-3-yl)propanoic acid;
2-amino-3-(1-methyl-5-morpholino-4-nitro-1H-indol-3-yl)propanoic acid;
2-amino-3-(1-methyl-6-morpholino-4-nitro-1H-indol-3-yl)propanoic acid;
2-amino-3-(1-methyl-7-morpholino-4-nitro-1H-indol-3-yl)propanoic acid;
2-amino-3-(1-methyl-4-morpholino-7-nitro-1H-indol-3-yl)propanoic acid;
2-amino-3-(1-methyl-5-(methylthio)-4-nitro-1H-indol-3-yl)propanoic acid;
2-amino-3-(1-methyl-6-(methylthio)-4-nitro-1H-indol-3-yl)propanoic acid;
2-amino-3-(1-methyl-7-(methylthio)-4-nitro-1H-indol-3-yl)propanoic acid;

2-amino-3-(1-methyl-4-(methylthio)-7-nitro-1H-indol-3-yl)propanoic acid;
2-amino-3-(1-methyl-4-nitro-5-(pyridin-4-yl)-1H-indol-3-yl)propanoic acid;
2-amino-3-(1-methyl-4-nitro-6-(pyridin-4-yl)-1H-indol-3-yl)propanoic acid;
2-amino-3-(1-methyl-4-nitro-7-(pyridin-4-yl)-1H-indol-3-yl)propanoic acid;
2-amino-3-(1-methyl-7-nitro-4-(pyridin-4-yl)-1H-indol-3-yl)propanoic acid;
2-amino-3-(2,5-dimethyl-4-nitro-1H-indol-3-yl)propanoic acid;
2-amino-3-(2,6-dimethyl-4-nitro-1H-indol-3-yl)propanoic acid;
2-amino-3-(2,7-dimethyl-4-nitro-1H-indol-3-yl)propanoic acid;
2-amino-3-(2,4-dimethyl-7-nitro-1H-indol-3-yl)propanoic acid;
2-amino-3-(6-fluoro-2-methyl-4-nitro-1H-indol-3-yl)propanoic acid;
2-amino-3-(7-fluoro-2-methyl-4-nitro-1H-indol-3-yl)propanoic acid;
2-amino-3-(4-fluoro-2-methyl-7-nitro-1H-indol-3-yl)propanoic acid;
2-amino-3-(5-chloro-2-methyl-4-nitro-1H-indol-3-yl)propanoic acid;
2-amino-3-(6-chloro-2-methyl-4-nitro-1H-indol-3-yl)propanoic acid;
2-amino-3-(7-chloro-2-methyl-4-nitro-1H-indol-3-yl)propanoic acid;
2-amino-3-(4-chloro-2-methyl-7-nitro-1H-indol-3-yl)propanoic acid;
2-amino-3-(5-bromo-2-methyl-4-nitro-1H-indol-3-yl)propanoic acid;
2-amino-3-(6-bromo-2-methyl-4-nitro-1H-indol-3-yl)propanoic acid;
2-amino-3-(7-bromo-2-methyl-4-nitro-1H-indol-3-yl)propanoic acid;
2-amino-3-(4-bromo-2-methyl-7-nitro-1H-indol-3-yl)propanoic acid;
2-amino-3-(5-methoxy-2-methyl-4-nitro-1H-indol-3-yl)propanoic acid;
2-amino-3-(6-methoxy-2-methyl-4-nitro-1H-indol-3-yl)propanoic acid;
2-amino-3-(7-methoxy-2-methyl-4-nitro-1H-indol-3-yl)propanoic acid;
2-amino-3-(4-methoxy-2-methyl-7-nitro-1H-indol-3-yl)propanoic acid;
2-amino-3-(5-amino-2-methyl-4-nitro-1H-indol-3-yl)propanoic acid;
2-amino-3-(6-amino-2-methyl-4-nitro-1H-indol-3-yl)propanoic acid;
2-amino-3-(7-amino-2-methyl-4-nitro-1H-indol-3-yl)propanoic acid;
2-amino-3-(4-amino-2-methyl-7-nitro-1H-indol-3-yl)propanoic acid;
2-amino-3-(5-hydroxy-2-methyl-4-nitro-1H-indol-3-yl)propanoic acid;
2-amino-3-(6-hydroxy-2-methyl-4-nitro-1H-indol-3-yl)propanoic acid;
2-amino-3-(7-hydroxy-2-methyl-4-nitro-1H-indol-3-yl)propanoic acid;
2-amino-3-(4-hydroxy-2-methyl-7-nitro-1H-indol-3-yl)propanoic acid;
2-amino-3-(2-methyl-4-nitro-5-phenyl-1H-indol-3-yl)propanoic acid;
2-amino-3-(2-methyl-4-nitro-6-phenyl-1H-indol-3-yl)propanoic acid;
2-amino-3-(2-methyl-4-nitro-7-phenyl-1H-indol-3-yl)propanoic acid;
2-amino-3-(2-methyl-7-nitro-4-phenyl-1H-indol-3-yl)propanoic acid;
2-amino-3-(5-cyclopropyl-2-methyl-4-nitro-1H-indol-3-yl)propanoic acid;
2-amino-3-(6-cyclopropyl-2-methyl-4-nitro-1H-indol-3-yl)propanoic acid;
2-amino-3-(7-cyclopropyl-2-methyl-4-nitro-1H-indol-3-yl)propanoic acid;
2-amino-3-(4-cyclopropyl-2-methyl-7-nitro-1H-indol-3-yl)propanoic acid;
2-amino-3-(2-methyl-4-nitro-5-vinyl-1H-indol-3-yl)propanoic acid;
2-amino-3-(2-methyl-4-nitro-6-vinyl-1H-indol-3-yl)propanoic acid;
2-amino-3-(2-methyl-4-nitro-7-vinyl-1H-indol-3-yl)propanoic acid;
2-amino-3-(2-methyl-7-nitro-4-vinyl-1H-indol-3-yl)propanoic acid;
2-amino-3-(5-ethynyl-2-methyl-4-nitro-1H-indol-3-yl)propanoic acid;
2-amino-3-(6-ethynyl-2-methyl-4-nitro-1H-indol-3-yl)propanoic acid;
2-amino-3-(7-ethynyl-2-methyl-4-nitro-1H-indol-3-yl)propanoic acid;
2-amino-3-(4-ethynyl-2-methyl-7-nitro-1H-indol-3-yl)propanoic acid;
2-amino-3-(2-methyl-5-morpholino-4-nitro-1H-indol-3-yl)propanoic acid;
2-amino-3-(2-methyl-6-morpholino-4-nitro-1H-indol-3-yl)propanoic acid;
2-amino-3-(2-methyl-7-morpholino-4-nitro-1H-indol-3-yl)propanoic acid;
2-amino-3-(2-methyl-4-morpholino-7-nitro-1H-indol-3-yl)propanoic acid;
2-amino-3-(2-methyl-5-(methylthio)-4-nitro-1H-indol-3-yl)propanoic acid;
2-amino-3-(2-methyl-6-(methylthio)-4-nitro-1H-indol-3-yl)propanoic acid;
2-amino-3-(2-methyl-7-(methylthio)-4-nitro-1H-indol-3-yl)propanoic acid;
2-amino-3-(2-methyl-4-(methylthio)-7-nitro-1H-indol-3-yl)propanoic acid;
2-amino-3-(2-methyl-4-nitro-5-(pyridin-4-yl)-1H-indol-3-yl)propanoic acid;
2-amino-3-(2-methyl-4-nitro-6-(pyridin-4-yl)-1H-indol-3-yl)propanoic acid;
2-amino-3-(2-methyl-4-nitro-7-(pyridin-4-yl)-1H-indol-3-yl)propanoic acid;
2-amino-3-(2-methyl-7-nitro-4-(pyridin-4-yl)-1H-indol-3-yl)propanoic acid;
2-amino-3-(1,2,5-trimethyl-4-nitro-1H-indol-3-yl)propanoic acid;
2-amino-3-(1,2,6-trimethyl-4-nitro-1H-indol-3-yl)propanoic acid;
2-amino-3-(1,2,7-trimethyl-4-nitro-1H-indol-3-yl)propanoic acid;
2-amino-3-(1,2,4-trimethyl-7-nitro-1H-indol-3-yl)propanoic acid;
2-amino-3-(6-fluoro-1,2-dimethyl-4-nitro-1H-indol-3-yl)propanoic acid;
2-amino-3-(7-fluoro-1,2-dimethyl-4-nitro-1H-indol-3-yl)propanoic acid;

2-amino-3-(4-fluoro-1,2-dimethyl-7-nitro-1H-indol-3-yl) propanoic acid;
2-amino-3-(5-chloro-1,2-dimethyl-4-nitro-1H-indol-3-yl) propanoic acid;
2-amino-3-(6-chloro-1,2-dimethyl-4-nitro-1H-indol-3-yl) propanoic acid;
2-amino-3-(7-chloro-1,2-dimethyl-4-nitro-1H-indol-3-yl) propanoic acid;
2-amino-3-(4-chloro-1,2-dimethyl-7-nitro-1H-indol-3-yl) propanoic acid;
2-amino-3-(5-bromo-1,2-dimethyl-4-nitro-1H-indol-3-yl) propanoic acid;
2-amino-3-(6-bromo-1,2-dimethyl-4-nitro-1H-indol-3-yl) propanoic acid;
2-amino-3-(7-bromo-1,2-dimethyl-4-nitro-1H-indol-3-yl) propanoic acid;
2-amino-3-(4-bromo-1,2-dimethyl-7-nitro-1H-indol-3-yl) propanoic acid;
2-amino-3-(5-methoxy-1,2-dimethyl-4-nitro-1H-indol-3-yl) propanoic acid;
2-amino-3-(6-methoxy-1,2-dimethyl-4-nitro-1H-indol-3-yl) propanoic acid;
2-amino-3-(7-methoxy-1,2-dimethyl-4-nitro-1H-indol-3-yl) propanoic acid;
2-amino-3-(4-methoxy-1,2-dimethyl-7-nitro-1H-indol-3-yl) propanoic acid;
2-amino-3-(5-amino-1,2-dimethyl-4-nitro-1H-indol-3-yl) propanoic acid;
2-amino-3-(6-amino-1,2-dimethyl-4-nitro-1H-indol-3-yl) propanoic acid;
2-amino-3-(7-amino-1,2-dimethyl-4-nitro-1H-indol-3-yl) propanoic acid;
2-amino-3-(4-amino-1,2-dimethyl-7-nitro-1H-indol-3-yl) propanoic acid;
2-amino-3-(5-hydroxy-1,2-dimethyl-4-nitro-1H-indol-3-yl) propanoic acid;
2-amino-3-(6-hydroxy-1,2-dimethyl-4-nitro-1H-indol-3-yl) propanoic acid;
2-amino-3-(7-hydroxy-1,2-dimethyl-4-nitro-1H-indol-3-yl) propanoic acid;
2-amino-3-(4-hydroxy-1,2-dimethyl-7-nitro-1H-indol-3-yl) propanoic acid;
2-amino-3-(1,2-dimethyl-4-nitro-5-phenyl-1H-indol-3-yl) propanoic acid;
2-amino-3-(1,2-dimethyl-4-nitro-6-phenyl-1H-indol-3-yl) propanoic acid;
2-amino-3-(1,2-dimethyl-4-nitro-7-phenyl-1H-indol-3-yl) propanoic acid;
2-amino-3-(1,2-dimethyl-7-nitro-4-phenyl-1H-indol-3-yl) propanoic acid;
2-amino-3-(5-cyclopropyl-1,2-dimethyl-4-nitro-1H-indol-3-yl)propanoic acid;
2-amino-3-(6-cyclopropyl-1,2-dimethyl-4-nitro-1H-indol-3-yl)propanoic acid;
2-amino-3-(7-cyclopropyl-1,2-dimethyl-4-nitro-1H-indol-3-yl)propanoic acid;
2-amino-3-(4-cyclopropyl-1,2-dimethyl-7-nitro-1H-indol-3-yl)propanoic acid;
2-amino-3-(1,2-dimethyl-4-nitro-5-vinyl-1H-indol-3-yl) propanoic acid;
2-amino-3-(1,2-dimethyl-4-nitro-6-vinyl-1H-indol-3-yl) propanoic acid;
2-amino-3-(1,2-dimethyl-4-nitro-7-vinyl-1H-indol-3-yl) propanoic acid;
2-amino-3-(1,2-dimethyl-7-nitro-4-vinyl-1H-indol-3-yl) propanoic acid;
2-amino-3-(5-ethynyl-1,2-dimethyl-4-nitro-1H-indol-3-yl) propanoic acid;
2-amino-3-(6-ethynyl-1,2-dimethyl-4-nitro-1H-indol-3-yl) propanoic acid;
2-amino-3-(7-ethynyl-1,2-dimethyl-4-nitro-1H-indol-3-yl) propanoic acid;
2-amino-3-(4-ethynyl-1,2-dimethyl-7-nitro-1H-indol-3-yl) propanoic acid;
2-amino-3-(1,2-dimethyl-5-morpholino-4-nitro-1H-indol-3-yl)propanoic acid;
2-amino-3-(1,2-dimethyl-6-morpholino-4-nitro-1H-indol-3-yl)propanoic acid;
2-amino-3-(1,2-dimethyl-7-morpholino-4-nitro-1H-indol-3-yl)propanoic acid;
2-amino-3-(1,2-dimethyl-4-morpholino-7-nitro-1H-indol-3-yl)propanoic acid;
2-amino-3-(1,2-dimethyl-5-(methylthio)-4-nitro-1H-indol-3-yl)propanoic acid;
2-amino-3-(1,2-dimethyl-6-(methylthio)-4-nitro-1H-indol-3-yl)propanoic acid;
2-amino-3-(1,2-dimethyl-7-(methylthio)-4-nitro-1H-indol-3-yl)propanoic acid;
2-amino-3-(1,2-dimethyl-4-(methylthio)-7-nitro-1H-indol-3-yl)propanoic acid;
2-amino-3-(1,2-dimethyl-4-nitro-5-(pyridin-4-yl)-1H-indol-3-yl)propanoic acid;
2-amino-3-(1,2-dimethyl-4-nitro-6-(pyridin-4-yl)-1H-indol-3-yl)propanoic acid;
2-amino-3-(1,2-dimethyl-4-nitro-7-(pyridin-4-yl)-1H-indol-3-yl)propanoic acid; or
2-amino-3-(1,2-dimethyl-7-nitro-4-(pyridin-4-yl)-1H-indol-3-yl)propanoic acid;
and a pharmaceutically acceptable salt, prodrug, hydrate, or solvate thereof.

In some embodiments of methods described by the disclosure, one or more compounds of Formula Ia or IVa. In some embodiments of methods described by the disclosure, one or more L-Trp analogue molecules are selected from the group consisting of α-Me-Trp, 4-F-Trp, 4-Me-Trp, 5-MeO-Trp, 5-Me-Trp, 5-F-Trp, 6-F-Trp, and 7-Me-Trp.

In some embodiments of methods described by the disclosure, the step of growing the bacterial cell culture comprises introducing one or more antibiotic and/or one or more inducer into the bacterial cell culture. In some embodiments, one or more antibiotic is selected from ampicillin and kanamycin. In some embodiments, one or more of the inducers is Isopropyl β-D-1-thiogalactopyranoside (IPTG).

In some embodiments of methods described by the disclosure, the step of growing a bacterial cell culture is performed at a temperature below 37° C. In some embodiments, the step of growing the bacterial cell culture is performed at a temperature between 10 to 30° C., optionally at a temperature of 28° C.

In some embodiments, a bacterial cell culture is grown for up to 25 hours (e.g., up to 25 hours post-transformation with one or more isolated nucleic acids).

In some embodiments, isolating nitrated L-Trp molecules and/or nitrated L-Trp analog molecules comprises lysing one or more recombinant bacterial cells. In some embodiments, isolating nitrated L-Trp molecules and/or nitrated L-Trp analog molecules further comprises performing high-pressure liquid chromatography (HPLC) on a bacterial cell lysate, or purifying a bacterial lysate by performing a liquid/solid (e.g., carbon-based, such as $C_{18}$) purification technique.

BRIEF DESCRIPTION OF DRAWINGS

FIG. 2A shows SDS-PAGE analysis of a whole cell nitration system. M, marker; 1, pETDUET-TB14-BsNOS+pET28b-GDH; 2, pETDUET-GDH-BsNOS+pET28b-TB14; 3, pACYCDUET-TB14-BsNOS+pET28b-GDH; 4, pACYCDUET-GDH-BsNOS+pET28b-TB14. Three soluble recombinant proteins (TB14, BsNOS, and GDH) are identified with arrows. FIG. 2B shows LCMS analysis of products in the whole cell nitration.

FIG. 3A is a schematic representation of plasmids combination used in different embodiments of a whole cell nitration system. FIG. 3B shows nitrated tryptophan concentration produced by different embodiments of a whole cell nitration system. Bacterial growth was supported by M9 medium.

FIG. 10A shows design of four Nitrotrp biosynthetic pathways comprising TB14, BsNOS, and GDH. These genes were cloned in pETDuet-1 and pET28b or pACYCDuet-1 and pET28b. FIG. 10B shows SDS-PAGE analysis of soluble protein fractions of E. coli cells transformed with the pathway I-IV. Protein expression in E. coli-I to -IV was induced by 0.5 mM IPTG in TB at 18° C., 250 rpm for 20 h. An equal volume of soluble protein fractions prepared from the same concentrations of cell resuspension solutions was used for SDS-PAGE analysis. Bands of three soluble recombinant proteins were indicated with arrows. FIG. 10C shows production of Nitrotrp by E. coli-I to -IV in the M9 medium at 20° C., 250 rpm. Aliquots (0.1 mL) of the fermentation culture were taken at days 1 to 4 and the concentration of Nitrotrp in the samples was measured in HPLC analysis. The data represent means±s.d. of at least two independent experiments.

FIG. 12A shows HPLC analysis of authentic Nitrotrp (I) and clear fermentation medium (II) demonstrated the production of Nitrotrp. FIG. 12B shows ESI-MS spectrum of Nitrotrp produced by E. coli. The calculated m/z of [M+H]+ is 250.1, identical to determined value.

FIG. 14A shows SDS-PAGE analysis of purified recombinant TnaA (around 56 kD). FIG. 14B shows HPLC analysis of TnaA reactions with L-Trp (I) and Nitrotrp (II) as substrates. The reactions contained 0.1 μM purified TnaA and 0.5 mM substrate and incubated at 37° C. for 10 min. No 4-nitro indole was produced in the enzyme reaction.

FIG. 16A shows the titers of Nitrotrp were varied when E. coli-II was fermented in M9, LB and TB media in the presence or absence of 5 mM L-Trp or L-Arg at 20° C., 250 rpm. FIG. 16B shows the titers of Nitrotrp were influenced by fermentation temperature. The fermentation was performed in TB medium at 15° C., 20° C., 28° C., or 37° C., and 250 rpm. Aliquots (0.1 mL) of the fermentation culture were taken at various time points and the concentration of Nitrotrp in the samples was measured in HPLC analysis. The data represent means±s.d. of at least two independent experiments.

DETAILED DESCRIPTION

Figure 1:
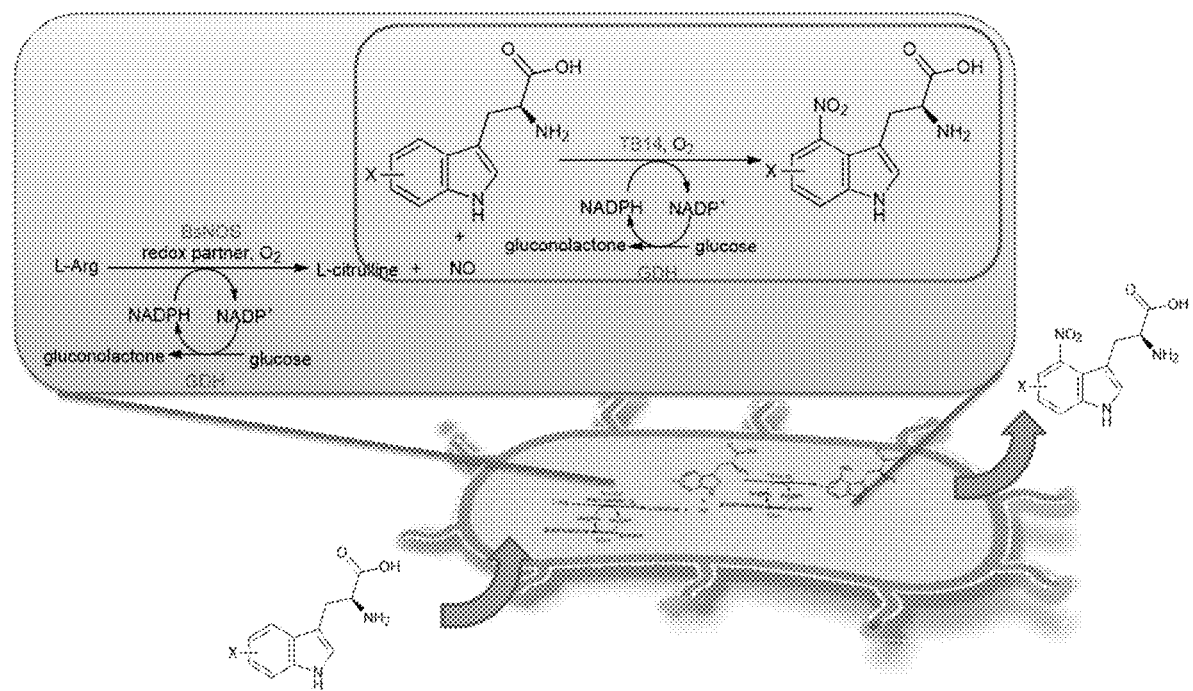
FIG. 1 is schematic overview of bacterial cell factories for the production of nitro-chemicals.

The disclosure relates, in some aspects, to compositions and methods useful for production of nitrated aromatic molecules. The disclosure is based, in part, on whole cell systems expressing artificial fusion proteins comprising cytochrome P450 enzymes linked to reductase enzymes. A significant advantage of whole cell nitration systems described by the disclosure compared to in vitro nitration reactions is the in situ production of NO from L-Arg, which enables recombinant bacterial cells to produce NO from L-Arg, which is synthesized by the bacterial cells from cheap carbon and nitrogen sources. Thus, it is believed that whole cell nitration systems described by the disclosure greatly lower the cost of biocatalytic nitration processes relative to currently utilized methods.

Recombinant Bacterial Cells

In some aspects, the disclosure relates to a recombinant bacterial cell comprising one or more isolated nucleic acids engineered to express: a fusion protein comprising a TxtE enzyme linked to a catalytic domain of a CYP102A1 (P450BM3) reductase enzyme via an amino acid linker sequence that is between 14 and 27 amino acids in length; and a nitric oxide synthase (NOS) enzyme.

As used herein "nucleic acid" refers to a DNA or RNA molecule. An "isolated nucleic acid" refers to a nucleic acid (e.g., DNA or RNA) that has been prepared in vitro, for example by recombinant technology. Nucleic acids are polymeric macromolecules comprising a plurality of nucleotides. In some embodiments, the nucleotides are deoxyribonucleotides or ribonucleotides. In some embodiments, the nucleotides comprising the nucleic acid are selected from the group consisting of adenine, guanine, cytosine, thymine, uracil and inosine. In some embodiments, the nucleotides comprising the nucleic acid are modified nucleotides. Non-limiting examples of natural nucleic acids include genomic DNA and plasmid DNA. In some embodiments, the nucleic acids of the instant disclosure are synthetic. As used herein, the term "synthetic nucleic acid" refers to a nucleic acid molecule that is constructed via joining nucleotides by a synthetic or non-natural method. One non-limiting example of a synthetic method is solid-phase oligonucleotide synthesis. In some embodiments, the nucleic acids of the instant disclosure are isolated.

In some aspects, the disclosure relates to bacterial cells (e.g., populations of bacterial cells) that have been genetically engineered to express biocatalysts useful for aromatic nitration in situ (e.g., aromatic nitration inside the bacterial cell(s)). Generally, a bacterial cell of the disclosure may be any Gram-negative bacterial cell, including but not limited to bacteria of the genus *Eschereria* sp. (e.g., *E. coli*), *Pseudomonas* sp., *Xanthomonas* sp., *Rhizobium* sp., *Azotobacter* sp., *Acetobacter* sp., *Gluconobacter* sp., *Methylococcus* sp., *Klebsiella* sp., *Bacteroides* sp., *Yersinia* sp., *Vibrio* sp., *Bacillus* sp., *Clostridium* sp., *Lactococcus* sp., *Lactobacillus* sp., *Staphylococcus* sp., and *Streptococcus* sp. In some embodiments, a bacterial cell is an *E. coli* cell. Examples of *E. coli* bacterial strains include *E. coli* Dh5α, *E. coli* BL21, *E. coli* DE3, *E. coli* Lemo21, *E. coli* NiCo21, *E. coli* Rosetta, etc. In some embodiments, a bacterial cell is an *E. coli* BL21-Gold cell.

In some embodiments, bacterial cells are genetically engineered to express certain biocatalysts (e.g., proteins, such as enzymes) capable of aromatic nitration. Typically, the biocatalyst comprises a self-sufficient cytochrome P450 enzyme, or a portion thereof. Previously described self-sufficient cytochrome P450 enzymes typically comprise (i) a cytochrome P450 enzyme which catalyzes transfer of a nitro functional group to aromatic moieties (e.g., indole); (ii) an amino acid linker; and, (iii) a catalytic domain of a reductase enzyme. For example, TxtE-P450BM3 (also referred to as TB13-Q) is described in PCT Publication WO 2016/134145, the entire contents of which are incorporated by reference herein. In another example a TxtE-450BM3 variant having a 14-amino acid linker (also referred to herein as TB14) is described in PCT International Application Number PCT/US2017/058579, the entire contents of which are incorporated herein by reference. In some embodiments, a fusion protein expressed by a recombinant bacterial cell described by the disclosure is a TB14 fusion protein having the sequence set forth in SEQ ID NO: 1.

As used herein, the term "TxtE enzyme" refers to a (i) polypeptide comprising the entire amino acid sequence of TxtE, (ii) a portion of TxtE which maintains the function of catalyzing transfer of a nitro functional group to aromatic moieties (e.g., indole), or (iii) an enzyme which catalyzes transfer of a nitro functional group to aromatic moieties (e.g., indole) and is at least 95% homologous to the amino acid sequence of TxtE. For example, in some embodiments, a TxtE enzyme comprises or consists of a sequence set forth in Genbank Accession No. CBG70284.1 or a portion thereof (e.g., SEQ ID NO: 14).

The skilled artisan recognizes that for a portion of TxtE to maintain the nitration function, the portion must include active site residues of TxtE, for example Arg59, Asn293, Thr296 and Glu394. However, genetic modification of residues at a location of the TxtE polypeptide remote from the active site may maintain the activity of the enzyme. As used herein, the term "genetic modification" refers to amino acid substitution (conservative, missense and/or non-sense), deletion and/or insertion. Thus in some embodiments, a portion of TxtE comprises at least 1, at least 2, at least 3, at least 4, at least 5, at least 10, at least 20, at least 30, at least 40, at least 50, at least 75, or at least 100 genetic modifications relative to wild-type TxtE. In some embodiments a portion of TxtE is truncated relative to wild-type TxtE. Truncations may occur at the N-terminus or C-terminus of the portion of TxtE. For example, a portion of TxtE may be truncated by 1, 2, 3, 4, 5, 10, 20, 30, 40, 50, 75, 100 or 200 amino acids at it N-terminus or C-terminus relative to wild-type TxtE.

In some embodiments, the disclosure provides a TxtE enzyme in which the loop region corresponding to residues A274 to V279 of GenBank Accession No. CBG70284.1 are replaced by the heme domain (e.g. loops "j" and "k") of CYP102A1 (e.g., P450BM3, PDB ID: 1BVY). In some embodiments, a TxtE enzyme (e.g., TxtE-P450BM3) comprises the sequence set forth in SEQ ID NO: 14 or 15.

Methods of genetically modifying TxtE or portions thereof and screening for retention of functional activity are known in the art and available to the skilled artisan. For example, TxtE may be modified by directed evolution or random mutagenesis and biochemically assayed for the capability to transfer a nitro group to aromatic moieties (e.g., indole). In some embodiments, a TxtE enzyme may be an enzyme which catalyzes transfer of a nitro functional group to aromatic moieties (e.g., indole) and has less than 95% homologous to the amino acid sequence of TxtE. In some embodiments, the enzyme has about 90%, about 80%, about 70%, about 60% or about 50% homology to the amino acid sequence of TxtE.

In some aspects, the disclosure provides fusion proteins comprising a catalytic domain of a reductase enzyme. As used herein, the term "reductase enzyme" refers to an enzyme that catalyzes a reduction reaction. Non-limiting examples of reductase enzymes include thioredoxn reductase, cytochrome P450 reductase and flavin adenine dinucleotide (FAD) reductase. In some embodiments, the reductase enzyme is a prokaryotic reductase enzyme. In some embodiments, the reductase enzyme is a bacterial reducatase enzyme. In some embodiments, the bacterial reductase enzyme naturally occurs in a self-sufficient cytochrome P450, for example CYP102A1 (P450BM3) reductase or a P450RhF reductase. In some embodiments, the catalytic domain of a reductase enzyme comprises or consists of the sequence set forth in SEQ ID NO: 15.

In some embodiments, the fusion protein comprises an amino acid linker. As used herein, the term "linker" refers to an amino acid sequence that joins two larger polypeptide domains to form a single fusion polypeptide. Amino acid linkers are well known to those skilled in the art and include flexible linkers (e.g. glycine rich linkers such as [GGGS]$_n$, where n>2), rigid linkers (e.g. poly-proline rich linkers) and cleavable linkers (e.g. photocleavable and enzyme-sensitive linkers). In some embodiments, an amino acid linker is derived from a TxtE enzyme or a reductase enzyme (e.g., CYP102A1). For example, in some embodiments, an amino acid linker may comprise between about 3 and about 27 continuous (e.g., covalently linked) amino acids of a reductase enzyme (e.g., between about 3 and about 27 contiguous amino acids the sequence set forth in UniProtKB/Swiss-Prot Accession No. P14779.2. In some embodiments, an amino acid linker comprises between about 3 and about 27 contiguous amino acids, for example between about 3 and about 25 contiguous amino acids of SEQ ID NO: 16.

In some embodiments, amino acid linker length affects the folding and orientation of fusion polypeptides. For example, a linker that is too long can prevent the interaction of a reductase domain with the cytochrome P450 enzyme to which it is linked. (It is also known that long linkers can fold and take on specific orientations that can be desirable.) Conversely, a linker that is too short can cause a reductase enzyme to sterically inhibit binding of substrate to the active site of the P450 enzyme to which it is linked. In some embodiments, TxtE-BM3 fusion proteins comprising linkers having a certain length (e.g., 11, 12, 14, 15, 16, 17, etc. amino acids in length) exhibit improved function (e.g., increased nitration activity, coupling efficiency, total turnover number (TTN), etc.) compared to previously described self-sufficient cytochrome p450 enzymes. Accordingly, in some embodiments, a fusion protein described by the disclosure comprises an amino acid linker between about 3 and about 27 amino acids in length. In some embodiments, an amino acid linker is between about 11 and about 17 amino acids in length. In some embodiments, an amino acid linker is between about 14 and 16 amino acids in length. In some embodiments, the length of the linker is 11, 12, 14, 15, 16, 17, 18, 19, 20, 21, 22, 23, 24, 25, 26, or 27 amino acids in length.

In some embodiments, the amino acid linker joins a catalytic domain of a reductase enzyme to a terminus of a cytochrome P450 enzyme. As used herein, the term "terminus" refers to the ends of a polypeptide sequence relative to the start codon of said polypeptide. For example, the N-terminus of a polypeptide is the end of the polypeptide containing the start codon (AUG) of the polypeptide, whereas the C-terminus of the polypeptide is the end of the polypeptide opposite of the start codon. In some embodiments, the amino acid linker joins the catalytic domain of a reductase enzyme to the C-terminus of a cytochrome P450 enzyme. In some embodiments, the amino acid linker joins CYP102A1 (P450BM3) reductase or P450RhF reductase to the C-terminus of a TxtE enzyme.

Generally, fusion proteins described by the disclosure can be produced by any suitable means known in the art. For example, in some embodiments, a fusion protein is produced by an overlap PCR method. As used herein, "overlap PCR" refers to the splicing (e.g., joining together) of two or more oligonucleotides by polymerase chain reaction employing primers that share complementarity with the terminus of each of the oligonucleotides, for example as described by Higuchi et al. (1988) Nucleic Acids Res. 16 (15): 7351-67.

In some embodiments, fusion proteins described by the disclosure are not produced by overlap PCR. In some embodiments, fusion proteins described by the disclosure are produced by a restriction digest-based method (e.g., traditional cloning), for example as described in Molecular Cloning: A Laboratory Manual, J. Sambrook, et al., eds., Second Edition, Cold Spring Harbor Laboratory Press, Cold Spring Harbor, New York, 1989.

The disclosure relates, in some aspects, to recombinant bacterial cells comprising an isolated nucleic acid engineered to express a nitric oxide synthase (NOS) enzyme. Generally, nitric oxide synthase (NOS) is a protein that catalyzes production of nitric oxide (NO) from L-arginine. Without wishing to be bound by any particular theory, NO is an important co-substrate for TxtE-based nitration reactions, and thus in some embodiments it is desirable to increase NO production in recombinant bacterial cells for the purpose of increasing nitration reaction yields. Generally, a NOS enzyme can be a prokaryotic or eukaryotic NOS enzyme. In some embodiments, a NOS enzyme is a bacterial NOS enzyme. Bacterial NOS enzymes are described, for example in Crane et al. (2010) *Annu Rev Biochem.* 79: 455-70. In some embodiments, a NOS enzyme is a *Bacillus subtilis* NOS enzyme. In some embodiments, a *Bacillus subtilis* NOS enzyme is encoded by the sequence set forth in SEQ ID NO: 3. In some embodiments, a *Bacillus subtilis* NOS enzyme comprises the amino acid sequence set forth in SEQ ID NO: 5. BsNOS enzymes are described, for example by Commichau et al. (2008) *J Bacteriol* 190(10):3557-3564.

In some aspects, the disclosure relates to recombinant bacterial cells comprising an isolated nucleic acid engineered to express a glucose dehydrogenase (GHD) enzyme. Glucose dehydrogenase (GDH) is an enzyme that catalyzes the reversible conversion of D-glucose to D-glucono-1,5-lactone while reducing NAD(P)+ to NAD(P)H. Without wishing to be bound by any particular theory, overexpression of GDH in recombinant bacterial cells (e.g., as part of a whole cell nitration system) may, in some embodiments, increase yield of nitration reactions by providing a sufficient supply of NADPH to fuel NOS-mediated conversion of L-Arg to L-citrulline. In some embodiments, a GDH enzyme is a bacterial GDH enzyme. In some embodiments, a bacterial GDH enzyme is a *Bacillus megaterium* GDH enzyme.

As used herein, the term "engineered to express" refers to an isolated nucleic acid that comprises a gene to be expressed (e.g., TB14, BsNOS, GDH, etc.) and, optionally, one or more expression control sequences. Examples of expression control sequences include but are not limited to promoter sequences, enhancer sequences, repressor sequences, poly A tail sequences, internal ribosomal entry sites, Kozak sequences, antibiotic resistance genes (e.g., ampR, kanR, a chloramphenicol resistance gene, a β-lactamase resistance gene, etc.), an origin of replication (ori), etc.

In some embodiments, one or more isolated nucleic acid is operably linked to a promoter sequence. A promoter can be a constitutive promoter or an inducible promoter. In some embodiments, a promoter is a constitutive promoter. Examples of constitutive promoters include but are not limited to constitutive *E. coli* σ$^{70}$ promoters, constitutive *E. coli* σ$^s$ promoters, constitutive *E. coli* σ$^{32}$ promoters, constitutive *E. coli* σ$^{54}$ promoters, constitutive *B. subtilis* σ$^A$ promoters, constitutive *B. subtilis* σ$^B$ promoters, constitutive bacteriophage T7 promoters, constitutive bacteriophage SP6 promoters, constitutive yeast promoters, etc.

In some embodiments, a promoter is an inducible promoter (e.g., induced in the presence of a small molecule, such as IPTG or tetracycline). Examples of inducible promoters include but are not limited to a promoter comprising a tetracycline responsive element (TRE), a pLac promoter, a pBad promoter, alcohol-regulated promoters (e.g., AlcA promoter), steroid-regulated promoters (e.g., LexA promoter), temperature-inducible promoters (e.g., Hsp70- or Hsp90-derived promoters, light-inducible promoters (e.g., YFI), etc.

In some embodiments, an isolated nucleic acid engineered to express a fusion protein is operably linked to a first promoter, an isolated nucleic acid engineered to express a NOS enzyme is operably linked to a second promoter, and an isolated nucleic acid engineered to express a GDH enzyme is operably linked to a third promoter. In some embodiments, a first promoter, a second promoter, and/or a third promoter is a T7 promoter.

In some embodiments, an isolated nucleic acid engineered to express a protein is a component of a vector. Examples of vectors include plasmids, viral vectors, cosmids, and artificial chromosomes. In some aspects, one or more isolated nucleic acids engineered to express a protein (e.g., TB14, NOS, GDH, etc.) are located (e.g., situated) on a plasmid, for example a bacterial plasmid. In some embodiments, the vector is a high-copy plasmid. In some embodiments, the vector is a low-copy plasmid. In some embodiments, a bacterial cell comprises one or more plasmids comprising the one or more isolated nucleic acids. For example, a plasmid may comprise 1, 2, 3, 4, 5, 6, 7, 8, 9, or 10 isolated nucleic acids. In some embodiments, a plasmid comprises 1, 2, or 3 isolated nucleic acids. In some embodiments, an isolated nucleic acid engineered to express the NOS enzyme and an isolated nucleic acid engineered to express the GDH enzyme are located on the same plasmid. In some embodiments, an isolated nucleic acid engineered to express the fusion protein is located on a plasmid that does not contain an isolated nucleic acid engineered to express the NOS enzyme and/or an isolated nucleic acid engineered to express the GDH enzyme. In some embodiments, a recombinant bacterial cell as described by the disclosure comprises a first plasmid comprising an isolated nucleic acid engineered to express a TxtE fusion protein (e.g. TB14), a second plasmid comprising an isolated nucleic acid engineered to express a NOS enzyme (e.g., BsNOS), and a third plasmid comprising an isolated nucleic acid engineered to express a GDH enzyme.

In some embodiments, one or more isolated nucleic acids (e.g., one or more isolated nucleic acids encoding a fusion protein, a NOS enzyme, and/or a GDH enzyme) are integrated into a chromosome of a bacterial cell. Methods of integrating exogenous (e.g., foreign) DNA into a bacterial chromosome are known in the art and are described, for example, by Gu et al. (2015) *Scientific Reports* 5; Article number 9684.

The disclosure is based, in part, on recombinant bacterial cells that are capable of producing nitrated aromatic compounds. In some embodiments, recombinant bacterial cells are produced from bacterial strains that have been metabolically modified. As used herein, "metabolically modified" refers to a bacterial cell (or strain) that has been manipulated using recombinant DNA technology or other genome engineering methodologies to lack one or more genes in a particular metabolic pathway. For example, in some embodiments, a recombinant bacterial cell may be produced using a bacterial strain that has been engineered to lack one or more genes relating to tryptophan metabolism, tryptophan biosynthesis, L-tyrosine biosynthesis, phenylalanine biosynthesis, or any combination of the foregoing. In some embodiments, a bacterial cell is genetically modified to lack expression of one or more of the following genes: traA (tryptophanase), trpR (tryptophan repressor), tyrA (T protein), and pheA (P protein). In some embodiments, a bacterial cell comprises the genotype ΔtrpRΔtyrAΔpheA (e.g., is a triple deletion mutant for trpR, tyrA, and pheA). In some embodiments, a bacterial cell comprises a tnaA gene, or a gene product (e.g., protein, enzyme, etc.) expressed from a tnaA gene.

Compositions Comprising Recombinant Bacterial Cells

In some aspects, the disclosure relates to a composition comprising one or more of a recombinant bacterial cell as described by the disclosure, and a bacterial culture media.

As used herein, a "bacterial culture media" is a nutrient rich composition that supports growth and reproduction of bacterial cells. Generally, bacterial culture media can be liquid or solid (e.g., culture media mixed with agar to form a gel). In some embodiments, bacterial culture media is a liquid. Examples of bacterial culture media include but are not limited to M9, Lysogeny Broth (LB), SOC media, Terrific Broth (TB), etc.

The volume of bacterial culture media in a composition comprising a recombinant bacterial cell can vary depending upon several factors including but not limited to the desired amount of nitrated aromatic compounds to be produced, the concentration (density) of bacterial cells desired in the composition, the volume of the container housing the composition, etc. In some embodiments, a composition comprises between about 10 µl and 1 L bacterial culture media. In some embodiments, a composition comprises between about 10 µl and about 1 mL bacterial culture media, for example about 10 µl, about 50 µl, about 100 µl, about 500 µl, about 750 µl, or about 1 mL (e.g., any volume between 10 µl and 1 mL, inclusive). In some embodiments, a composition comprises between about 750 µl and 5 mL (e.g., any volume between 750 µl and 5 mL, inclusive). In some embodiments, a composition comprises between about 2 mL and about 20 mL bacterial culture media (e.g., any volume between 2 mL and 20 mL, inclusive). In some embodiments, a composition comprises between about 10 mL and about 200 mL bacterial culture media (e.g., any volume between 10 mL and 200 mL, inclusive). In some embodiments, a composition comprises between about 100 mL and about 500 mL bacterial culture media (e.g., any volume between 100 mL and 500 mL, inclusive). In some embodiments, a composition comprises between about 250 mL and about 1 L bacterial culture media (e.g., any volume between 250 mL and 1 L, inclusive). In some embodiments, a composition comprises more than 1 L (e.g., 5 L, 10 L, 100 L, 200 L, 1000 L, 10,000 L, 50,000 L, etc.) bacterial culture media.

In some embodiments, a composition further comprises one or more antibiotic agents. In some embodiments, one or more antibiotic agent is ampicillin or kanamycin. A composition may comprise 1, 2, 3, 4, 5, 6, 7, 8, 9, 10, or more antibiotic agents. The concentration of an antibiotic agent can vary. In some embodiments, the concentration of an antibiotic agent ranges from about 0 (e.g., lacking antibiotic) to about 125 µg/ml.

Aspects of the disclosure relate to uptake and subsequent nitration of L-tryptophan (and L-tryptophan analogues) by recombinant bacterial cells described herein. Without wishing to be bound by any particular theory, compositions comprising recombinant bacterial cells described herein and bacterial culture media may be "fed" with exogenous L-tryptophan or analogues thereof, which are internalized by the bacteria (e.g., via permease transport across the bacterial cell membrane) and subsequently nitrated by a fusion protein (e.g., a TxtE fusion protein, such as TB14). Thus, in some embodiments, a composition further comprises one or more of the following: L-tryptophan (L-Trp), L-arginine (L-Arg), or an analogue of L-tryptophan. In some embodiments, a composition further comprises one or more compounds of Formula Ia or IVa. In some embodiments, an analogue of L-tryptophan is selected from the group consisting of α-Me-Trp, 4-F-Trp, 4-Me-Trp, 5-MeO-Trp, 5-Me-Trp, 5-F-Trp, 6-F-Trp, and 7-Me-Trp.

In some embodiments, a composition further comprises one or more compounds of Formulae I-VI. In some embodiments, a composition further comprises one or more of the following: 4-NO$_2$-L-Trp, α-Me-4-NO$_2$-Trp, 4-F-7-NO$_2$-Trp, 4-Me-7-NO$_2$-Trp, 5-MeO-4-NO$_2$-Trp, 5-Me-4-NO$_2$-Trp, 5-F-4-NO$_2$-Trp, 6-F-4-NO$_2$-Trp, or 7-Me-4-NO$_2$-Trp. In some embodiments, the compound of Formulae I-VI is selected from:

(S)-2-amino-3-(4-methyl-5-nitro-1H-indol-3-yl)propanoic acid;
(S)-2-amino-3-(5-methyl-4-nitro-1H-indol-3-yl)propanoic acid;
(S)-2-amino-3-(6-methyl-4-nitro-1H-indol-3-yl)propanoic acid;
(S)-2-amino-3-(7-methyl-4-nitro-1H-indol-3-yl)propanoic acid;
(S)-2-amino-3-(4-methyl-7-nitro-1H-indol-3-yl)propanoic acid;
(S)-2-amino-3-(5-fluoro-4-nitro-1H-indol-3-yl)propanoic acid;
(S)-2-amino-3-(6-fluoro-4-nitro-1H-indol-3-yl)propanoic acid;
(S)-2-amino-3-(7-fluoro-4-nitro-1H-indol-3-yl)propanoic acid;
(S)-2-amino-3-(4-fluoro-7-nitro-1H-indol-3-yl)propanoic acid;
(S)-2-amino-3-(5-chloro-4-nitro-1H-indol-3-yl)propanoic acid;
(S)-2-amino-3-(6-chloro-4-nitro-1H-indol-3-yl)propanoic acid;
(S)-2-amino-3-(7-chloro-4-nitro-1H-indol-3-yl)propanoic acid;
(S)-2-amino-3-(4-chloro-7-nitro-1H-indol-3-yl)propanoic acid;
(S)-2-amino-3-(5-bromo-4-nitro-1H-indol-3-yl)propanoic acid;
(S)-2-amino-3-(6-bromo-4-nitro-1H-indol-3-yl)propanoic acid;
(S)-2-amino-3-(7-bromo-4-nitro-1H-indol-3-yl)propanoic acid;
(S)-2-amino-3-(4-bromo-7-nitro-1H-indol-3-yl)propanoic acid;
(S)-2-amino-3-(5-methoxy-4-nitro-1H-indol-3-yl)propanoic acid;
(S)-2-amino-3-(6-methoxy-4-nitro-1H-indol-3-yl)propanoic acid;
(S)-2-amino-3-(7-methoxy-4-nitro-1H-indol-3-yl)propanoic acid;
(S)-2-amino-3-(4-methoxy-7-nitro-1H-indol-3-yl)propanoic acid;
(S)-2-amino-3-(5-amino-4-nitro-1H-indol-3-yl)propanoic acid;
(S)-2-amino-3-(6-amino-4-nitro-1H-indol-3-yl)propanoic acid;
(S)-2-amino-3-(7-amino-4-nitro-1H-indol-3-yl)propanoic acid;
(S)-2-amino-3-(4-amino-7-nitro-1H-indol-3-yl)propanoic acid;
(S)-2-amino-3-(5-hydroxy-4-nitro-1H-indol-3-yl)propanoic acid;
(S)-2-amino-3-(6-hydroxy-4-nitro-1H-indol-3-yl)propanoic acid;
(S)-2-amino-3-(7-hydroxy-4-nitro-1H-indol-3-yl)propanoic acid;
(S)-2-amino-3-(4-hydroxy-7-nitro-1H-indol-3-yl)propanoic acid;
(S)-2-amino-3-(4-nitro-5-phenyl-1H-indol-3-yl)propanoic acid;
(S)-2-amino-3-(4-nitro-6-phenyl-1H-indol-3-yl)propanoic acid;
(S)-2-amino-3-(4-nitro-7-phenyl-1H-indol-3-yl)propanoic acid;
(S)-2-amino-3-(7-nitro-4-phenyl-1H-indol-3-yl)propanoic acid;
(S)-2-amino-3-(5-cyclopropyl-4-nitro-1H-indol-3-yl)propanoic acid;
(S)-2-amino-3-(6-cyclopropyl-4-nitro-1H-indol-3-yl)propanoic acid;
(S)-2-amino-3-(7-cyclopropyl-4-nitro-1H-indol-3-yl)propanoic acid;
(S)-2-amino-3-(4-cyclopropyl-7-nitro-1H-indol-3-yl)propanoic acid;
(S)-2-amino-3-(4-nitro-5-vinyl-1H-indol-3-yl)propanoic acid;
(S)-2-amino-3-(4-nitro-6-vinyl-1H-indol-3-yl)propanoic acid;
(S)-2-amino-3-(4-nitro-7-vinyl-1H-indol-3-yl)propanoic acid;
(S)-2-amino-3-(7-nitro-4-vinyl-1H-indol-3-yl)propanoic acid;
(S)-2-amino-3-(5-ethynyl-4-nitro-1H-indol-3-yl)propanoic acid;
(S)-2-amino-3-(6-ethynyl-4-nitro-1H-indol-3-yl)propanoic acid;
(S)-2-amino-3-(7-ethynyl-4-nitro-1H-indol-3-yl)propanoic acid;
(S)-2-amino-3-(4-ethynyl-7-nitro-1H-indol-3-yl)propanoic acid;
(S)-2-amino-3-(5-morpholino-4-nitro-1H-indol-3-yl)propanoic acid;
(S)-2-amino-3-(6-morpholino-4-nitro-1H-indol-3-yl)propanoic acid;
(S)-2-amino-3-(7-morpholino-4-nitro-1H-indol-3-yl)propanoic acid;
(S)-2-amino-3-(4-morpholino-7-nitro-1H-indol-3-yl)propanoic acid;
(S)-2-amino-3-(5-(methylthio)-4-nitro-1H-indol-3-yl)propanoic acid;
(S)-2-amino-3-(6-(methylthio)-4-nitro-1H-indol-3-yl)propanoic acid;
(S)-2-amino-3-(7-(methylthio)-4-nitro-1H-indol-3-yl)propanoic acid;
(S)-2-amino-3-(4-(methylthio)-7-nitro-1H-indol-3-yl)propanoic acid;
(S)-2-amino-3-(4-nitro-5-(pyridin-4-yl)-1H-indol-3-yl)propanoic acid;
(S)-2-amino-3-(4-nitro-6-(pyridin-4-yl)-1H-indol-3-yl)propanoic acid;
(S)-2-amino-3-(4-nitro-7-(pyridin-4-yl)-1H-indol-3-yl)propanoic acid;
(S)-2-amino-3-(7-nitro-4-(pyridin-4-yl)-1H-indol-3-yl)propanoic acid;
2-amino-3-(4-methyl-5-nitro-1H-indol-3-yl)propanoic acid;
2-amino-3-(5-methyl-4-nitro-1H-indol-3-yl)propanoic acid;
2-amino-3-(6-methyl-4-nitro-1H-indol-3-yl)propanoic acid;

2-amino-3-(7-methyl-4-nitro-1H-indol-3-yl)propanoic acid;
2-amino-3-(4-methyl-7-nitro-1H-indol-3-yl)propanoic acid;
2-amino-3-(6-fluoro-4-nitro-1H-indol-3-yl)propanoic acid;
2-amino-3-(7-fluoro-4-nitro-1H-indol-3-yl)propanoic acid;
2-amino-3-(4-fluoro-7-nitro-1H-indol-3-yl)propanoic acid;
2-amino-3-(5-chloro-4-nitro-1H-indol-3-yl)propanoic acid;
2-amino-3-(6-chloro-4-nitro-1H-indol-3-yl)propanoic acid;
2-amino-3-(7-chloro-4-nitro-1H-indol-3-yl)propanoic acid;
2-amino-3-(4-chloro-7-nitro-1H-indol-3-yl)propanoic acid;
2-amino-3-(5-bromo-4-nitro-1H-indol-3-yl)propanoic acid;
2-amino-3-(6-bromo-4-nitro-1H-indol-3-yl)propanoic acid;
2-amino-3-(7-bromo-4-nitro-1H-indol-3-yl)propanoic acid;
2-amino-3-(4-bromo-7-nitro-1H-indol-3-yl)propanoic acid;
2-amino-3-(5-methoxy-4-nitro-1H-indol-3-yl)propanoic acid;
2-amino-3-(6-methoxy-4-nitro-1H-indol-3-yl)propanoic acid;
2-amino-3-(7-methoxy-4-nitro-1H-indol-3-yl)propanoic acid;
2-amino-3-(4-methoxy-7-nitro-1H-indol-3-yl)propanoic acid;
2-amino-3-(5-amino-4-nitro-1H-indol-3-yl)propanoic acid;
2-amino-3-(6-amino-4-nitro-1H-indol-3-yl)propanoic acid;
2-amino-3-(7-amino-4-nitro-1H-indol-3-yl)propanoic acid;
2-amino-3-(4-amino-7-nitro-1H-indol-3-yl)propanoic acid;
2-amino-3-(5-hydroxy-4-nitro-1H-indol-3-yl)propanoic acid;
2-amino-3-(6-hydroxy-4-nitro-1H-indol-3-yl)propanoic acid;
2-amino-3-(7-hydroxy-4-nitro-1H-indol-3-yl)propanoic acid;
2-amino-3-(4-hydroxy-7-nitro-1H-indol-3-yl)propanoic acid;
2-amino-3-(4-nitro-5-phenyl-1H-indol-3-yl)propanoic acid;
2-amino-3-(4-nitro-6-phenyl-1H-indol-3-yl)propanoic acid;
2-amino-3-(4-nitro-7-phenyl-1H-indol-3-yl)propanoic acid;
2-amino-3-(7-nitro-4-phenyl-1H-indol-3-yl)propanoic acid;
2-amino-3-(5-cyclopropyl-4-nitro-1H-indol-3-yl)propanoic acid;
2-amino-3-(6-cyclopropyl-4-nitro-1H-indol-3-yl)propanoic acid;
2-amino-3-(7-cyclopropyl-4-nitro-1H-indol-3-yl)propanoic acid;
2-amino-3-(4-cyclopropyl-7-nitro-1H-indol-3-yl)propanoic acid;
2-amino-3-(4-nitro-5-vinyl-1H-indol-3-yl)propanoic acid;
2-amino-3-(4-nitro-6-vinyl-1H-indol-3-yl)propanoic acid;
2-amino-3-(4-nitro-7-vinyl-1H-indol-3-yl)propanoic acid;
2-amino-3-(7-nitro-4-vinyl-1H-indol-3-yl)propanoic acid;
2-amino-3-(5-ethynyl-4-nitro-1H-indol-3-yl)propanoic acid;
2-amino-3-(6-ethynyl-4-nitro-1H-indol-3-yl)propanoic acid;
2-amino-3-(7-ethynyl-4-nitro-1H-indol-3-yl)propanoic acid;
2-amino-3-(4-ethynyl-7-nitro-1H-indol-3-yl)propanoic acid;
2-amino-3-(5-morpholino-4-nitro-1H-indol-3-yl)propanoic acid;
2-amino-3-(6-morpholino-4-nitro-1H-indol-3-yl)propanoic acid;
2-amino-3-(7-morpholino-4-nitro-1H-indol-3-yl)propanoic acid;
2-amino-3-(4-morpholino-7-nitro-1H-indol-3-yl)propanoic acid;
2-amino-3-(5-(methylthio)-4-nitro-1H-indol-3-yl)propanoic acid;
2-amino-3-(6-(methylthio)-4-nitro-1H-indol-3-yl)propanoic acid;
2-amino-3-(7-(methylthio)-4-nitro-1H-indol-3-yl)propanoic acid;
2-amino-3-(4-(methylthio)-7-nitro-1H-indol-3-yl)propanoic acid;
2-amino-3-(4-nitro-5-(pyridin-4-yl)-1H-indol-3-yl)propanoic acid;
2-amino-3-(4-nitro-6-(pyridin-4-yl)-1H-indol-3-yl)propanoic acid;
2-amino-3-(4-nitro-7-(pyridin-4-yl)-1H-indol-3-yl)propanoic acid;
2-amino-3-(7-nitro-4-(pyridin-4-yl)-1H-indol-3-yl)propanoic acid;
2-amino-3-(1,5-dimethyl-4-nitro-1H-indol-3-yl)propanoic acid;
2-amino-3-(1,6-dimethyl-4-nitro-1H-indol-3-yl)propanoic acid;
2-amino-3-(1,7-dimethyl-4-nitro-1H-indol-3-yl)propanoic acid;
2-amino-3-(1,4-dimethyl-7-nitro-1H-indol-3-yl)propanoic acid;
2-amino-3-(6-fluoro-1-methyl-4-nitro-1H-indol-3-yl)propanoic acid;
2-amino-3-(7-fluoro-1-methyl-4-nitro-1H-indol-3-yl)propanoic acid;
2-amino-3-(4-fluoro-1-methyl-7-nitro-1H-indol-3-yl)propanoic acid;
2-amino-3-(5-chloro-1-methyl-4-nitro-1H-indol-3-yl)propanoic acid;
2-amino-3-(6-chloro-1-methyl-4-nitro-1H-indol-3-yl)propanoic acid;
2-amino-3-(7-chloro-1-methyl-4-nitro-1H-indol-3-yl)propanoic acid;
2-amino-3-(4-chloro-1-methyl-7-nitro-1H-indol-3-yl)propanoic acid;
2-amino-3-(5-bromo-1-methyl-4-nitro-1H-indol-3-yl)propanoic acid;
2-amino-3-(6-bromo-1-methyl-4-nitro-1H-indol-3-yl)propanoic acid;
2-amino-3-(7-bromo-1-methyl-4-nitro-1H-indol-3-yl)propanoic acid;
2-amino-3-(4-bromo-1-methyl-7-nitro-1H-indol-3-yl)propanoic acid;
2-amino-3-(5-methoxy-1-methyl-4-nitro-1H-indol-3-yl)propanoic acid;
2-amino-3-(6-methoxy-1-methyl-4-nitro-1H-indol-3-yl)propanoic acid;
2-amino-3-(7-methoxy-1-methyl-4-nitro-1H-indol-3-yl)propanoic acid;
2-amino-3-(4-methoxy-1-methyl-7-nitro-1H-indol-3-yl)propanoic acid;
2-amino-3-(5-amino-1-methyl-4-nitro-1H-indol-3-yl)propanoic acid;
2-amino-3-(6-amino-1-methyl-4-nitro-1H-indol-3-yl)propanoic acid;
2-amino-3-(7-amino-1-methyl-4-nitro-1H-indol-3-yl)propanoic acid;
2-amino-3-(4-amino-1-methyl-7-nitro-1H-indol-3-yl)propanoic acid;
2-amino-3-(5-hydroxy-1-methyl-4-nitro-1H-indol-3-yl)propanoic acid;
2-amino-3-(6-hydroxy-1-methyl-4-nitro-1H-indol-3-yl)propanoic acid;
2-amino-3-(7-hydroxy-1-methyl-4-nitro-1H-indol-3-yl)propanoic acid;

2-amino-3-(4-hydroxy-1-methyl-7-nitro-1H-indol-3-yl)propanoic acid;
2-amino-3-(1-methyl-4-nitro-5-phenyl-1H-indol-3-yl)propanoic acid;
2-amino-3-(1-methyl-4-nitro-6-phenyl-1H-indol-3-yl)propanoic acid;
2-amino-3-(1-methyl-4-nitro-7-phenyl-1H-indol-3-yl)propanoic acid;
2-amino-3-(1-methyl-7-nitro-4-phenyl-1H-indol-3-yl)propanoic acid;
2-amino-3-(5-cyclopropyl-1-methyl-4-nitro-1H-indol-3-yl)propanoic acid;
2-amino-3-(6-cyclopropyl-1-methyl-4-nitro-1H-indol-3-yl)propanoic acid;
2-amino-3-(7-cyclopropyl-1-methyl-4-nitro-1H-indol-3-yl)propanoic acid;
2-amino-3-(4-cyclopropyl-1-methyl-7-nitro-1H-indol-3-yl)propanoic acid;
2-amino-3-(1-methyl-4-nitro-5-vinyl-1H-indol-3-yl)propanoic acid;
2-amino-3-(1-methyl-4-nitro-6-vinyl-1H-indol-3-yl)propanoic acid;
2-amino-3-(1-methyl-4-nitro-7-vinyl-1H-indol-3-yl)propanoic acid;
2-amino-3-(1-methyl-7-nitro-4-vinyl-1H-indol-3-yl)propanoic acid;
2-amino-3-(5-ethynyl-1-methyl-4-nitro-1H-indol-3-yl)propanoic acid;
2-amino-3-(6-ethynyl-1-methyl-4-nitro-1H-indol-3-yl)propanoic acid;
2-amino-3-(7-ethynyl-1-methyl-4-nitro-1H-indol-3-yl)propanoic acid;
2-amino-3-(4-ethynyl-1-methyl-7-nitro-1H-indol-3-yl)propanoic acid;
2-amino-3-(1-methyl-5-morpholino-4-nitro-1H-indol-3-yl)propanoic acid;
2-amino-3-(1-methyl-6-morpholino-4-nitro-1H-indol-3-yl)propanoic acid;
2-amino-3-(1-methyl-7-morpholino-4-nitro-1H-indol-3-yl)propanoic acid;
2-amino-3-(1-methyl-4-morpholino-7-nitro-1H-indol-3-yl)propanoic acid;
2-amino-3-(1-methyl-5-(methylthio)-4-nitro-1H-indol-3-yl)propanoic acid;
2-amino-3-(1-methyl-6-(methylthio)-4-nitro-1H-indol-3-yl)propanoic acid;
2-amino-3-(1-methyl-7-(methylthio)-4-nitro-1H-indol-3-yl)propanoic acid;
2-amino-3-(1-methyl-4-(methylthio)-7-nitro-1H-indol-3-yl)propanoic acid;
2-amino-3-(1-methyl-4-nitro-5-(pyridin-4-yl)-1H-indol-3-yl)propanoic acid;
2-amino-3-(1-methyl-4-nitro-6-(pyridin-4-yl)-1H-indol-3-yl)propanoic acid;
2-amino-3-(1-methyl-4-nitro-7-(pyridin-4-yl)-1H-indol-3-yl)propanoic acid;
2-amino-3-(1-methyl-7-nitro-4-(pyridin-4-yl)-1H-indol-3-yl)propanoic acid;
2-amino-3-(2,5-dimethyl-4-nitro-1H-indol-3-yl)propanoic acid;
2-amino-3-(2,6-dimethyl-4-nitro-1H-indol-3-yl)propanoic acid;
2-amino-3-(2,7-dimethyl-4-nitro-1H-indol-3-yl)propanoic acid;
2-amino-3-(2,4-dimethyl-7-nitro-1H-indol-3-yl)propanoic acid;
2-amino-3-(6-fluoro-2-methyl-4-nitro-1H-indol-3-yl)propanoic acid;
2-amino-3-(7-fluoro-2-methyl-4-nitro-1H-indol-3-yl)propanoic acid;
2-amino-3-(4-fluoro-2-methyl-7-nitro-1H-indol-3-yl)propanoic acid;
2-amino-3-(5-chloro-2-methyl-4-nitro-1H-indol-3-yl)propanoic acid;
2-amino-3-(6-chloro-2-methyl-4-nitro-1H-indol-3-yl)propanoic acid;
2-amino-3-(7-chloro-2-methyl-4-nitro-1H-indol-3-yl)propanoic acid;
2-amino-3-(4-chloro-2-methyl-7-nitro-1H-indol-3-yl)propanoic acid;
2-amino-3-(5-bromo-2-methyl-4-nitro-1H-indol-3-yl)propanoic acid;
2-amino-3-(6-bromo-2-methyl-4-nitro-1H-indol-3-yl)propanoic acid;
2-amino-3-(7-bromo-2-methyl-4-nitro-1H-indol-3-yl)propanoic acid;
2-amino-3-(4-bromo-2-methyl-7-nitro-1H-indol-3-yl)propanoic acid;
2-amino-3-(5-methoxy-2-methyl-4-nitro-1H-indol-3-yl)propanoic acid;
2-amino-3-(6-methoxy-2-methyl-4-nitro-1H-indol-3-yl)propanoic acid;
2-amino-3-(7-methoxy-2-methyl-4-nitro-1H-indol-3-yl)propanoic acid;
2-amino-3-(4-methoxy-2-methyl-7-nitro-1H-indol-3-yl)propanoic acid;
2-amino-3-(5-amino-2-methyl-4-nitro-1H-indol-3-yl)propanoic acid;
2-amino-3-(6-amino-2-methyl-4-nitro-1H-indol-3-yl)propanoic acid;
2-amino-3-(7-amino-2-methyl-4-nitro-1H-indol-3-yl)propanoic acid;
2-amino-3-(4-amino-2-methyl-7-nitro-1H-indol-3-yl)propanoic acid;
2-amino-3-(5-hydroxy-2-methyl-4-nitro-1H-indol-3-yl)propanoic acid;
2-amino-3-(6-hydroxy-2-methyl-4-nitro-1H-indol-3-yl)propanoic acid;
2-amino-3-(7-hydroxy-2-methyl-4-nitro-1H-indol-3-yl)propanoic acid;
2-amino-3-(4-hydroxy-2-methyl-7-nitro-1H-indol-3-yl)propanoic acid;
2-amino-3-(2-methyl-4-nitro-5-phenyl-1H-indol-3-yl)propanoic acid;
2-amino-3-(2-methyl-4-nitro-6-phenyl-1H-indol-3-yl)propanoic acid;
2-amino-3-(2-methyl-4-nitro-7-phenyl-1H-indol-3-yl)propanoic acid;
2-amino-3-(2-methyl-7-nitro-4-phenyl-1H-indol-3-yl)propanoic acid;
2-amino-3-(5-cyclopropyl-2-methyl-4-nitro-1H-indol-3-yl)propanoic acid;
2-amino-3-(6-cyclopropyl-2-methyl-4-nitro-1H-indol-3-yl)propanoic acid;
2-amino-3-(7-cyclopropyl-2-methyl-4-nitro-1H-indol-3-yl)propanoic acid;
2-amino-3-(4-cyclopropyl-2-methyl-7-nitro-1H-indol-3-yl)propanoic acid;
2-amino-3-(2-methyl-4-nitro-5-vinyl-1H-indol-3-yl)propanoic acid;
2-amino-3-(2-methyl-4-nitro-6-vinyl-1H-indol-3-yl)propanoic acid;

2-amino-3-(2-methyl-4-nitro-7-vinyl-1H-indol-3-yl)propanoic acid;
2-amino-3-(2-methyl-7-nitro-4-vinyl-1H-indol-3-yl)propanoic acid;
2-amino-3-(5-ethynyl-2-methyl-4-nitro-1H-indol-3-yl)propanoic acid;
2-amino-3-(6-ethynyl-2-methyl-4-nitro-1H-indol-3-yl)propanoic acid;
2-amino-3-(7-ethynyl-2-methyl-4-nitro-1H-indol-3-yl)propanoic acid;
2-amino-3-(4-ethynyl-2-methyl-7-nitro-1H-indol-3-yl)propanoic acid;
2-amino-3-(2-methyl-5-morpholino-4-nitro-1H-indol-3-yl)propanoic acid;
2-amino-3-(2-methyl-6-morpholino-4-nitro-1H-indol-3-yl)propanoic acid;
2-amino-3-(2-methyl-7-morpholino-4-nitro-1H-indol-3-yl)propanoic acid;
2-amino-3-(2-methyl-4-morpholino-7-nitro-1H-indol-3-yl)propanoic acid;
2-amino-3-(2-methyl-5-(methylthio)-4-nitro-1H-indol-3-yl)propanoic acid;
2-amino-3-(2-methyl-6-(methylthio)-4-nitro-1H-indol-3-yl)propanoic acid;
2-amino-3-(2-methyl-7-(methylthio)-4-nitro-1H-indol-3-yl)propanoic acid;
2-amino-3-(2-methyl-4-(methylthio)-7-nitro-1H-indol-3-yl)propanoic acid;
2-amino-3-(2-methyl-4-nitro-5-(pyridin-4-yl)-1H-indol-3-yl)propanoic acid;
2-amino-3-(2-methyl-4-nitro-6-(pyridin-4-yl)-1H-indol-3-yl)propanoic acid;
2-amino-3-(2-methyl-4-nitro-7-(pyridin-4-yl)-1H-indol-3-yl)propanoic acid;
2-amino-3-(2-methyl-7-nitro-4-(pyridin-4-yl)-1H-indol-3-yl)propanoic acid;
2-amino-3-(1,2,5-trimethyl-4-nitro-1H-indol-3-yl)propanoic acid;
2-amino-3-(1,2,6-trimethyl-4-nitro-1H-indol-3-yl)propanoic acid;
2-amino-3-(1,2,7-trimethyl-4-nitro-1H-indol-3-yl)propanoic acid;
2-amino-3-(1,2,4-trimethyl-7-nitro-1H-indol-3-yl)propanoic acid;
2-amino-3-(6-fluoro-1,2-dimethyl-4-nitro-1H-indol-3-yl)propanoic acid;
2-amino-3-(7-fluoro-1,2-dimethyl-4-nitro-1H-indol-3-yl)propanoic acid;
2-amino-3-(4-fluoro-1,2-dimethyl-7-nitro-1H-indol-3-yl)propanoic acid;
2-amino-3-(5-chloro-1,2-dimethyl-4-nitro-1H-indol-3-yl)propanoic acid;
2-amino-3-(6-chloro-1,2-dimethyl-4-nitro-1H-indol-3-yl)propanoic acid;
2-amino-3-(7-chloro-1,2-dimethyl-4-nitro-1H-indol-3-yl)propanoic acid;
2-amino-3-(4-chloro-1,2-dimethyl-7-nitro-1H-indol-3-yl)propanoic acid;
2-amino-3-(5-bromo-1,2-dimethyl-4-nitro-1H-indol-3-yl)propanoic acid;
2-amino-3-(6-bromo-1,2-dimethyl-4-nitro-1H-indol-3-yl)propanoic acid;
2-amino-3-(7-bromo-1,2-dimethyl-4-nitro-1H-indol-3-yl)propanoic acid;
2-amino-3-(4-bromo-1,2-dimethyl-7-nitro-1H-indol-3-yl)propanoic acid;
2-amino-3-(5-methoxy-1,2-dimethyl-4-nitro-1H-indol-3-yl)propanoic acid;
2-amino-3-(6-methoxy-1,2-dimethyl-4-nitro-1H-indol-3-yl)propanoic acid;
2-amino-3-(7-methoxy-1,2-dimethyl-4-nitro-1H-indol-3-yl)propanoic acid;
2-amino-3-(4-methoxy-1,2-dimethyl-7-nitro-1H-indol-3-yl)propanoic acid;
2-amino-3-(5-amino-1,2-dimethyl-4-nitro-1H-indol-3-yl)propanoic acid;
2-amino-3-(6-amino-1,2-dimethyl-4-nitro-1H-indol-3-yl)propanoic acid;
2-amino-3-(7-amino-1,2-dimethyl-4-nitro-1H-indol-3-yl)propanoic acid;
2-amino-3-(4-amino-1,2-dimethyl-7-nitro-1H-indol-3-yl)propanoic acid;
2-amino-3-(5-hydroxy-1,2-dimethyl-4-nitro-1H-indol-3-yl)propanoic acid;
2-amino-3-(6-hydroxy-1,2-dimethyl-4-nitro-1H-indol-3-yl)propanoic acid;
2-amino-3-(7-hydroxy-1,2-dimethyl-4-nitro-1H-indol-3-yl)propanoic acid;
2-amino-3-(4-hydroxy-1,2-dimethyl-7-nitro-1H-indol-3-yl)propanoic acid;
2-amino-3-(1,2-dimethyl-4-nitro-5-phenyl-1H-indol-3-yl)propanoic acid;
2-amino-3-(1,2-dimethyl-4-nitro-6-phenyl-1H-indol-3-yl)propanoic acid;
2-amino-3-(1,2-dimethyl-4-nitro-7-phenyl-1H-indol-3-yl)propanoic acid;
2-amino-3-(1,2-dimethyl-7-nitro-4-phenyl-1H-indol-3-yl)propanoic acid;
2-amino-3-(5-cyclopropyl-1,2-dimethyl-4-nitro-1H-indol-3-yl)propanoic acid;
2-amino-3-(6-cyclopropyl-1,2-dimethyl-4-nitro-1H-indol-3-yl)propanoic acid;
2-amino-3-(7-cyclopropyl-1,2-dimethyl-4-nitro-1H-indol-3-yl)propanoic acid;
2-amino-3-(4-cyclopropyl-1,2-dimethyl-7-nitro-1H-indol-3-yl)propanoic acid;
2-amino-3-(1,2-dimethyl-4-nitro-5-vinyl-1H-indol-3-yl)propanoic acid;
2-amino-3-(1,2-dimethyl-4-nitro-6-vinyl-1H-indol-3-yl)propanoic acid;
2-amino-3-(1,2-dimethyl-4-nitro-7-vinyl-1H-indol-3-yl)propanoic acid;
2-amino-3-(1,2-dimethyl-7-nitro-4-vinyl-1H-indol-3-yl)propanoic acid;
2-amino-3-(5-ethynyl-1,2-dimethyl-4-nitro-1H-indol-3-yl)propanoic acid;
2-amino-3-(6-ethynyl-1,2-dimethyl-4-nitro-1H-indol-3-yl)propanoic acid;
2-amino-3-(7-ethynyl-1,2-dimethyl-4-nitro-1H-indol-3-yl)propanoic acid;
2-amino-3-(4-ethynyl-1,2-dimethyl-7-nitro-1H-indol-3-yl)propanoic acid;
2-amino-3-(1,2-dimethyl-5-morpholino-4-nitro-1H-indol-3-yl)propanoic acid;
2-amino-3-(1,2-dimethyl-6-morpholino-4-nitro-1H-indol-3-yl)propanoic acid;
2-amino-3-(1,2-dimethyl-7-morpholino-4-nitro-1H-indol-3-yl)propanoic acid;
2-amino-3-(1,2-dimethyl-4-morpholino-7-nitro-1H-indol-3-yl)propanoic acid;
2-amino-3-(1,2-dimethyl-5-(methylthio)-4-nitro-1H-indol-3-yl)propanoic acid;

2-amino-3-(1,2-dimethyl-6-(methylthio)-4-nitro-1H-indol-3-yl)propanoic acid;
2-amino-3-(1,2-dimethyl-7-(methylthio)-4-nitro-1H-indol-3-yl)propanoic acid;
2-amino-3-(1,2-dimethyl-4-(methylthio)-7-nitro-1H-indol-3-yl)propanoic acid;
2-amino-3-(1,2-dimethyl-4-nitro-5-(pyridin-4-yl)-1H-indol-3-yl)propanoic acid;
2-amino-3-(1,2-dimethyl-4-nitro-6-(pyridin-4-yl)-1H-indol-3-yl)propanoic acid;
2-amino-3-(1,2-dimethyl-4-nitro-7-(pyridin-4-yl)-1H-indol-3-yl)propanoic acid; or
2-amino-3-(1,2-dimethyl-7-nitro-4-(pyridin-4-yl)-1H-indol-3-yl)propanoic acid;
and a pharmaceutically acceptable salt, prodrug, hydrate, or solvate thereof.

The skilled artisan recognizes that the conditions under which a composition as described herein is maintained may affect the production and/or stability of nitrated aromatic compounds by the recombinant bacterial cell(s). The disclosure is based, in part, on the recognition that production of nitrated aromatic compounds is reduced or absent at temperatures at which bacterial cells are generally cultured (e.g., 37° C.). In some embodiments, a composition has a temperature below 37° C. (e.g., the temperature of the bacterial culture media of a composition is below 37° C.). The disclosure is based, in part, on the recognition that production of nitrated aromatic compounds is increased at temperatures between 10 to 30° C. (e.g., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., or 30° C.). In some embodiments, a composition has a temperature of 28° C. (e.g., the temperature of the bacterial culture media of a composition is 28° C.).

In some embodiments, a composition as described by the disclosure comprises additional components, for example one or more cryopreservatives (e.g., glycol, DMSO, PEG, glycerol, etc.), antifungals, etc.

Methods of Producing Recombinant Bacterial Cells

In some embodiments, the disclosure relates to methods of producing a recombinant bacterial cell as described by the disclosure. Typically, the methods comprise the steps of: transforming a bacterial cell with an isolated nucleic acid engineered to express a fusion protein comprising a TxtE enzyme linked to a catalytic domain of a CYP102A1 (P450BM3) reductase enzyme via an amino acid linker sequence that is between 14 and 27 amino acids in length; and an isolated nucleic acid engineered to express a nitric oxide synthase (NOS) enzyme; and culturing (e.g., growing) the bacterial cell.

Methods of introducing vectors into bacteria are well known in the art and described, for example, in Current Protocols in Molecular Biology, Ausubel et al. (Eds), John Wiley and Sons, New York, 2007.

In some embodiments of methods described by the disclosure, a bacterial cell is transformed with one or more an isolated nucleic acids comprising the sequence set forth in any one of SEQ ID NOs: 8-13.

Whole Cell-Based Nitration of L-Tryptophan and L-Tryptophan Analogues

In some aspects, the disclosure relates to methods for producing a nitrated L-tryptophan or nitrated L-tryptophan analogue, comprising the steps of: introducing into a bacterial cell culture comprising a one or more of a recombinant bacterial cell as described by the disclosure one or more L-Trp molecules and/or one or more L-Trp analogue molecules; and growing the bacterial cell culture under conditions under which a fusion protein expressed by the recombinant bacterial cell catalyzes a nitration reaction which produces one or more nitrated L-Trp molecules and/or one or more nitrated L-Trp analog molecules. In some embodiments, methods further comprise the step of isolating nitrated L-Trp molecules and/or nitrated L-Trp analog molecules from the bacterial cell culture.

In some embodiments of methods described by the disclosure, one or more L-Trp analogue molecules are selected from the group consisting of α-Me-Trp, 4-F-Trp, 4-Me-Trp, 5-MeO-Trp, 5-Me-Trp, 5-F-Trp, 6-F-Trp, and 7-Me-Trp. The concentration of L-Trp or L-Trp analog added (introduced into) a bacterial cell culture can vary. In some embodiments, L-Trp or an L-Trp analogue is added to a bacterial cell culture in an amount such that the final concentration of L-Trp or L-Trp analogue in the bacterial cell culture ranges from about 1 μM to a saturation concentration or above (e.g., 1 μM, 10 μM, 50 μM, 100 μM, 500 μM, 750 μM, 1 mM, 10 mM, 100 mM, etc.).

In some embodiments, the order in which the proteins encoded by the isolated nucleic acids of the recombinant bacterial cell are expressed affects the production of nitrated aromatic compounds. In some embodiments, a TxtE fusion protein, NOS enzyme, and optionally GDH, are simultaneously expressed in a recombinant bacterial cell. In some embodiments, a TxtE fusion protein, NOS enzyme, and optionally GDH, are expressed sequentially in a recombinant bacterial cell. The order of sequential expression of the proteins can vary. For example a TxtE fusion protein may be expressed first prior to NOS and/or GDH. In some embodiments, a NOS enzyme is expressed prior to expression of a TxtE fusion protein. In some embodiments, a TxtE fusion protein, NOS enzyme, and optionally GDH, are expressed in a recombinant bacterial cell prior to addition of L-Trp or L-Trp analogue. In some embodiments, a TxtE fusion protein, NOS enzyme, and optionally GDH, are expressed in a recombinant bacterial cell after addition of L-Trp or L-Trp analogue.

In some embodiments of methods described by the disclosure, the step of growing the bacterial cell culture comprises introducing one or more antibiotic and/or one or more inducer into the bacterial cell culture. In some embodiments, one or more antibiotic is selected from ampicillin and kanamycin. In some embodiments, one or more of the inducers is Isopropyl β-D-1-thiogalactopyranoside (IPTG).

The skilled artisan recognizes that the conditions under which a composition as described herein is maintained may affect the production and/or stability of nitrated aromatic compounds by the recombinant bacterial cell(s). The disclosure is based, in part, on the recognition that production of nitrated aromatic compounds is reduced or absent at temperatures at which bacterial cells are generally cultured (e.g., 37° C.). In some embodiments, a composition has a temperature below 37° C. (e.g., the temperature of the bacterial culture media of a composition is below 37° C.). The disclosure is based, in part, on the recognition that production of nitrated aromatic compounds is increased at temperatures between 10 to 30° C. (e.g., 10° C., 11° C., 12° C., 13° C., 14° C., 15° C., 16° C., 17° C., 18° C., 19° C., 20° C., 21° C., 22° C., 23° C., 24° C., 25° C., 26° C., 27° C., 28° C., 29° C., or 30° C.). In some embodiments, a composition has a temperature of 28° C. (e.g., the temperature of the bacterial culture media of a composition is 28° C.).

The length of time a bacterial cell culture is grown after addition of L-Trp or a L-Trp analogue can vary. In some embodiments, a bacterial cell culture is grown for about 1 hour to about 30 hours (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 hours) after the addition of L-Trp or L-Trp analogue. In some embodiments, a bacterial cell culture is grown for about 1 hour to about 30 hours (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 hours) post-transformation with one or more isolated nucleic acids. In some embodiments, a bacterial cell culture is grown for up to 25 hours (e.g., up to 25 hours post-transformation with one or more isolated nucleic acids).

In some embodiments, isolating nitrated L-Trp molecules and/or nitrated L-Trp analog molecules comprises lysing one or more recombinant bacterial cells. Lysis of bacterial cells is generally known in the art and may be achieved, for example, by incubating bacterial cells in a lysis buffer (e.g., a hypertonic solution, a solution containing lysozyme, a solution containing detergent, etc.) or by centrifugation.

In some embodiments, nitrated L-Trp molecules and/or nitrated L-Trp analog molecules are isolated from a bacterial cell lysate by performing high-pressure liquid chromatography (HPLC) or other liquid extraction methods known in the art. Additional methods for purification and/or analysis of nitrated aromatic compounds (e.g., 4-NO$_2$-L-Trp, etc.) include mass spectroscopy and nuclear magnetic resonance (NMR) analysis.

The present invention is further illustrated by the following Examples, which in no way should be construed as further limiting.

EXAMPLES

Example 1: Materials and Methods

General Chemicals, DNA Sub-Cloning, and Bacterial Strains

Molecular biology reagents and enzymes were purchased from Fisher Scientific. Primers (Table 1) were ordered from Sigma-Aldrich. 4-Me-DLTrp was from MP Biomedical (Santa Ana, CA), while NOC-5 (3-(Aminopropyl)-1-hydroxy-3-isopropyl-2-oxo-1-triazene) was purchased from EMD Millipore. Other chemicals and solvents were purchased from Sigma-Aldrich and Fisher Scientific. *Escherichia coli* DH5α (Life Technologies) was used for cloning and plasmid harvesting. *E. coli* BL21-GOLD (DE3) (Agilent) was used for protein overexpression. *E. coli* strains were grown in Luria-Bertani broth or Terrific broth. DNA sequencing was performed at Eurofins. A Shimadzu Prominence UHPLC system (Kyoto, Japan) fitted with an Agilent Poroshell 120 EC-C$_{18}$ column (2.7 μm, 3.0×50 mm), coupled with a PDA detector was used for HPLC analysis.

Construction of Plasmids for Whole Cell Transformation

TB14 gene was amplified from TB14/pET28b using a pair of TB14FN and TB14RH primers in PCR reactions (Table 1). The PCR product was analyzed by agarose gel and extracted with a GeneJET Gel Extraction Kit (Thermo). Purified PCR products, pACYCDuet and pETDuet were digested with the restriction enzymes NcoI and HindIII, and corresponding linear DNAs were ligated to generate expression constructs. GDH gene was amplified from GDH/pET21b using a pair of GDHFB and GDHRH primers in PCR reactions (Table 1). The PCR product was analyzed by agarose gel and extracted with a GeneJET Gel Extraction Kit (Thermo). Purified PCR products, pET28b, pACYCDuet and pETDuet were digested with the restriction enzymes BamHI and HindIII, and corresponding linear DNAs were ligated to generate expression constructs. BsNOS gene was amplified from BsNOS/pET15b using a pair of BsNOSFN and BsNOSRH primers in PCR reactions (Table 1). The PCR product was analyzed by agarose gel and extracted with a GeneJET Gel Extraction Kit (Thermo). Purified PCR products, pET28b, pACYCDuet and pETDuet were digested with the restriction enzymes NdeI and HindIII, and corresponding linear DNAs were ligated to generate expression constructs. SsTxtD and StTxtD were amplified from genomic DNA of *S. scabies* 87.22 (NRRL B-24449) and *S. turgidiscabies* Car8 using a pair of SsTxtDFN/SsTxtDRH and StTxtDFN/25 StTxtDRH primers in PCR reactions (Table 1). The PCR product was analyzed by agarose gel and extracted with a GeneJET Gel Extraction Kit (Thermo). Purified PCR products and pET28b were digested with the restriction enzymes NdeI and HindIII, and corresponding linear DNAs were ligated to generate expression constructs. All inserts in the constructs were sequenced to exclude mutations introduced during PCR amplification and gene manipulation.

Heterologous Expression and Purification of Recombinant Proteins

Protein expression and purification followed established protocols. The purified proteins were exchanged into storage buffer (25 mM Tris-HCl, pH 8.0, 100 mM NaCl, 3 mM βME, and 10% glycerol) by PD-10 column, aliquoted and stored at −80° C. until needed. CO difference spectroscopy was used to measure the concentrations of functional P450s.

Analytical HPLC Analysis

For analytical analysis, an HPLC column was kept at 40° C., water with 0.1% formic acid was used as solvent A and acetonitrile with 0.1% formic acid was used as solvent B. The column was eluted first with 1% solvent B for 1 min and then with a linear gradient of 1-20% solvent B in 8 min, followed by another linear gradient of 20-99% solvent B in 2 min. The column was further cleaned with 99% solvent B for 2 min and then re-equilibrated with 1% solvent B for 2 min. The flow rate was set as 1 mL/min, and the products were detected at 211 nm with a PDA detector.

Whole-Cell Biotransformation

*E. coli* BL21 Gold cells containing pETDuet and pET28b derived plasmids were grown from glycerol stock overnight in 5 mL Luria broth with 0.1 mg/mL ampicillin and 0.05 mg/mL kanamycin (37° C., 250 rpm). The pre-culture was used to inoculate 100 mL of Terrific broth medium (0.1 mg/mL ampicillin and 0.05 mg/mL kanamycin) in a 500 mL flask; this culture was incubated at 37° C., 250 rpm to OD$_{600}$=0.6-0.8. The cultures were cooled on water-ice mixture and induced with 0.5 mM IPTG. Expression was conducted at 18° C., 250 rpm, for 20 h. For the culture of *E. coli* BL21 Gold cells containing pACYCDuet and pET28b derived plasmids, 0.05 mg/mL chloramphenicol was used instead of 0.05 mg/mL kanamycin. The cultures were then harvested and resuspended to OD$_{600}$=30 in test medium. Aliquots of the cell suspension were used in the whole cell transformation. To a test tube was added 5 mL cell suspension, 25 μL 100 mM L-Trp or L-Trp analogues, and 25 μL 100 mM L-Arg when necessary. The mixture was then incubated at different conditions. The reactions were quenched by adding equal volume of methanol and the resulting mixture was aliquoted and transferred to a microcentrifuge tube and centrifuged at 14,000 rpm for 10 minutes. The supernatant was transferred to an HPLC vial and analyzed by LC-MS.

TABLE 1

Primers for construction of whole cell transformation plasmids.

| Name | Sequence (5'→3') | Function |
|---|---|---|
| TB14FN | ATACCATGGTGACCGTCCCCTCGCCG (SEQ ID NO: 17) | TB14 cloning |
| TB14RH | ATCAAGCTTCCCAGCCCACACGTCTTTTGC (SEQ ID NO: 18) | TB14 cloning |
| GDHFB | CAGGATCC GATGTATAAAGATCTGGAAGGTAAAGTGGTG (SEQ ID NO: 19) | GDH cloning |
| GDHRH | CAAAGCTTTTAGCCACGACCTGCCTGAAAG (SEQ ID NO: 20) | GDH cloning |
| BsNOSFN | ACTCATATGATGGAAGAAAAAGAAATC (SEQ ID NO: 21) | BsNOS cloning |
| BsNOSRH | ACTAAGCTT CTATTCATACGGTTTGTC (SEQ ID NO: 22) | BsNOS cloning |
| SsTxtDFN | CTACATATGGTGACTTTCGAAGTCGC (SEQ ID NO: 23) | SsTxtD cloning |
| SsTxtDRH | CTCAAGCTTCTGATGAGGGTAAAAGTTG (SEQ ID NO: 24) | SsTxtD cloning |
| StTxtDFN | ACTCATATGGTGACTTTCGAAGTCGCCCTG (SEQ ID NO: 25) | StTxtD cloning |
| StTxtDRH | ACTAAGCTTCTGATGAGGGTAAAAGTTGGGG (SEQ ID NO: 26) | StTxtD cloning |

Example 2: Whole Cell Nitration System

This example describes an *E. coli*-based biotransformation system for the production of nitrated L-Trp was developed (FIG. 1). The engineered *E. coli* strain contained three functional genes, TB14 (TB14), nitro oxide synthase (NOS), and Glucose Dehydrogenase 1 (GDH). TB14 is a self-sufficient nitration biocatalyst that is a fusion protein comprising a cytochrome P450 (e.g., a *Streptomyces* TxtE enzyme) and a catalytic domain of a reductase enzyme (e.g., a prokaryotic reductase enzyme, such as a CYP102A1 (P450BM3) reductase). TB14 is soluble in *E. coli*. In some embodiments, TB14 is represented by SEQ ID NO: 1.

The co-substrate NO is indispensable for a TxtE nitration reaction. In the in vitro assays, NO was derived from the NO precursor NOC-5 that is expensive, has a short-life, and is often incompatible with bacterial cells (e.g., NO at high concentration is toxic to bacterial cells). The thaxtomin biosynthetic gene cluster in *Streptomyces* scabies contains a TxtD gene encoding a nitric oxide synthase that converts L-Arg into L-citrulline and NO along with the consumption of NADPH. The expression of the NOS gene in *E. coli* can, in some embodiments, provide a sustainable and environment-friendly approach to eliminate the dependence of the high-cost and unstable NO precursors in whole cell nitration biotransformation.

It was observed that expression of the TxtD gene from two thaxtomin-producing *Streptomyces* strains (*Streptomyces* scabies and *Streptomyces turgidiscabies*) and yielded only insoluble proteins after optimizing expression conditions. However, expression of a codon-optimized NOS gene from *Bacillus subtilis* resulted in production of soluble NOS protein in *E. coli* and was used in the subsequent experiments.

The reaction of NOS requires redox partners for transferring electrons from NADPH. It was observed that non-specific redox partners of *E. coli* effectively support the BsNOS reaction, making BsNOS containing *E. coli* strain a viable biosystem to supply NO for the nitration reaction. In some embodiments, insufficient supply of NADPH limits the productivity of biotransformation. Thus, in some embodiments of whole cell nitration systems described in this example, the GDH gene from *Bacillus megaterium* was also engineered into *E. coli* to regenerate NADPH that is consumed in both TB14 and BsNOS reactions. GDH catalyzes the oxidation of β-D-glucose to β-D-glucono-1,5-lactone with simultaneous reduction of the cofactor NADP$^+$ to NADPH, and may be applied in biocatalysis procedures to regenerate NADPH.

Figure 2A:
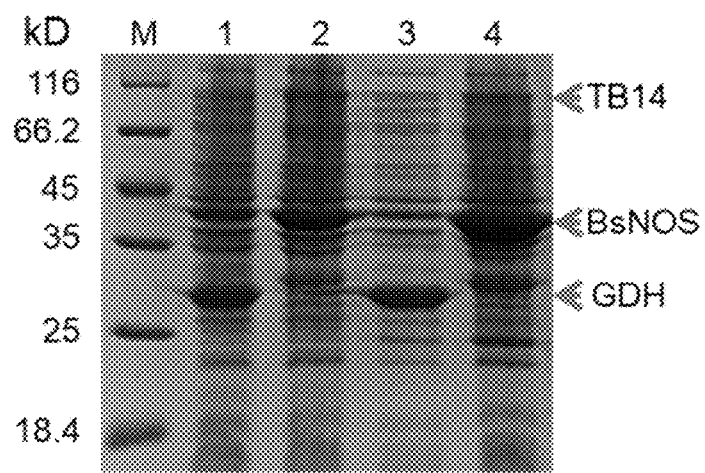
FIGS. 2A-2B show representative data for activity testing of a whole cell nitration system.
Figure 2B:
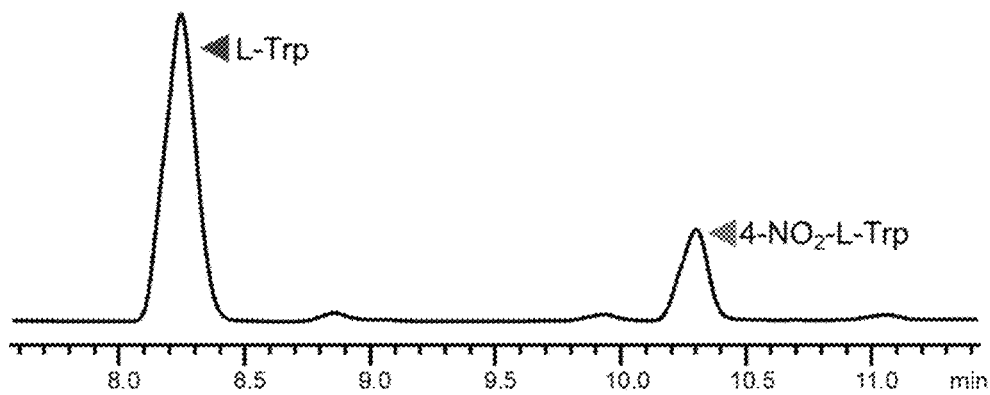

In some experiments, TB14 and BsNOS genes were co-expressed using vector pETDuet, while the GDH gene was separately expressed in the vector pET28b. Both vectors have the same, medium copy numbers (15 to 60) in the host and drive the expression of each gene with a strong inducible promoter T7. In addition, the different antibiotic resistant markers (ampicillin R and kanamycin R) in these two vectors make them suitable for simultaneous expression of three genes in the same host. The two constructs described above were transformed into *E. coli* BL21-GOLD strain. The overexpression of the three enzymes was induced by IPTG. SDS-PAGE analysis of the soluble crude extract (FIG. 2A, lane 1) indicated successful overexpression of BsNOS (42 kD) and GDH (28 kD). Soluble TB14 (110 kD) expression was also observed. In some embodiments, co-expression of BsNOS and/or GDH negatively influences the expression of TB14. Nevertheless, this engineered *E. coli* strain was used in whole-cell biotransformation to produce 4-NO$_2$-L-Trp from fed L-Trp. After 20-h incubation, the successful production of 4-NO$_2$-L-Trp was confirmed by LC-MS (FIG. 2B).

Optimization of Heterologous Enzyme Expression

Figure 3A:
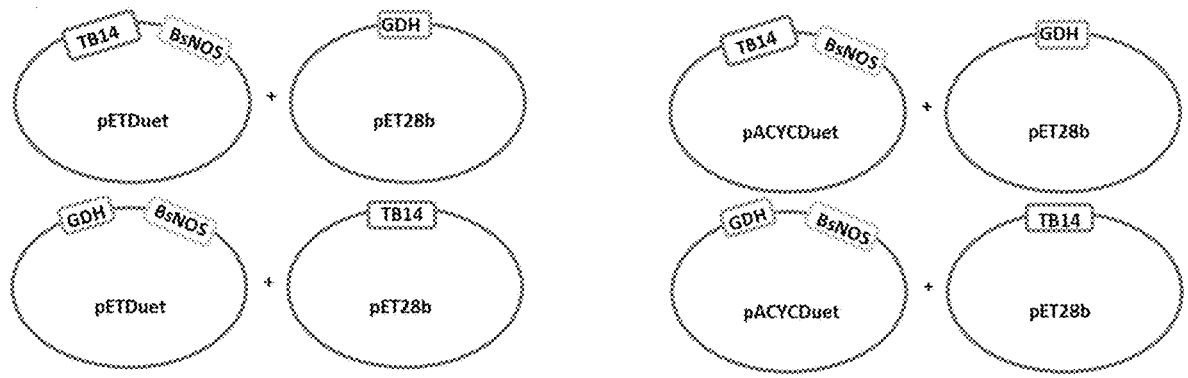
FIGS. 3A-3B show analysis of different embodiments of a whole cell nitration system.
Figure 3B:
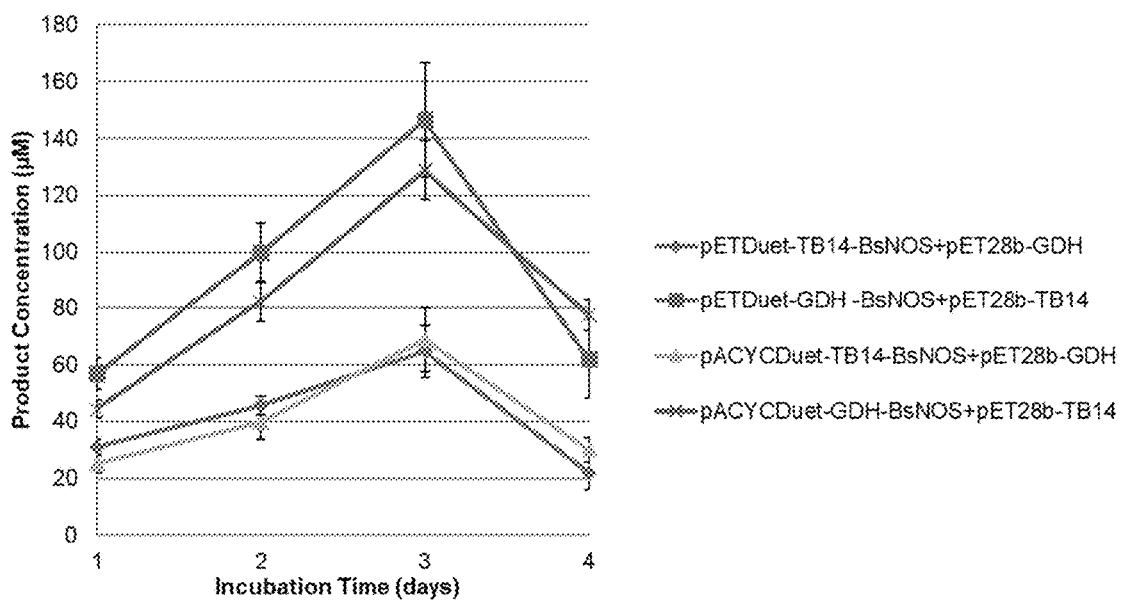

Next, the copy numbers of the three genes (e.g., TB14, BsNOS, GDH) were varied in order to improve TB14 expression and to improve plasmid stability. Plasmid pACYCDuet was used for the co-expression of two target genes. The pACYCDuet plasmid includes two T7 promoters to drive the proteins expression carries the P15A replicon instead of pBR322-derived ColE1 replicon as in pETDuet and pET28b, which can provide higher plasmid stability when two plasmids are used. Three new pairs of expression constructs were created, pETDuet-GDH-BsNOS+pET28b-TB14, pACYCDuet-TB14-BsNOS+pET28b-GDH, and pACYCDuet-GDH-BsNOS+pET28b-TB14, and the corresponding engineered *E. coli* strains (FIG. 3A). Protein expression levels in these strains was then examined by SDS-PAGE (FIG. 2A). The bacterial strain transformed with the pair of pETDuet-GDH-BsNOS and pET28b-TB14 plasmids showed significantly increased TB14 expression level, and it also demonstrated the high nitration activity (FIG. 3B). This strain was used in the following experiments.

Optimization of Fermentation Conditions

Fermentation conditions, including medium, temperature, substrate supplement, and harvesting time were then investigated. Minimal medium M9 was used in previously described experiments. As M9 medium is nutritiously poor, it was investigated whether nutrition availability could influence the whole cell nitration efficiency. Three nutrition rich media, including LB medium, SOC medium and TB medium, were tested along with the M9 medium in a whole cell nitration system. As shown in (FIG. 4), transformations supported by nutrition richer media generally had higher efficiency than those supported by the M9. Notably, TB medium supported transformation yielded as high as 600 µM of nitrated tryptophan (149 mg/L) after 20-hour fermentation.

The time profile of the product formation (FIG. 4) was then tested. In all the nutrition rich media, the highest productivity was observed at approximately 20 hours. By contrast, it required 3 days in the M9 medium. Notably, the concentration of nitrated tryptophan in the rich media started to decrease after 30-hour fermentation. In some embodiments, *E. coli* endogenous tryptophanase (EC 4.1.99.1), which converts tryptophan to indole, pyruvate and $NH_3$, mediates production decomposition. *E. coli* tryptophanase (tnaA) was cloned and recombinant enzyme was prepared. In vitro biochemical assay data indicated that TnaA was not able to decompose 4-$NO_2$-Trp.

Figure 4:
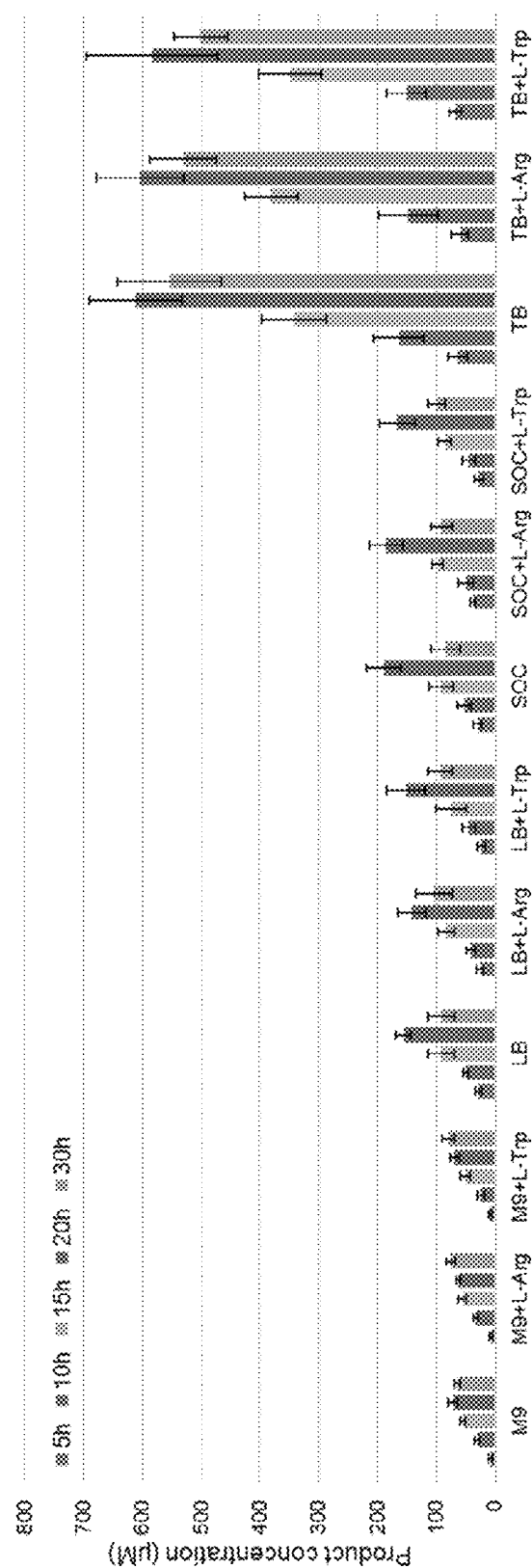
FIG. 4 shows nitrated tryptophan concentration produced by one embodiment of a whole cell nitration system supported by different types of growth medium (e.g., M9, LB, SOC, TB, each with or without supplemented L-Arg or L-Trp).

In TB14 reactions, the co-substrate NO is generated from L-arginine by BsNOS. The effect of increasing the concentration of L-Arg was then tested (FIG. 4). No significant change in nitro-tryptophan production was observed when 5 mM of L-Arg was added to each of the transformation systems tested. This result indicates that L-Arg or NO is not the limiting factor in the whole cell transformation. The effect of increased concentration of the substrate L-Trp was also tested (FIG. 4). No significant change of the production was observed when 5 mM of L-Trp was added to the transformation system.

Figure 5:
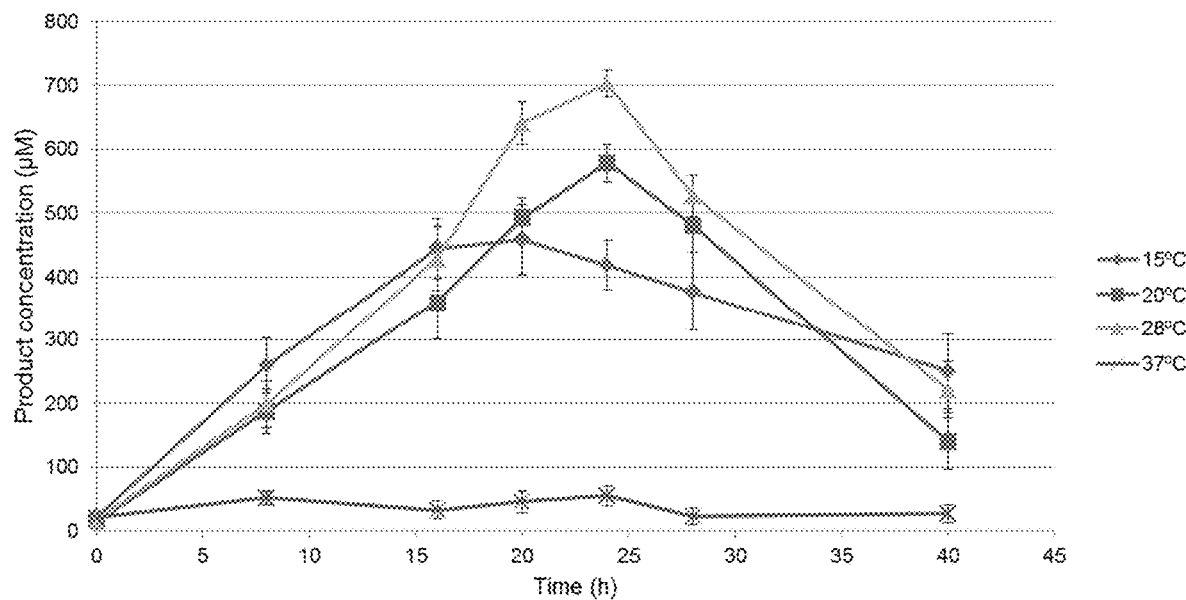
FIG. 5 shows nitrated tryptophan concentration produced by one embodiment of a whole cell nitration system fermented at different temperatures.

The temperature effects on the whole cell nitration were also investigated. In vitro studies indicated TB14 was active at temperatures between 10 to 30° C. All previous experiments were performed at 20° C. Productivity of the whole cell system at four different fermentation temperatures (15° C., 20° C., 28° C. and 37° C.) at different time points was investigated (FIG. 5). The transformations at 15° C., 20° C. and 28° C. each resulted in product yield. At 28° C., product concentration was observed to be 700 µM after 24-hour fermentation. Interestingly, the optimal growth temperature of *E. coli*, 37° C., almost completely abolished the nitration transformation.

Production of Nitrated Tryptophan Analogues by Whole Cell Nitration System

Figure 6:
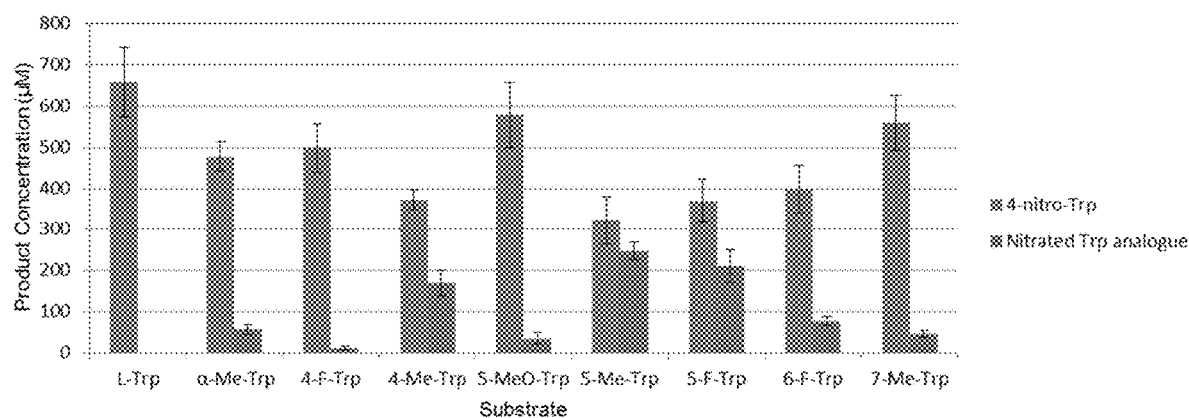
FIG. 6 shows production of nitrated tryptophan analogues by one embodiment of a whole cell nitration system.

A series of tryptophan analogues that can be nitrated by TxtE and its variants in vitro have been identified. In this example, the substrate scope of whole cell systems was investigated using these tryptophan analogues. These unnatural analogues generally compete with the native substrate L-Trp abundant in the TB medium in the whole cell transformation. However, data indicate that α-Me-Trp, 4-F-Trp, 4-Me-Trp, 5-MeO-Trp, 5-Me-Trp, 5-F-Trp, 6-F-Trp, and 7-Me-Trp all were successfully nitrated using the whole cell nitration system. Similar to observations in the in vitro enzymatic reactions, whole cell-based nitration demonstrated the highest conversion rates with 4-Me-Trp, 5-Me-Trp and 5-F-Trp (FIG. 6). The substrate 5-Me-Trp product concentration reached approximately 250 µM after 24-hour fermentation, along with approximately 320 µM of nitrated tryptophan (FIG. 6). The following nitro-tryptophan and nitro-tryptophan analogs can be synthesized using any of the methods delineated herein:

Example 3: Preparation of (S)-2-amino-3-(5-methyl-4-nitro-1H-indol-3-yl)propanoic acid (3)

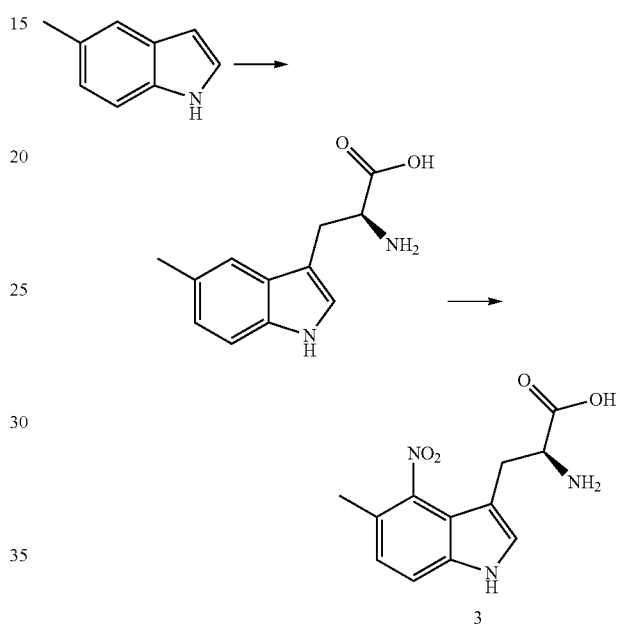

Example 3 can be prepared from 5-methylindole as shown above.

Example 4: Preparation of (S)-2-amino-3-(6-methyl-4-nitro-1H-indol-3-yl)propanoic acid (4)

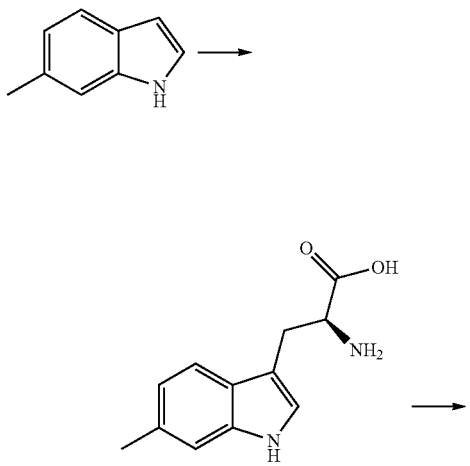

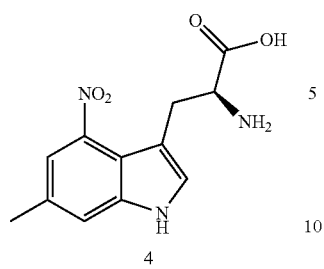
4

Example 4 can be prepared from 6-methylindole as shown above.

Example 5: Preparation of (S)-2-amino-3-(7-methyl-4-nitro-1H-indol-3-yl)propanoic acid (5)

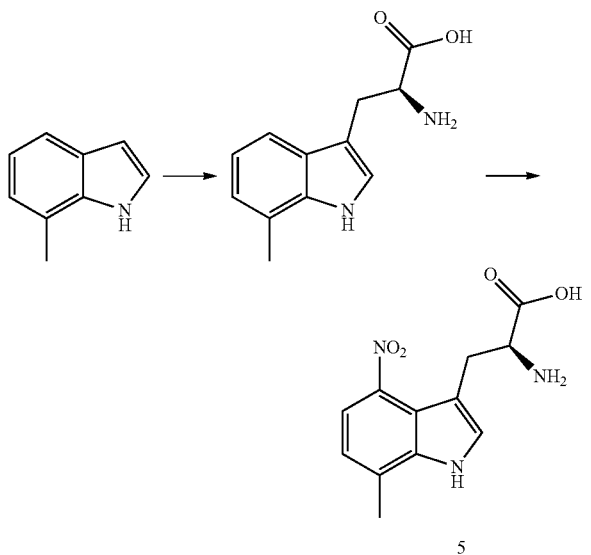
5

Example 5 can be prepared from 7-methylindole as shown above.

Example 6: Preparation of (S)-2-amino-3-(5-fluoro-4-nitro-1H-indol-3-yl)propanoic acid (6)

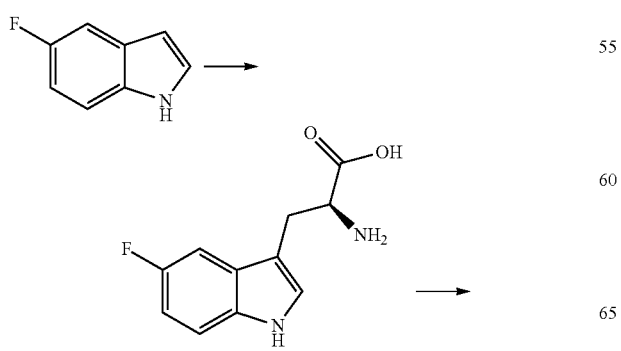

6

Example 6 can be prepared from 5-fluoroindole as shown above.

Example 7: Preparation of (S)-2-amino-3-(6-fluoro-4-nitro-1H-indol-3-yl)propanoic acid (7)

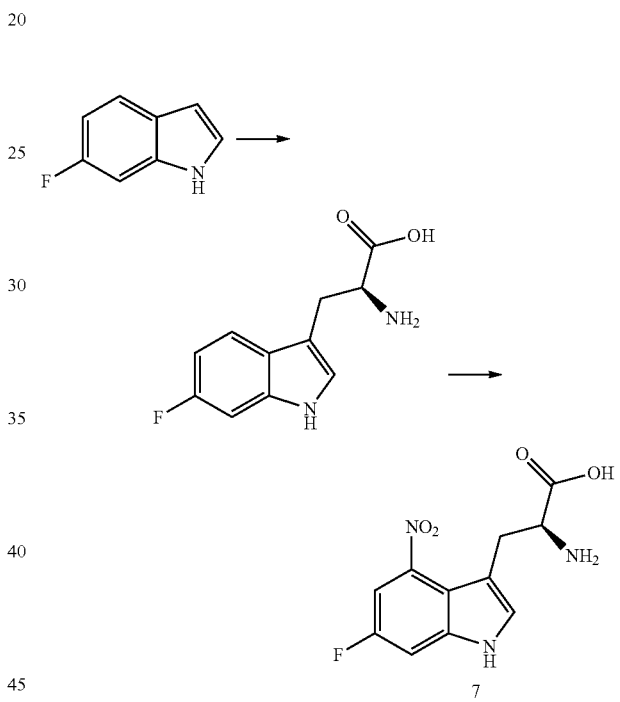
7

Example 7 can be prepared from 6-fluoroindole.

Example 8: Preparation of (S)-2-amino-3-(7-fluoro-4-nitro-1H-indol-3-yl)propanoic acid (8)

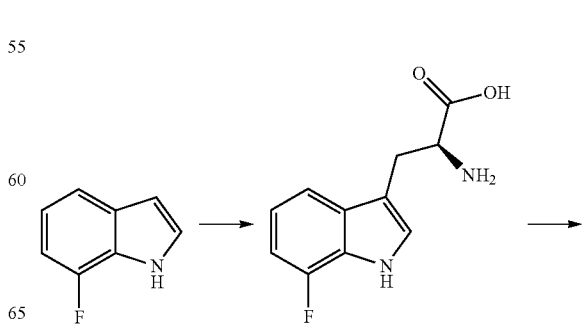

53

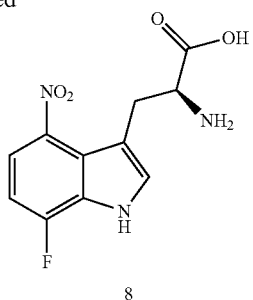

8

Example 8 can be prepared from 7-fluoroindole as shown above.

Example 9: Preparation of (S)-2-amino-3-(4-fluoro-7-nitro-1H-indol-3-yl)propanoic acid (9)

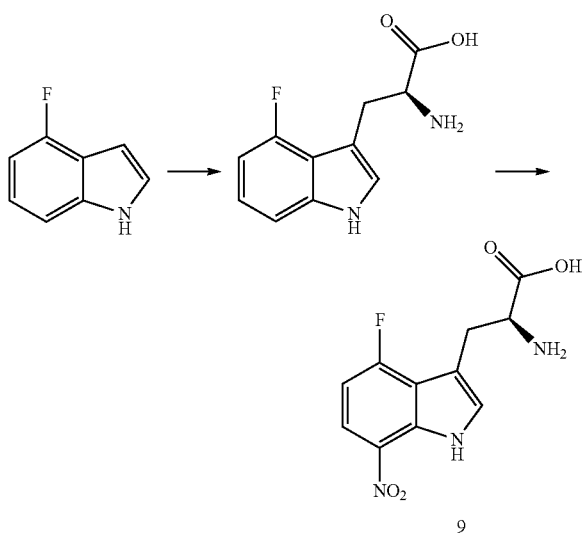

9

Example 9 can be prepared from 4-fluoroindole as shown above.

Example 10: Preparation of (S)-2-amino-3-(5-chloro-4-nitro-1H-indol-3-yl)propanoic acid (10)

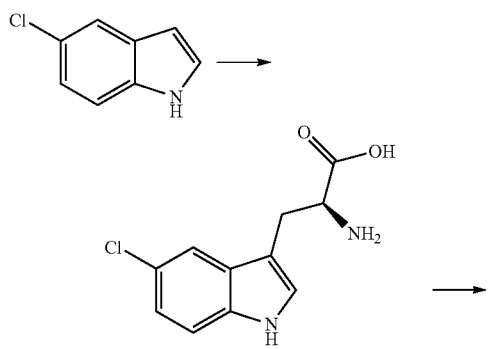

54

10

Example 10 can be prepared from 5-chloroindole as shown above.

Example 11: Preparation of (S)-2-amino-3-(6-chloro-4-nitro-1H-indol-3-yl)propanoic acid (11)

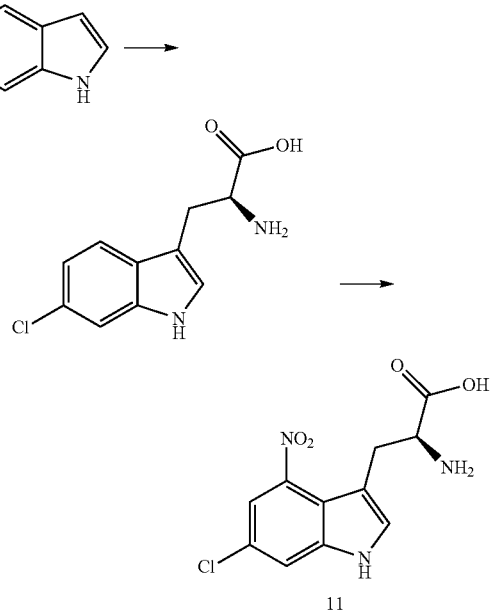

11

Example 11 can be prepared from 6-chloroindole as shown above.

Example 12: Preparation of (S)-2-amino-3-(7-chloro-4-nitro-1H-indol-3-yl)propanoic acid (12)

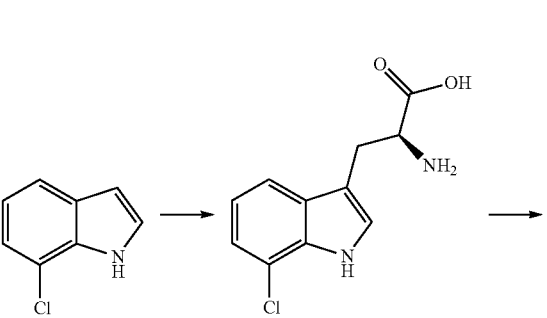

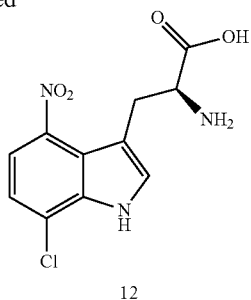

Example 12 can be prepared from 7-chloroindole as shown above.

Example 13: Preparation of (S)-2-amino-3-(4-chloro-7-nitro-1H-indol-3-yl)propanoic acid (13)

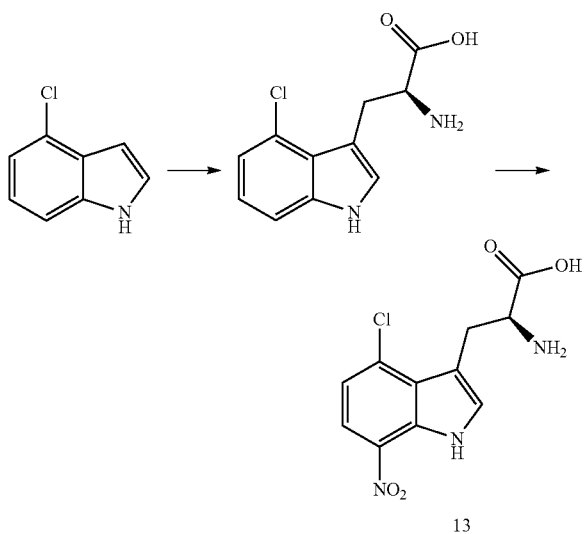

Example 13 can be prepared from 4-chloroindole as shown above.

Example 14: Preparation of (S)-2-amino-3-(5-bromo-4-nitro-1H-indol-3-yl)propanoic acid (14)

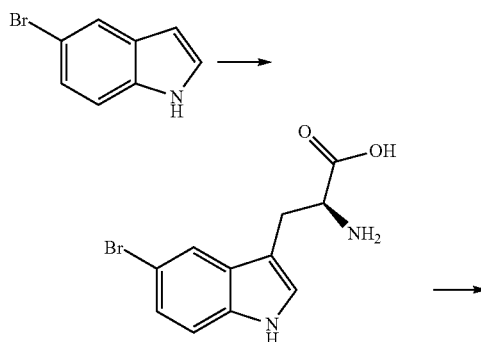

Example 14 can be prepared from 5-bromoindole as shown above.

Example 15: Preparation of (S)-2-amino-3-(6-bromo-4-nitro-1H-indol-3-yl)propanoic acid (15)

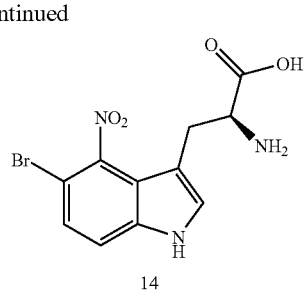

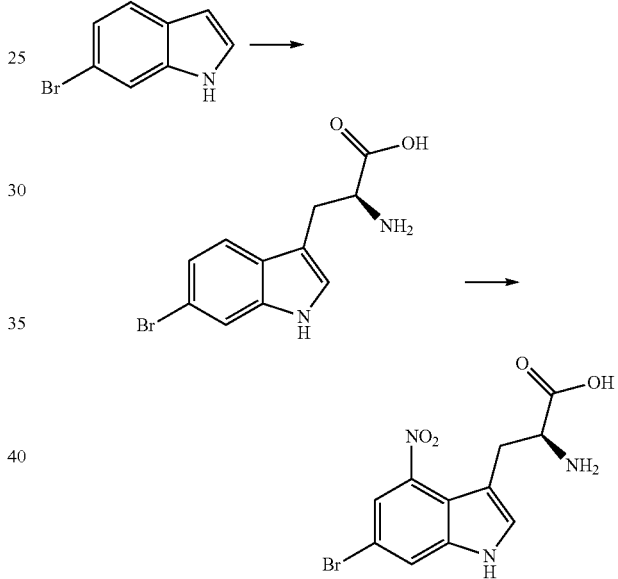

Example 15 can be prepared from 6-bromoindole as shown.

Example 16: Preparation of (S)-2-amino-3-(7-bromo-4-nitro-1H-indol-3-yl)propanoic acid (16)

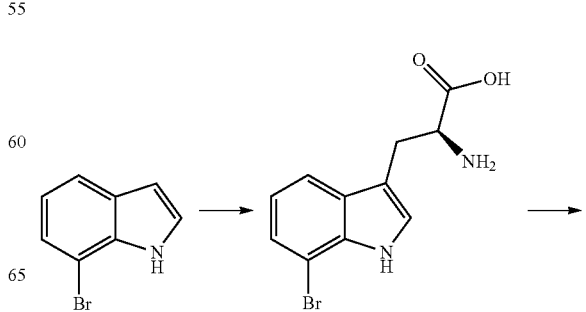

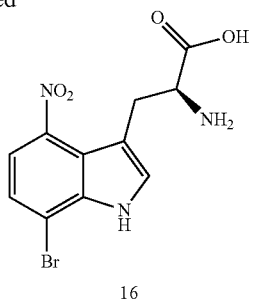

Example 16 can be prepared from 7-bromoindole as shown above.

Example 17: Preparation of (S)-2-amino-3-(4-bromo-7-nitro-1H-indol-3-yl)propanoic acid (17)

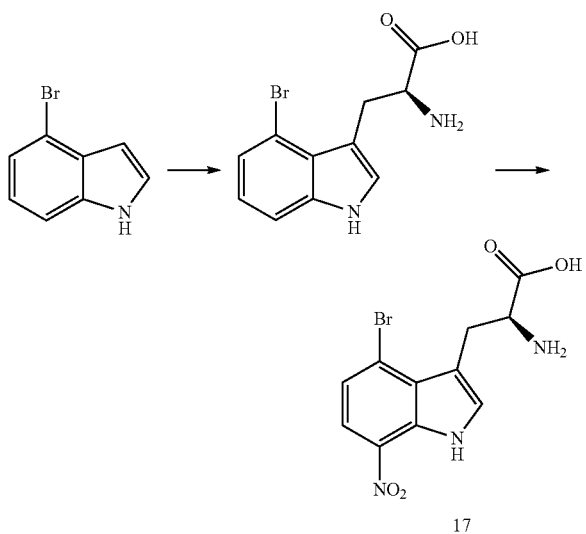

Example 17 can be prepared from 4-bromoindole as shown above.

Example 18: Preparation of (S)-2-amino-3-(5-methoxy-4-nitro-1H-indol-3-yl)propanoic acid (18)

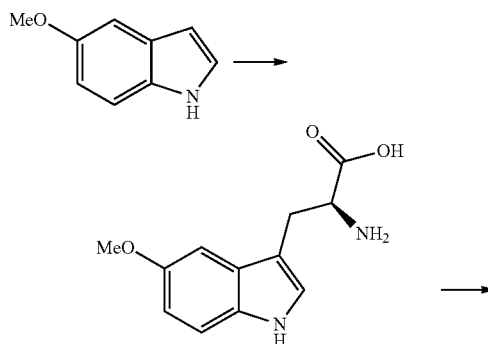

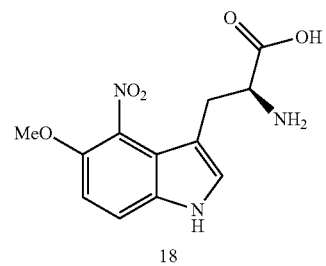

Example 18 can be prepared from 5-methoxyindole as shown above.

Example 19: Preparation of (S)-2-amino-3-(6-methoxy-4-nitro-1H-indol-3-yl)propanoic acid (19)

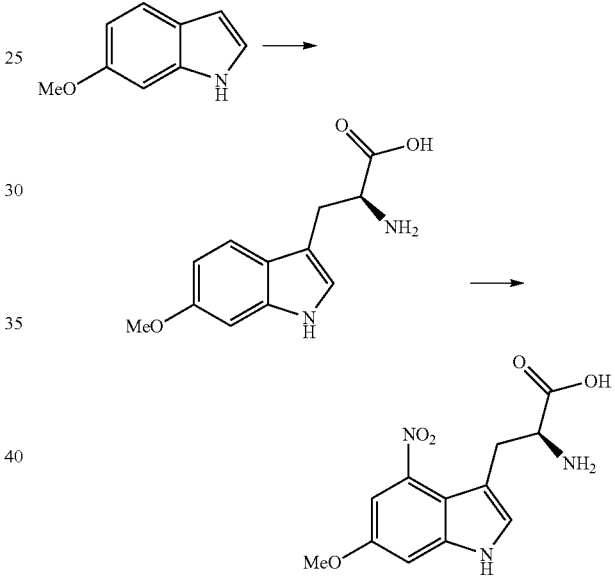

Example 19 can be prepared from 6-methoxyindole as shown above.

Example 20: Preparation of (S)-2-amino-3-(7-methoxy-4-nitro-1H-indol-3-yl)propanoic acid (20)

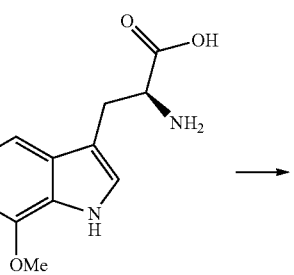

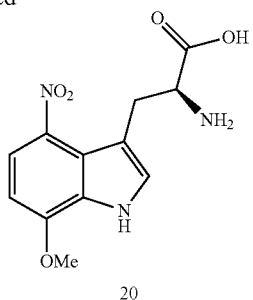

Example 20 can be prepared from 7-methoxyindole as shown above.

Example 21: Preparation of (S)-2-amino-3-(4-methoxy-7-nitro-1H-indol-3-yl)propanoic acid (21)

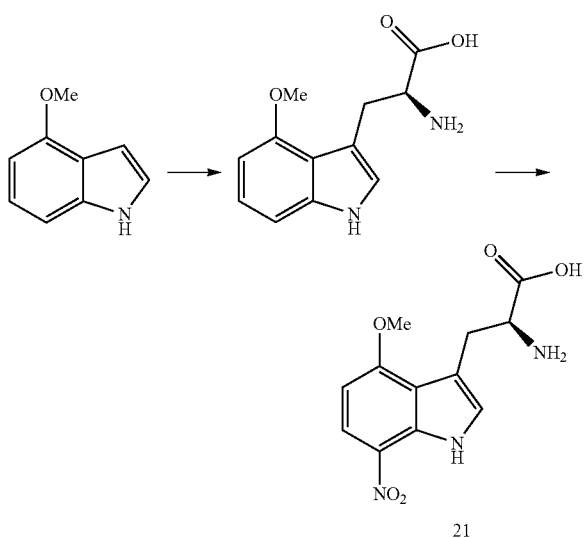

Example 21 can be prepared from 4-methoxyindole as shown above.

Example 22: Preparation of (S)-2-amino-3-(5-amino-4-nitro-1H-indol-3-yl)propanoic acid (22)

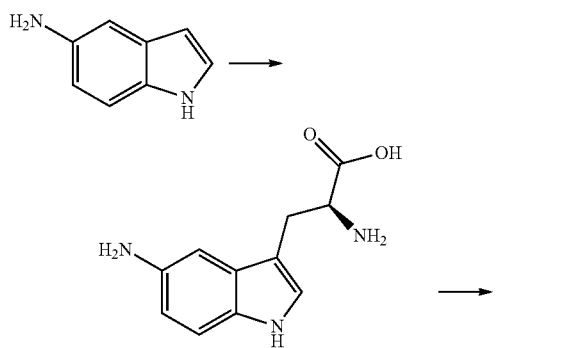

Example 22 can be prepared from 5-aminoindole as shown above.

Example 23: Preparation of (S)-2-amino-3-(6-amino-4-nitro-1H-indol-3-yl)propanoic acid (23)

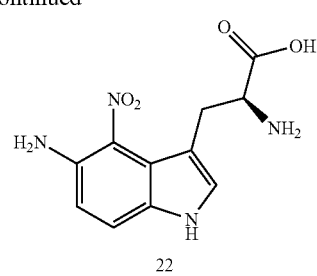

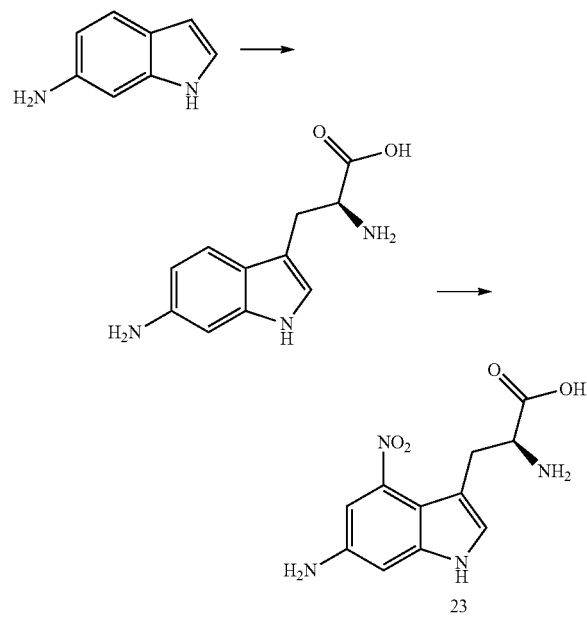

Example 23 can be prepared from 6-aminoindole as shown above.

Example 24: Preparation of (S)-2-amino-3-(7-amino-4-nitro-1H-indol-3-yl)propanoic acid (24)

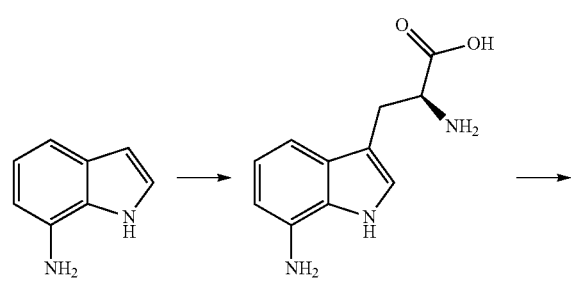

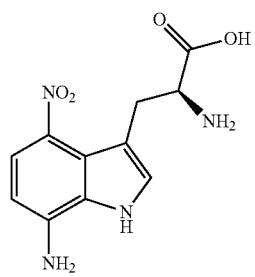

Example 24 can be prepared from 7-aminoindole as shown above.

Example 25: Preparation of (S)-2-amino-3-(4-amino-7-nitro-1H-indol-3-yl)propanoic acid (25)

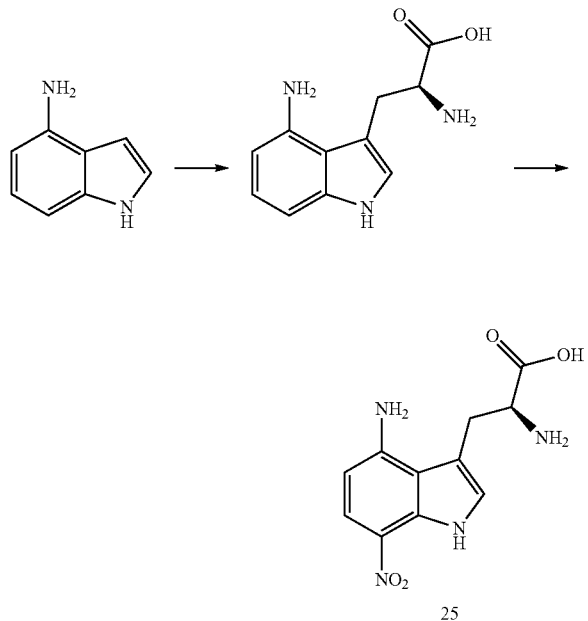 [SMILES: Nc1cccc2[nH]ccc12 ; Nc1cccc2[nH]cc(C[C@H](N)C(=O)O)c12 ; Nc1ccc([N+](=O)[O-])c2[nH]cc(C[C@H](N)C(=O)O)c12]

Example 25 can be prepared from 4-aminoindole as shown above.

Example 26: Preparation of (S)-2-amino-3-(5-hydroxy-4-nitro-1H-indol-3-yl)propanoic acid (26)

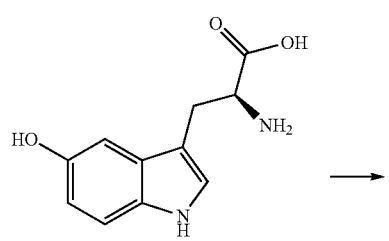

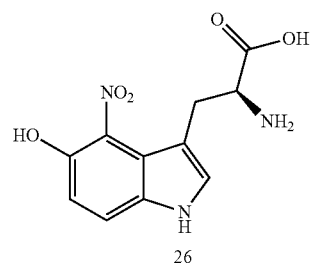

Example 26 can be prepared from (S)-2-amino-3-(5-hydroxy-1H-indol-3-yl)propanoic acid as shown above.

Example 27: Preparation of (S)-2-amino-3-(6-hydroxy-4-nitro-1H-indol-3-yl)propanoic acid (27)

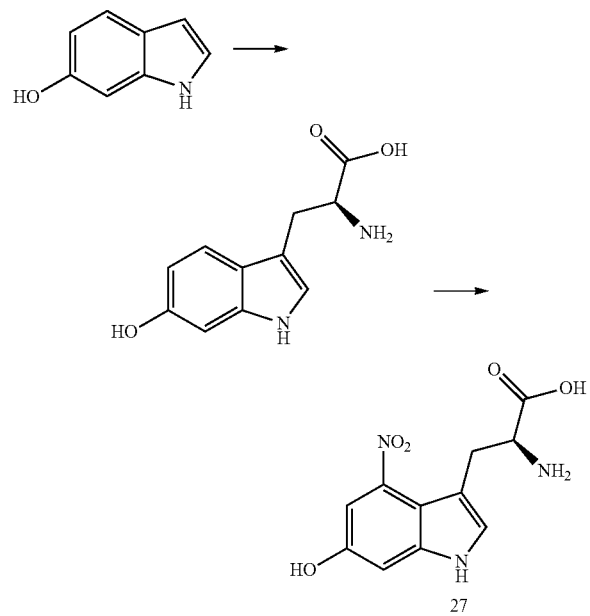

Example 27 can be prepared from 6-hydroxyindole as shown above.

Example 28: Preparation of (S)-2-amino-3-(7-hydroxy-4-nitro-1H-indol-3-yl)propanoic acid (28)

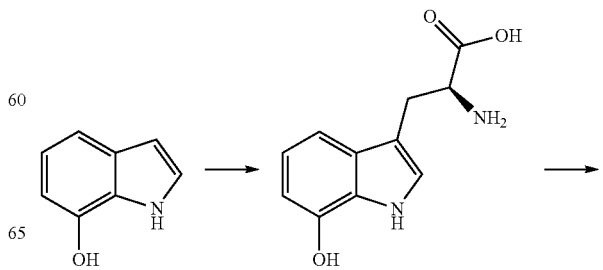

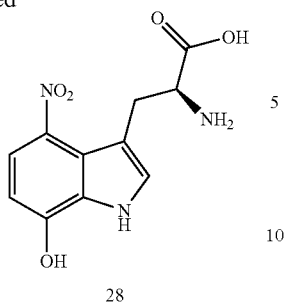

28

Example 28 can be prepared from 7-hydroxyindole as shown above.

Example 29: Preparation of (S)-2-amino-3-(4-hydroxy-7-nitro-1H-indol-3-yl)propanoic acid (29)

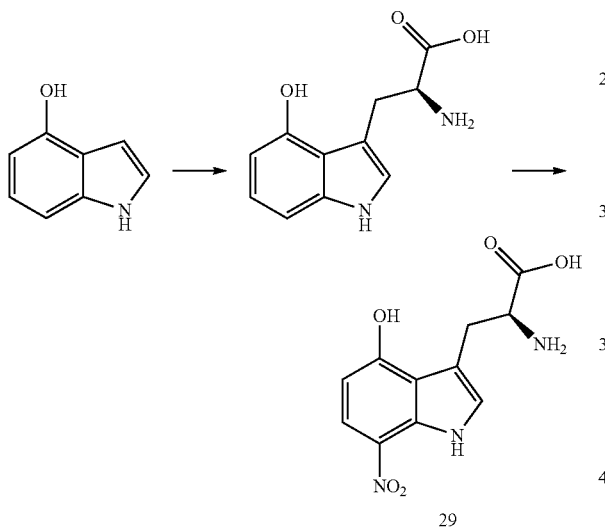

29

Example 29 can be prepared from 4-hydroxyindole as shown above.

Example 30: Preparation of (S)-2-amino-3-(4-nitro-5-phenyl-1H-indol-3-yl)propanoic acid (30)

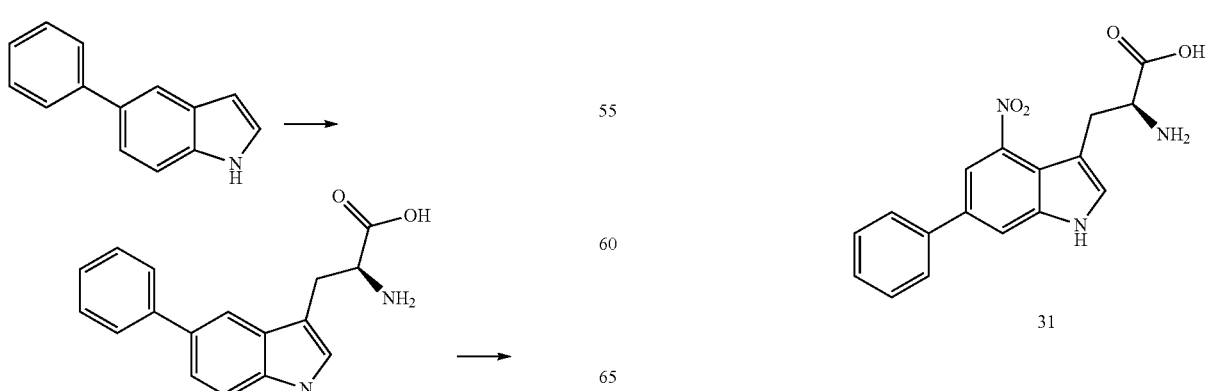

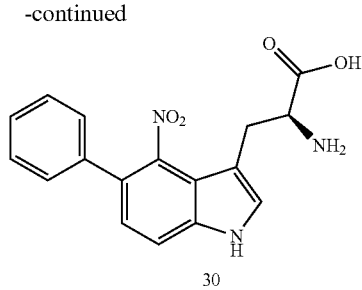

30

Example 30 can be prepared from 5-phenylindole as shown above.

Example 31: Preparation of (S)-2-amino-3-(4-nitro-6-phenyl-1H-indol-3-yl)propanoic acid (31)

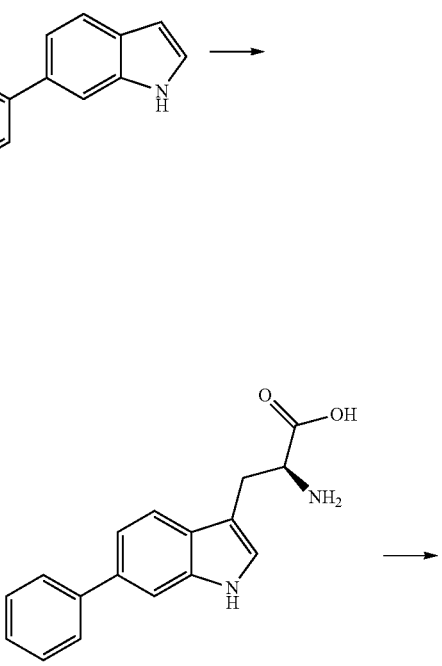

31

Example 31 can be prepared from 6-phenylindole as shown above.

Example 32: Preparation of (S)-2-amino-3-(4-nitro-7-phenyl-1H-indol-3-yl)propanoic acid (32)

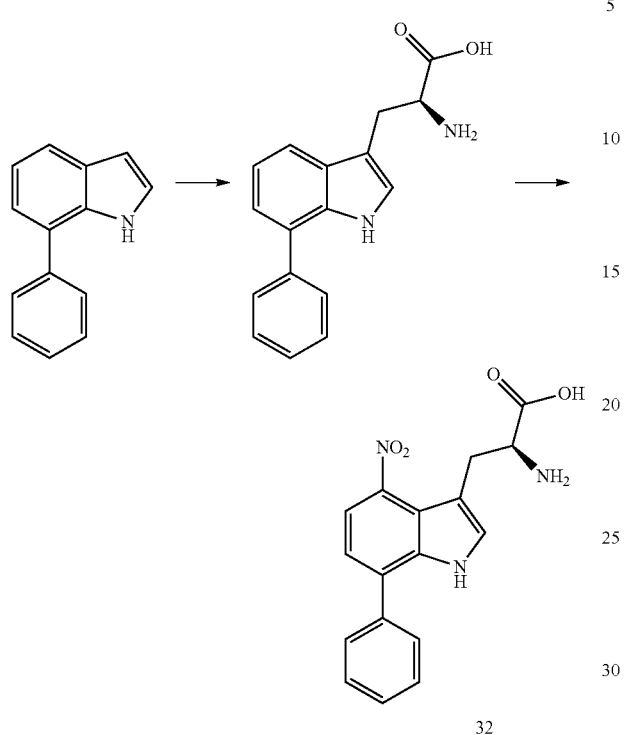

Example 32 can be prepared from 7-phenylindole as shown above.

Example 33: Preparation of (S)-2-amino-3-(7-nitro-4-phenyl-1H-indol-3-yl)propanoic acid (33)

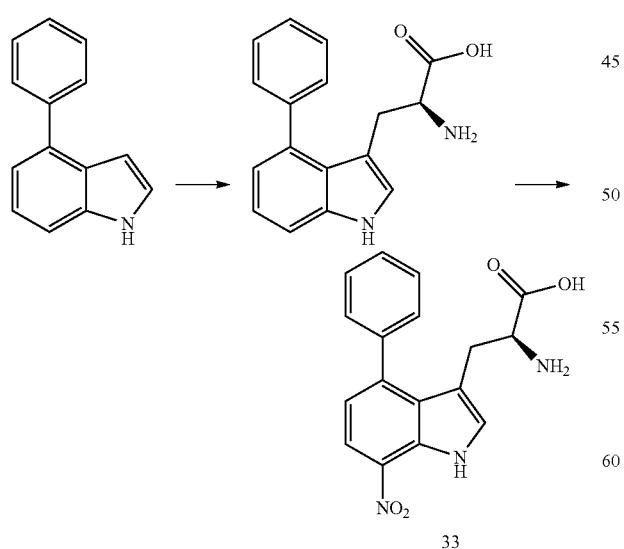

Example 33 can be prepared from 4-phenylindole as shown above.

Example 34: Preparation of (S)-2-amino-3-(5-cyclopropyl-4-nitro-1H-indol-3-yl)propanoic acid (34)

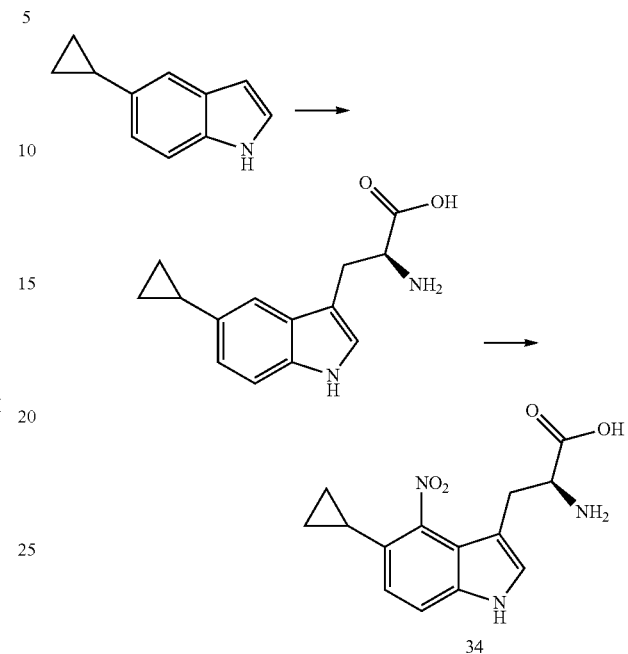

Example 34 can be prepared from 5-cyclopropylindole as shown above.

Example 35: Preparation of (S)-2-amino-3-(6-cyclopropyl-4-nitro-1H-indol-3-yl)propanoic acid (35)

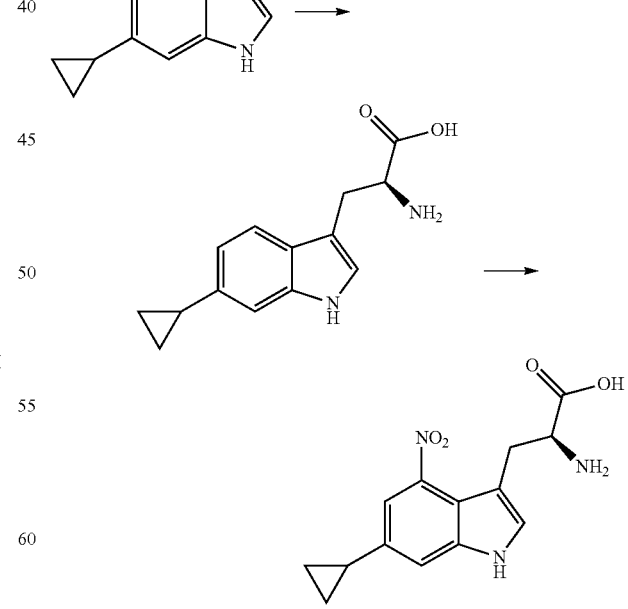

Example 35 can be prepared from 6-cyclopropylindole as shown above.

Example 36: Preparation of (S)-2-amino-3-(7-cyclopropyl-4-nitro-1H-indol-3-yl)propanoic acid (36)

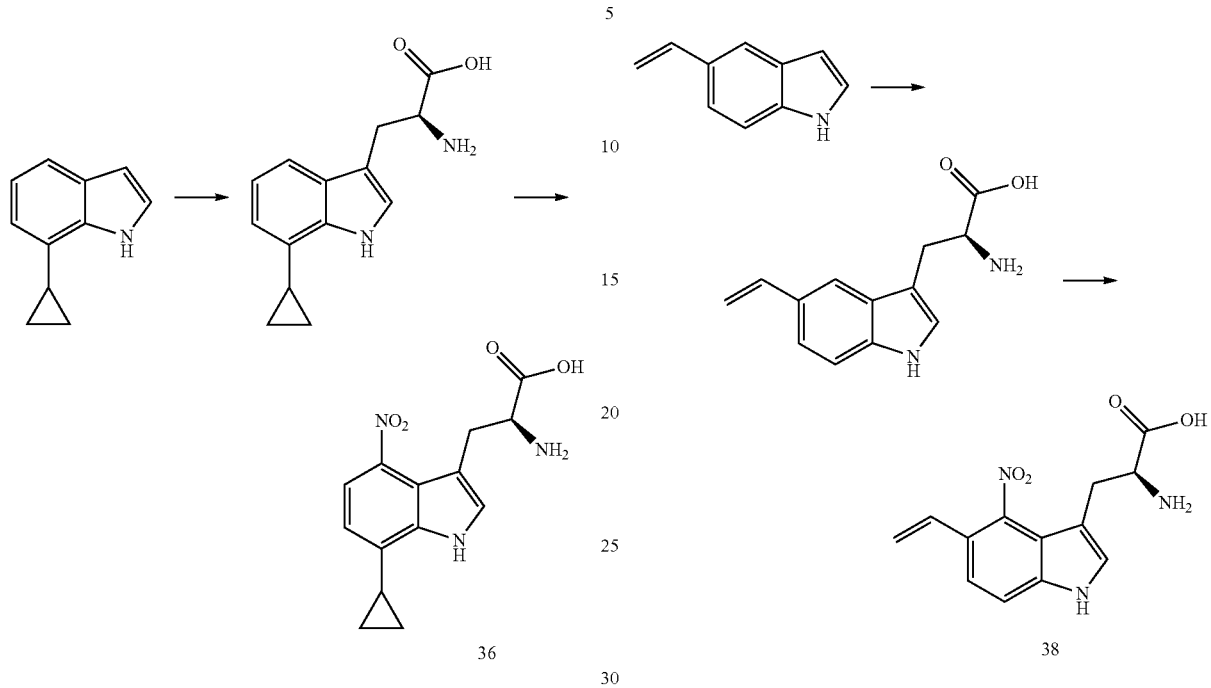

Example 36 can be prepared from 7-cyclopropylindole as shown above.

Example 37: Preparation of (S)-2-amino-3-(4-cyclopropyl-7-nitro-1H-indol-3-yl)propanoic acid (37)

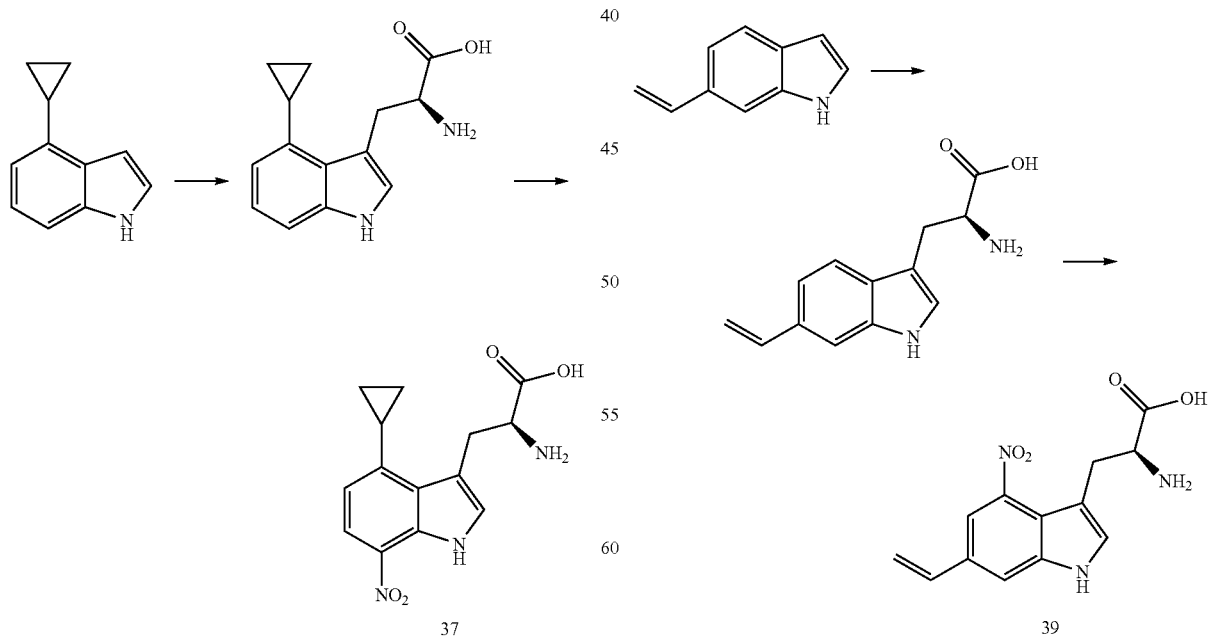

Example 37 can be prepared from 4-cyclopropylindole as shown above.

Example 38: Preparation of (S)-2-amino-3-(4-nitro-5-vinyl-1H-indol-3-yl)propanoic acid (38)

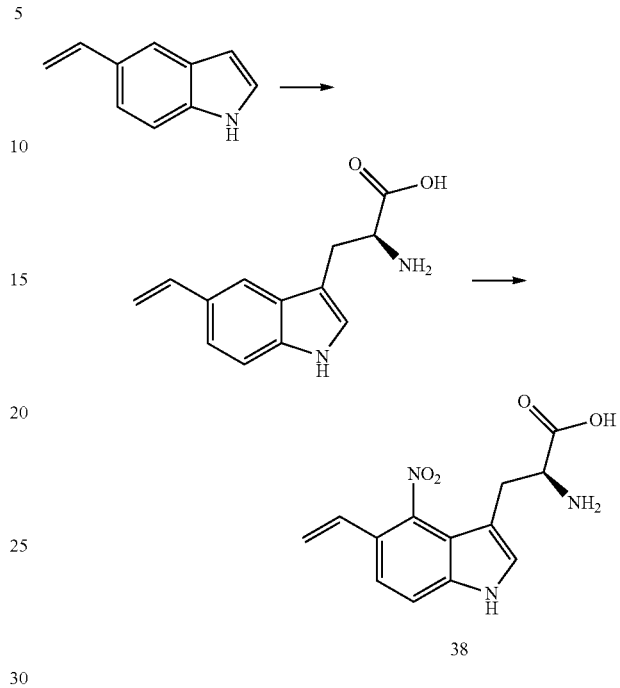

Example 38 can be prepared from 5-vinylindole as shown above.

Example 39: Preparation of (S)-2-amino-3-(4-nitro-6-vinyl-1H-indol-3-yl)propanoic acid (39)

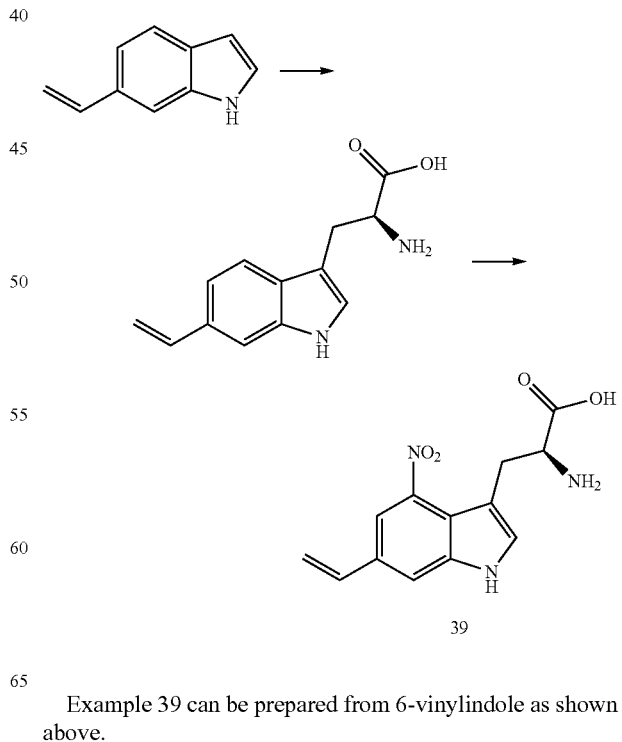

Example 39 can be prepared from 6-vinylindole as shown above.

Example 40: Preparation of (S)-2-amino-3-(4-nitro-7-vinyl-1H-indol-3-yl)propanoic acid (40)

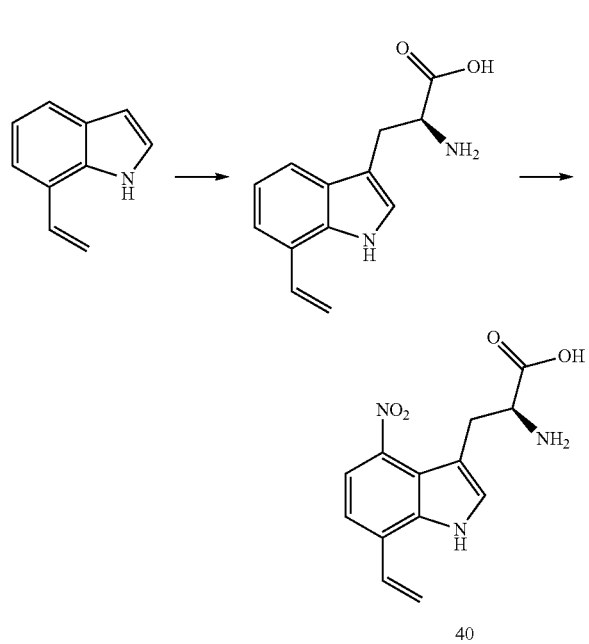

40

Example 40 can be prepared from 7-vinylindole as shown above.

Example 41: Preparation of (S)-2-amino-3-(7-nitro-4-vinyl-1H-indol-3-yl)propanoic acid (41)

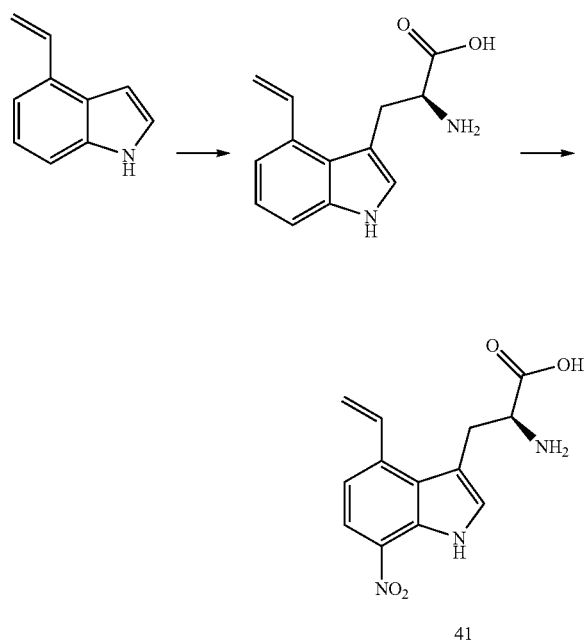

41

Example 41 can be prepared from 4-vinylindole as shown above.

Example 42: Preparation of (S)-2-amino-3-(5-ethynyl-4-nitro-1H-indol-3-yl)propanoic acid (42)

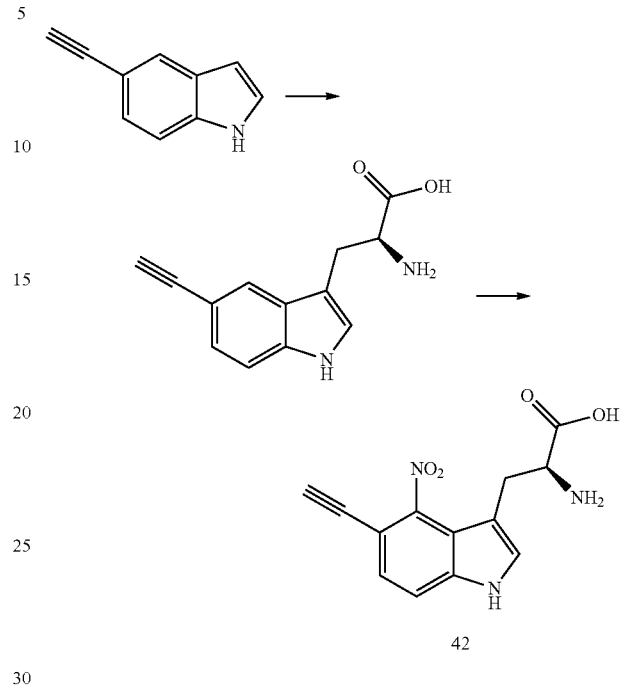

42

Example 42 can be prepared from 5-ethynylindole as shown above.

Example 43: Preparation of (S)-2-amino-3-(6-ethynyl-4-nitro-1H-indol-3-yl)propanoic acid (43)

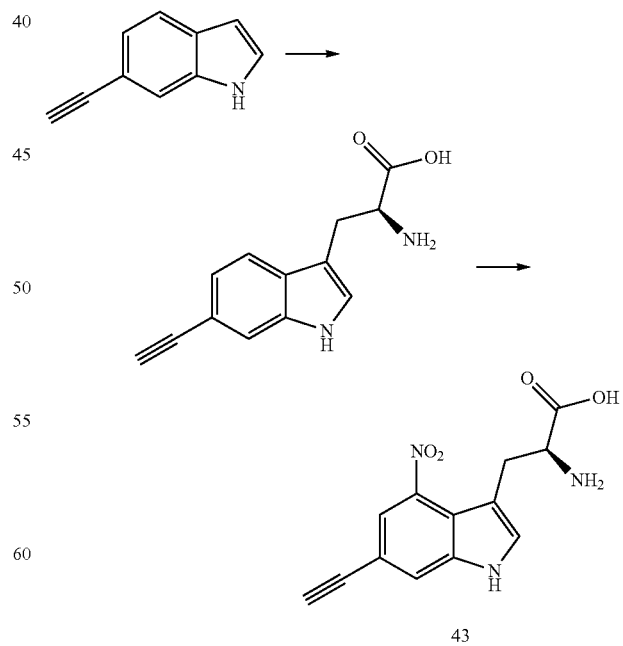

43

Example 43 can be prepared from 6-ethynylindole as shown above.

Example 44: Preparation of (S)-2-amino-3-(7-ethynyl-4-nitro-1H-indol-3-yl)propanoic acid (44)

Example 46: Preparation of (S)-2-amino-3-(5-morpholino-4-nitro-1H-indol-3-yl)propanoic acid (46)

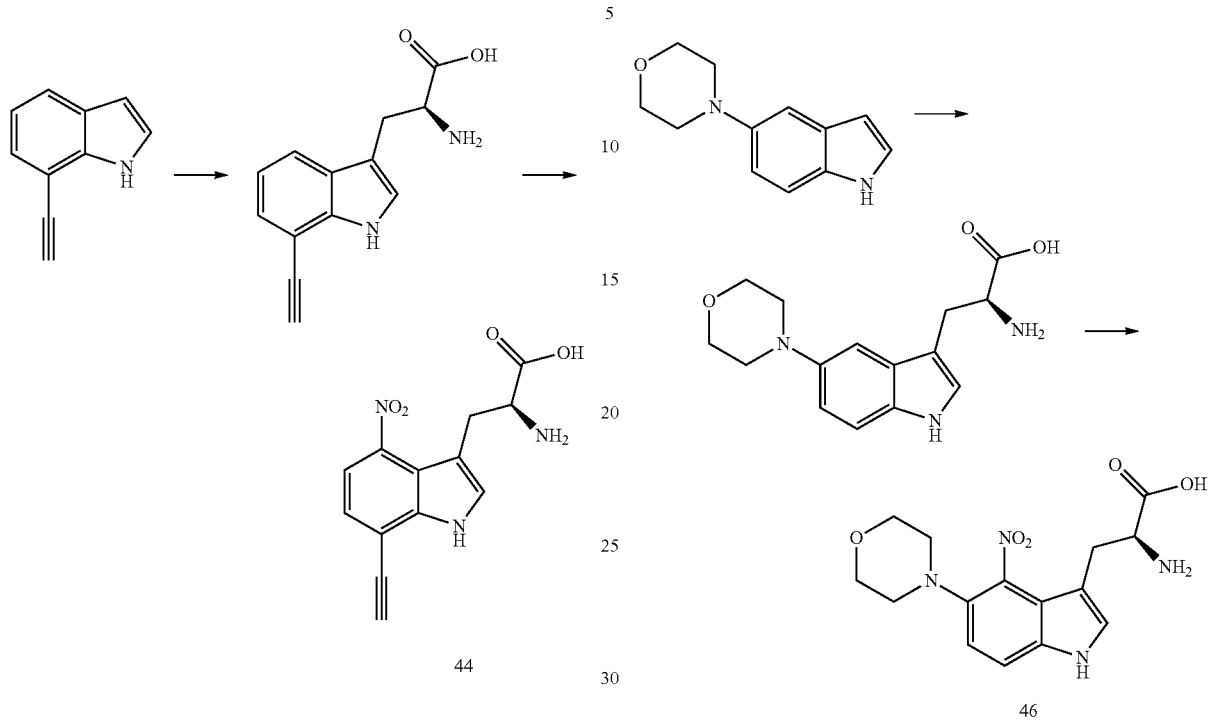

Example 44 can be prepared from 7-ethynylindole as shown above.

Example 46 can be prepared from 5-morpholinoindole as shown above.

Example 45: Preparation of (S)-2-amino-3-(4-ethynyl-7-nitro-1H-indol-3-yl)propanoic acid (45)

Example 47: Preparation of (S)-2-amino-3-(6-morpholino-4-nitro-1H-indol-3-yl)propanoic acid (47)

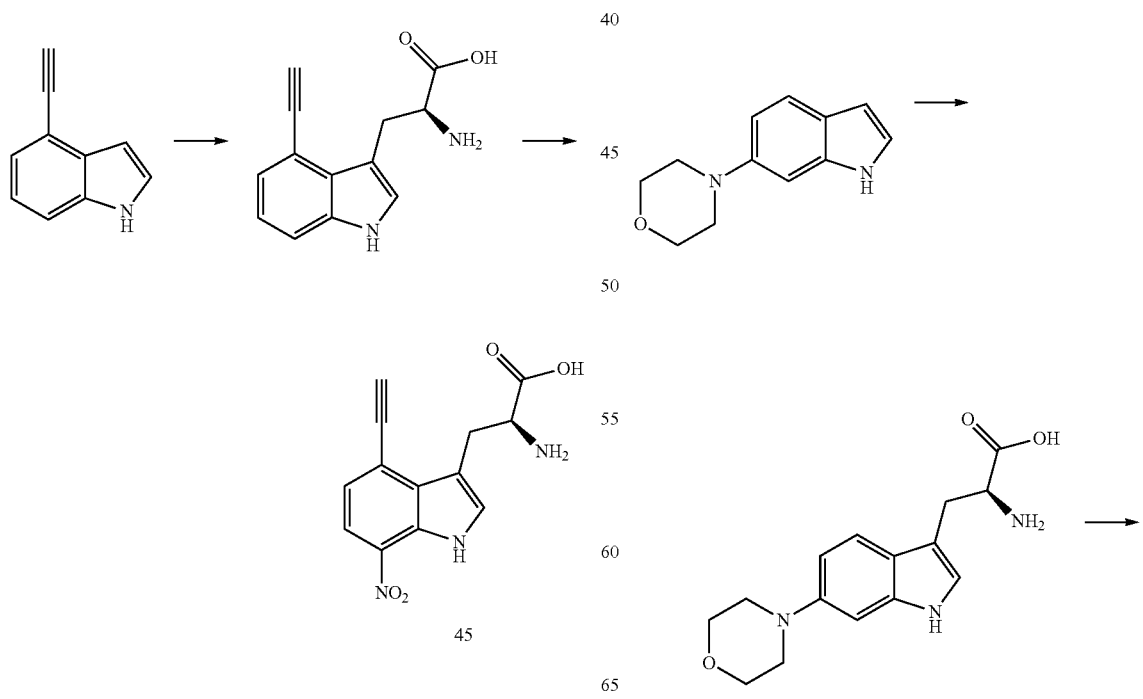

Example 45 can be prepared from 4-ethynylindole as shown above.

-continued

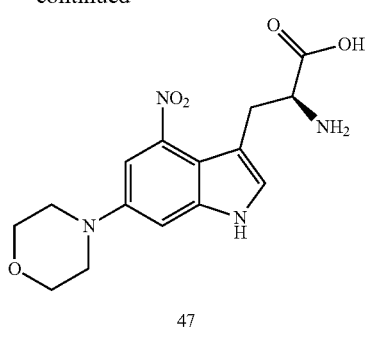

Example 47 can be prepared from 6-morpholinoindole as shown above.

Example 48: Preparation of (S)-2-amino-3-(7-morpholino-4-nitro-1H-indol-3-yl)propanoic acid (48)

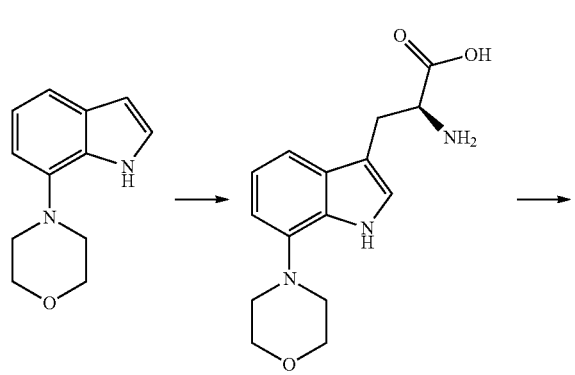

Example 48 can be prepared from 7-morpholinoindole as shown above.

Example 49: Preparation of (S)-2-amino-3-(4-morpholino-7-nitro-1H-indol-3-yl)propanoic acid (49)

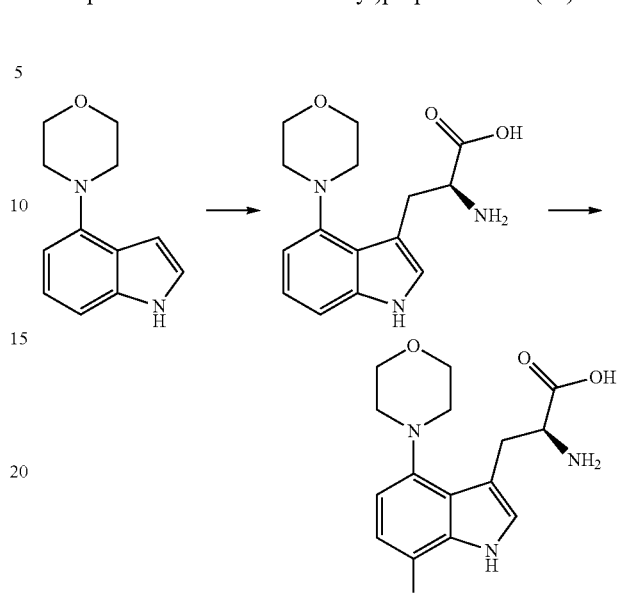

Example 49 can be prepared from 4-morpholinoindole as shown above.

Example 50: Preparation of (S)-2-amino-3-(5-(methylthio)-4-nitro-1H-indol-3-yl)propanoic acid (50)

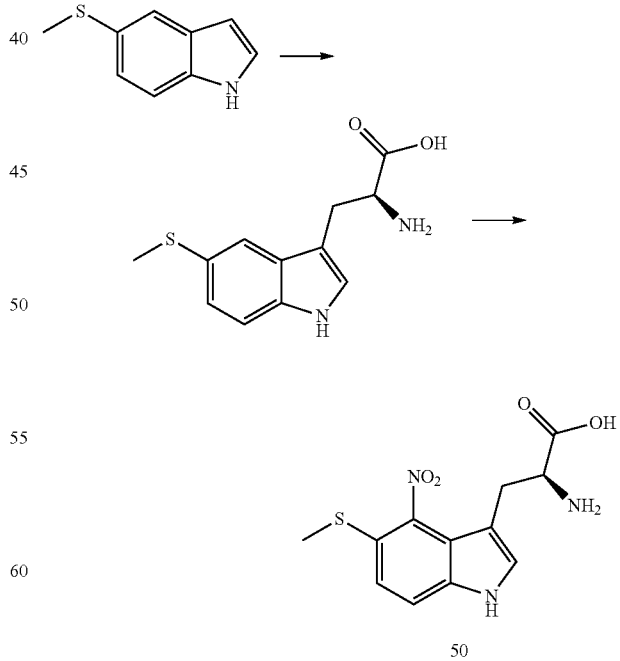

Example 50 can be prepared from 5-(methylthio)indole as shown above.

Example 51: Preparation of (S)-2-amino-3-(6-(methylthio)-4-nitro-1H-indol-3-yl)propanoic acid (51)

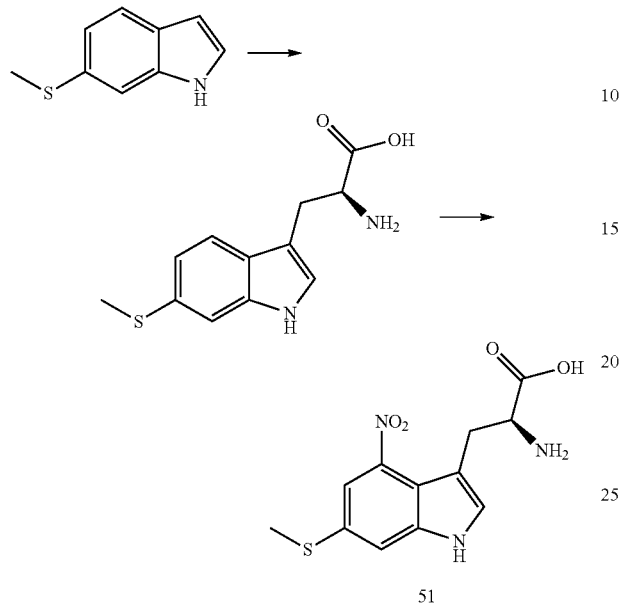

Example 51 can be prepared from 6-(methylthio)indole as shown above.

Example 52: Preparation of (S)-2-amino-3-(7-(methylthio)-4-nitro-1H-indol-3-yl)propanoic acid (52)

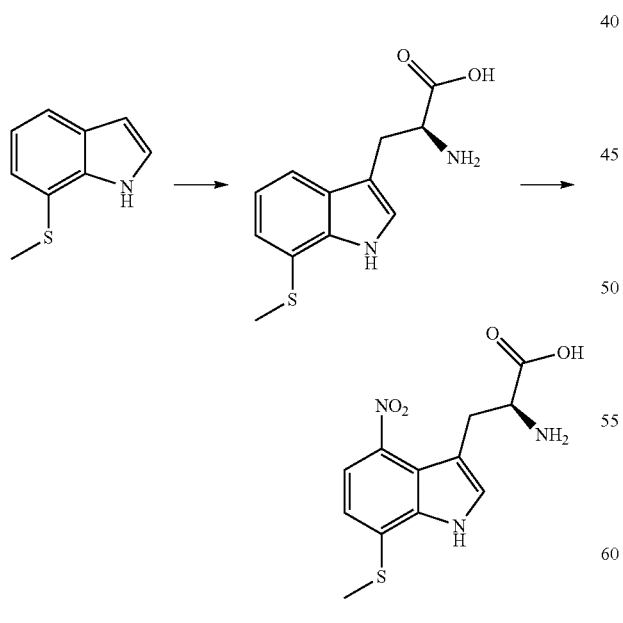

Example 52 can be prepared from 7-(methylthio)indole as shown above.

Example 53: Preparation of (S)-2-amino-3-(4-(methylthio)-7-nitro-1H-indol-3-yl)propanoic acid (53)

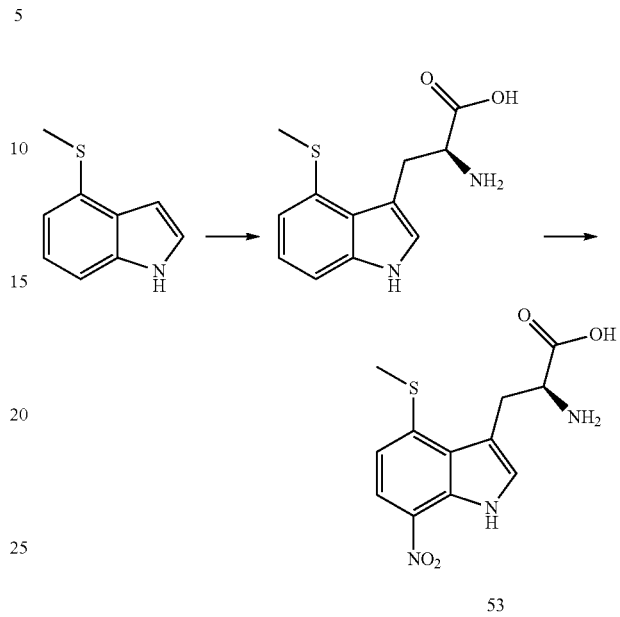

Example 53 can be prepared from 4-(methylthio)indole as shown above.

Example 54: Preparation of (S)-2-amino-3-(4-nitro-5-(pyridin-4-yl)-1H-indol-3-yl)propanoic acid (54)

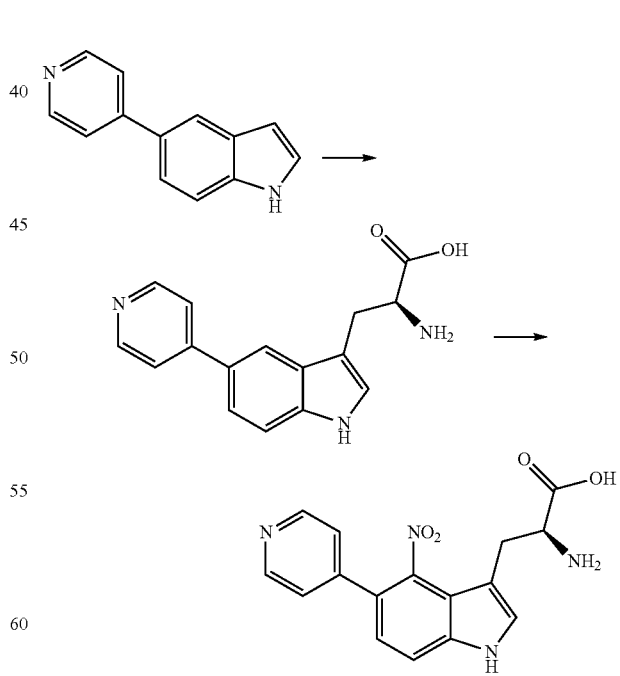

Example 54 can be prepared from 5-(pyridin-4-yl)indole as shown above.

Example 55: Preparation of (S)-2-amino-3-(4-nitro-6-(pyridin-4-yl)-1H-indol-3-yl)propanoic acid (55)

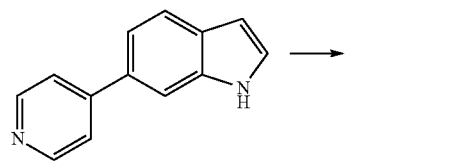

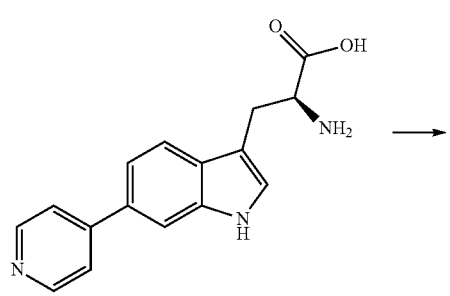

55

Example 55 can be prepared from 6-(pyridin-4-yl)indole as shown above.

Example 56: Preparation of (S)-2-amino-3-(4-nitro-7-(pyridin-4-yl)-1H-indol-3-yl)propanoic acid (56)

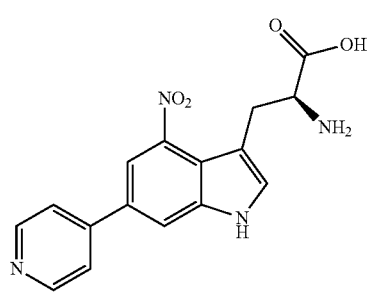

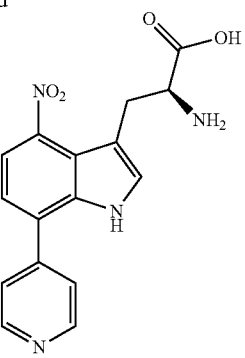

56

Example 56 can be prepared from 7-(pyridin-4-yl)indole as shown above.

Example 57: Preparation of (S)-2-amino-3-(7-nitro-4-(pyridin-4-yl)-1H-indol-3-yl)propanoic acid (57)

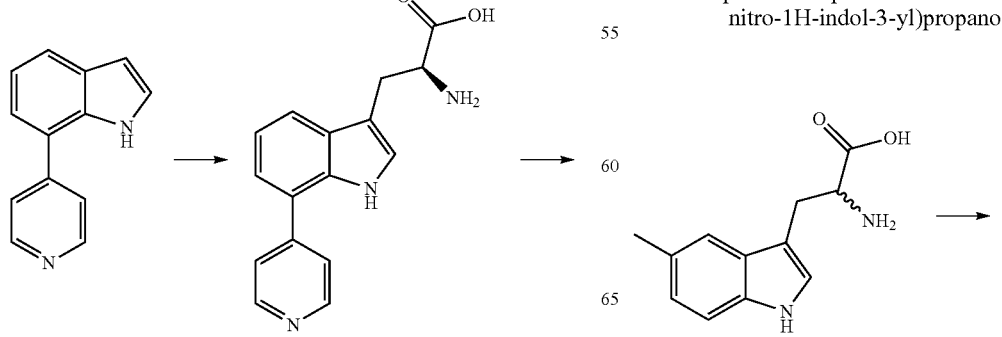

57

Example 57 can be prepared from 4-(pyridin-4-yl)indole as shown above.

Example 58: Preparation of 2-amino-3-(5-methyl-4-nitro-1H-indol-3-yl)propanoic acid (58)

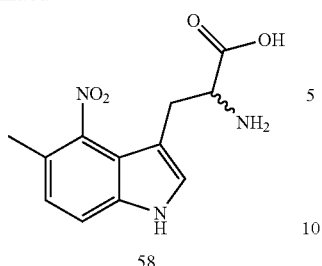

58

Example 58 can be prepared from 2-amino-3-(5-methyl-1H-indol-3-yl)propanoic acid as shown above.

Example 59: Preparation of 2-amino-3-(6-methyl-4-nitro-1H-indol-3-yl)propanoic acid (59)

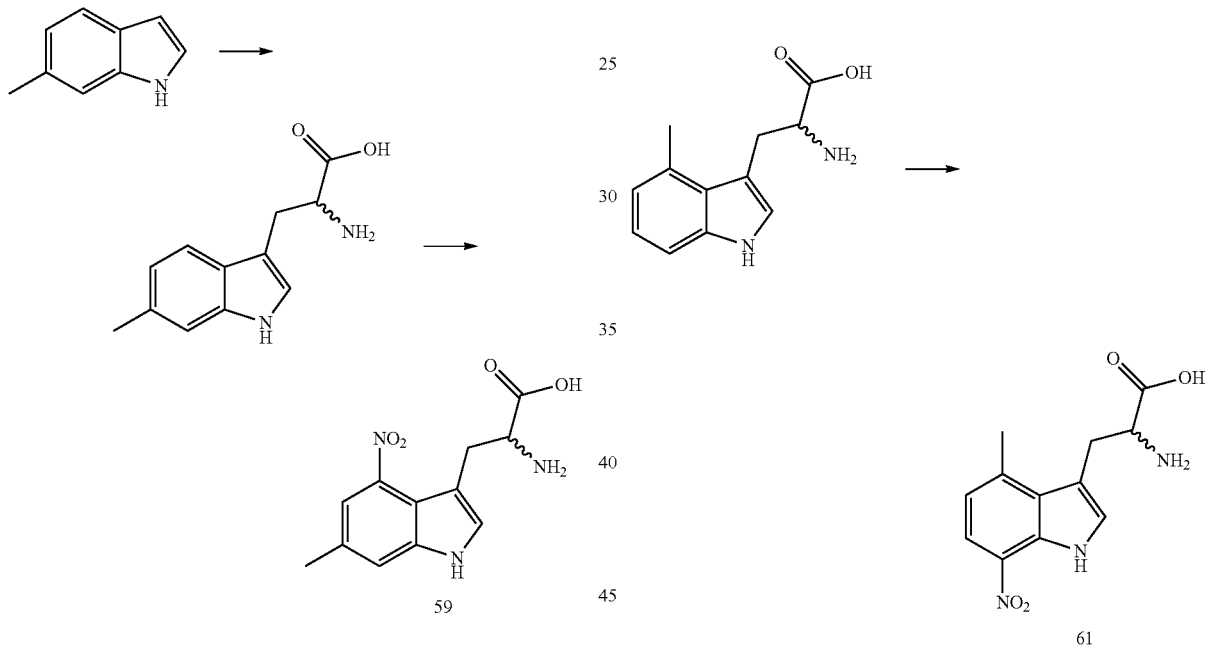

59

Example 59 can be prepared from 6-methylindole as shown above.

Example 60: Preparation of 2-amino-3-(7-methyl-4-nitro-1H-indol-3-yl)propanoic acid (60)

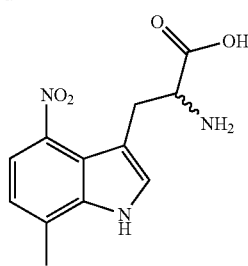

60

Example 60 can be prepared from 2-amino-3-(7-methyl-1H-indol-3-yl)propanoic acid as shown above.

Example 61: Preparation of 2-amino-3-(4-methyl-7-nitro-1H-indol-3-yl)propanoic acid (61)

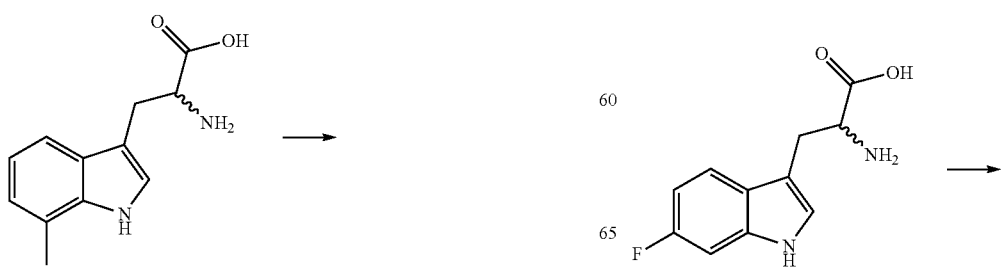

61

Example 61 was prepared from 2-amino-3-(4-methyl-1H-indol-3-yl)propanoic acid as shown above.

Example 62: Preparation of 2-amino-3-(6-fluoro-4-nitro-1H-indol-3-yl)propanoic acid (62)

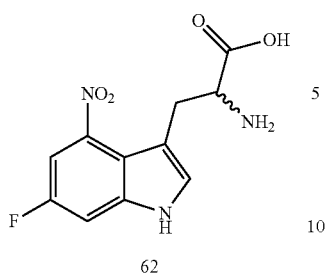

Example 62 can be prepared from 2-amino-3-(6-fluoro-1H-indol-3-yl)propanoic acid as shown above.

Example 63: Preparation of 2-amino-3-(7-fluoro-4-nitro-1H-indol-3-yl)propanoic acid (63)

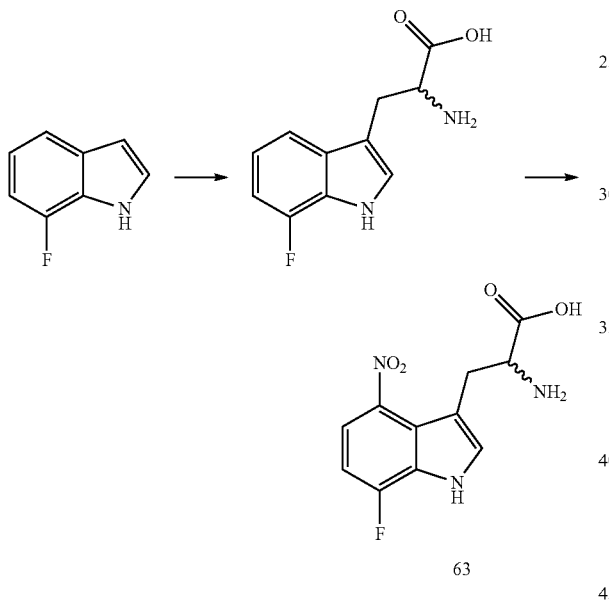

Example 63 can be prepared from 7-fluoroindole as shown above.

Example 64: Preparation of 2-amino-3-(4-fluoro-7-nitro-1H-indol-3-yl)propanoic acid (64)

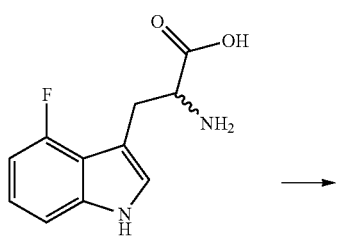

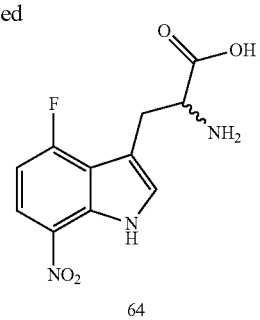

Example 64 can be prepared from 2-amino-3-(4-fluoro-1H-indol-3-yl)propanoic acid as shown above.

Example 65: Preparation of 2-amino-3-(5-chloro-4-nitro-1H-indol-3-yl)propanoic acid (65)

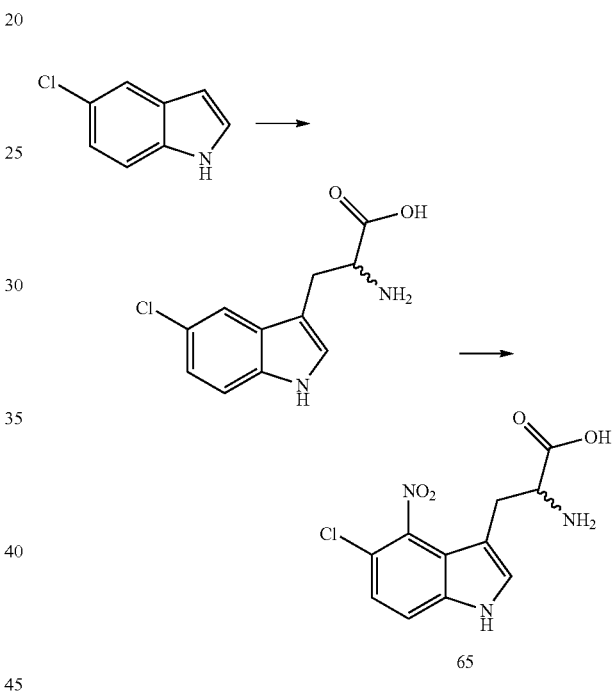

Example 65 can be prepared from 5-chloroindole as shown above.

Example 66: Preparation of 2-amino-3-(6-chloro-4-nitro-1H-indol-3-yl)propanoic acid (66)

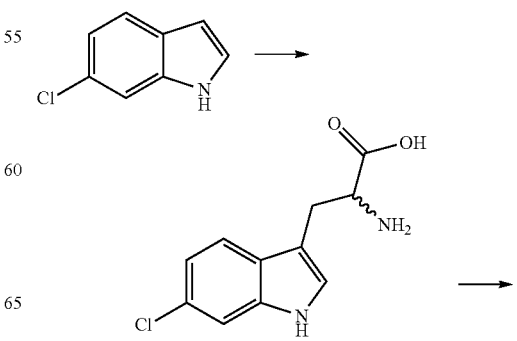

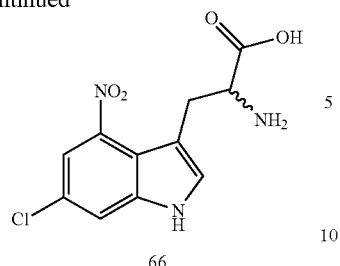

66

Example 66 can be prepared from 6-chloroindole as shown above.

Example 67: Preparation of 2-amino-3-(7-chloro-4-nitro-1H-indol-3-yl)propanoic acid (67)

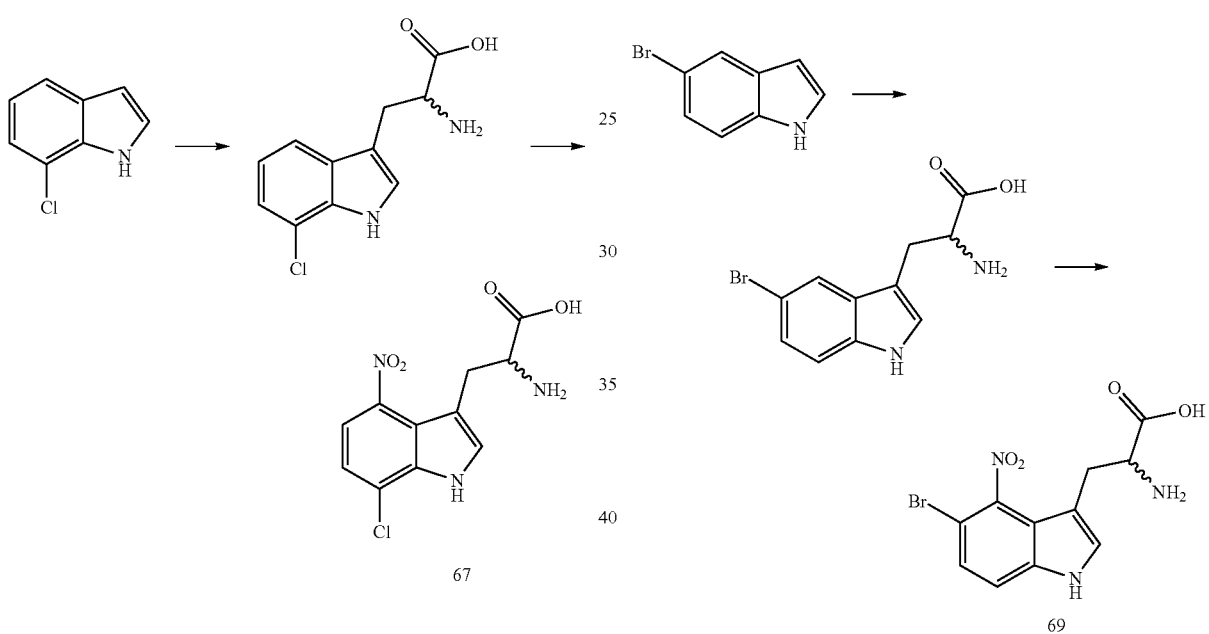

67

Example 67 can be prepared from 7-chloroindole as shown above.

Example 68: Preparation of 2-amino-3-(4-chloro-7-nitro-1H-indol-3-yl)propanoic acid (68)

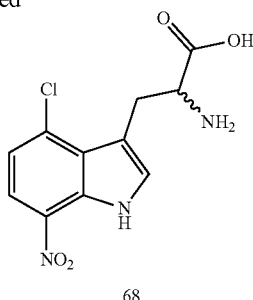

68

Example 68 can be prepared from 4-chloroindole as shown above.

Example 69: Preparation of 2-amino-3-(5-bromo-4-nitro-1H-indol-3-yl)propanoic acid (69)

69

Example 69 can be prepared from 5-bromoindole as shown above.

Example 70: Preparation of 2-amino-3-(6-bromo-4-nitro-1H-indol-3-yl)propanoic acid (70)

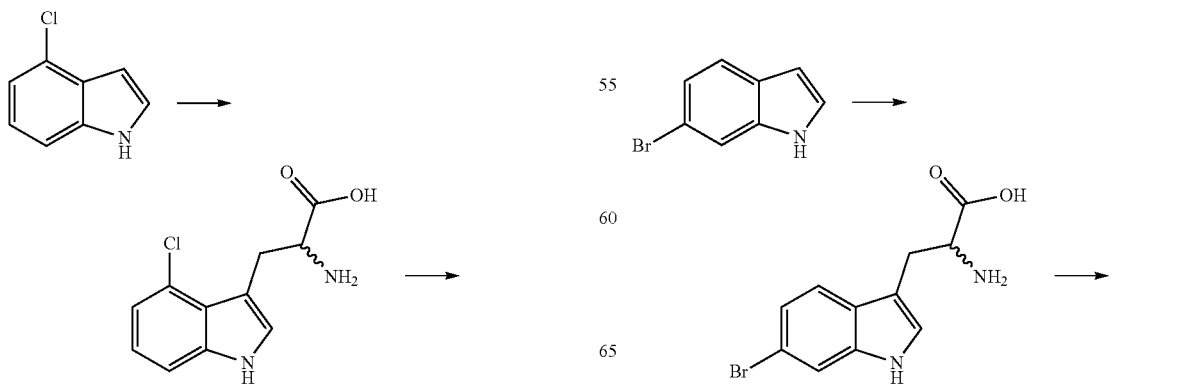

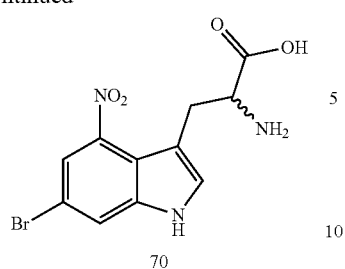
70

Example 70 can be prepared from 6-bromoindole as shown above.

Example 71: Preparation of 2-amino-3-(7-bromo-4-nitro-1H-indol-3-yl)propanoic acid (71)

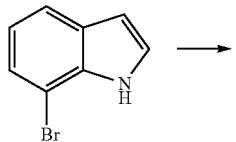

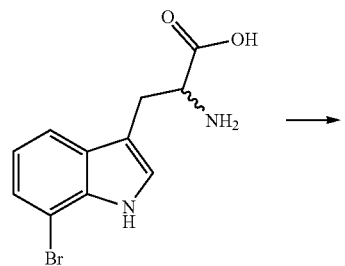
71

Example 71 can be prepared from 7-bromoindole as shown above.

Example 72: Preparation of 2-amino-3-(4-bromo-7-nitro-1H-indol-3-yl)propanoic acid (72)

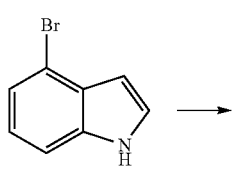

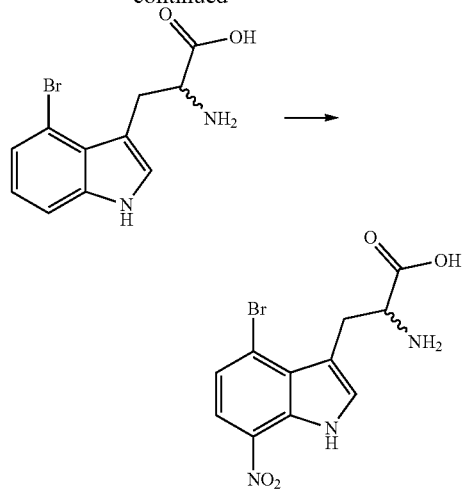
72

Example 72 can be prepared from 4-bromoindole as shown above.

Example 73: Preparation of 2-amino-3-(5-methoxy-4-nitro-1H-indol-3-yl)propanoic acid (73)

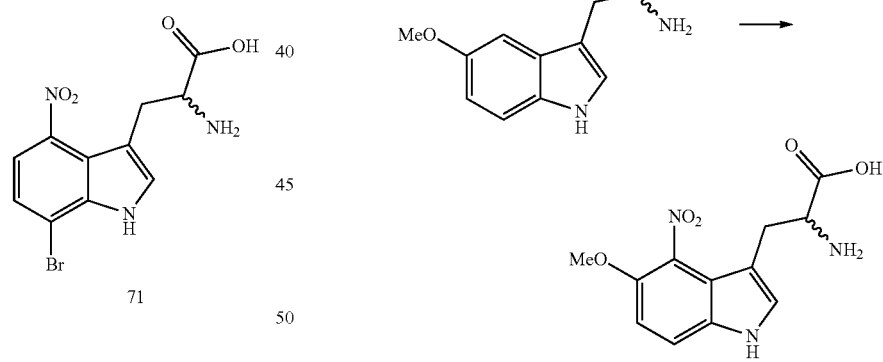
73

Example 73 can be prepared from 5-methoxyindole as shown above.

Example 74: Preparation of 2-amino-3-(6-methoxy-4-nitro-1H-indol-3-yl)propanoic acid (74)

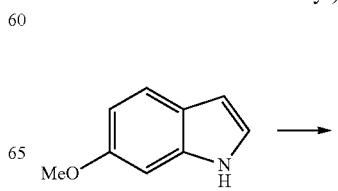

-continued

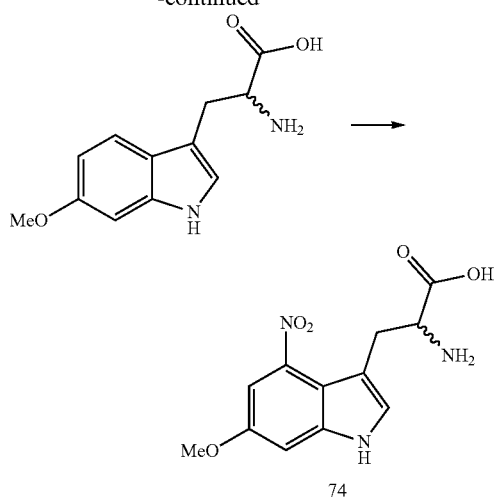

Example 74 can be prepared from 6-methoxyindole as shown above.

Example 75: Preparation of 2-amino-3-(7-methoxy-4-nitro-1H-indol-3-yl)propanoic acid (75)

Example 76: Preparation of 2-amino-3-(4-methoxy-7-nitro-1H-indol-3-yl)propanoic acid (76)

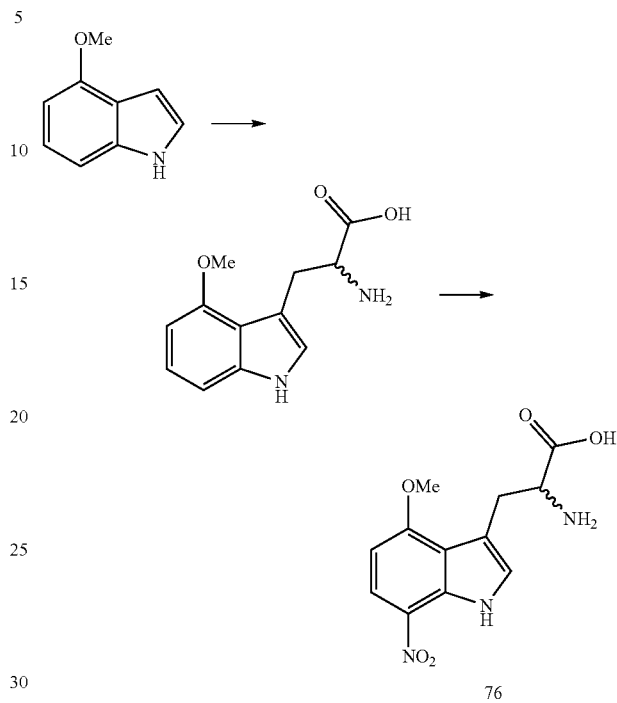

Example 76 can be prepared from 4-methoxyindole as shown above.

Example 77: Preparation of 2-amino-3-(5-amino-4-nitro-1H-indol-3-yl)propanoic acid (77)

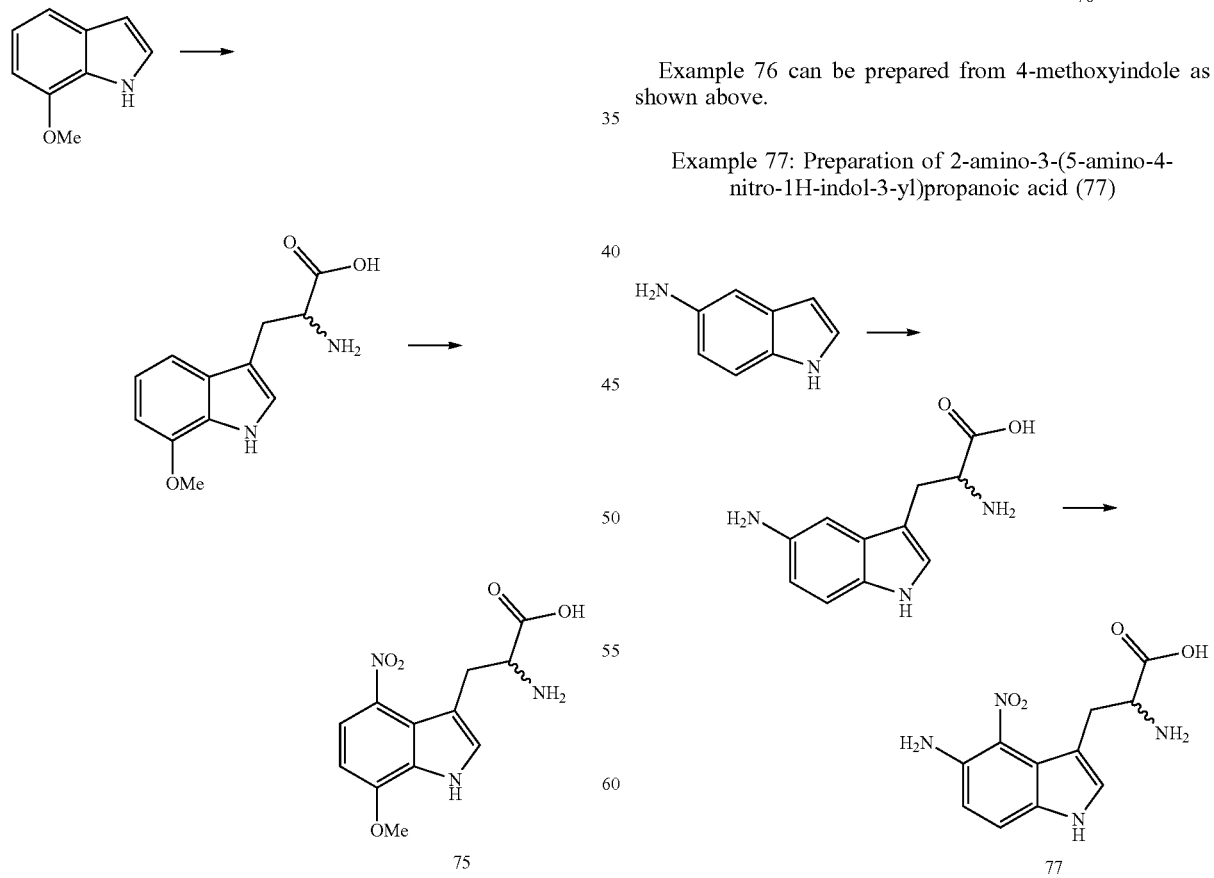

Example 75 can be prepared from 7-methoxyindole as shown above.

Example 77 can be prepared from 5-aminoindole as shown above.

Example 78: Preparation of 2-amino-3-(6-amino-4-nitro-1H-indol-3-yl)propanoic acid (78)

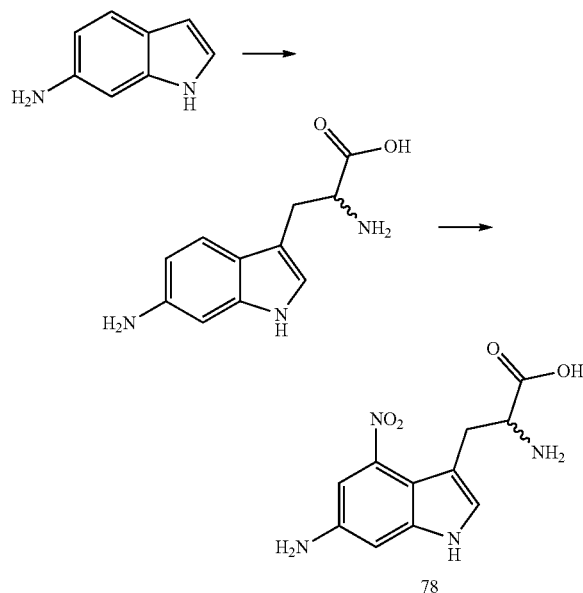

Example 78 can be prepared from 6-aminoindole as shown above.

Example 79: Preparation of 2-amino-3-(7-amino-4-nitro-1H-indol-3-yl)propanoic acid (79)

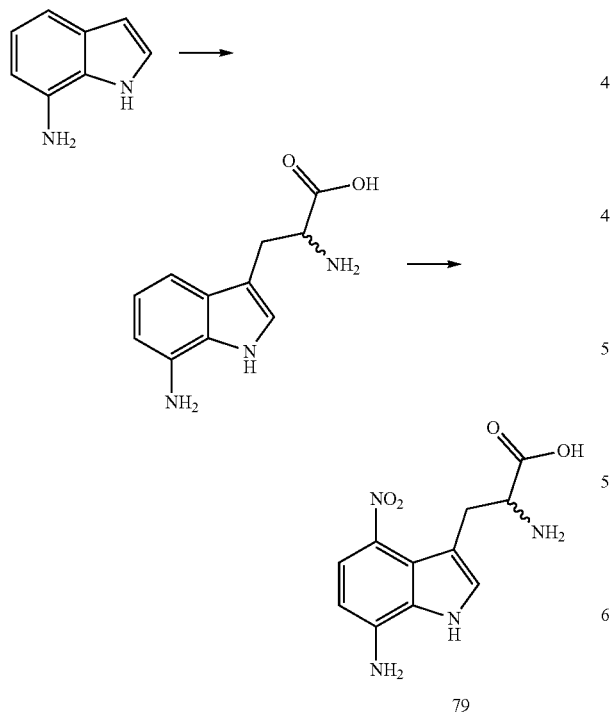

Example 79 can be prepared from 7-aminoindole as shown above.

Example 80: Preparation of 2-amino-3-(4-amino-7-nitro-1H-indol-3-yl)propanoic acid (80)

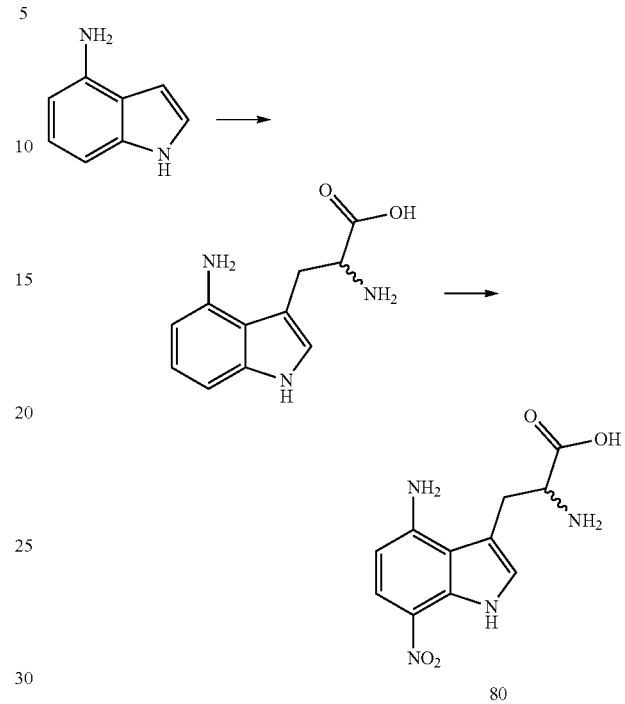

Example 80 can be prepared from 4-aminoindole as shown above.

Example 81: Preparation of 2-amino-3-(5-hydroxy-4-nitro-1H-indol-3-yl)propanoic acid (81)

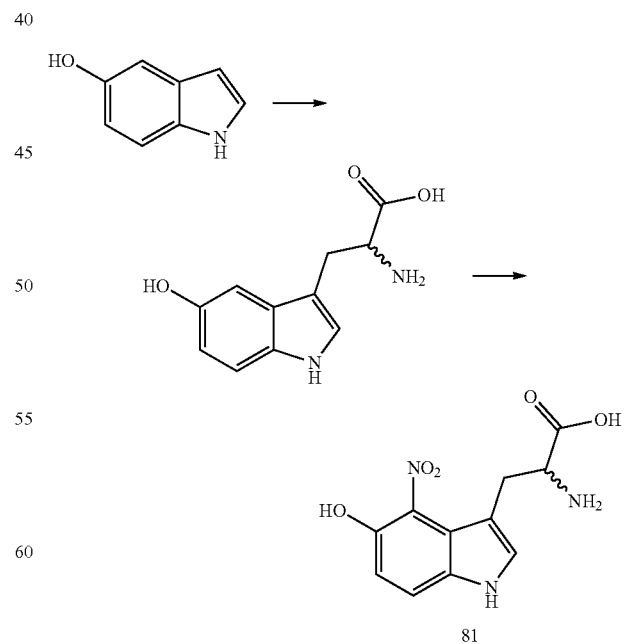

Example 81 can be prepared from 5-hydroxyindole as shown above.

Example 82: Preparation of 2-amino-3-(6-hydroxy-4-nitro-1H-indol-3-yl)propanoic acid (82)

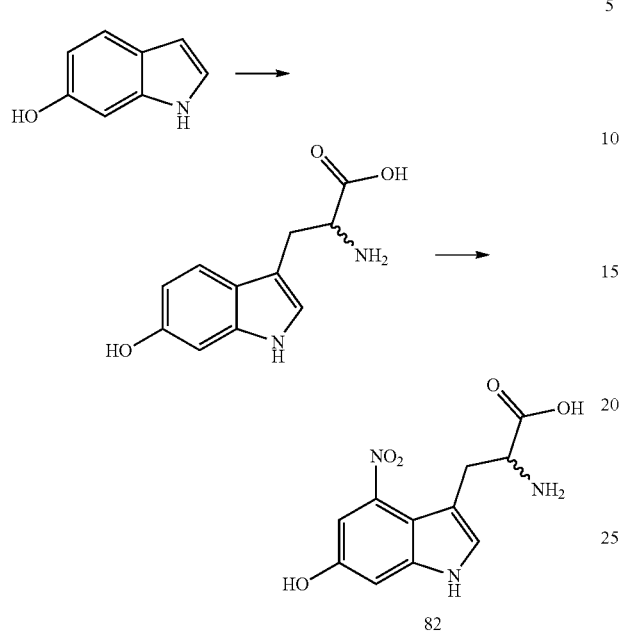

Example 82 can be prepared from 6-hydroxyindole as shown above.

Example 83: Preparation of 2-amino-3-(7-hydroxy-4-nitro-1H-indol-3-yl)propanoic acid (83)

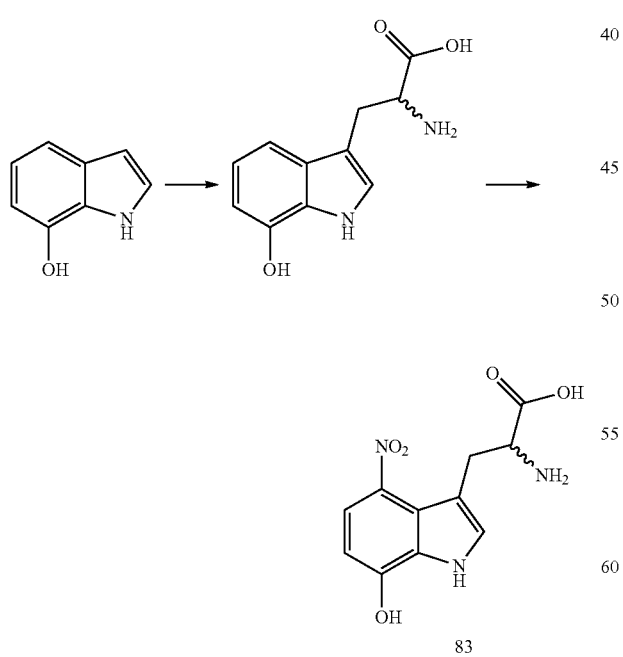

Example 83 can be prepared from 7-hydroxyindole as shown above.

Example 84: Preparation of 2-amino-3-(4-hydroxy-7-nitro-1H-indol-3-yl)propanoic acid (84)

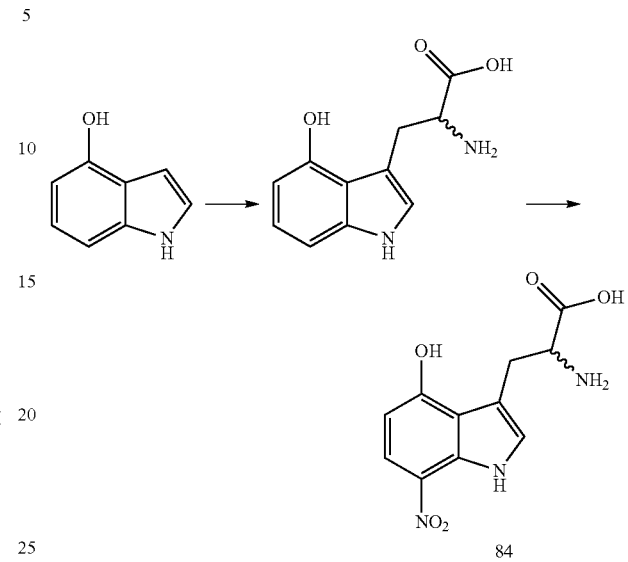

Example 84 can be prepared from 4-hydroxyindole as shown above.

Example 85: Preparation of 2-amino-3-(4-nitro-5-phenyl-1H-indol-3-yl)propanoic acid (85)

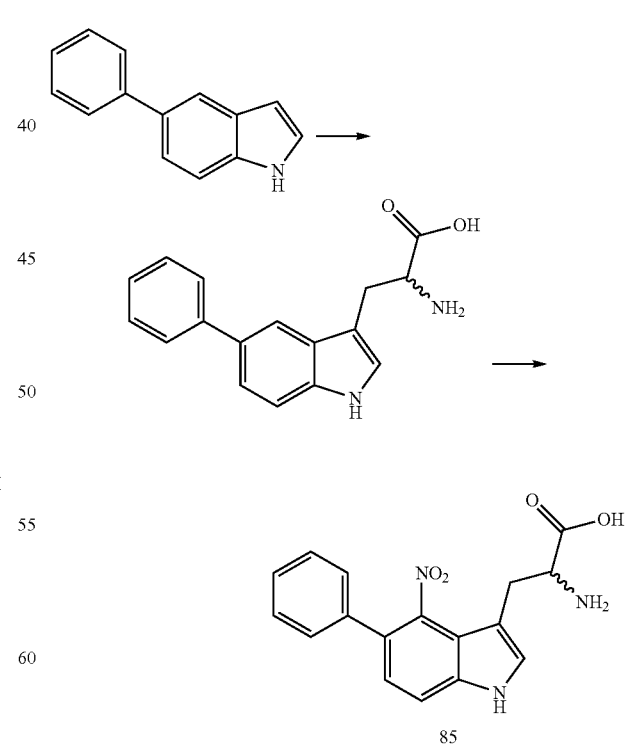

Example 85 can be prepared from 5-phenylindole as shown above.

Example 86: Preparation of 2-amino-3-(4-nitro-6-phenyl-1H-indol-3-yl)propanoic acid (86)

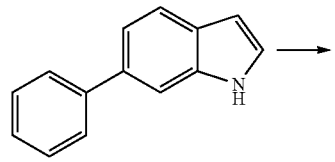

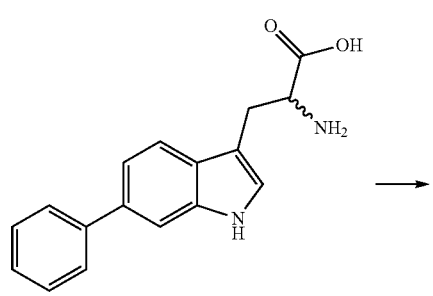

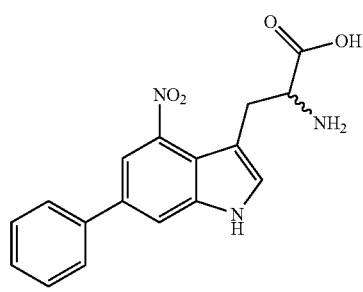

86

Example 86 can be prepared from 6-phenylindole as shown above.

Example 87: Preparation of 2-amino-3-(4-nitro-7-phenyl-1H-indol-3-yl)propanoic acid (87)

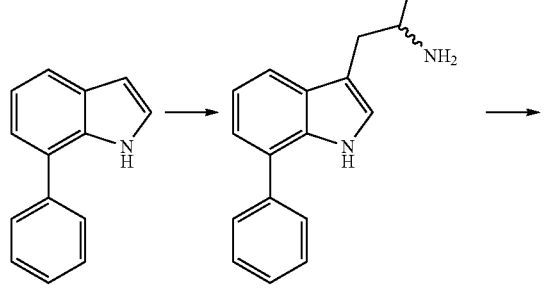

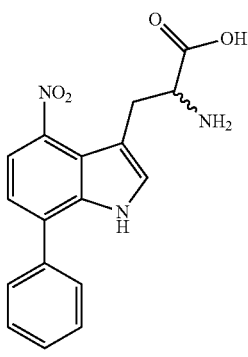

87

Example 87 can be prepared from 7-phenylindole as shown above.

Example 88: Preparation of 2-amino-3-(7-nitro-4-phenyl-1H-indol-3-yl)propanoic acid (88)

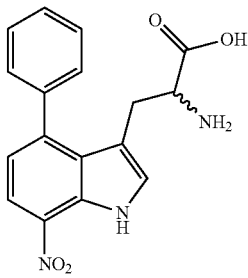

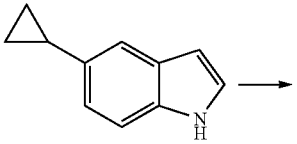

88

Example 88 can be prepared from 4-phenylindole as shown above.

Example 89: Preparation of 2-amino-3-(5-cyclopropyl-4-nitro-1H-indol-3-yl)propanoic acid (89)

-continued

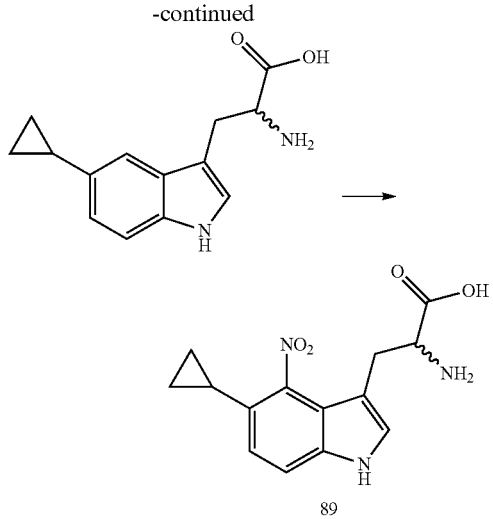

89

Example 89 can be prepared from 5-cyclopropylindole as shown above.

Example 90: Preparation of 2-amino-3-(6-cyclopropyl-4-nitro-1H-indol-3-yl)propanoic acid (90)

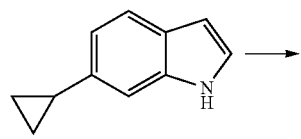

90

Example 90 can be prepared from 6-cyclopropylindole as shown above.

Example 91: Preparation of 2-amino-3-(7-cyclopropyl-4-nitro-1H-indol-3-yl)propanoic acid (91)

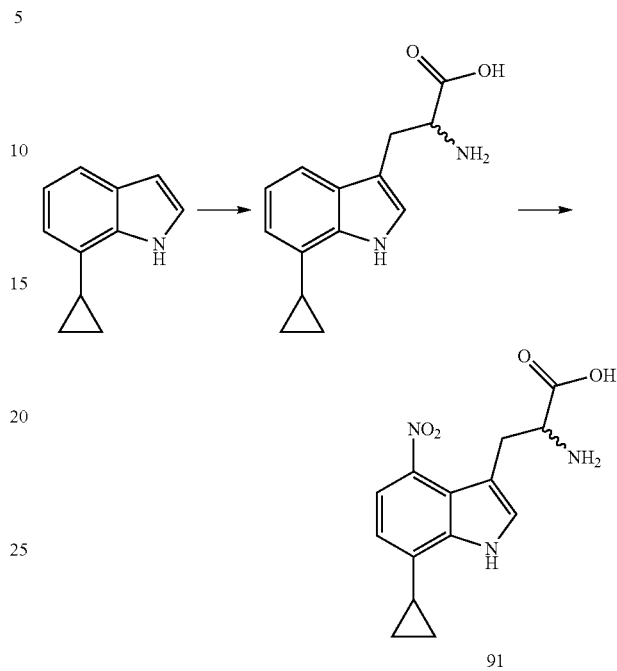

91

Example 91 can be prepared from 7-cyclopropylindole as shown above.

Example 92: Preparation of 2-amino-3-(4-cyclopropyl-7-nitro-1H-indol-3-yl)propanoic acid (92)

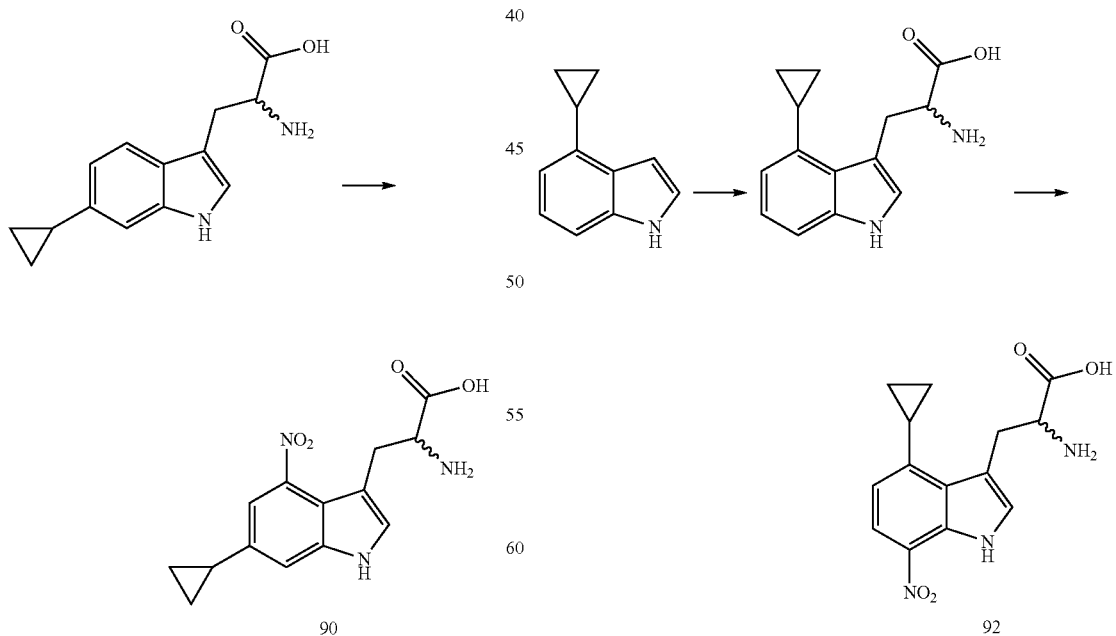

92

Example 92 can be prepared from 4-cyclopropylindole as shown above.

Example 93: Preparation of 2-amino-3-(4-nitro-5-vinyl-1H-indol-3-yl)propanoic acid (93)

Example 95: Preparation of 2-amino-3-(4-nitro-7-vinyl-1H-indol-3-yl)propanoic acid (95)

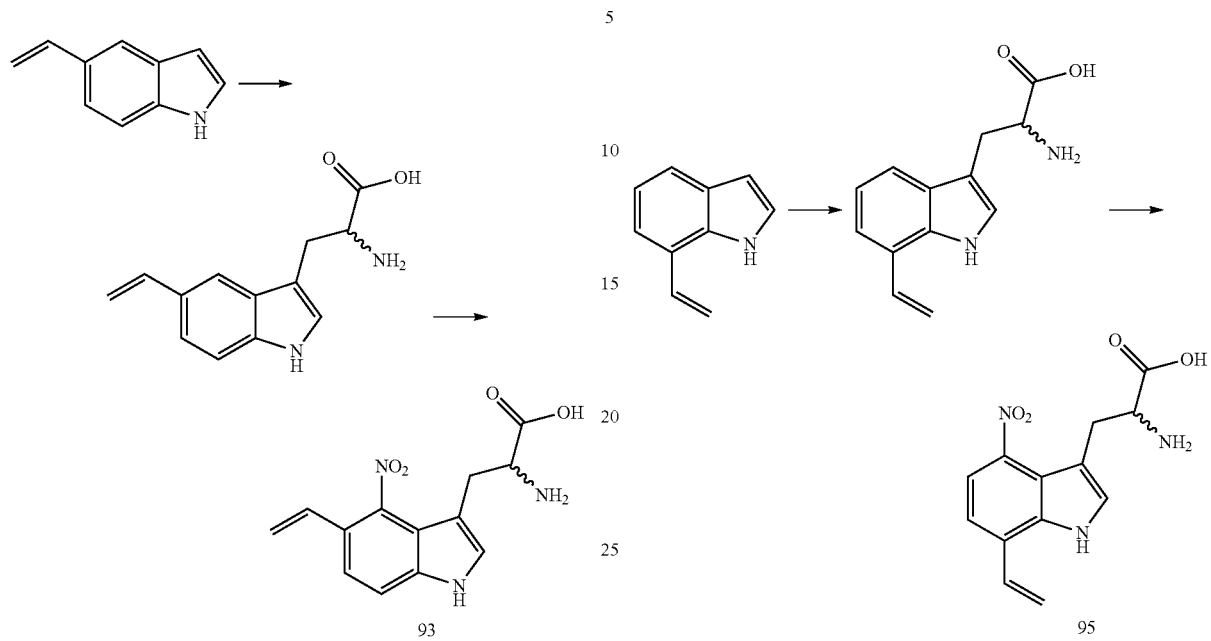

Example 93 can be prepared from 5-vinylindole as shown above.

Example 95 can be prepared from 7-vinylindole as shown above.

Example 94: Preparation of 2-amino-3-(4-nitro-6-vinyl-1H-indol-3-yl)propanoic acid (94)

Example 96: Preparation of 2-amino-3-(7-nitro-4-vinyl-1H-indol-3-yl)propanoic acid (96)

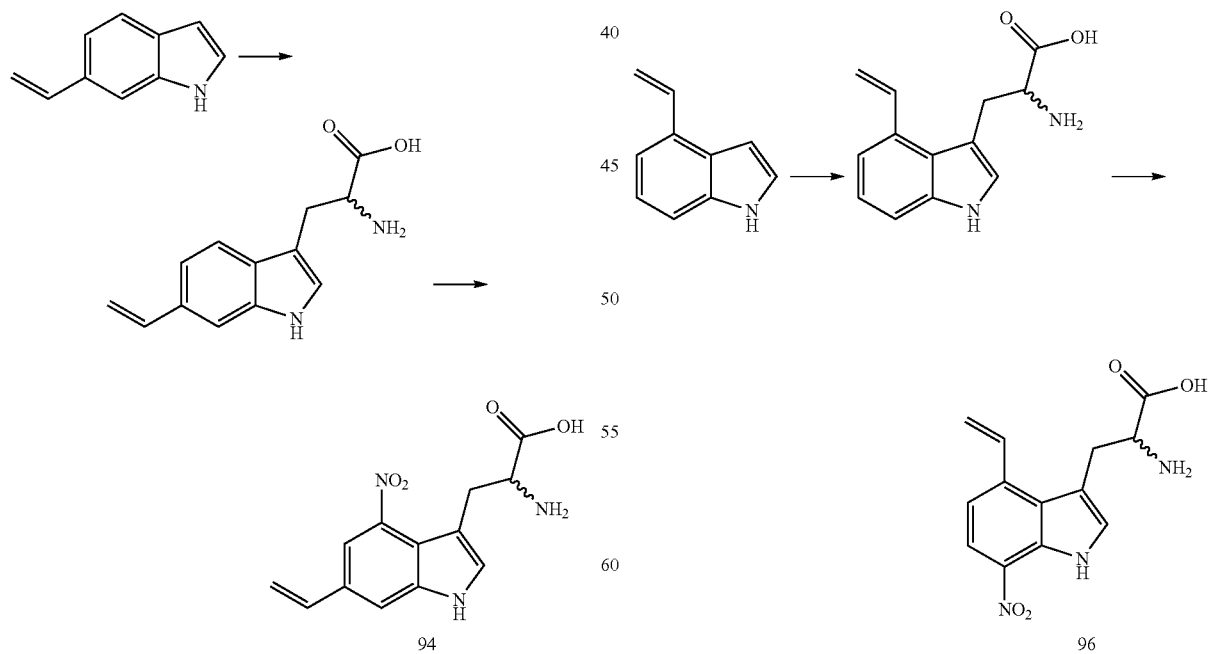

Example 94 can be prepared from 6-vinylindole as shown above.

Example 96 can be prepared from 4-vinylindole as shown above.

Example 97: Preparation of 2-amino-3-(5-ethynyl-4-nitro-1H-indol-3-yl)propanoic acid (97)

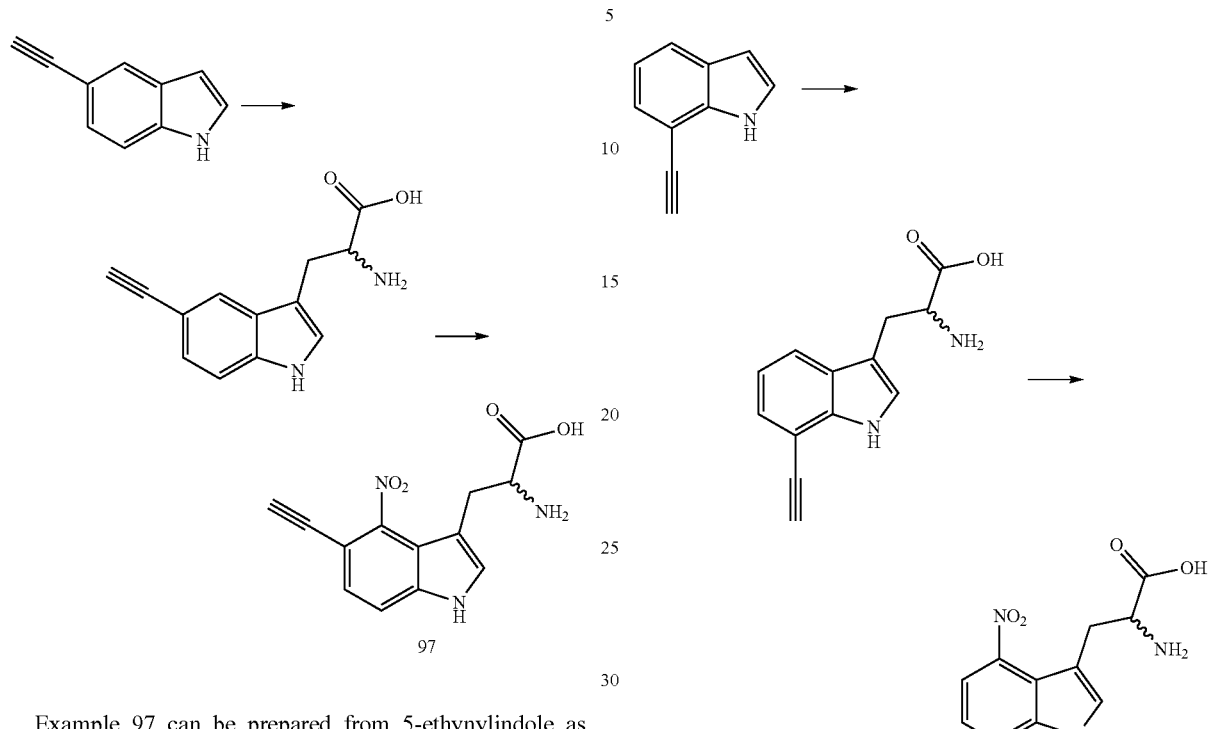

Example 97 can be prepared from 5-ethynylindole as shown above.

Example 98: Preparation of 2-amino-3-(6-ethynyl-4-nitro-1H-indol-3-yl)propanoic acid (98)

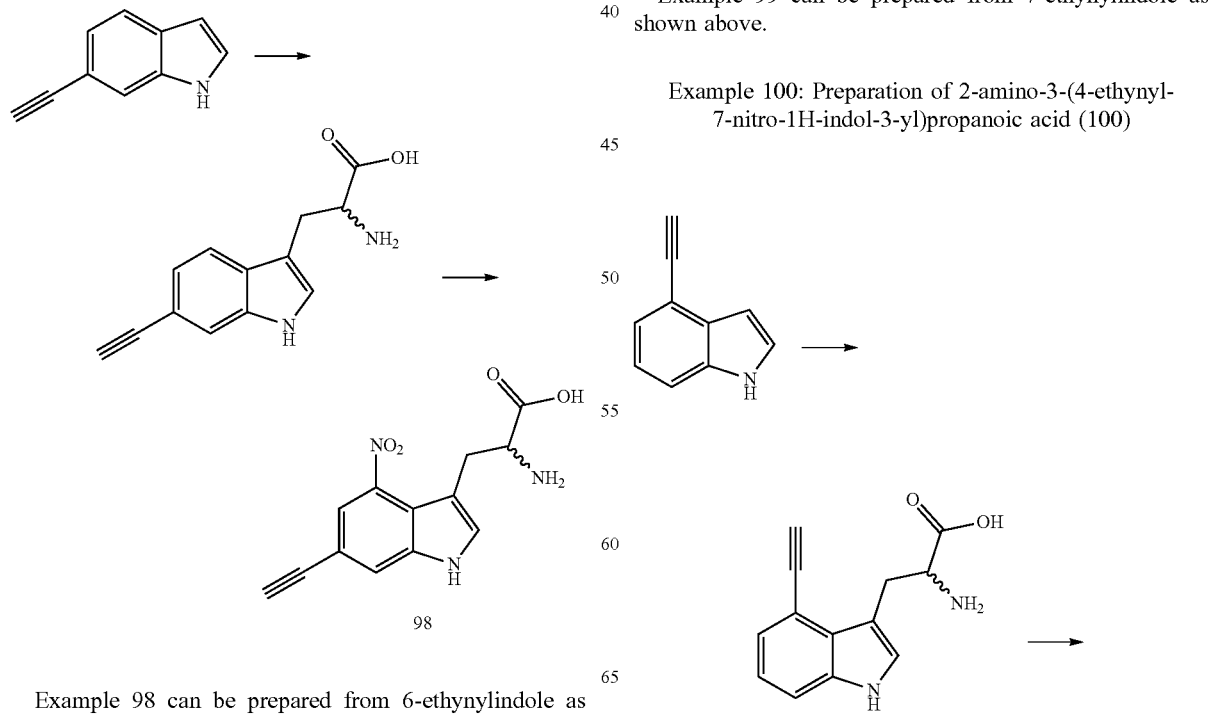

Example 98 can be prepared from 6-ethynylindole as shown above.

Example 99: Preparation of 2-amino-3-(7-ethynyl-4-nitro-1H-indol-3-yl)propanoic acid (99)

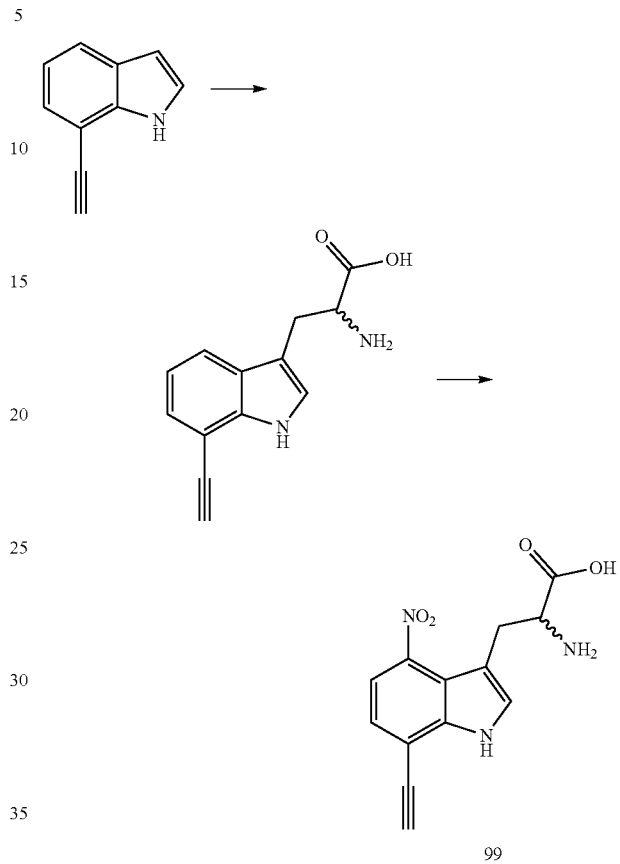

Example 99 can be prepared from 7-ethynylindole as shown above.

Example 100: Preparation of 2-amino-3-(4-ethynyl-7-nitro-1H-indol-3-yl)propanoic acid (100)

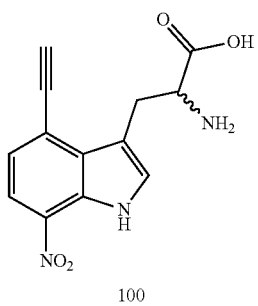

100

Example 100 can be prepared from 4-ethynylindole as shown above.

Example 101: Preparation of 2-amino-3-(5-morpholino-4-nitro-1H-indol-3-yl)propanoic acid (101)

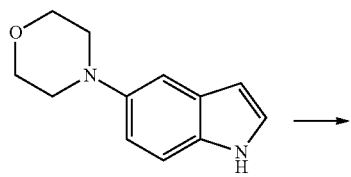

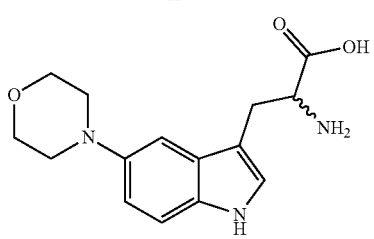

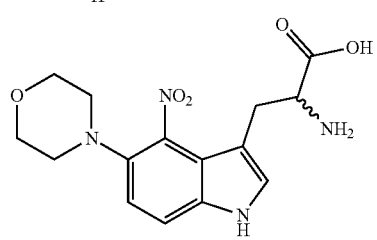

101

Example 101 can be prepared from 5-morpholinoindole as shown above.

Example 102: Preparation of 2-amino-3-(6-morpholino-4-nitro-1H-indol-3-yl)propanoic acid (102)

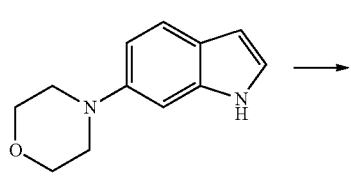

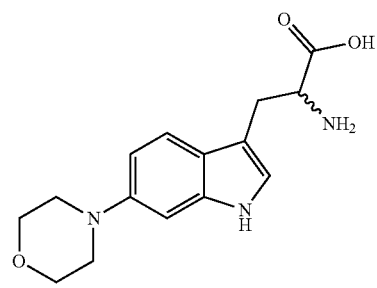

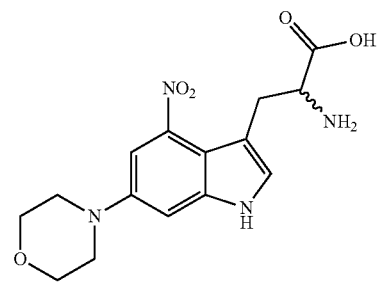

102

Example 102 can be prepared from 6-morpholinoindole as shown above.

Example 103: Preparation of 2-amino-3-(7-morpholino-4-nitro-1H-indol-3-yl)propanoic acid (103)

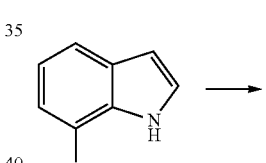

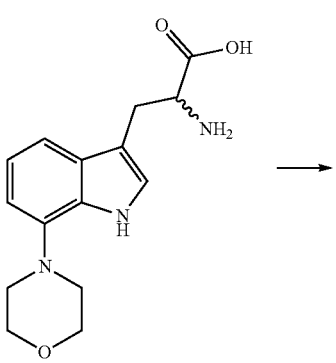

-continued

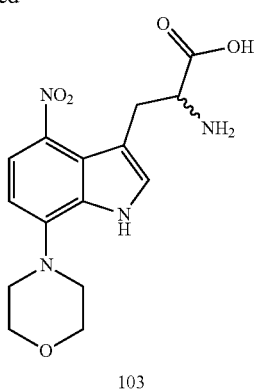
103

Example 103 can be prepared from 7-morpholinoindole as shown above.

Example 104: Preparation of 2-amino-3-(4-morpholino-7-nitro-1H-indol-3-yl)propanoic acid (104)

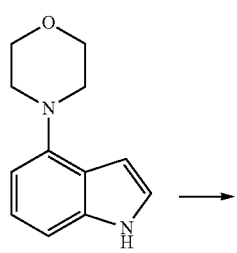

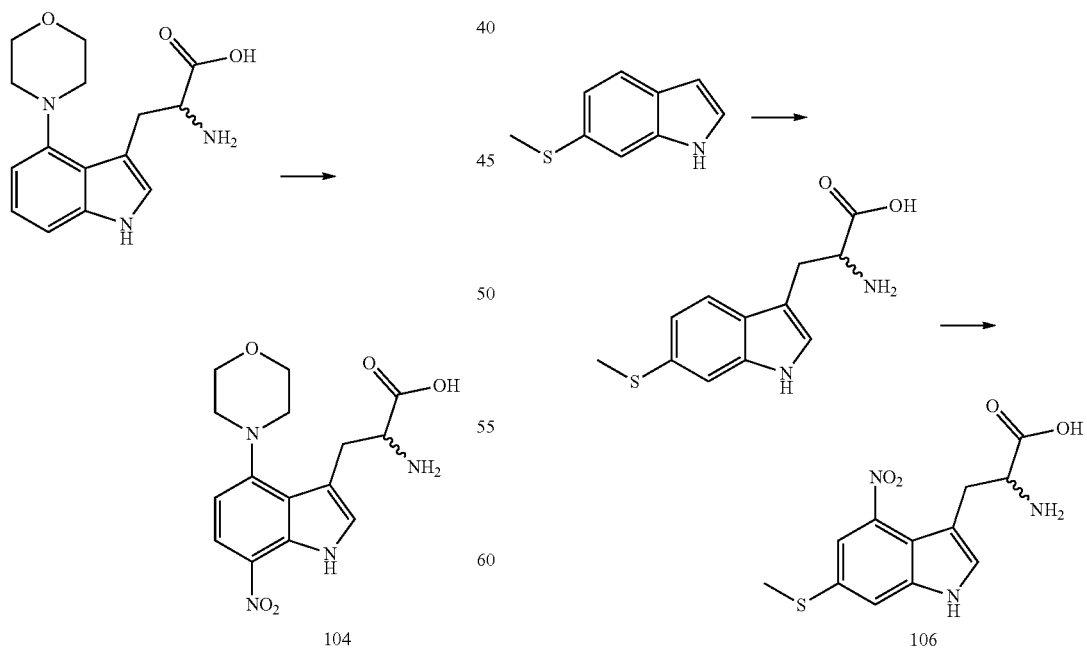
104

Example 104 can be prepared from 4-morpholinoindole as shown above.

Example 105: Preparation of 2-amino-3-(5-(methylthio)-4-nitro-1H-indol-3-yl)propanoic acid (105)

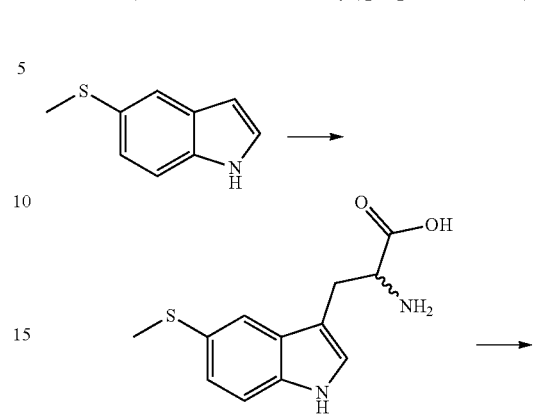
105

Example 105 can be prepared from 5-(methylthio)indole as shown above.

Example 106: Preparation of 2-amino-3-(6-(methylthio)-4-nitro-1H-indol-3-yl)propanoic acid (106)

106

Example 106 can be prepared from 6-(methylthio)indole as shown above.

Example 107: Preparation of 2-amino-3-(7-(methylthio)-4-nitro-1H-indol-3-yl)propanoic acid (107)

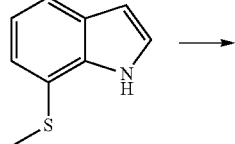

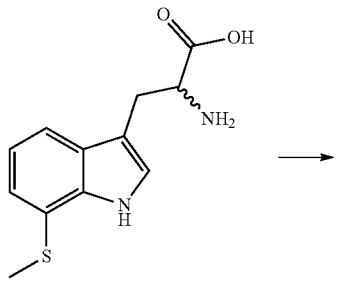

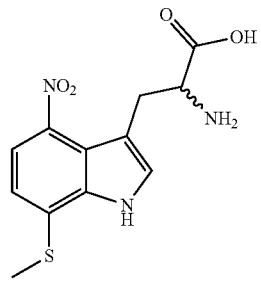

Example 107 can be prepared from 7-(methylthio)indole as shown above.

Example 108: Preparation of 2-amino-3-(4-(methylthio)-7-nitro-1H-indol-3-yl)propanoic acid (108)

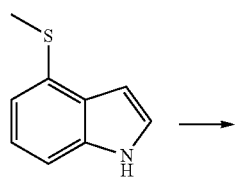

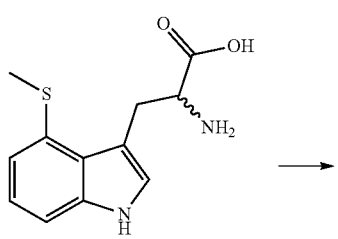

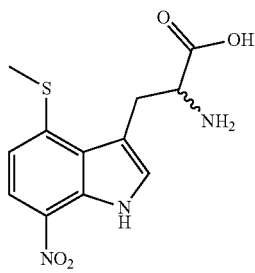

Example 108 can be prepared from 4-(methylthio)indole as shown above.

Example 109: Preparation of 2-amino-3-(4-nitro-5-(pyridin-4-yl)-1H-indol-3-yl)propanoic acid (109)

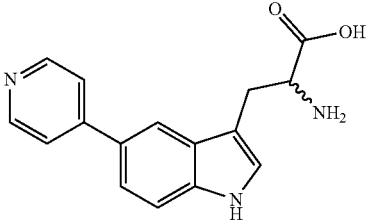

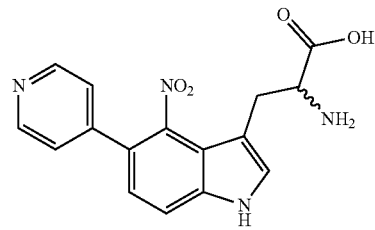

Example 109 can be prepared from 5-(pyridin-4-yl)indole as shown above.

Example 110: Preparation of 2-amino-3-(4-nitro-6-(pyridin-4-yl)-1H-indol-3-yl)propanoic acid (110)

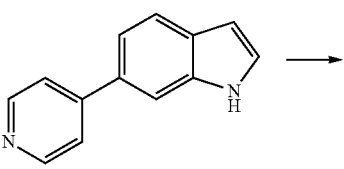

-continued
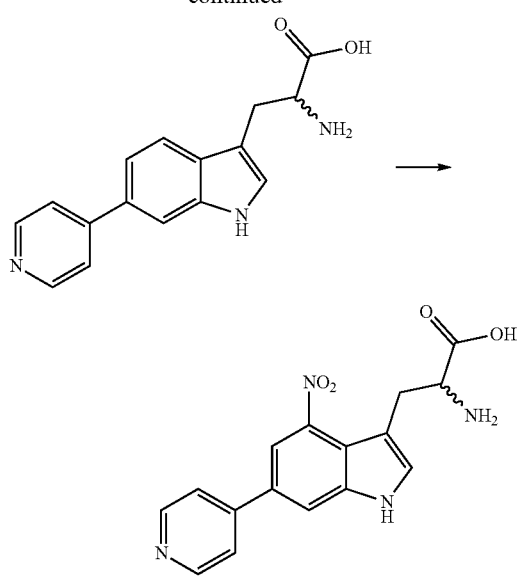
110
Example 110 can be prepared from 6-(pyridin-4-yl)indole as shown above.
Example 111: Preparation of 2-amino-3-(4-nitro-7-(pyridin-4-yl)-1H-indol-3-yl)propanoic acid (111)
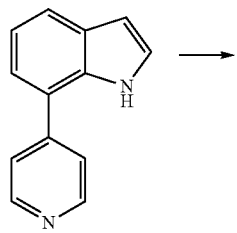
-continued
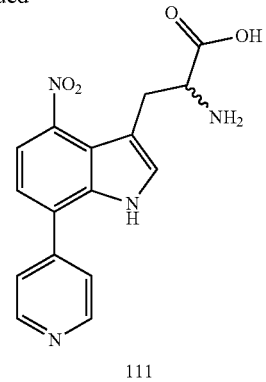
111
Example 111 can be prepared from 7-(pyridin-4-yl)indole as shown above.
Example 112: Preparation of 2-amino-3-(7-nitro-4-(pyridin-4-yl)-1H-indol-3-yl)propanoic acid (112)
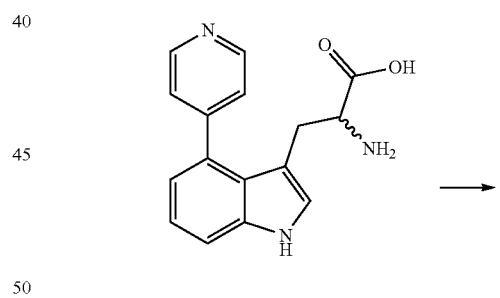
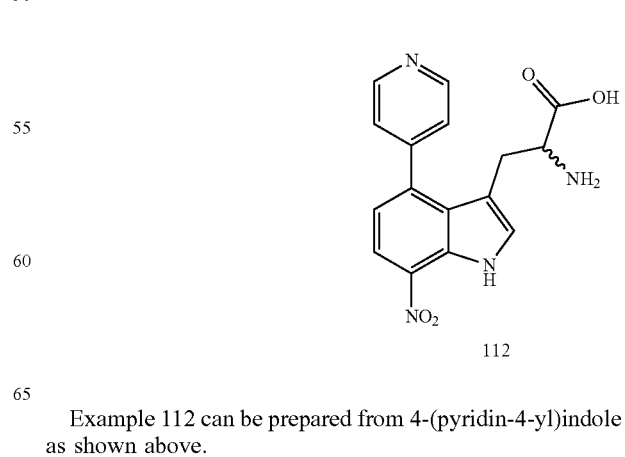
112
Example 112 can be prepared from 4-(pyridin-4-yl)indole as shown above.

Example 113: Preparation of 2-amino-3-(1,5-dimethyl-4-nitro-1H-indol-3-yl)propanoic acid (113)

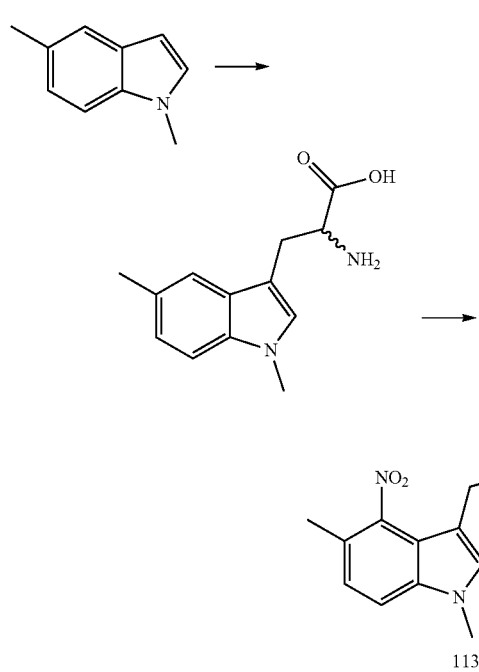

Example 113 can be prepared from 1,5-dimethyl-1H-indole as shown above.

Example 114: Preparation of 2-amino-3-(1,6-dimethyl-4-nitro-1H-indol-3-yl)propanoic acid (114)

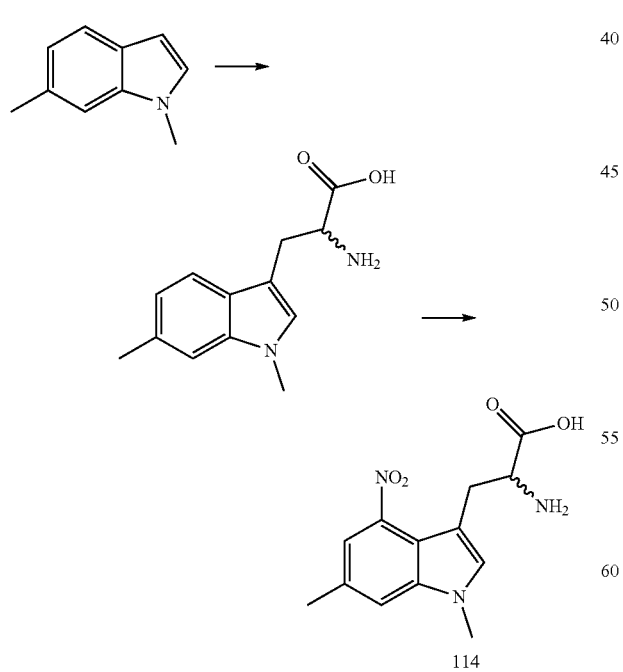

Example 114 can be prepared from 1,6-dimethyl-1H-indole as shown above.

Example 115: Preparation of 2-amino-3-(1,7-dimethyl-4-nitro-1H-indol-3-yl)propanoic acid (115)

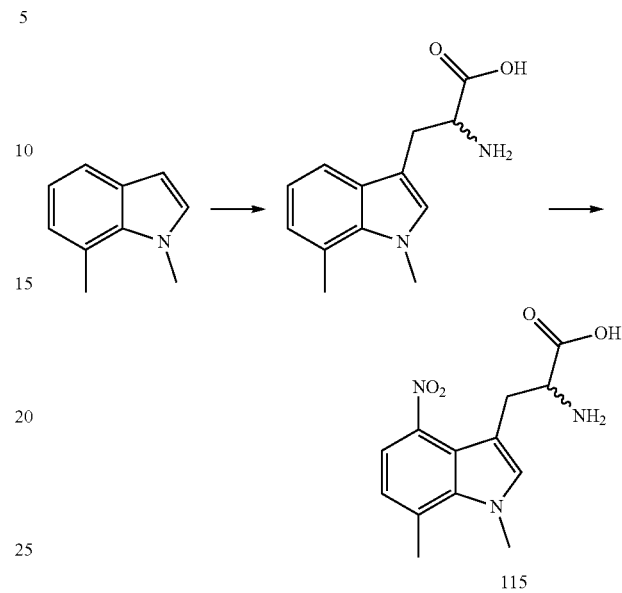

Example 115 can be prepared from 1,7-dimethyl-1H-indole as shown above.

Example 116: Preparation of 2-amino-3-(1,4-dimethyl-7-nitro-1H-indol-3-yl)propanoic acid (116)

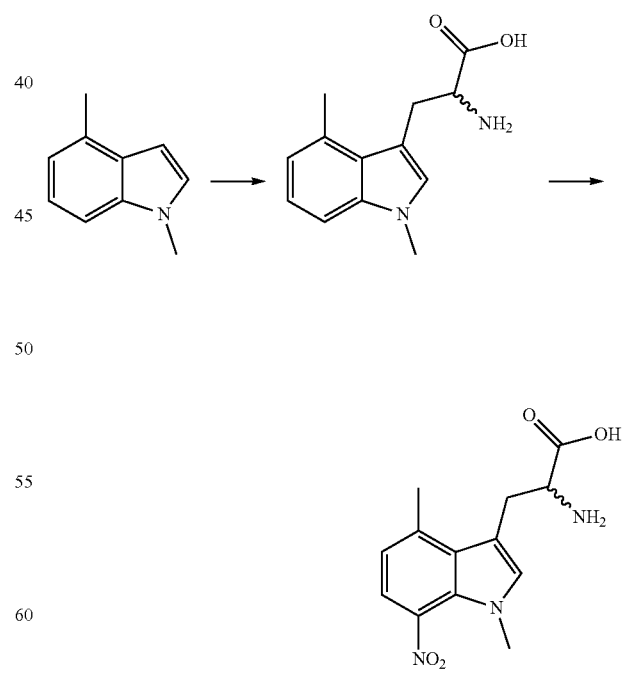

Example 116 can be prepared from 1,4-dimethyl-1H-indole as shown above.

Example 117: Preparation of 2-amino-3-(6-fluoro-1-methyl-4-nitro-1H-indol-3-yl)propanoic acid (117)

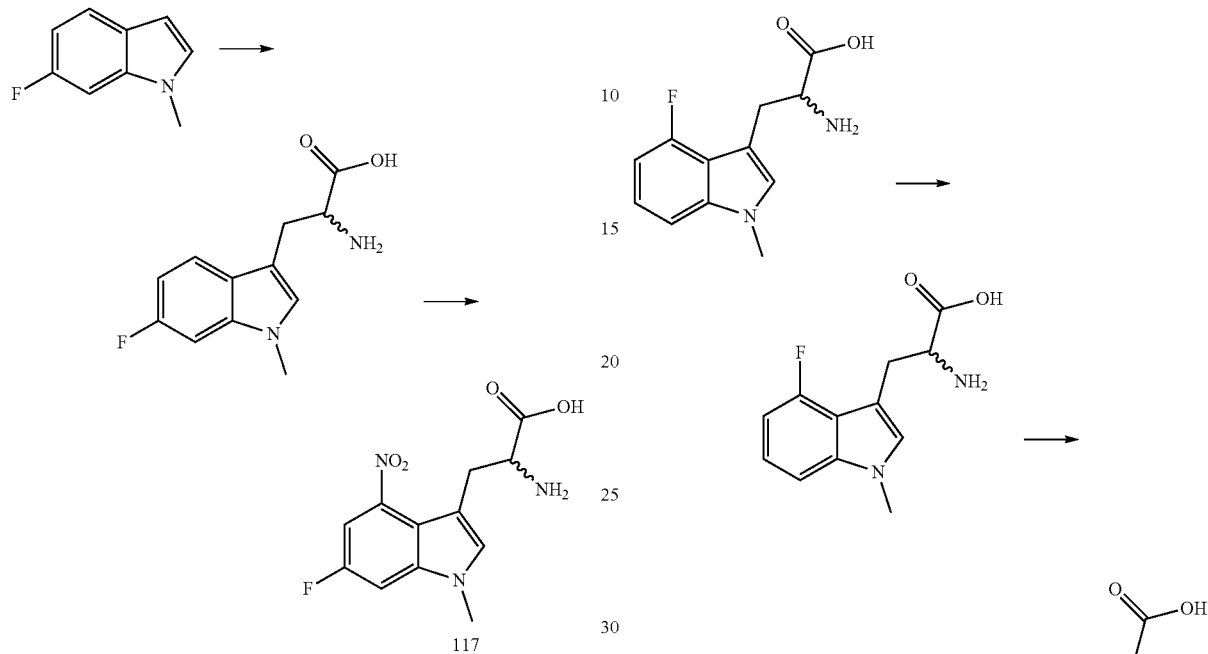

Example 117 can be prepared from 6-fluoro-1-methyl-1H-indole as shown above.

Example 118: Preparation of 2-amino-3-(7-fluoro-1-methyl-4-nitro-1H-indol-3-yl)propanoic acid (118)

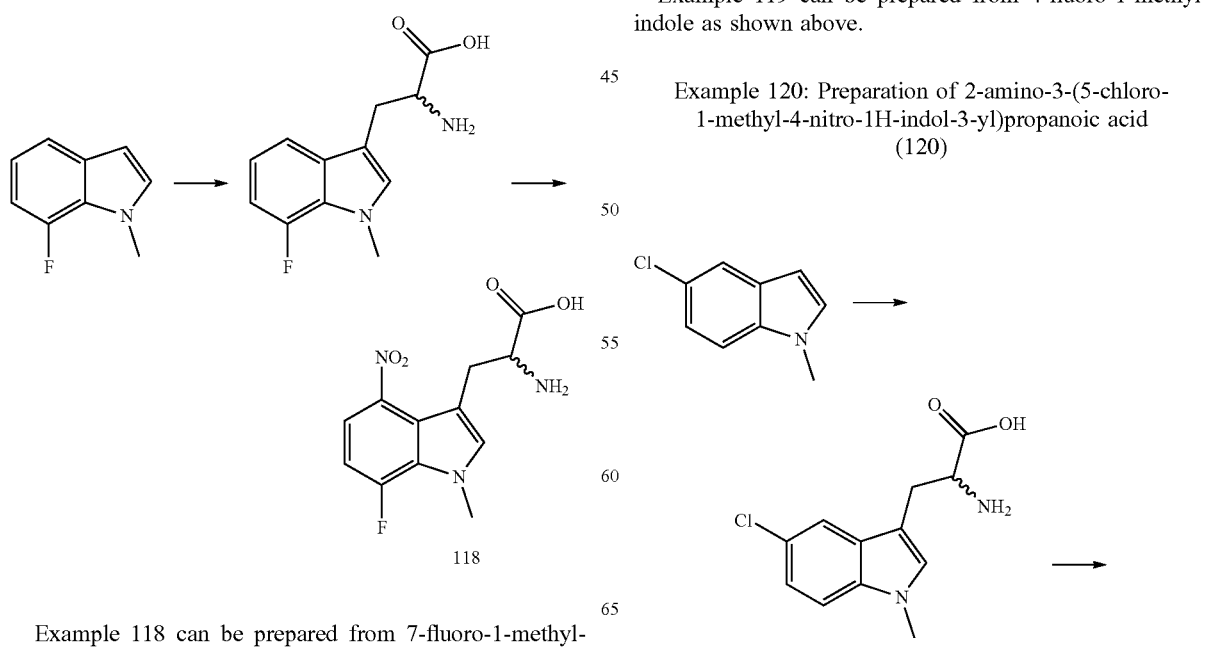

Example 118 can be prepared from 7-fluoro-1-methyl-indole as shown above.

Example 119: Preparation of 2-amino-3-(4-fluoro-1-methyl-7-nitro-1H-indol-3-yl)propanoic acid (119)

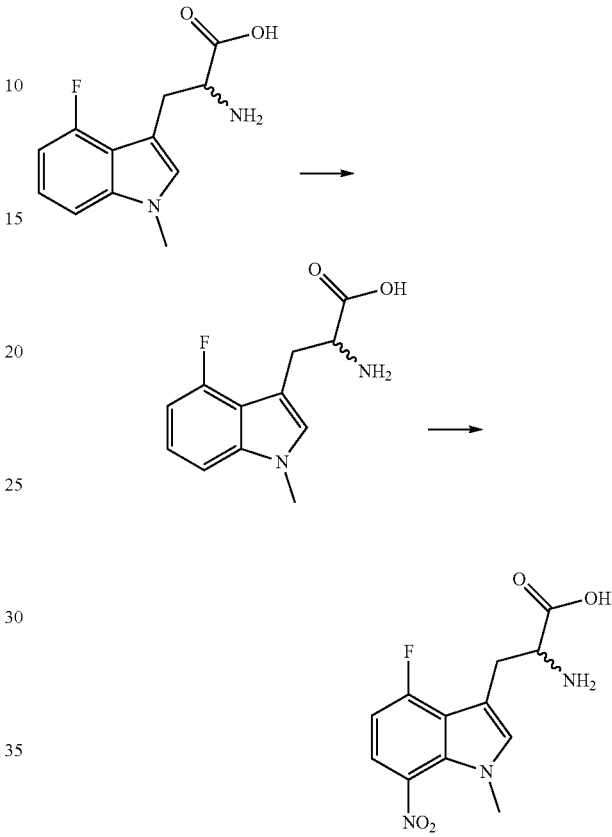

Example 119 can be prepared from 4-fluoro-1-methyl-indole as shown above.

Example 120: Preparation of 2-amino-3-(5-chloro-1-methyl-4-nitro-1H-indol-3-yl)propanoic acid (120)

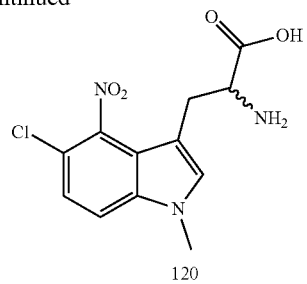

120

Example 120 can be prepared from 5-chloro-1-methyl-indole as shown above.

Example 121: Preparation of 2-amino-3-(6-chloro-1-methyl-4-nitro-1H-indol-3-yl)propanoic acid (121)

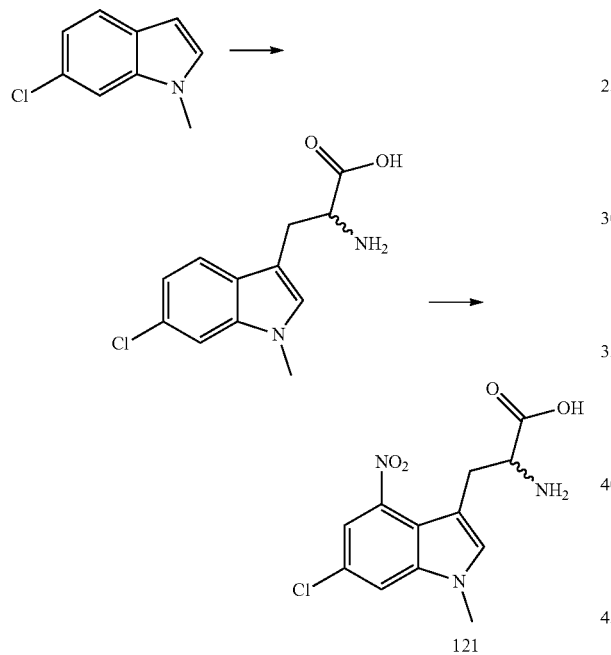

121

Example 121 can be prepared from 6-chloro-1-methyl-indole as shown above.

Example 122: Preparation of 2-amino-3-(7-chloro-1-methyl-4-nitro-1H-indol-3-yl)propanoic acid (122)

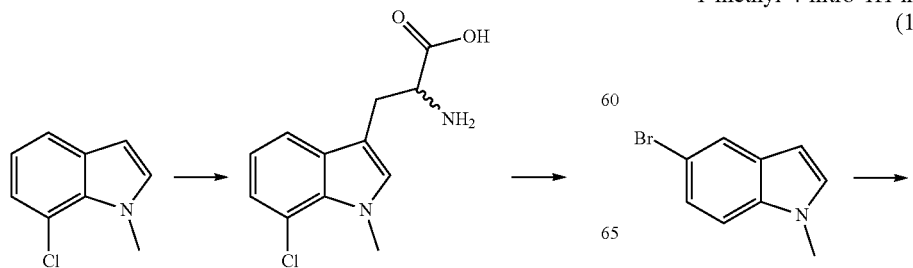

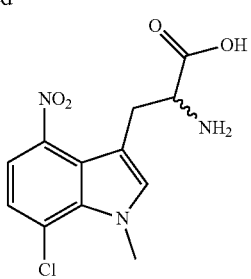

122

Example 122 can be prepared from 7-chloro-1-methyl-indole as shown above.

Example 123: Preparation of 2-amino-3-(4-chloro-1-methyl-7-nitro-1H-indol-3-yl)propanoic acid (123)

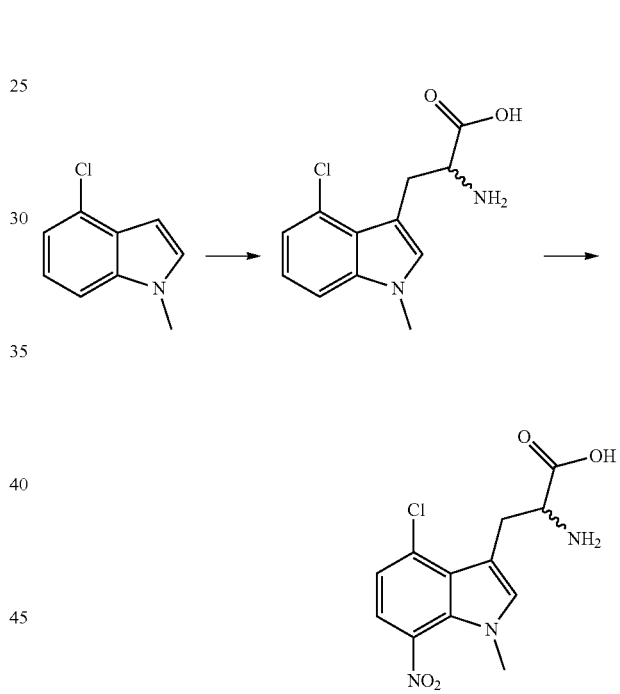

123

Example 123 can be prepared from 4-chloro-1-methyl-indole as shown above.

Example 124: Preparation of 2-amino-3-(5-bromo-1-methyl-4-nitro-1H-indol-3-yl)propanoic acid (124)

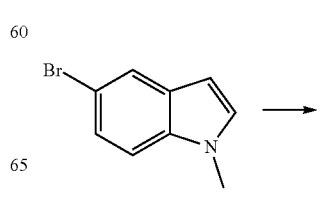

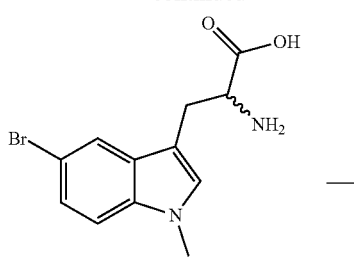

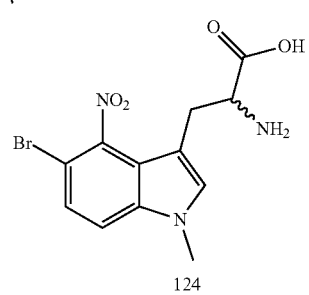

124

Example 124 can be prepared from 5-bromo-1-methyl-indole as shown above.

Example 125: Preparation of 2-amino-3-(6-bromo-1-methyl-4-nitro-1H-indol-3-yl)propanoic acid (125)

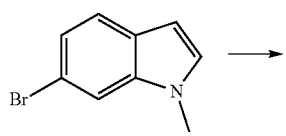

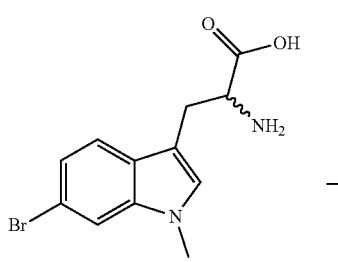

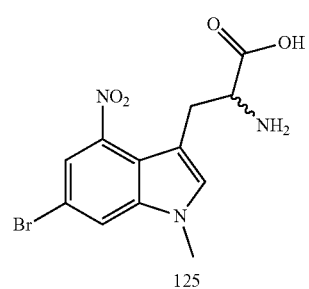

125

Example 125 can be prepared from 6-bromo-1-methyl-indole as shown above.

Example 126: Preparation of 2-amino-3-(7-bromo-1-methyl-4-nitro-1H-indol-3-yl)propanoic acid (126)

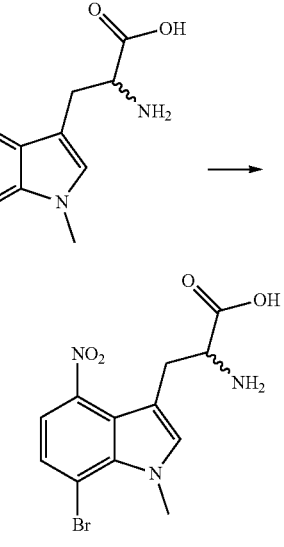

126

Example 126 can be prepared from 7-bromo-1-methyl-indole as shown above.

Example 127: Preparation of 2-amino-3-(4-bromo-1-methyl-7-nitro-1H-indol-3-yl)propanoic acid (127)

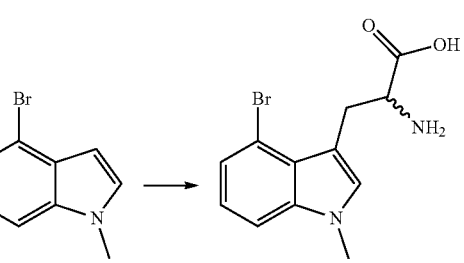

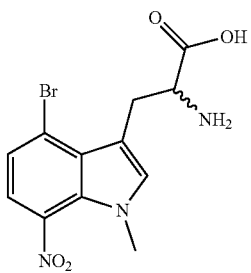

127

Example 127 can be prepared from 4-bromo-1-methyl-indole as shown above.

Example 128: Preparation of 2-amino-3-(5-methoxy-1-methyl-4-nitro-1H-indol-3-yl)propanoic acid (128)

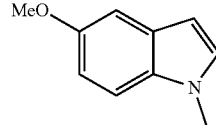

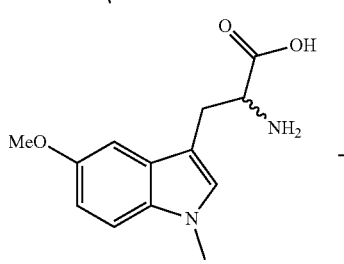

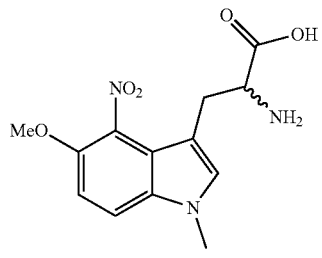

128

Example 128 can be prepared from 5-methoxy-1-methyl-indole as shown above.

Example 129: Preparation of 2-amino-3-(6-methoxy-1-methyl-4-nitro-1H-indol-3-yl)propanoic acid (129)

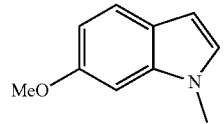

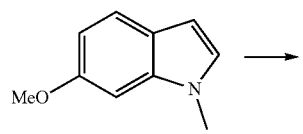

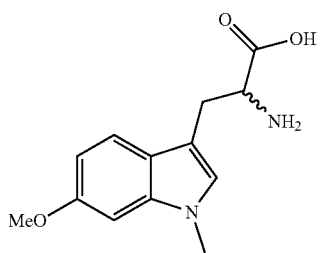

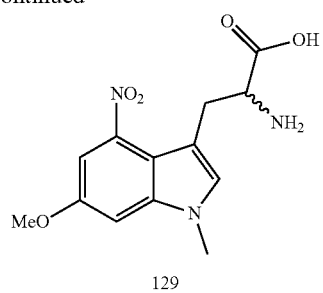

129

Example 129 can be prepared from 6-methoxy-1-methyl-indole as shown above.

Example 130: Preparation of 2-amino-3-(7-methoxy-1-methyl-4-nitro-1H-indol-3-yl)propanoic acid (130)

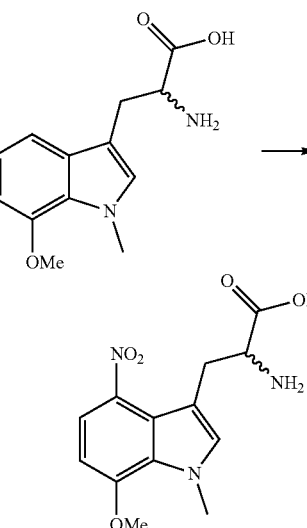

130

Example 130 can be prepared from 7-methoxy-1-methyl-indole as shown above.

Example 131: Preparation of 2-amino-3-(4-methoxy-1-methyl-7-nitro-1H-indol-3-yl)propanoic acid (131)

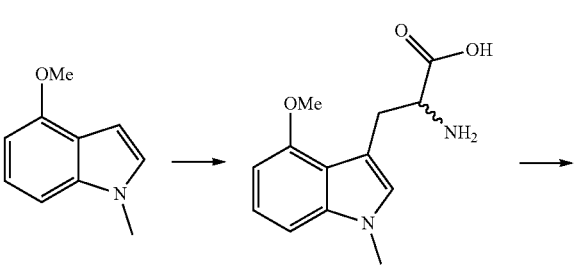

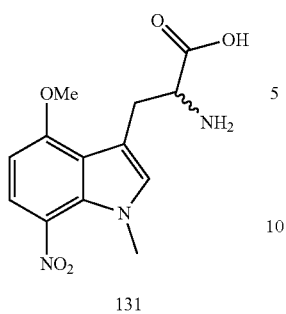

131

Example 131 can be prepared from 4-methoxy-1-methyl-indole as shown above.

Example 132: Preparation of 2-amino-3-(5-amino-1-methyl-4-nitro-1H-indol-3-yl)propanoic acid (132)

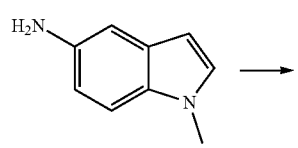

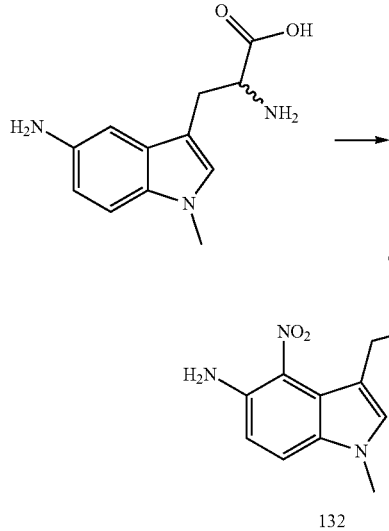

132

Example 132 can be prepared from 5-amino-1-methyl-indole as shown above.

Example 133: Preparation of 2-amino-3-(6-amino-1-methyl-4-nitro-1H-indol-3-yl)propanoic acid (133)

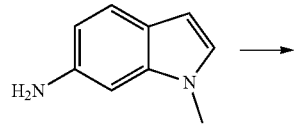

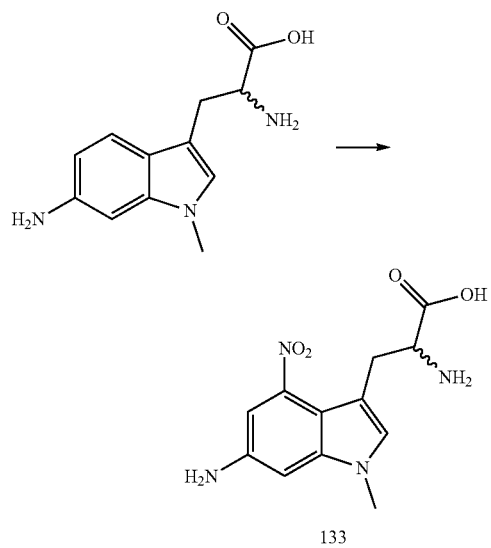

133

Example 133 can be prepared from 6-amino-1-methyl-indole as shown above.

Example 134: Preparation of 2-amino-3-(7-amino-1-methyl-4-nitro-1H-indol-3-yl)propanoic acid (134)

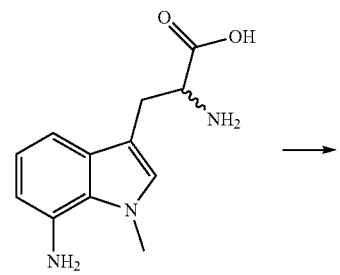

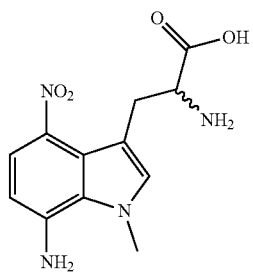

134

Example 134 can be prepared from 7-amino-1-methyl-indole as shown above.

Example 135: Preparation of 2-amino-3-(4-amino-1-methyl-7-nitro-1H-indol-3-yl)propanoic acid (135)

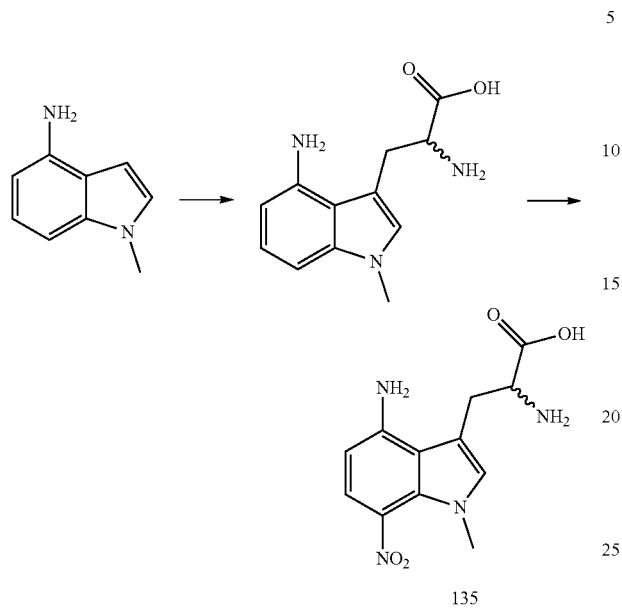

Example 135 can be prepared from 4-amino-1-methyl-indole as shown above.

Example 136: Preparation of 2-amino-3-(5-hydroxy-1-methyl-4-nitro-1H-indol-3-yl)propanoic acid (136)

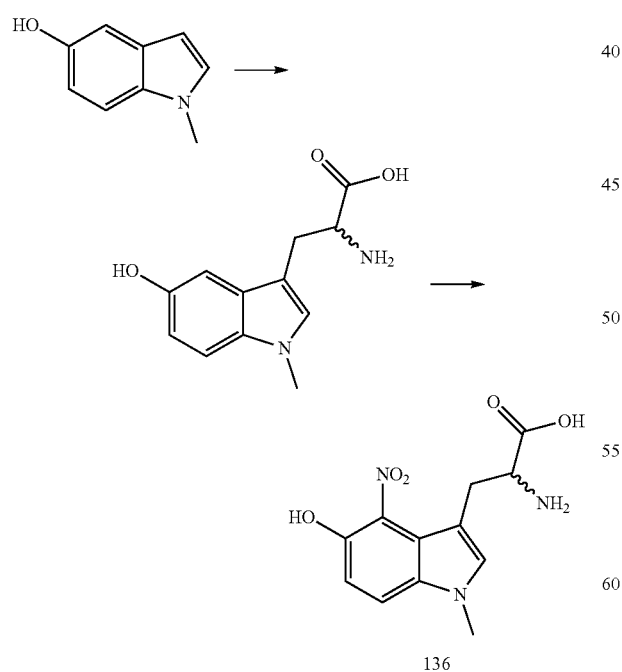

Example 136 can be prepared from 5-hydroxy-1-methyl-indole as shown above.

Example 137: Preparation of 2-amino-3-(6-hydroxy-1-methyl-4-nitro-1H-indol-3-yl)propanoic acid (137)

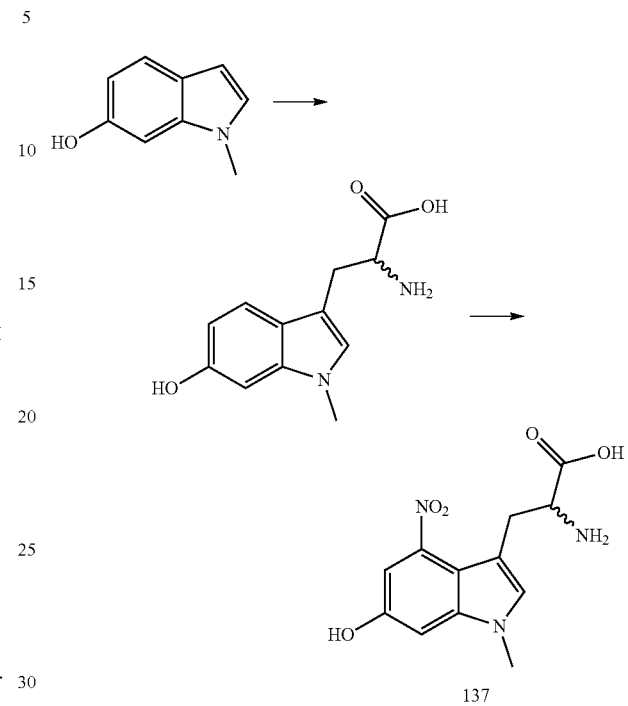

Example 137 can be prepared from 6-hydroxy-1-methyl-indole as shown above.

Example 138: Preparation of 2-amino-3-(7-hydroxy-1-methyl-4-nitro-1H-indol-3-yl)propanoic acid (138)

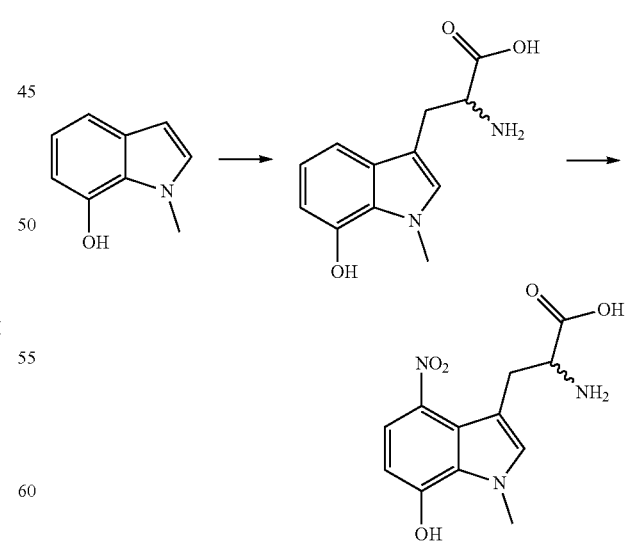

Example 138 can be prepared from 7-hydroxy-1-methyl-indole as shown above.

Example 139: Preparation of 2-amino-3-(4-hydroxy-1-methyl-7-nitro-1H-indol-3-yl)propanoic acid (139)

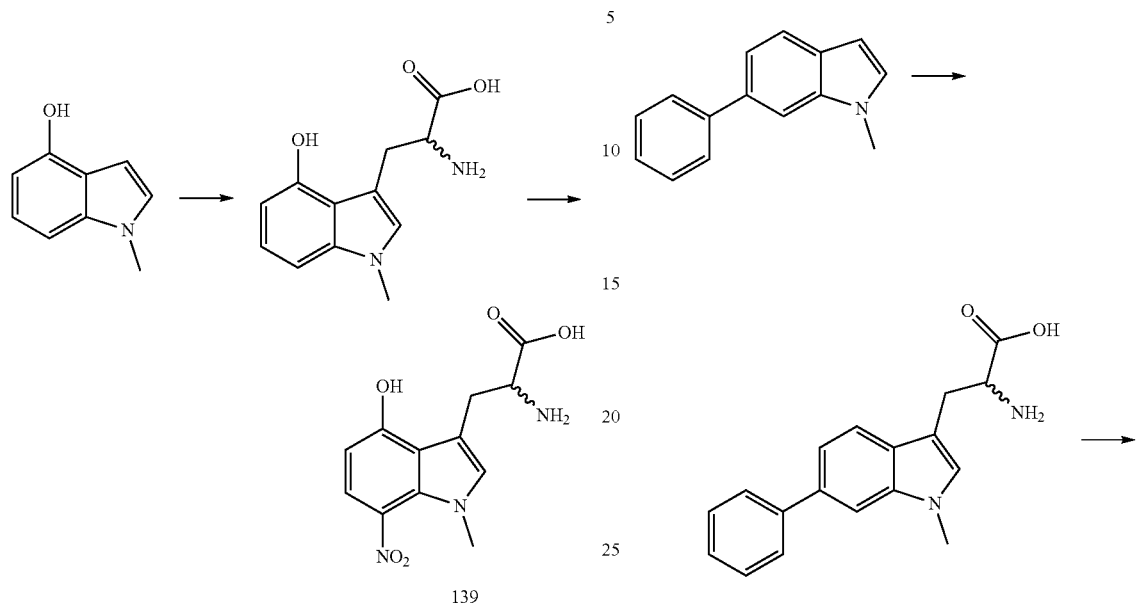

Example 139 can be prepared from 4-hydroxy-1-methyl-indole as shown above.

Example 140: Preparation of 2-amino-3-(1-methyl-4-nitro-5-phenyl-1H-indol-3-yl)propanoic acid (140)

Example 140 can be prepared from 5-phenyl-1-methyl-indole as shown above.

Example 141: Preparation of 2-amino-3-(1-methyl-4-nitro-6-phenyl-1H-indol-3-yl)propanoic acid (141)

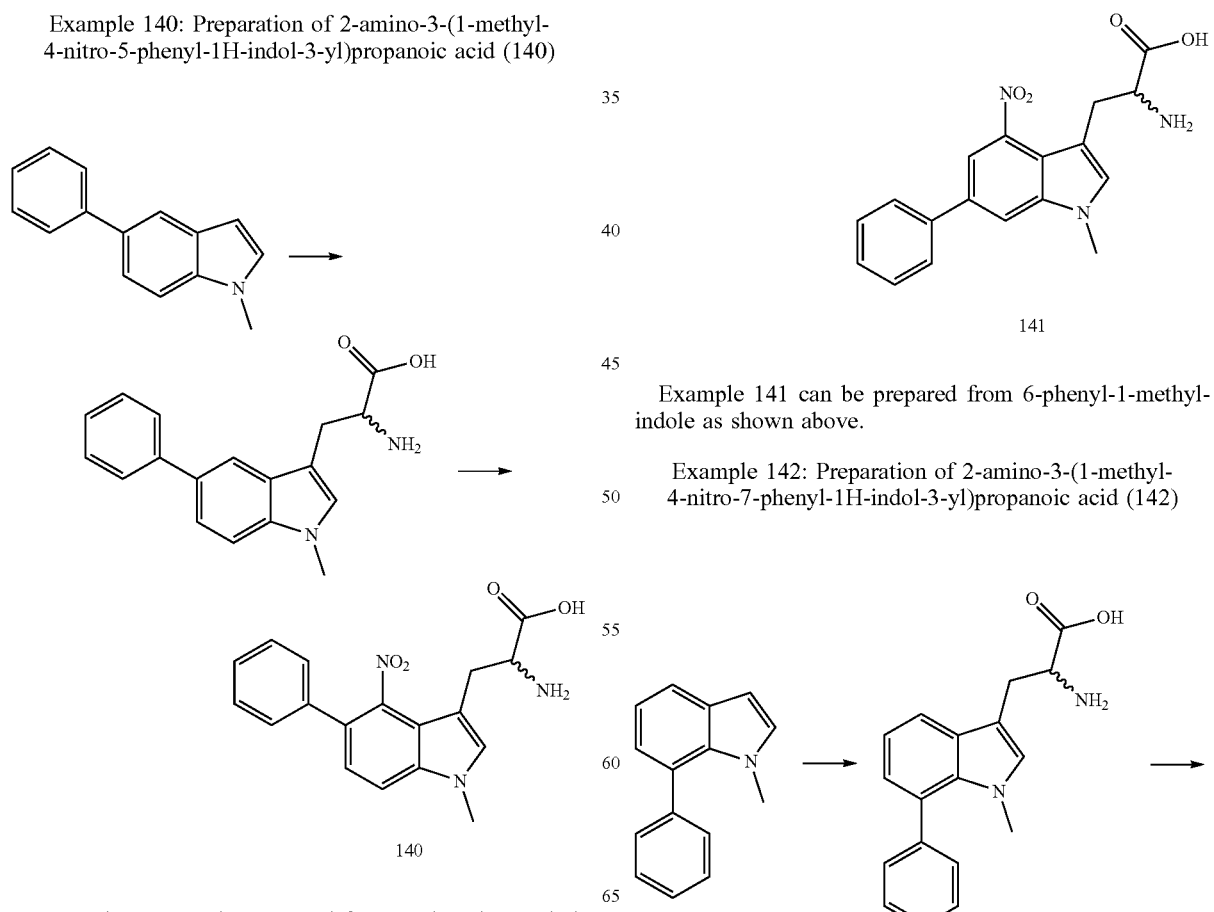

Example 141 can be prepared from 6-phenyl-1-methyl-indole as shown above.

Example 142: Preparation of 2-amino-3-(1-methyl-4-nitro-7-phenyl-1H-indol-3-yl)propanoic acid (142)

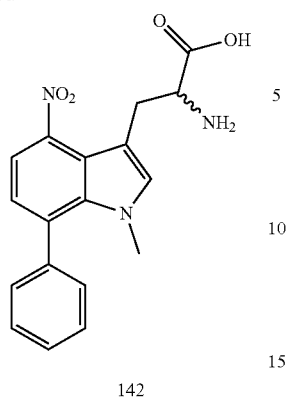

142

Example 142 can be prepared from 7-phenyl-1-methyl-indole as shown above.

Example 143: Preparation of 2-amino-3-(1-methyl-7-nitro-4-phenyl-1H-indol-3-yl)propanoic acid (143)

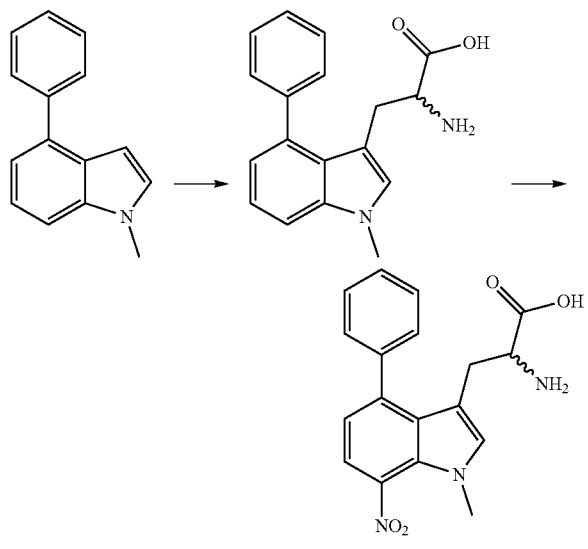

143

Example 143 can be prepared from 4-phenyl-1-methyl-indole as shown above.

Example 144: Preparation of 2-amino-3-(5-cyclo-propyl-1-methyl-4-nitro-1H-indol-3-yl)propanoic acid (144)

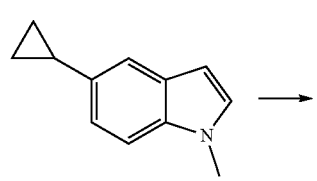

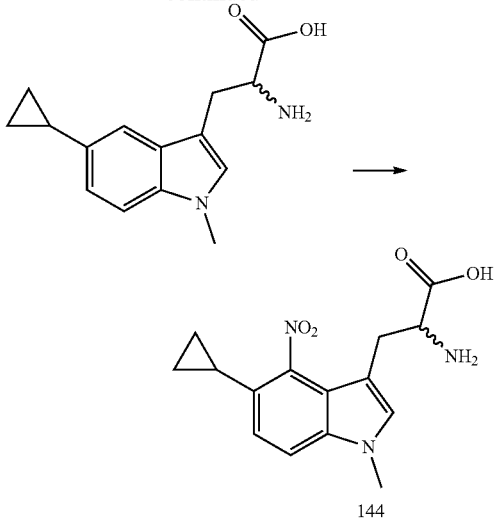

144

Example 144 can be prepared from 5-cyclopropyl-1-methyl-indole as shown above.

Example 145: Preparation of 2-amino-3-(6-cyclo-propyl-1-methyl-4-nitro-1H-indol-3-yl)propanoic acid (145)

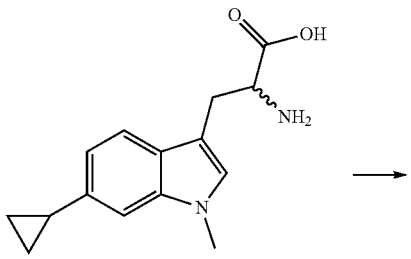

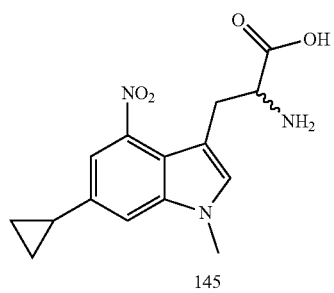

145

Example 145 can be prepared from 6-cyclopropyl-1-methyl-indole as shown above.

Example 146: Preparation of 2-amino-3-(7-cyclopropyl-1-methyl-4-nitro-1H-indol-3-yl)propanoic acid (146)

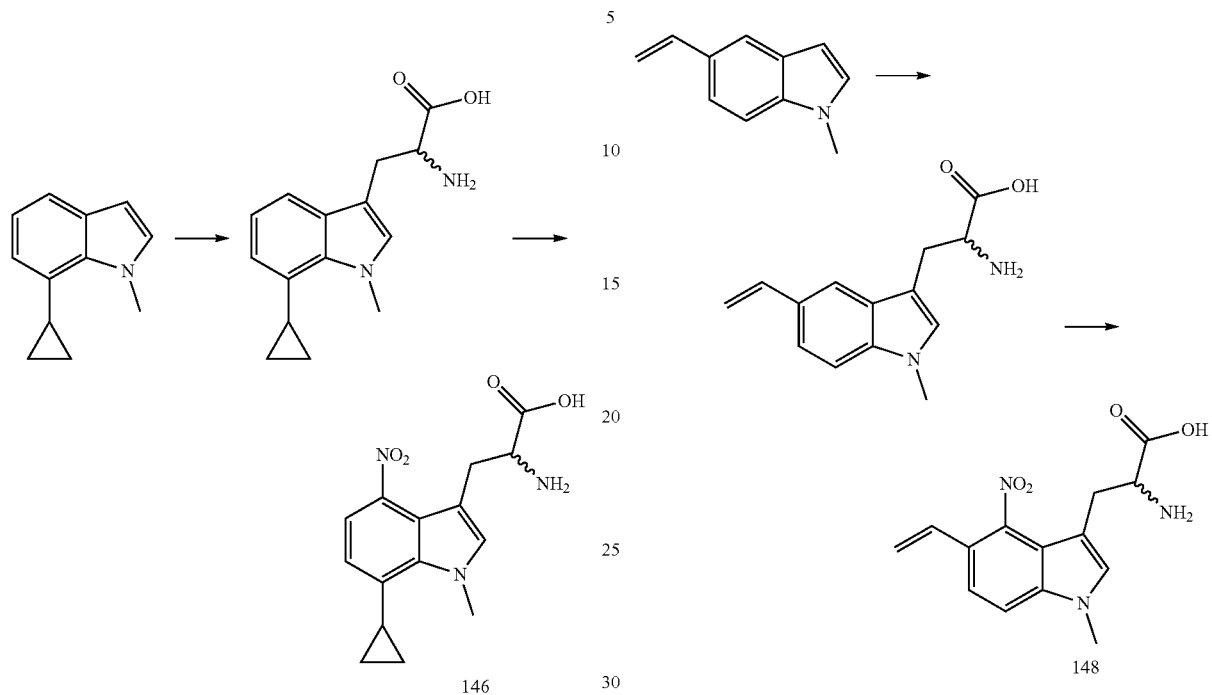

Example 146 can be prepared from 7-cyclopropyl-1-methyl-indole as shown above.

Example 147: Preparation of 2-amino-3-(4-cyclopropyl-1-methyl-7-nitro-1H-indol-3-yl)propanoic acid (147)

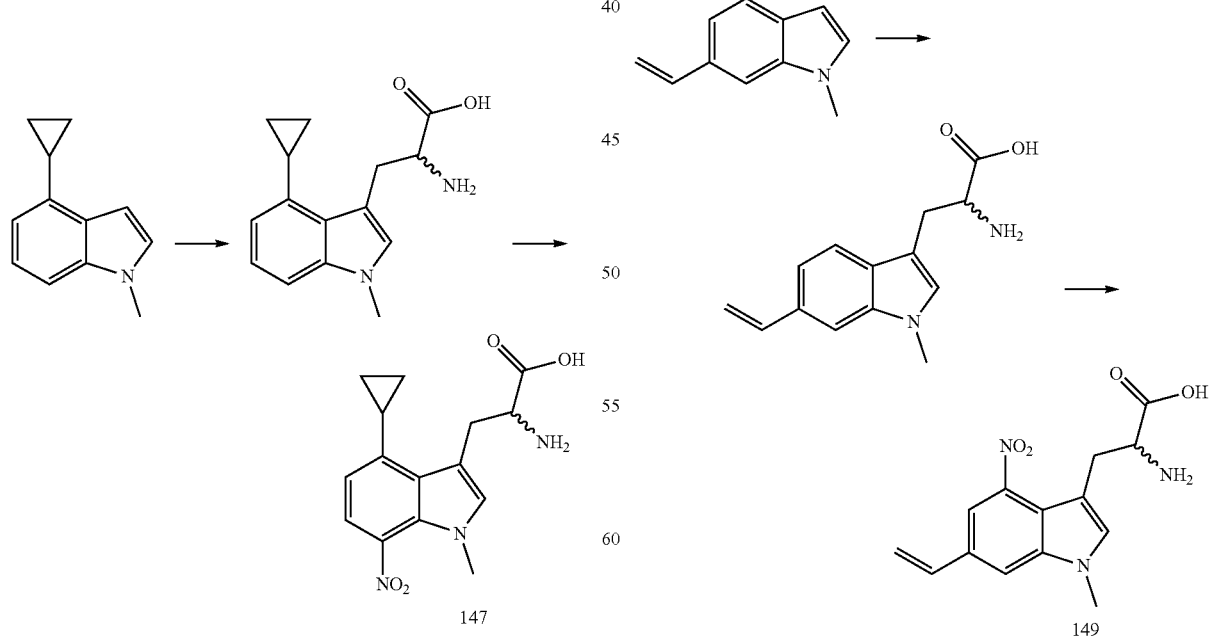

Example 147 can be prepared from 4-cyclopropyl-1-methyl-indole as shown above.

Example 148: Preparation of 2-amino-3-(1-methyl-4-nitro-5-vinyl-1H-indol-3-yl)propanoic acid (148)

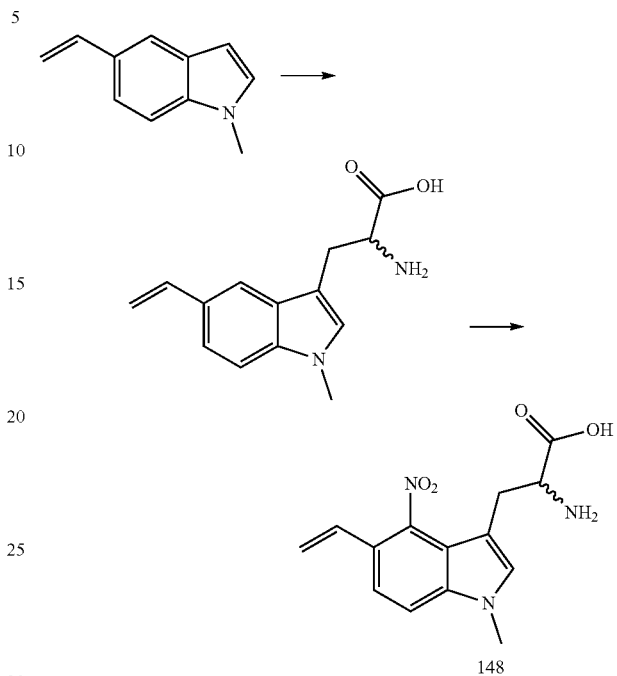

Example 148 can be prepared from 5-vinyl-1-methyl-indole as shown above.

Example 149: Preparation of 2-amino-3-(1-methyl-4-nitro-6-vinyl-1H-indol-3-yl)propanoic acid (149)

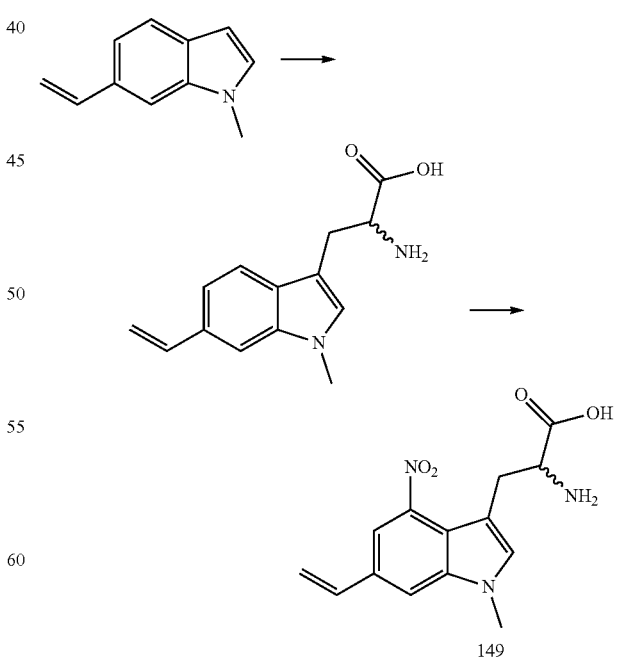

Example 149 can be prepared from 6-vinyl-1-methyl-indole as shown above.

129

Example 150: Preparation of 2-amino-3-(1-methyl-4-nitro-7-vinyl-1H-indol-3-yl)propanoic acid (150)

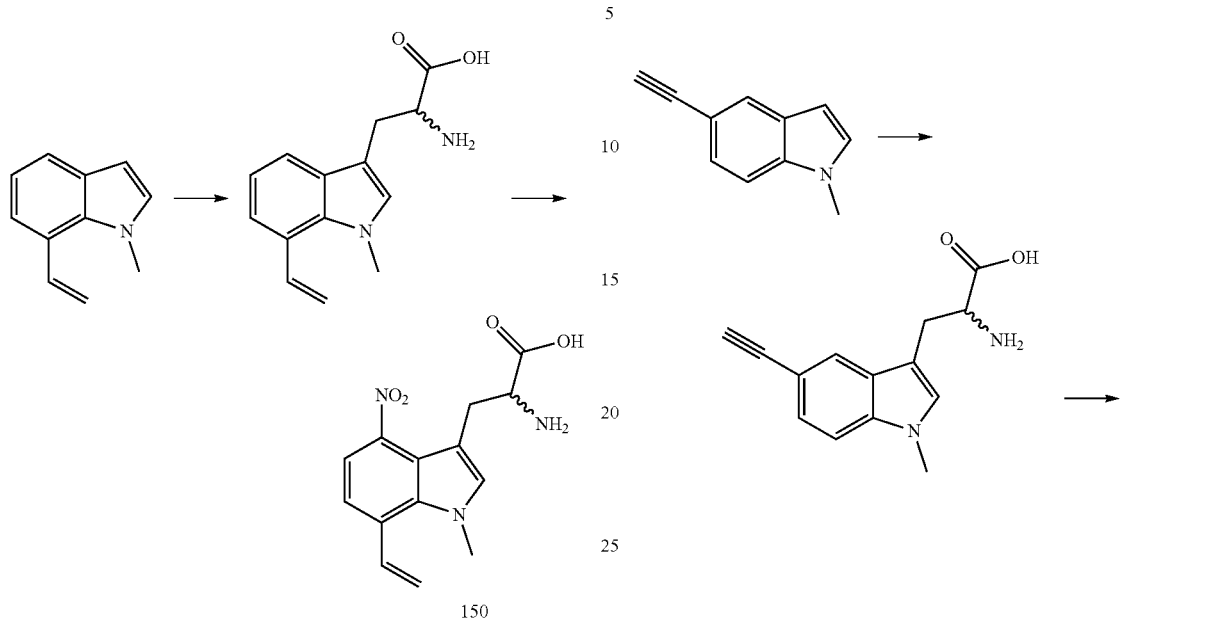

150

Example 150 can be prepared from 7-vinyl-1-methyl-indole as shown above.

Example 151: Preparation of 2-amino-3-(1-methyl-7-nitro-4-vinyl-1H-indol-3-yl)propanoic acid (151)

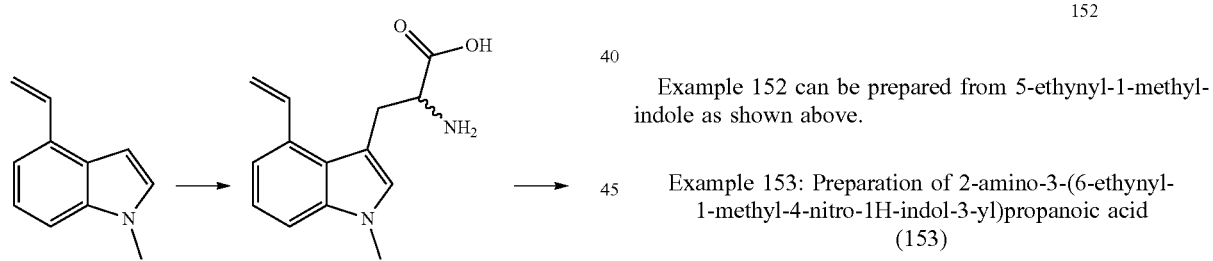

151

Example 151 can be prepared from 4-vinyl-1-methyl-indole as shown above.

130

Example 152: Preparation of 2-amino-3-(5-ethynyl-1-methyl-4-nitro-1H-indol-3-yl)propanoic acid (152)

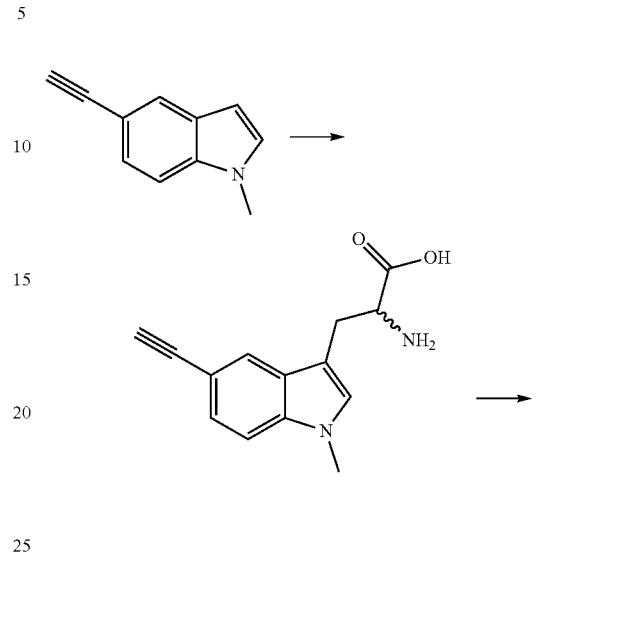

152

Example 152 can be prepared from 5-ethynyl-1-methyl-indole as shown above.

Example 153: Preparation of 2-amino-3-(6-ethynyl-1-methyl-4-nitro-1H-indol-3-yl)propanoic acid (153)

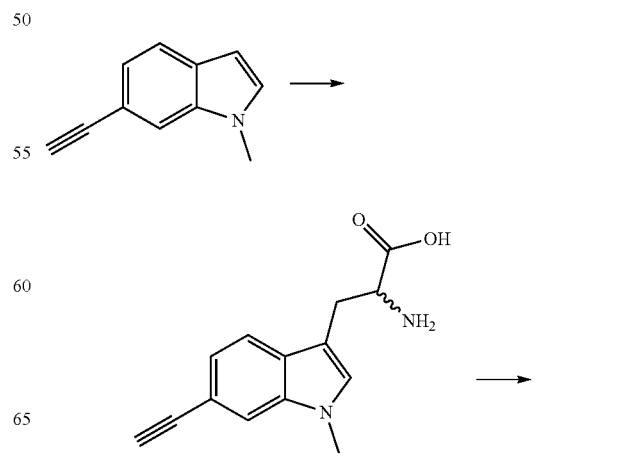

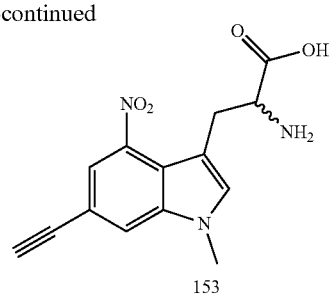

153

Example 153 can be prepared from 6-ethynyl-1-methyl-indole as shown above.

Example 154: Preparation of 2-amino-3-(7-ethynyl-1-methyl-4-nitro-1H-indol-3-yl)propanoic acid (154)

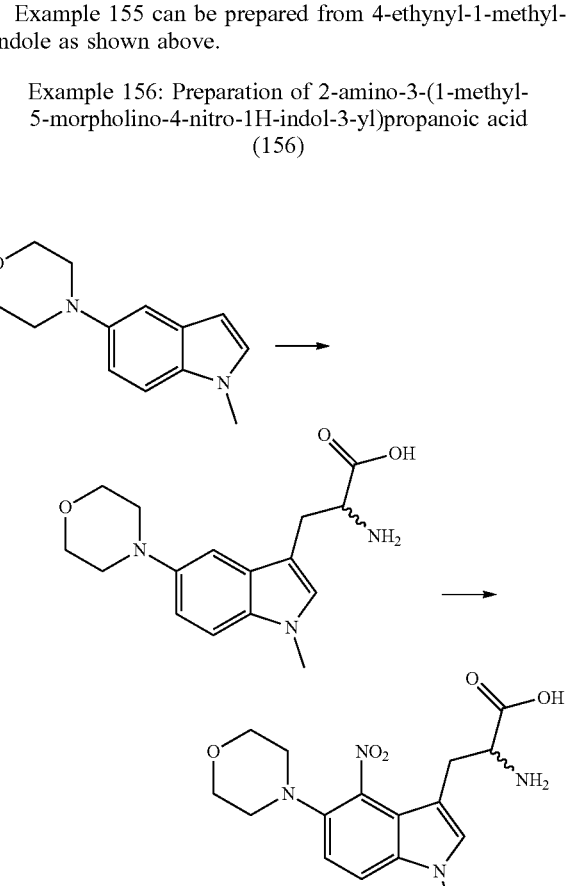

Example 154 can be prepared from 7-ethynyl-1-methyl-indole as shown above.

Example 155: Preparation of 2-amino-3-(4-ethynyl-1-methyl-7-nitro-1H-indol-3-yl)propanoic acid (155)

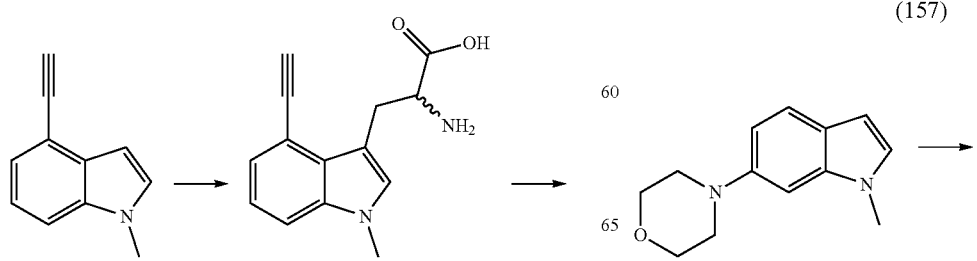

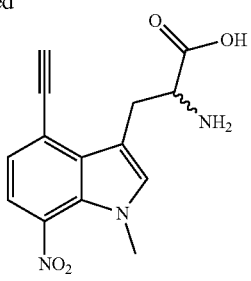

155

Example 155 can be prepared from 4-ethynyl-1-methyl-indole as shown above.

Example 156: Preparation of 2-amino-3-(1-methyl-5-morpholino-4-nitro-1H-indol-3-yl)propanoic acid (156)

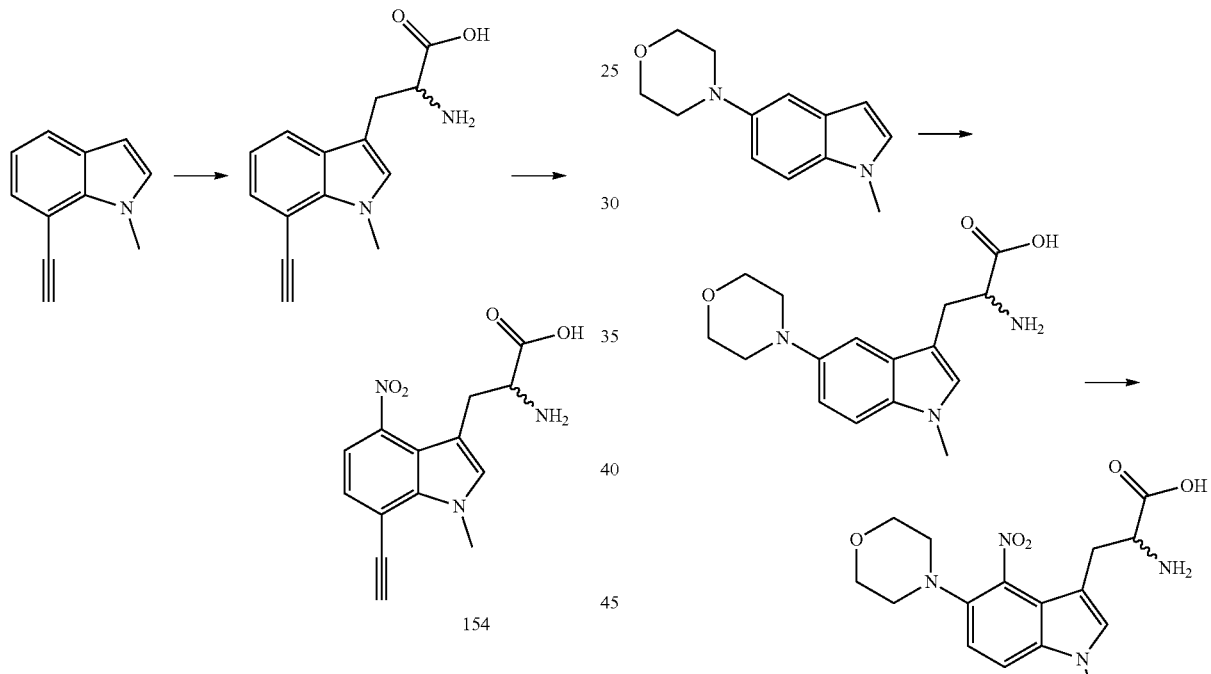

156

Example 156 can be prepared from 5-morpholino-1-methyl-indole as shown above.

Example 157: Preparation of 2-amino-3-(1-methyl-6-morpholino-4-nitro-1H-indol-3-yl)propanoic acid (157)

133

-continued

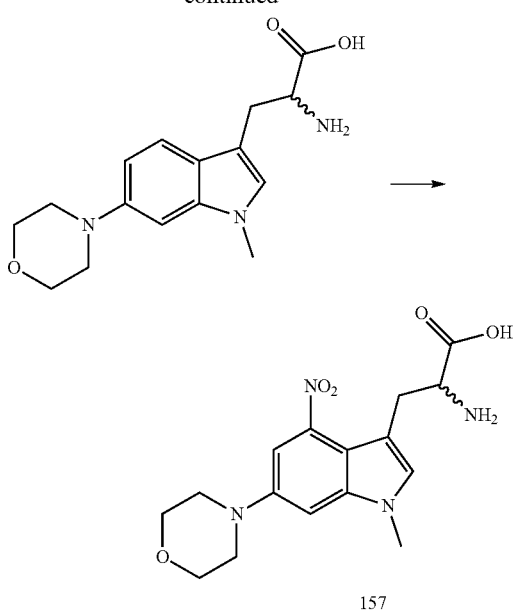

157

Example 157 can be prepared from 6-morpholino-1-methyl-indole as shown above.

Example 158: Preparation of 2-amino-3-(1-methyl-7-morpholino-4-nitro-1H-indol-3-yl)propanoic acid (158)

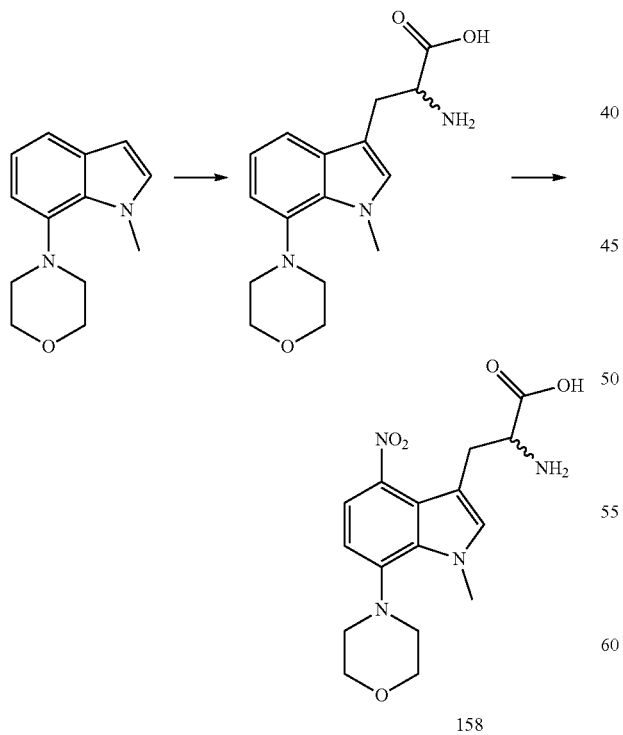

158

Example 158 can be prepared from 7-morpholino-1-methyl-indole as shown above.

134

Example 159: Preparation of 2-amino-3-(1-methyl-4-morpholino-7-nitro-1H-indol-3-yl)propanoic acid (159)

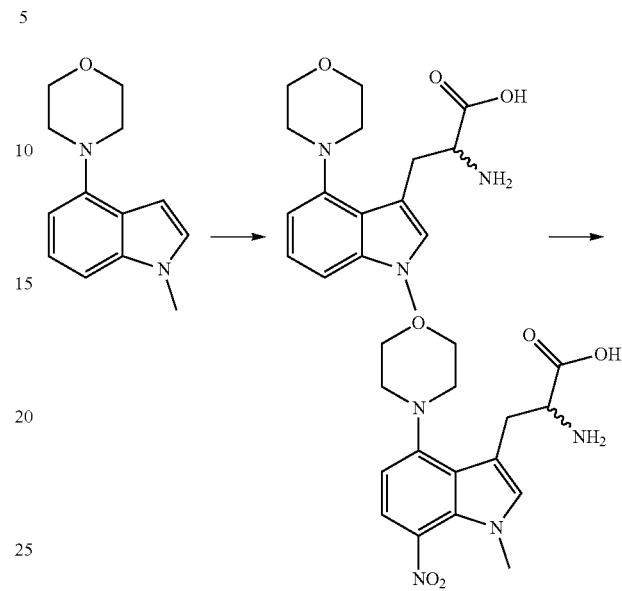

159

Example 159 can be prepared from 4-morpholino-1-methyl-indole as shown above.

Example 160: Preparation of 2-amino-3-(1-methyl-5-(methylthio)-4-nitro-1H-indol-3-yl)propanoic acid (160)

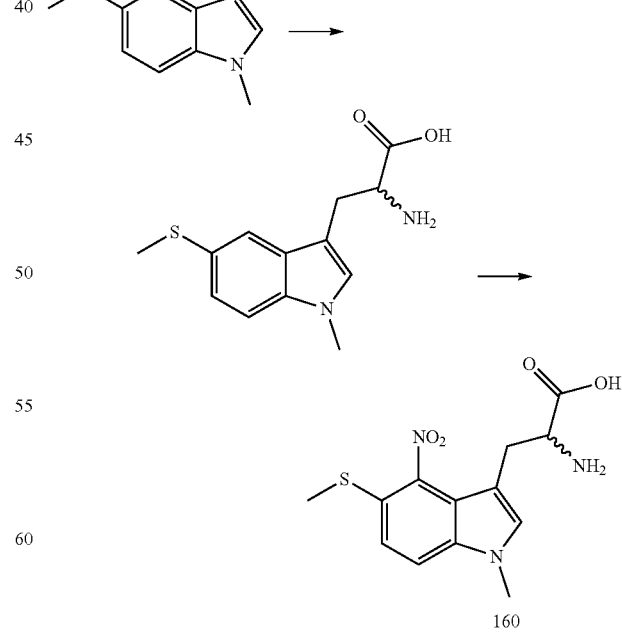

160

Example 160 can be prepared from 5-(methylthio)-1-methyl-indole as shown above.

Example 161: Preparation of 2-amino-3-(1-methyl-6-(methylthio)-4-nitro-1H-indol-3-yl)propanoic acid (161)

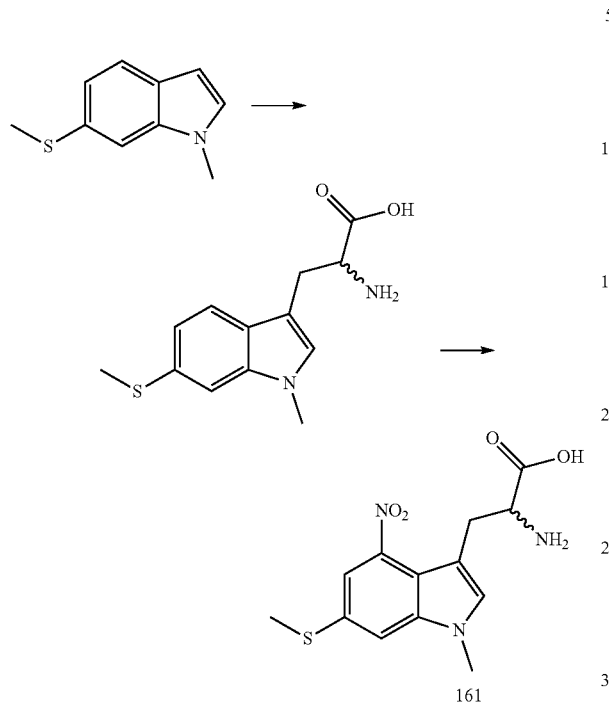

Example 161 can be prepared from 6-(methylthio)-1-methyl-indole as shown above.

Example 162: Preparation of 2-amino-3-(1-methyl-7-(methylthio)-4-nitro-1H-indol-3-yl)propanoic acid (162)

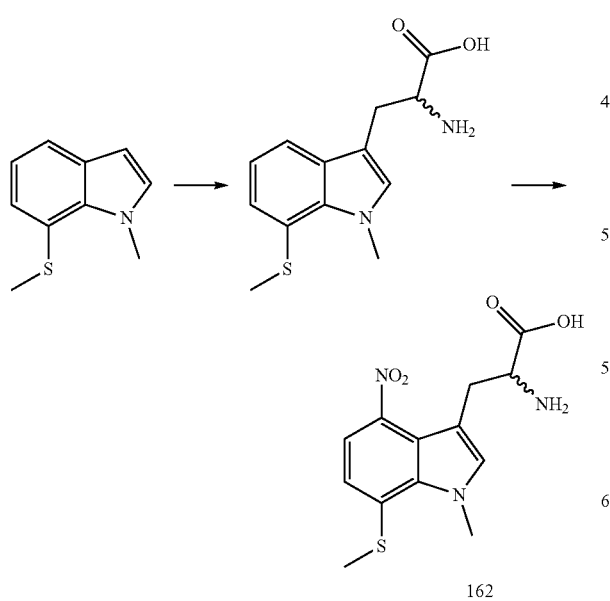

Example 162 can be prepared from 7-(methylthio)-1-methyl-indole as shown above.

Example 163: Preparation of 2-amino-3-(1-methyl-4-(methylthio)-7-nitro-1H-indol-3-yl)propanoic acid (163)

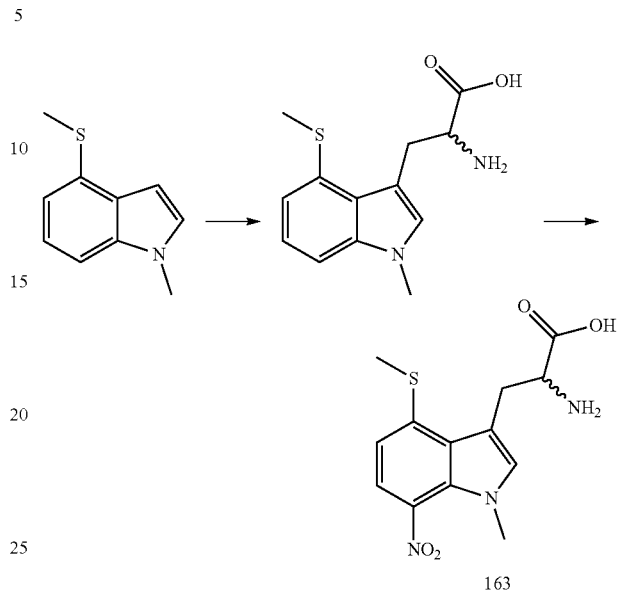

Example 163 can be prepared from 4-(methylthio)-1-methyl-indole as shown above.

Example 164: Preparation of 2-amino-3-(1-methyl-4-nitro-5-(pyridin-4-yl)-1H-indol-3-yl)propanoic acid (164)

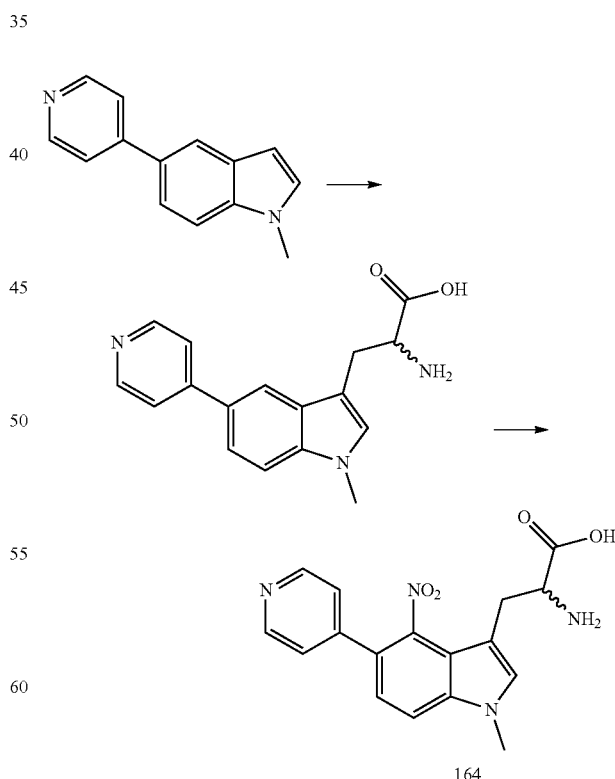

Example 164 can be prepared from 5-(pyridin-4-yl)-1-methyl-indole as shown above.

Example 165: Preparation of 2-amino-3-(1-methyl-4-nitro-6-(pyridin-4-yl)-1H-indol-3-yl)propanoic acid (165)

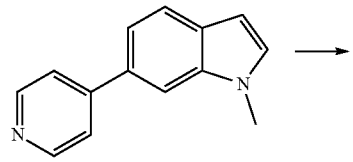

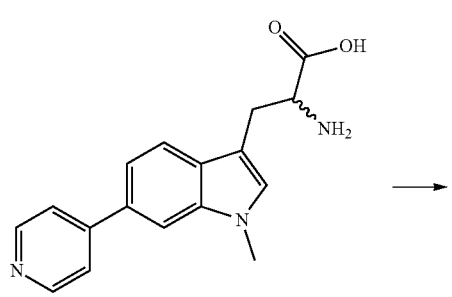

165

Example 165 can be prepared from 6-(pyridin-4-yl)-1-methyl-indole as shown above.

Example 166: Preparation of 2-amino-3-(1-methyl-4-nitro-7-(pyridin-4-yl)-1H-indol-3-yl)propanoic acid (166)

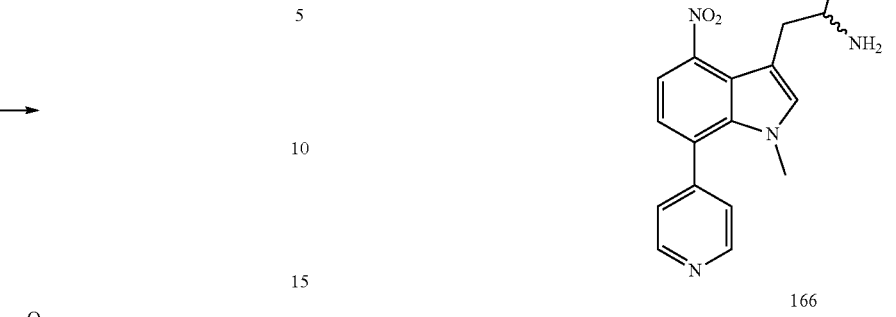

166

Example 166 can be prepared from 7-(pyridin-4-yl)-1-methyl-indole as shown above.

Example 167: Preparation of 2-amino-3-(1-methyl-7-nitro-4-(pyridin-4-yl)-1H-indol-3-yl)propanoic acid (167)

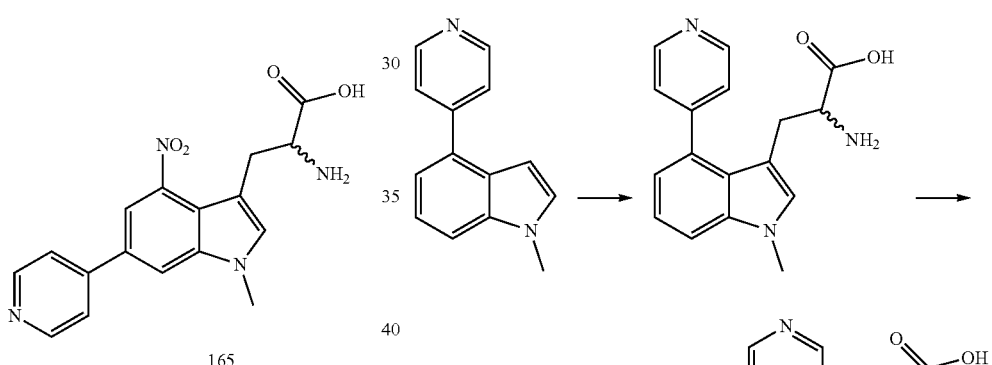

167

Example 167 can be prepared from 4-(pyridin-4-yl)-1-methyl-indole as shown above.

Example 168: Preparation of 2-amino-3-(2,5-dimethyl-4-nitro-1H-indol-3-yl)propanoic acid (168)

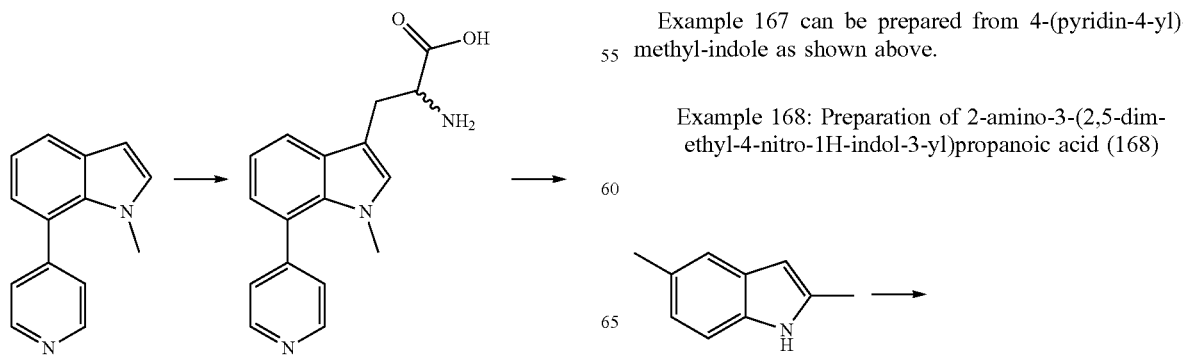

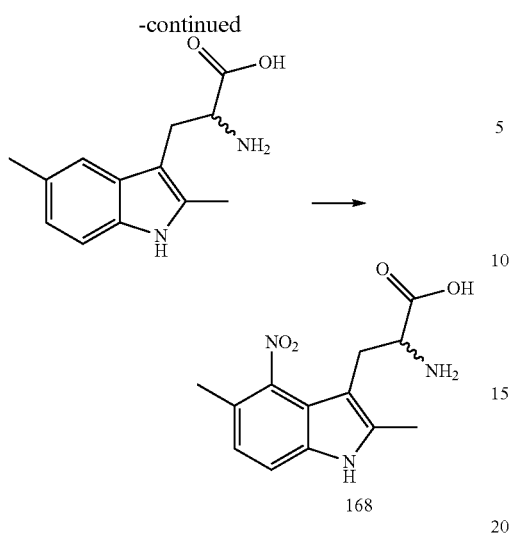

Example 168 can be prepared from 2,5-dimethyl-1H-indole as shown above.

Example 169: Preparation of 2-amino-3-(2,6-dimethyl-4-nitro-1H-indol-3-yl)propanoic acid (169)

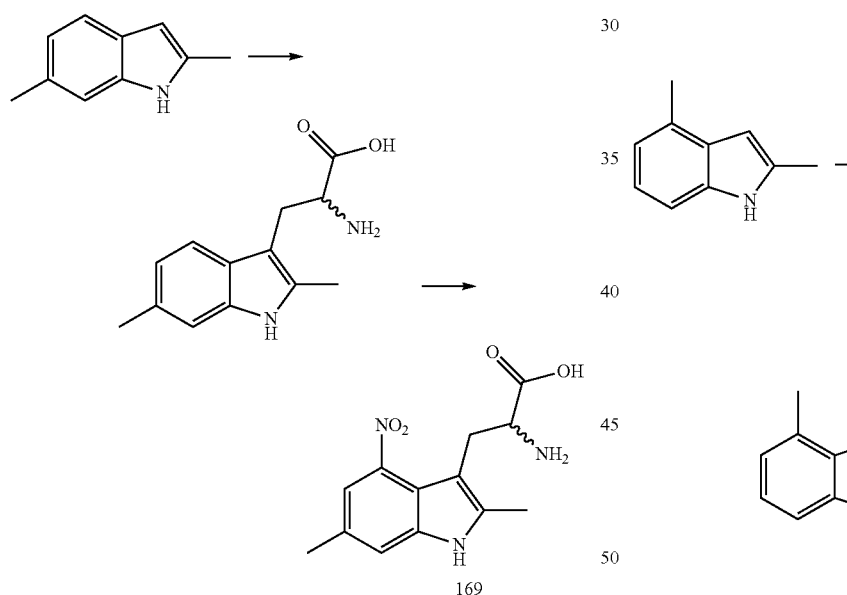

Example 169 can be prepared from 2,6-dimethyl-1H-indole as shown above.

Example 170: Preparation of 2-amino-3-(2,7-dimethyl-4-nitro-1H-indol-3-yl)propanoic acid (170)

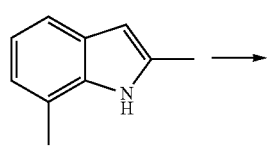

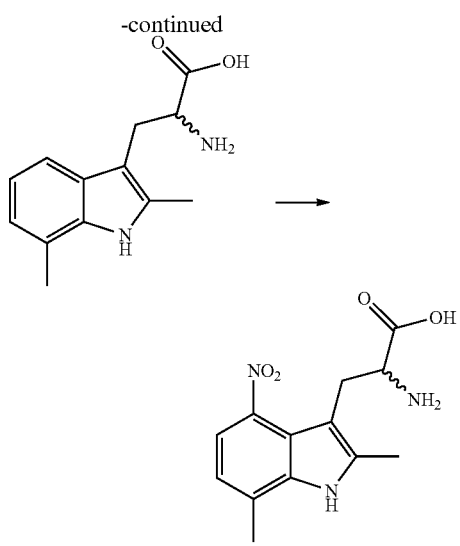

Example 170 can be prepared from 2,7-dimethyl-1H-indole as shown above.

Example 171: Preparation of 2-amino-3-(2,4-dimethyl-7-nitro-1H-indol-3-yl)propanoic acid (171)

Example 171 can be prepared from 2,4-dimethyl-1H-indole as shown above.

Example 172: Preparation of 2-amino-3-(6-fluoro-2-methyl-4-nitro-1H-indol-3-yl)propanoic acid (172)

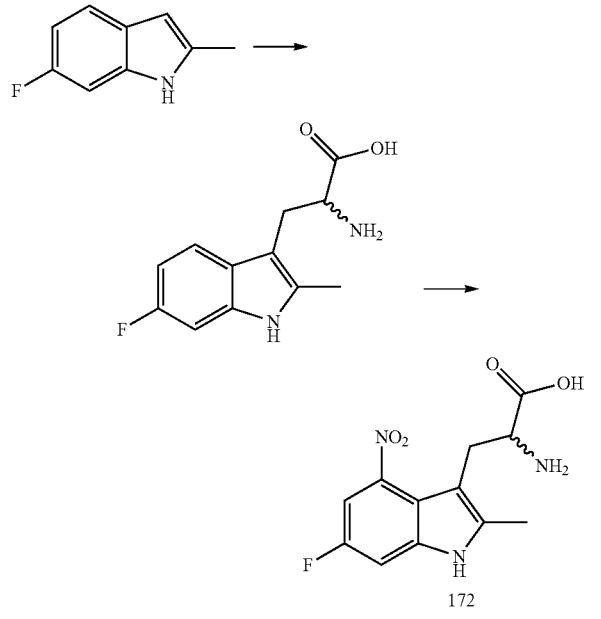

172

Example 172 can be prepared from 6-fluoro-2-methyl-1H-indole as shown above.

Example 173: Preparation of 2-amino-3-(7-fluoro-2-methyl-4-nitro-1H-indol-3-yl)propanoic acid (173)

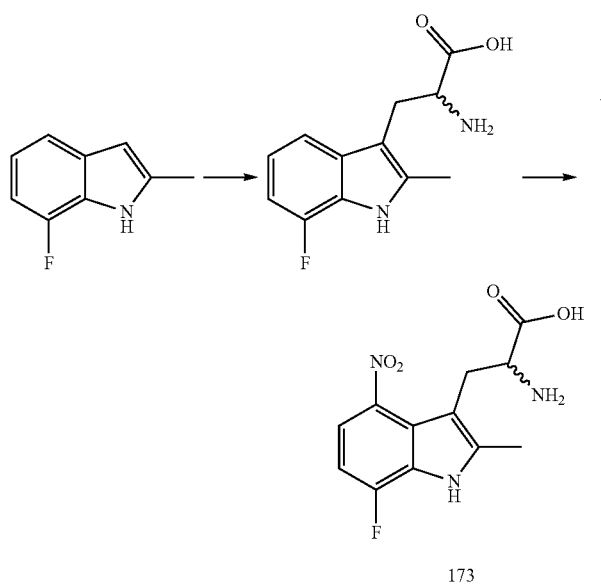

173

Example 173 can be prepared from 7-fluoro-2-methyl-indole as shown above.

Example 174: Preparation of 2-amino-3-(4-fluoro-2-methyl-7-nitro-1H-indol-3-yl)propanoic acid (174)

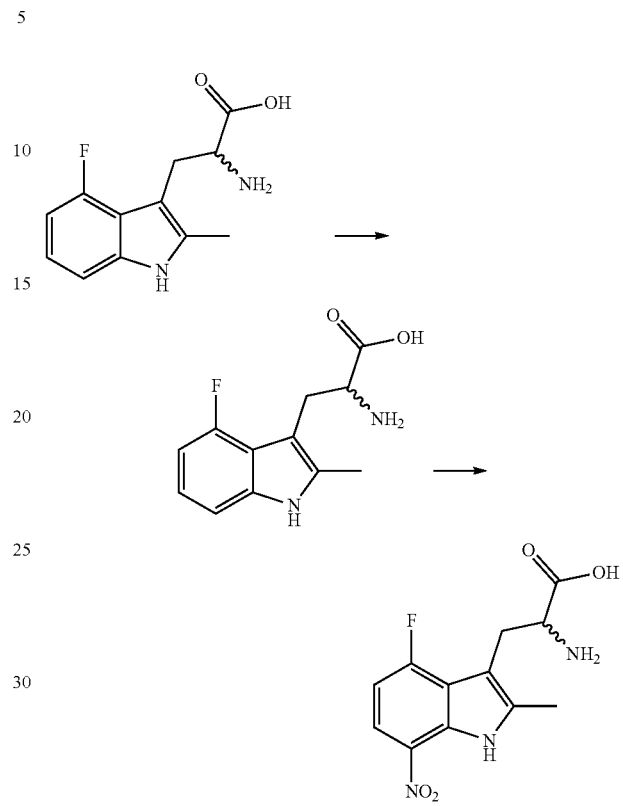

174

Example 174 can be prepared from 4-fluoro-2-methyl-indole as shown above.

Example 175: Preparation of 2-amino-3-(5-chloro-2-methyl-4-nitro-1H-indol-3-yl)propanoic acid (175)

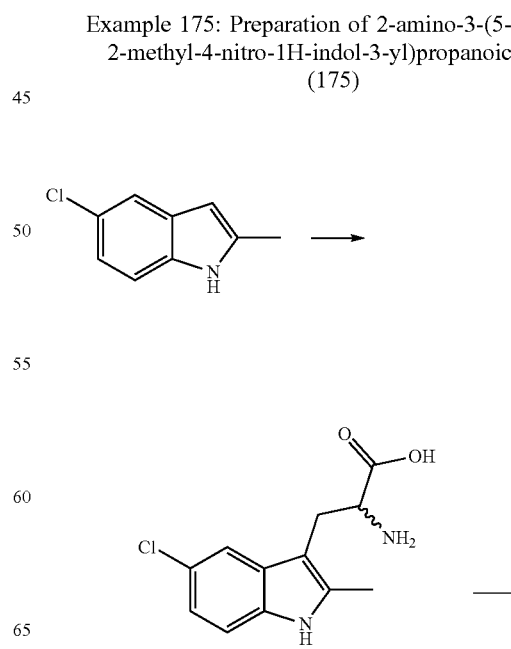

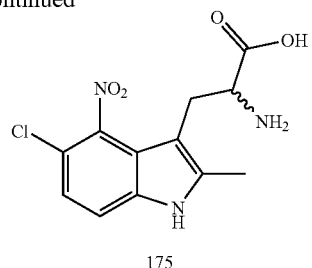

175

Example 175 can be prepared from 5-chloro-2-methyl-indole as shown above.

Example 176: Preparation of 2-amino-3-(6-chloro-2-methyl-4-nitro-1H-indol-3-yl)propanoic acid (176)

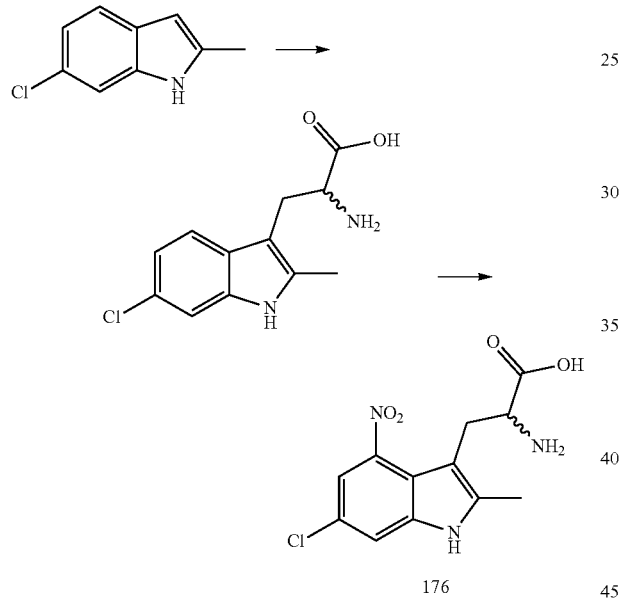

176

Example 176 can be prepared from 6-chloro-2-methyl-indole as shown above.

Example 177: Preparation of 2-amino-3-(7-chloro-2-methyl-4-nitro-1H-indol-3-yl)propanoic acid (177)

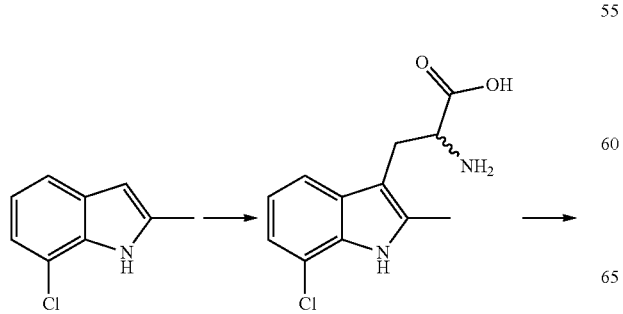

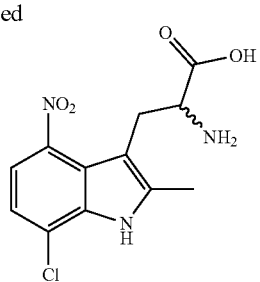

177

Example 177 can be prepared from 7-chloro-2-methyl-indole as shown above.

Example 178: Preparation of 2-amino-3-(4-chloro-2-methyl-7-nitro-1H-indol-3-yl)propanoic acid (178)

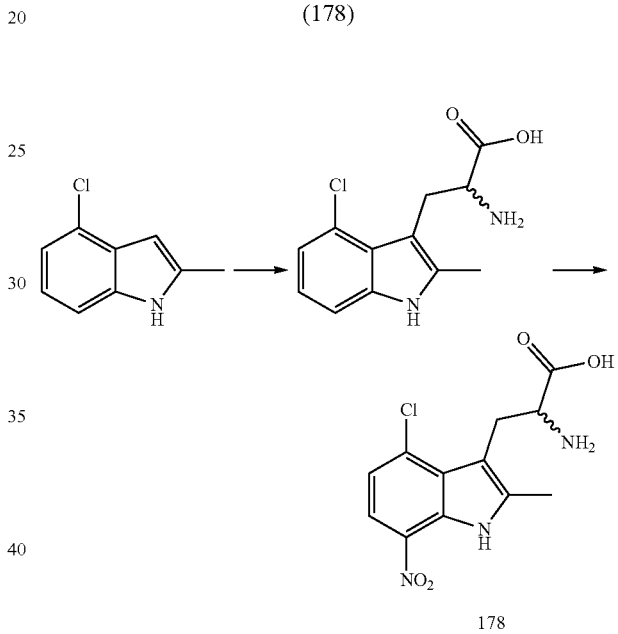

178

Example 178 can be prepared from 4-chloro-2-methyl-indole as shown above.

Example 179: Preparation of 2-amino-3-(5-bromo-2-methyl-4-nitro-1H-indol-3-yl)propanoic acid (179)

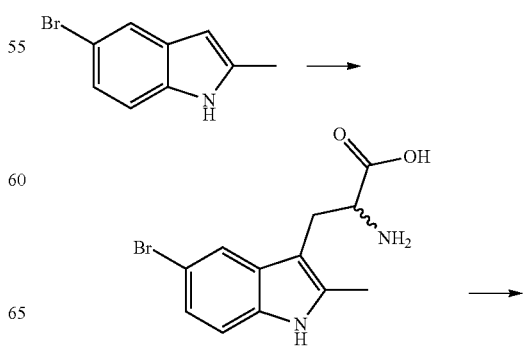

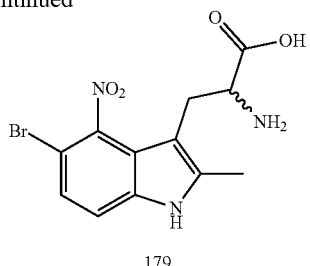

179

Example 179 can be prepared from 5-bromo-2-methyl-indole as shown above.

Example 180: Preparation of 2-amino-3-(6-bromo-2-methyl-4-nitro-1H-indol-3-yl)propanoic acid (180)

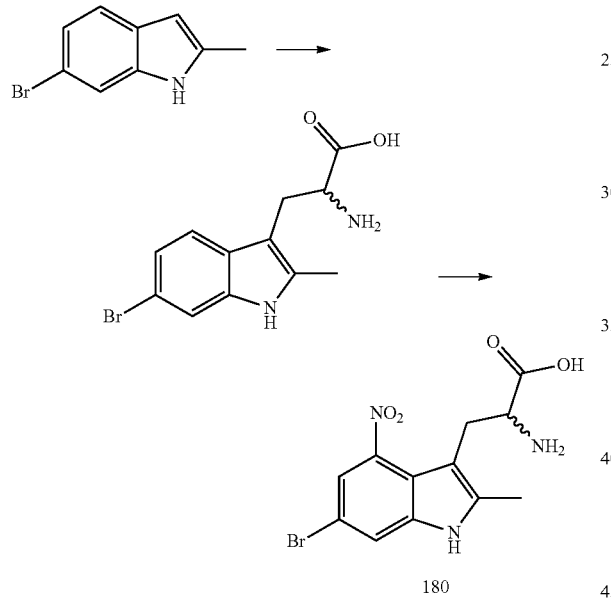

180

Example 180 can be prepared from 6-bromo-2-methyl-indole as shown above.

Example 181: Preparation of 2-amino-3-(7-bromo-2-methyl-4-nitro-1H-indol-3-yl)propanoic acid (181)

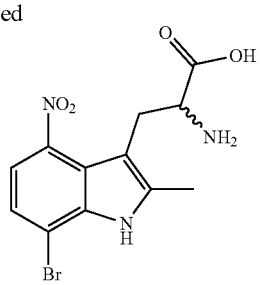

181

Example 181 can be prepared from 7-bromo-2-methyl-indole as shown above.

Example 182: Preparation of 2-amino-3-(4-bromo-2-methyl-7-nitro-1H-indol-3-yl)propanoic acid (182)

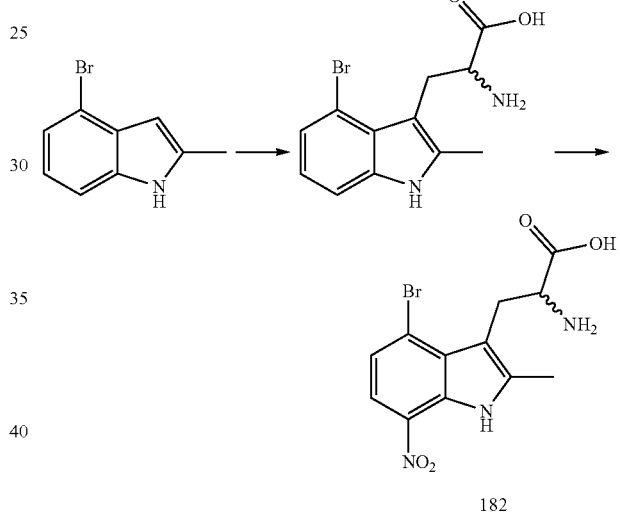

182

Example 182 can be prepared from 4-bromo-2-methyl-indole as shown above.

Example 183: Preparation of 2-amino-3-(5-methoxy-2-methyl-4-nitro-1H-indol-3-yl)propanoic acid (183)

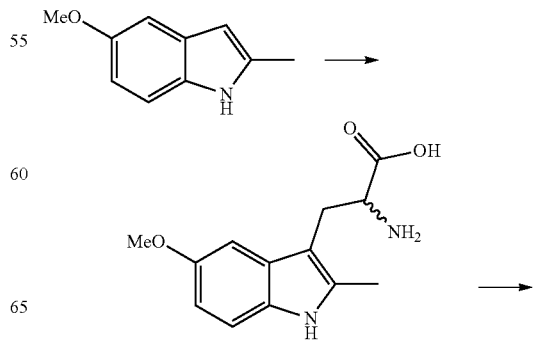

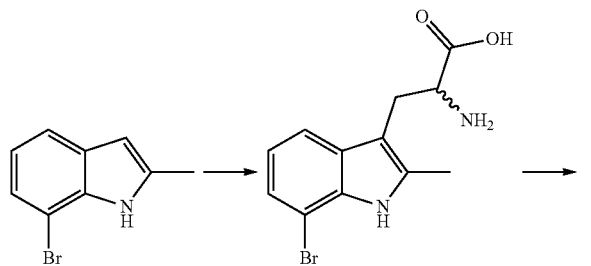

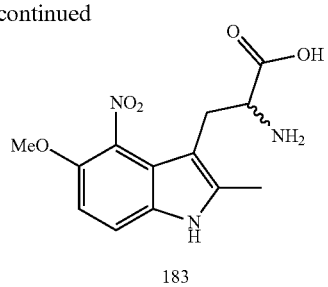

183

Example 183 can be prepared from 5-methoxy-2-methyl-indole as shown above.

Example 184: Preparation of 2-amino-3-(6-methoxy-2-methyl-4-nitro-1H-indol-3-yl)propanoic acid (184)

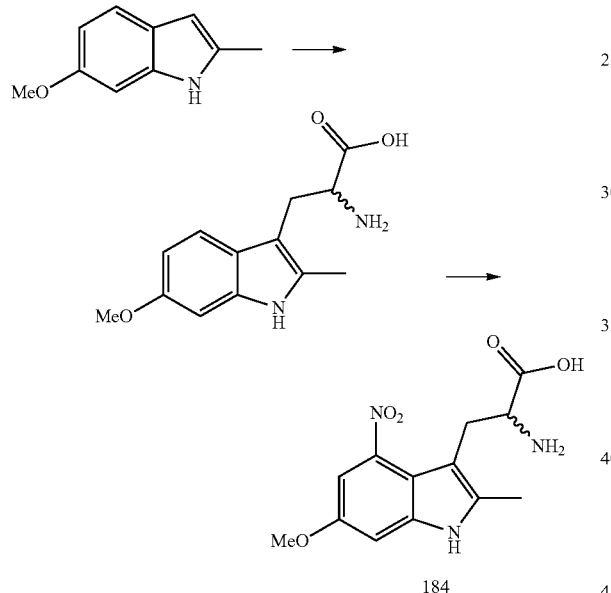

184

Example 184 can be prepared from 6-methoxy-2-methyl-indole as shown above.

Example 185: Preparation of 2-amino-3-(7-methoxy-2-methyl-4-nitro-1H-indol-3-yl)propanoic acid (185)

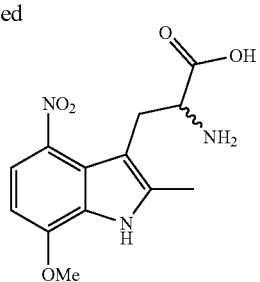

185

Example 185 can be prepared from 7-methoxy-2-methyl-indole as shown above.

Example 186: Preparation of 2-amino-3-(4-methoxy-2-methyl-7-nitro-1H-indol-3-yl)propanoic acid (186)

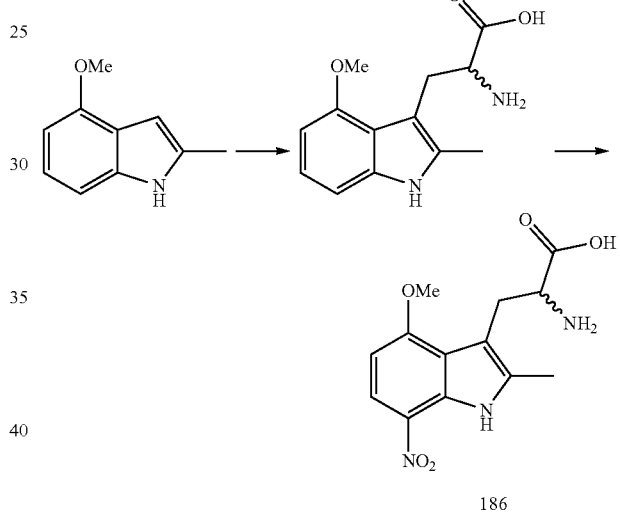

186

Example 186 can be prepared from 4-methoxy-2-methyl-indole as shown above.

Example 187: Preparation of 2-amino-3-(5-amino-2-methyl-4-nitro-1H-indol-3-yl)propanoic acid (187)

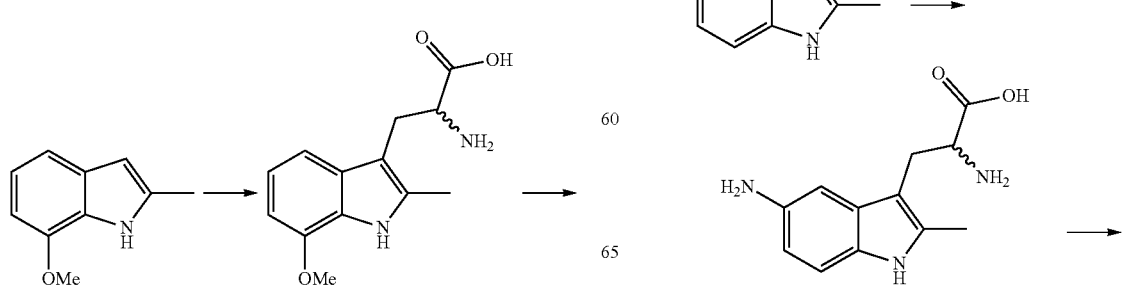

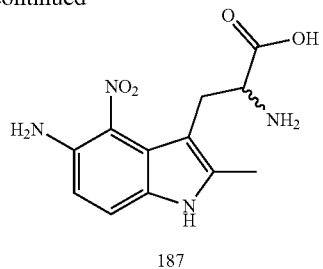

187

Example 187 can be prepared from 5-amino-2-methyl-indole as shown above.

Example 188: Preparation of 2-amino-3-(6-amino-2-methyl-4-nitro-1H-indol-3-yl)propanoic acid (188)

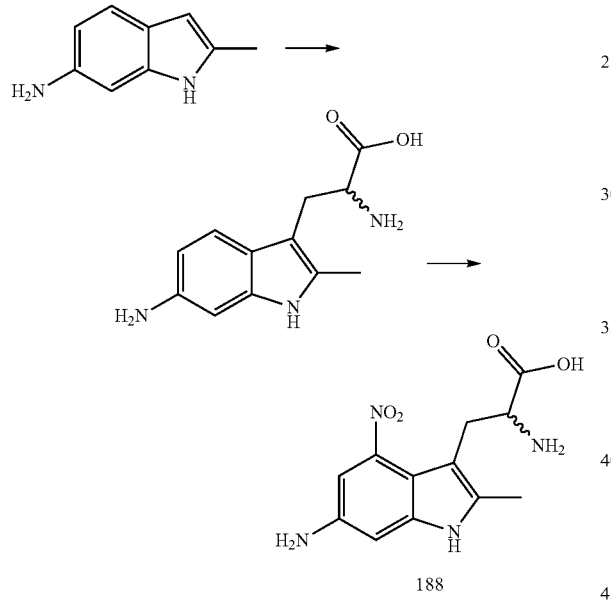

188

Example 188 can be prepared from 6-amino-2-methyl-indole as shown above.

Example 189: Preparation of 2-amino-3-(7-amino-2-methyl-4-nitro-1H-indol-3-yl)propanoic acid (189)

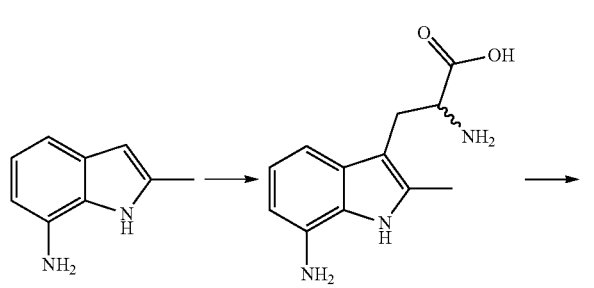

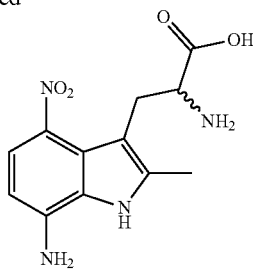

189

Example 189 can be prepared from 7-amino-2-methyl-indole as shown above.

Example 190: Preparation of 2-amino-3-(4-amino-2-methyl-7-nitro-1H-indol-3-yl)propanoic acid (190)

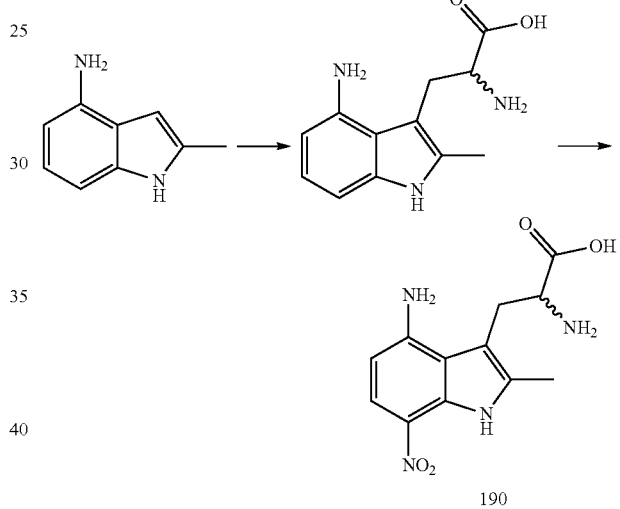

190

Example 190 can be prepared from 4-amino-2-methyl-indole as shown above.

Example 191: Preparation of 2-amino-3-(5-hydroxy-2-methyl-4-nitro-1H-indol-3-yl)propanoic acid (191)

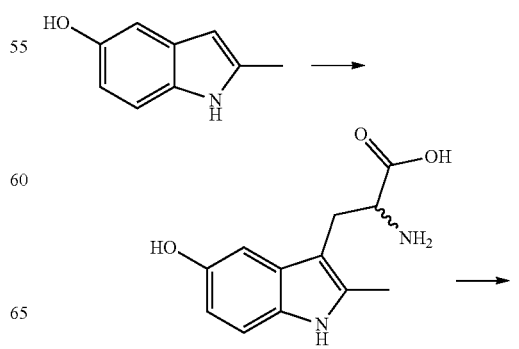

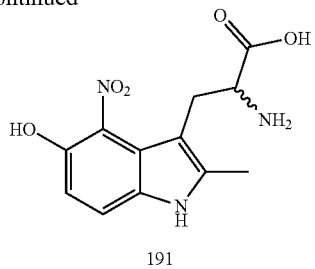
191

Example 191 can be prepared from 5-hydroxy-2-methyl-indole as shown above.

Example 192: Preparation of 2-amino-3-(6-hydroxy-2-methyl-4-nitro-1H-indol-3-yl)propanoic acid (192)

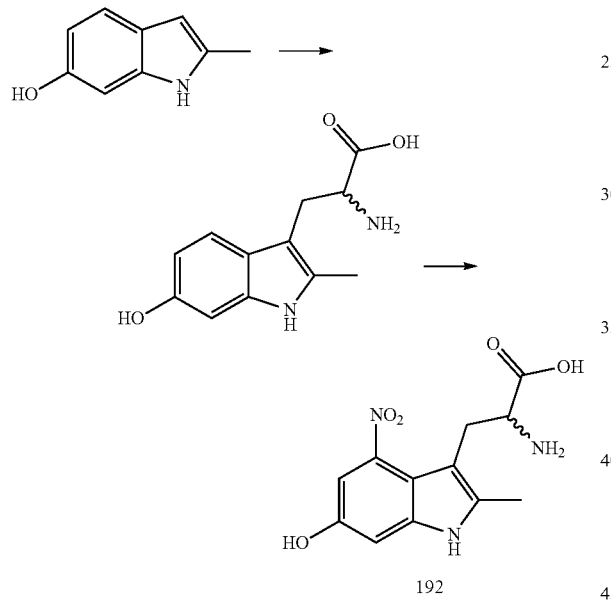
192

Example 192 can be prepared from 6-hydroxy-2-methyl-indole as shown above.

Example 193: Preparation of 2-amino-3-(7-hydroxy-2-methyl-4-nitro-1H-indol-3-yl)propanoic acid (193)

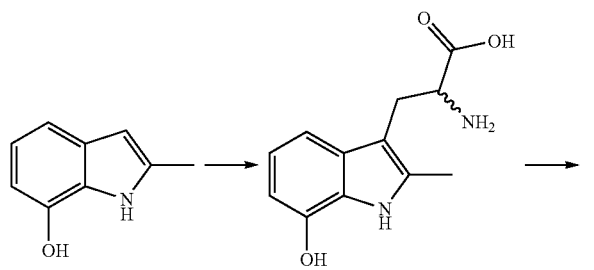

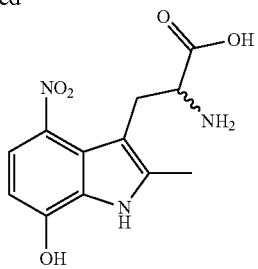
193

Example 193 can be prepared from 7-hydroxy-2-methyl-indole as shown above.

Example 194: Preparation of 2-amino-3-(4-hydroxy-2-methyl-7-nitro-1H-indol-3-yl)propanoic acid (194)

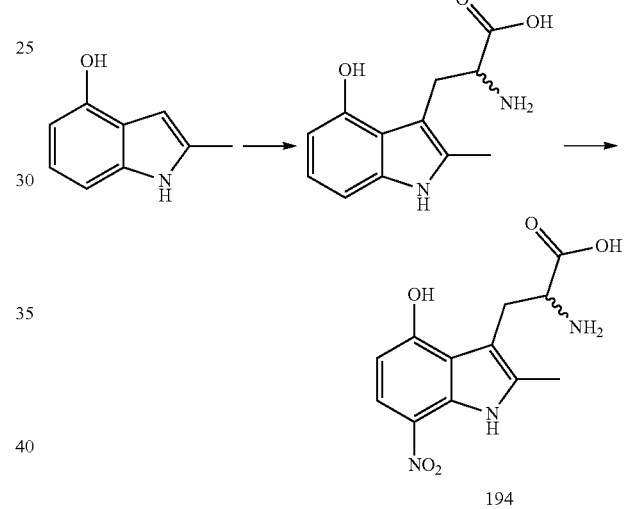
194

Example 194 can be prepared from 4-hydroxy-2-methyl-indole as shown above.

Example 195: Preparation of 2-amino-3-(2-methyl-4-nitro-5-phenyl-1H-indol-3-yl)propanoic acid (195)

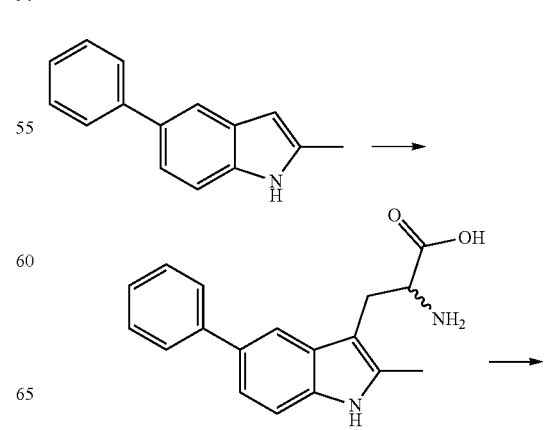

153

-continued

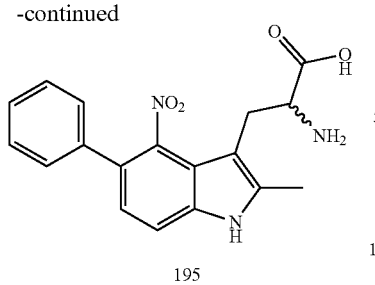

195

Example 195 can be prepared from 5-phenyl-2-methyl-indole as shown above.

Example 196: Preparation of 2-amino-3-(2-methyl-4-nitro-6-phenyl-1H-indol-3-yl)propanoic acid (196)

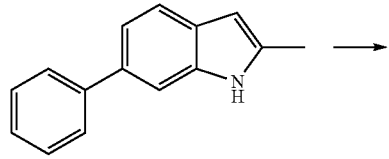

154

Example 197: Preparation of 2-amino-3-(2-methyl-4-nitro-7-phenyl-1H-indol-3-yl)propanoic acid (197)

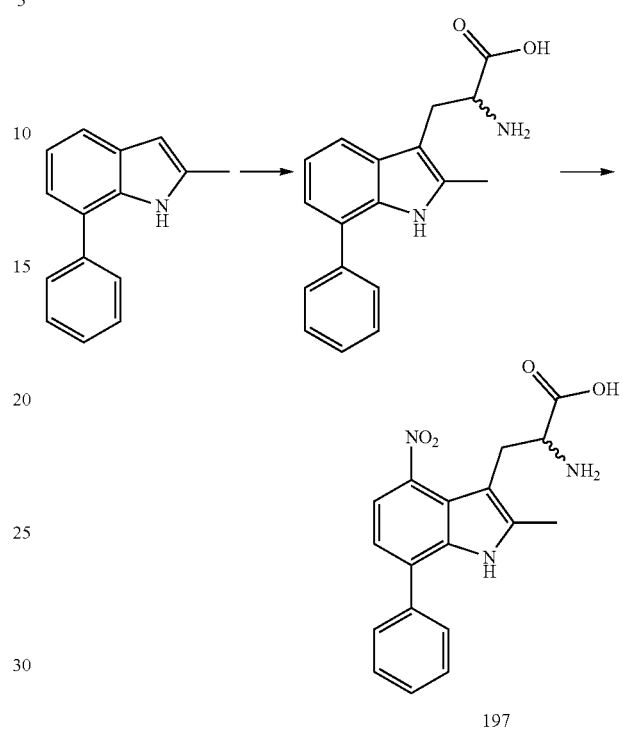

197

Example 197 can be prepared from 7-phenyl-2-methyl-indole as shown above.

Example 198: Preparation of 2-amino-3-(2-methyl-7-nitro-4-phenyl-1H-indol-3-yl)propanoic acid (198)

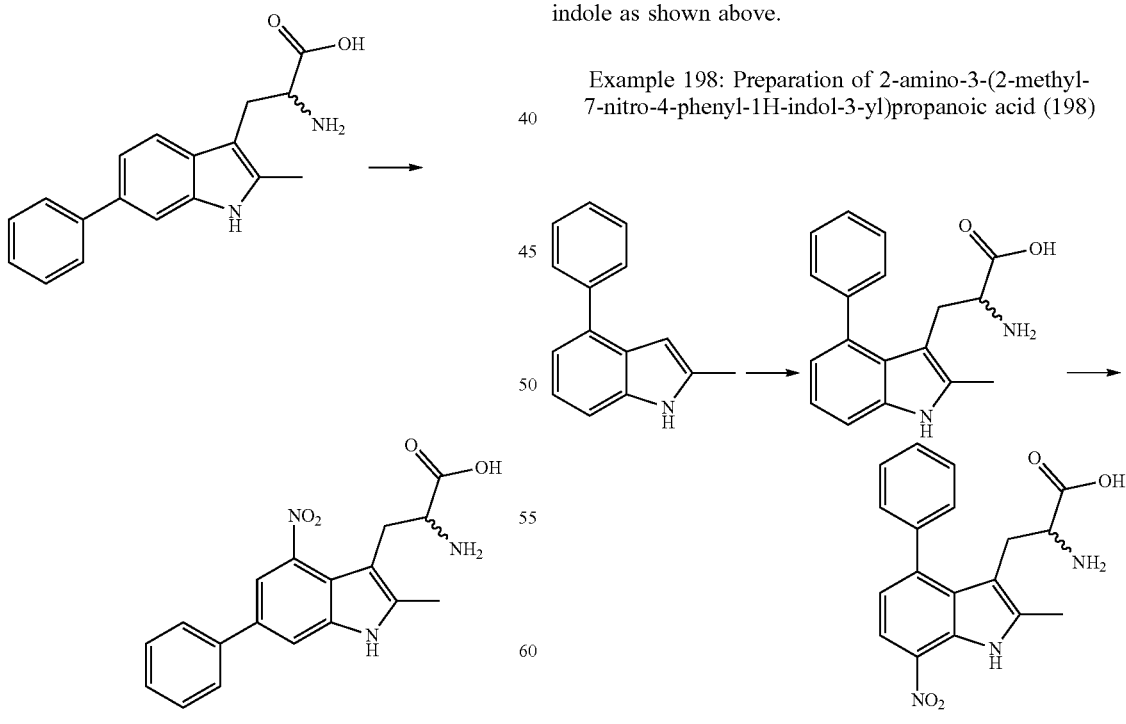

196

198

Example 196 can be prepared from 6-phenyl-2-methyl-indole as shown above.

Example 198 can be prepared from 4-phenyl-2-methyl-indole as shown above.

Example 199: Preparation of 2-amino-3-(5-cyclopropyl-2-methyl-4-nitro-1H-indol-3-yl)propanoic acid (199)

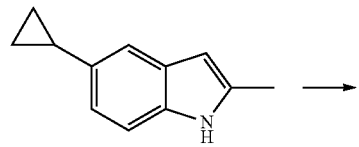

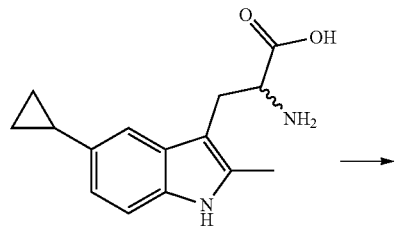

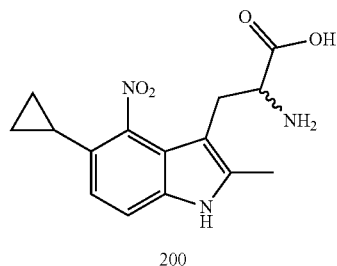

200

Example 199 can be prepared from 5-cyclopropyl-2-methyl-indole as shown above.

Example 200: Preparation of 2-amino-3-(6-cyclopropyl-2-methyl-4-nitro-1H-indol-3-yl)propanoic acid (200)

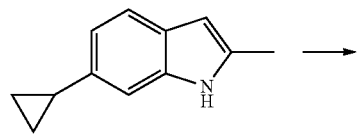

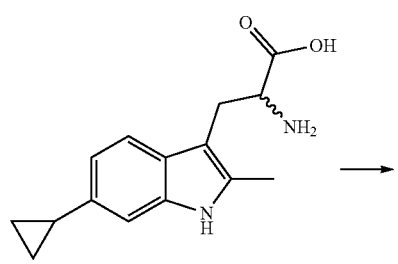

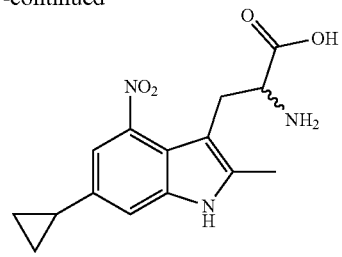

200

Example 200 can be prepared from 6-cyclopropyl-2-methyl-indole as shown above.

Example 201: Preparation of 2-amino-3-(7-cyclopropyl-2-methyl-4-nitro-1H-indol-3-yl)propanoic acid (201)

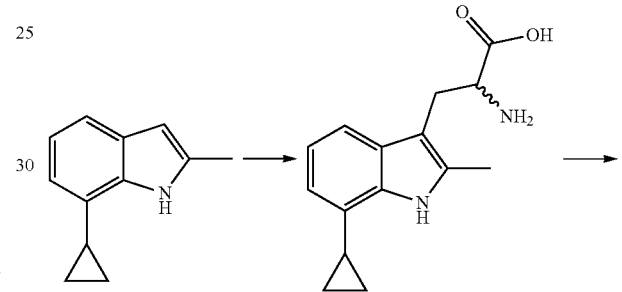

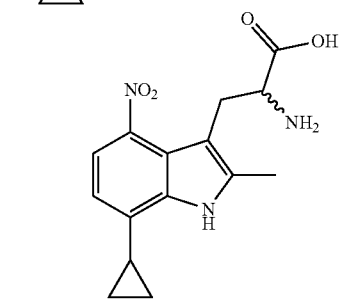

201

Example 201 can be prepared from 7-cyclopropyl-2-methyl-indole as shown above.

Example 202: Preparation of 2-amino-3-(4-cyclopropyl-2-methyl-7-nitro-1H-indol-3-yl)propanoic acid (202)

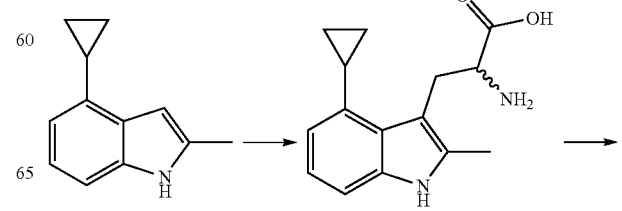

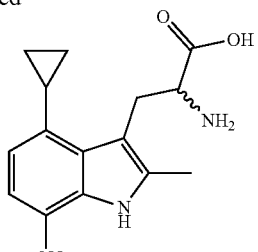

202

Example 202 can be prepared from 4-cyclopropyl-2-methyl-indole as shown above.

Example 203: Preparation of 2-amino-3-(2-methyl-4-nitro-5-vinyl-1H-indol-3-yl)propanoic acid (203)

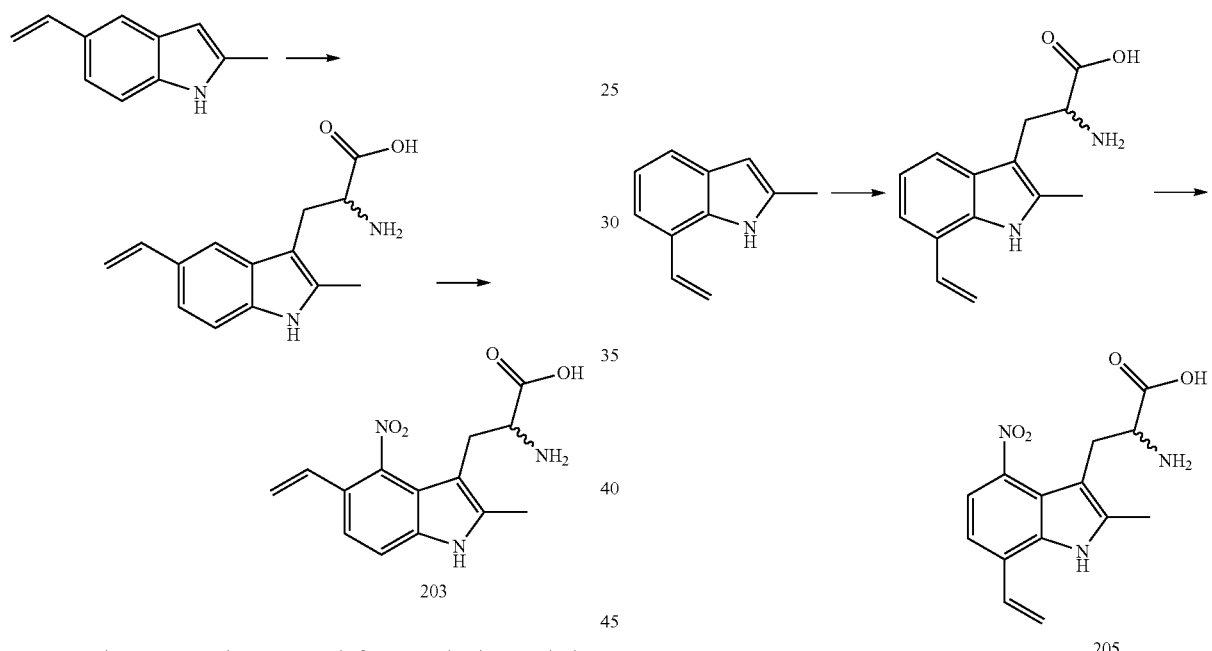

203

Example 203 can be prepared from 5-vinyl-2-methyl-indole as shown above.

Example 204: Preparation of 2-amino-3-(2-methyl-4-nitro-6-vinyl-1H-indol-3-yl)propanoic acid (204)

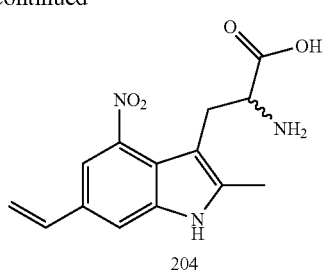

204

Example 204 can be prepared from 6-vinyl-2-methyl-indole as shown above.

Example 205: Preparation of 2-amino-3-(2-methyl-4-nitro-7-vinyl-1H-indol-3-yl)propanoic acid (205)

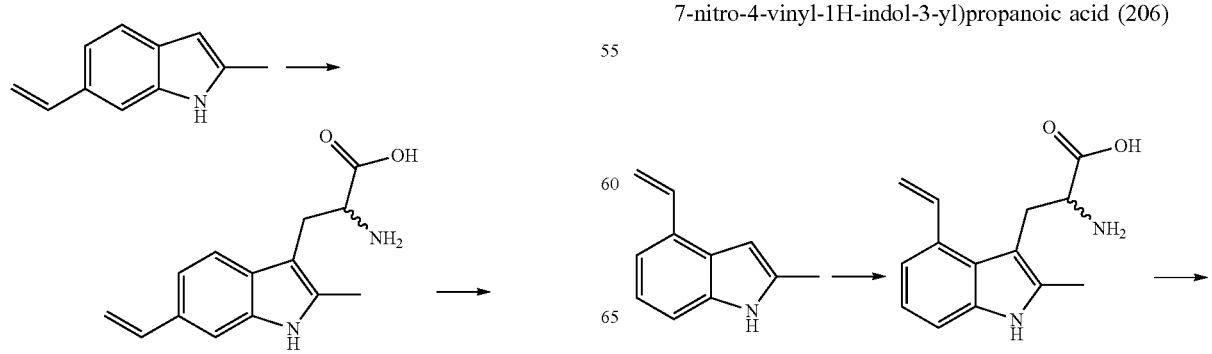

205

Example 205 can be prepared from 7-vinyl-2-methyl-indole as shown above.

Example 206: Preparation of 2-amino-3-(2-methyl-7-nitro-4-vinyl-1H-indol-3-yl)propanoic acid (206)

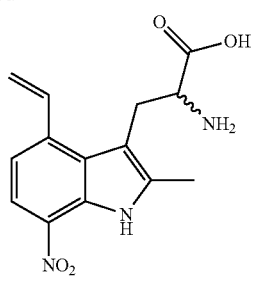

206

Example 206 can be prepared from 4-vinyl-2-methyl-indole as shown above.

Example 207: Preparation of 2-amino-3-(5-ethynyl-2-methyl-4-nitro-1H-indol-3-yl)propanoic acid (207)

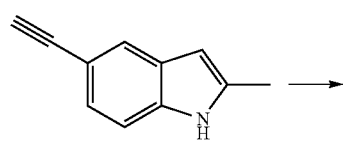

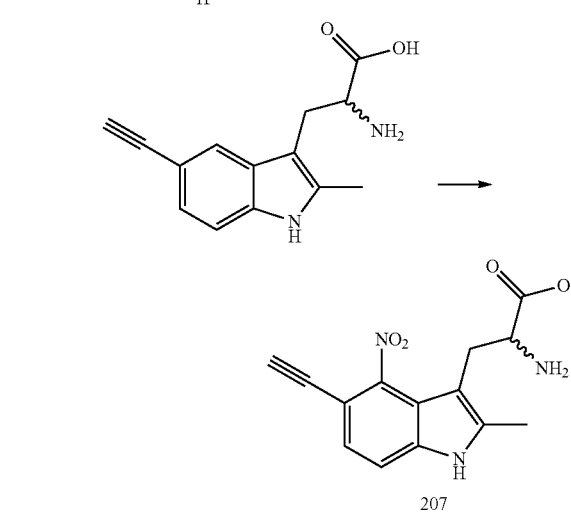

207

Example 207 can be prepared from 5-ethynyl-2-methyl-indole as shown above.

Example 208: Preparation of 2-amino-3-(6-ethynyl-2-methyl-4-nitro-1H-indol-3-yl)propanoic acid (208)

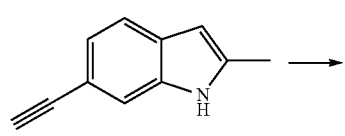

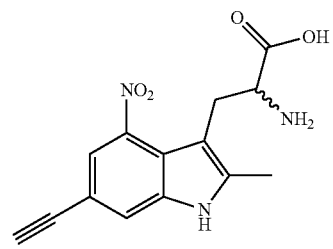

208

Example 208 can be prepared from 6-ethynyl-2-methyl-indole as shown above.

Example 209: Preparation of 2-amino-3-(7-ethynyl-2-methyl-4-nitro-1H-indol-3-yl)propanoic acid (209)

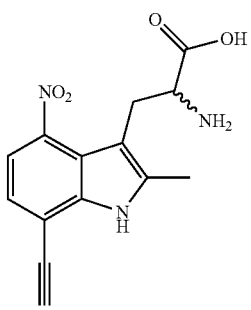

209

Example 209 can be prepared from 7-ethynyl-2-methyl-indole as shown above.

Example 210: Preparation of 2-amino-3-(4-ethynyl-2-methyl-7-nitro-1H-indol-3-yl)propanoic acid (210)

Example 212: Preparation of 2-amino-3-(2-methyl-6-morpholino-4-nitro-1H-indol-3-yl)propanoic acid (212)

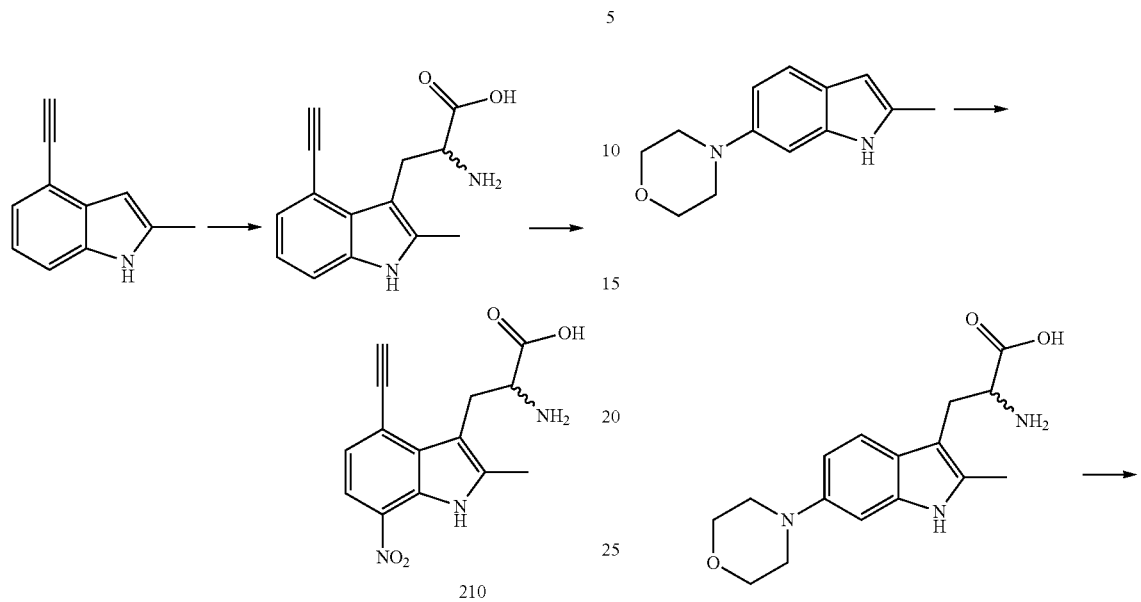

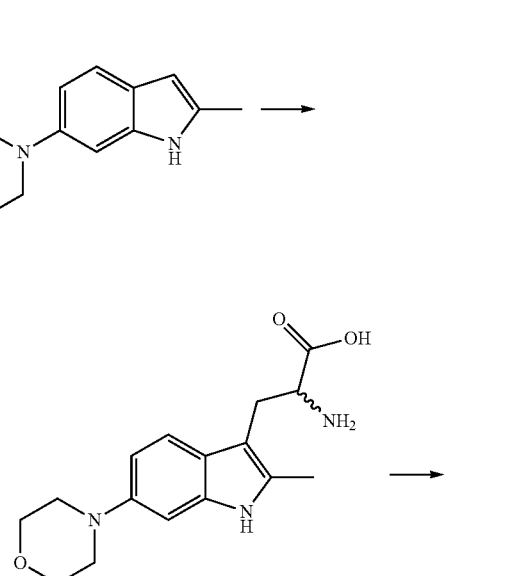

Example 210 can be prepared from 4-ethynyl-2-methyl-indole as shown above.

Example 211: Preparation of 2-amino-3-(2-methyl-5-morpholino-4-nitro-1H-indol-3-yl)propanoic acid (211)

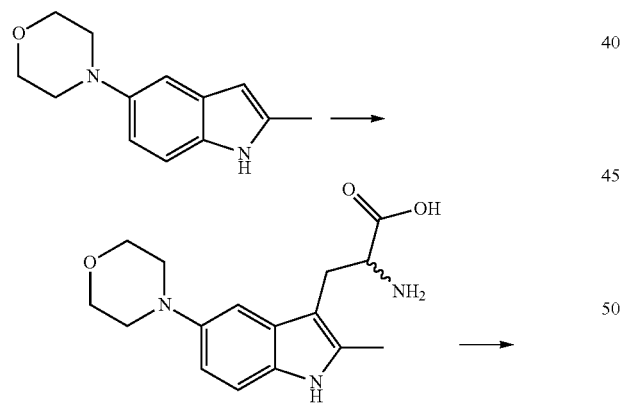

Example 211 can be prepared from 5-morpholino-2-methyl-indole as shown above.

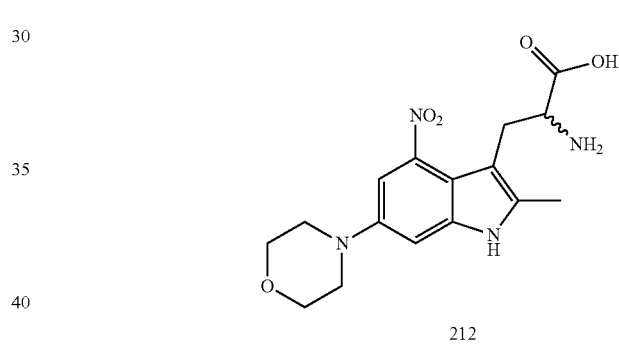

Example 212 can be prepared from 6-morpholino-2-methyl-indole as shown above.

Example 213: Preparation of 2-amino-3-(2-methyl-7-morpholino-4-nitro-1H-indol-3-yl)propanoic acid (213)

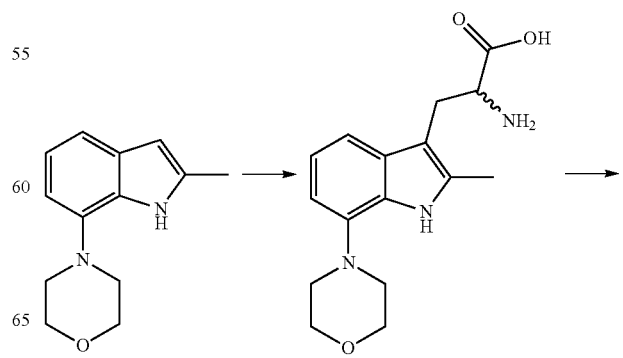

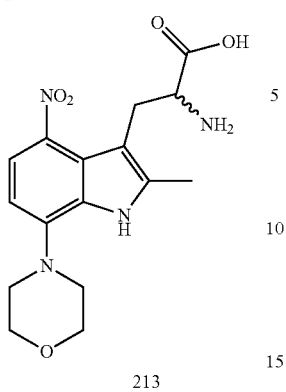

213

Example 213 can be prepared from 7-morpholino-2-methyl-indole as shown above.

Example 214: Preparation of 2-amino-3-(2-methyl-4-morpholino-7-nitro-1H-indol-3-yl)propanoic acid (214)

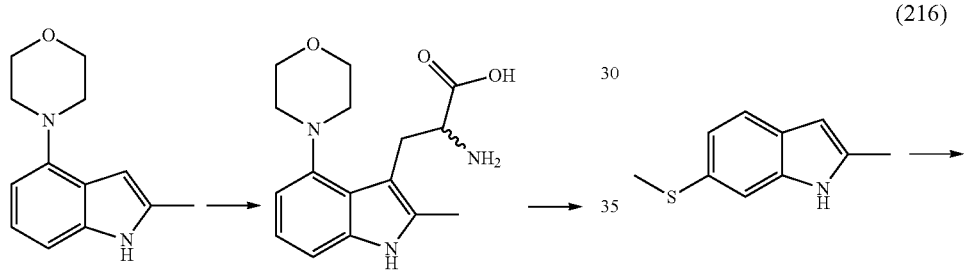

214

Example 214 can be prepared from 4-morpholino-2-methyl-indole as shown above.

Example 215: Preparation of 2-amino-3-(2-methyl-5-(methylthio)-4-nitro-1H-indol-3-yl)propanoic acid (215)

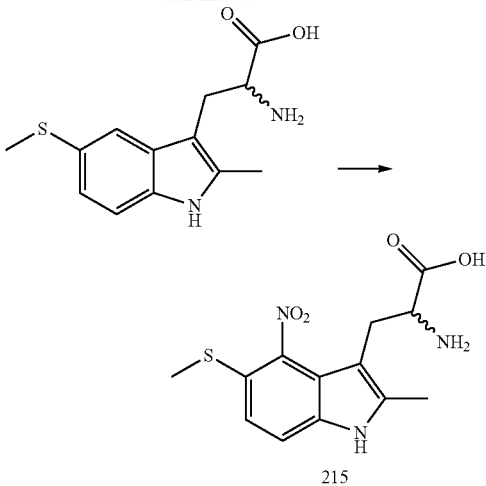

215

Example 215 can be prepared from 5-(methylthio)-2-methyl-indole as shown above.

Example 216: Preparation of 2-amino-3-(2-methyl-6-(methylthio)-4-nitro-1H-indol-3-yl)propanoic acid (216)

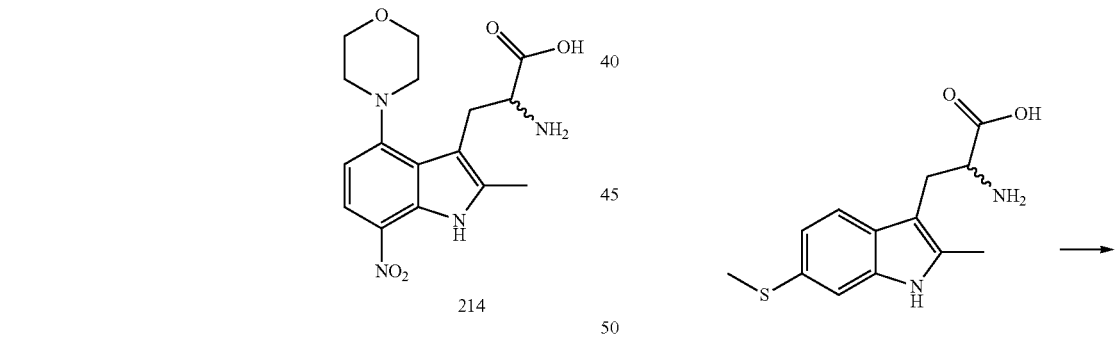

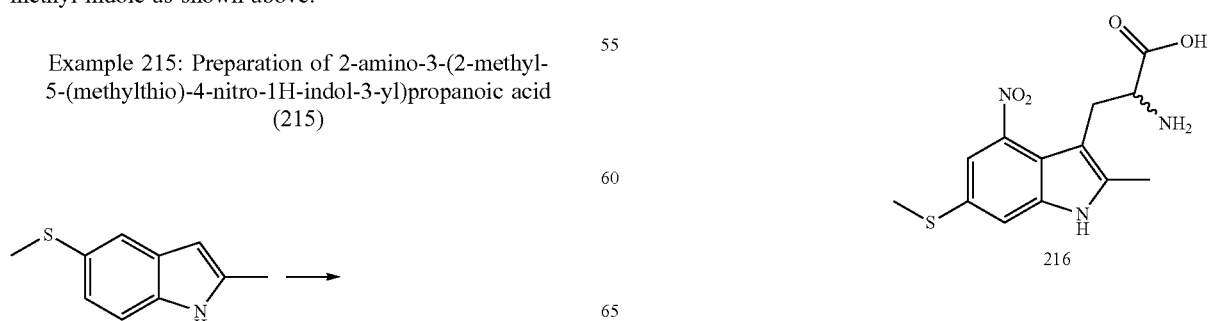

216

Example 216 can be prepared from 6-(methylthio)-2-methyl-indole as shown above.

Example 217: Preparation of 2-amino-3-(2-methyl-7-(methylthio)-4-nitro-1H-indol-3-yl)propanoic acid (217)

Example 219: Preparation of 2-amino-3-(2-methyl-4-nitro-5-(pyridin-4-yl)-1H-indol-3-yl)propanoic acid (219)

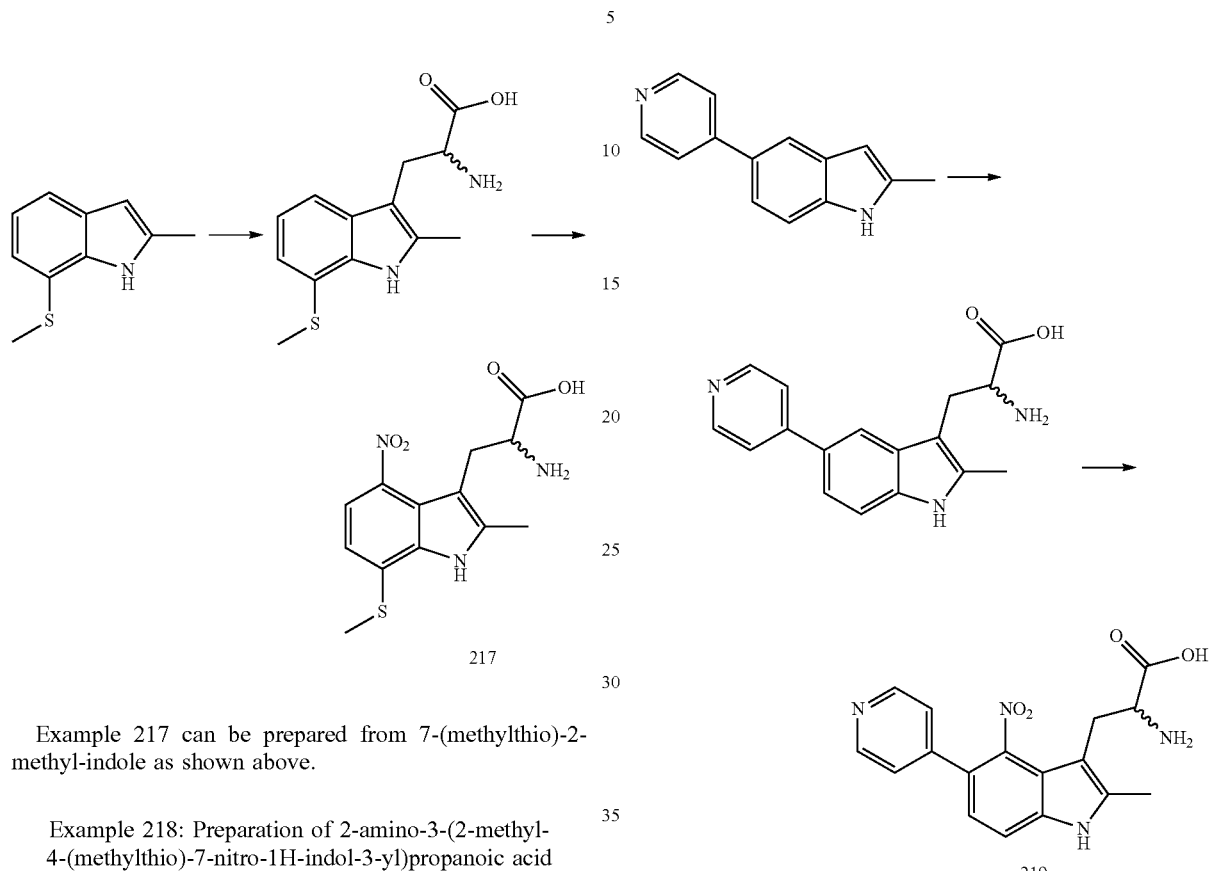

Example 217 can be prepared from 7-(methylthio)-2-methyl-indole as shown above.

Example 218: Preparation of 2-amino-3-(2-methyl-4-(methylthio)-7-nitro-1H-indol-3-yl)propanoic acid (218)

Example 219 can be prepared from 5-(pyridin-4-yl)-2-methyl-indole as shown above.

Example 220: Preparation of 2-amino-3-(2-methyl-4-nitro-6-(pyridin-4-yl)-1H-indol-3-yl)propanoic acid (220)

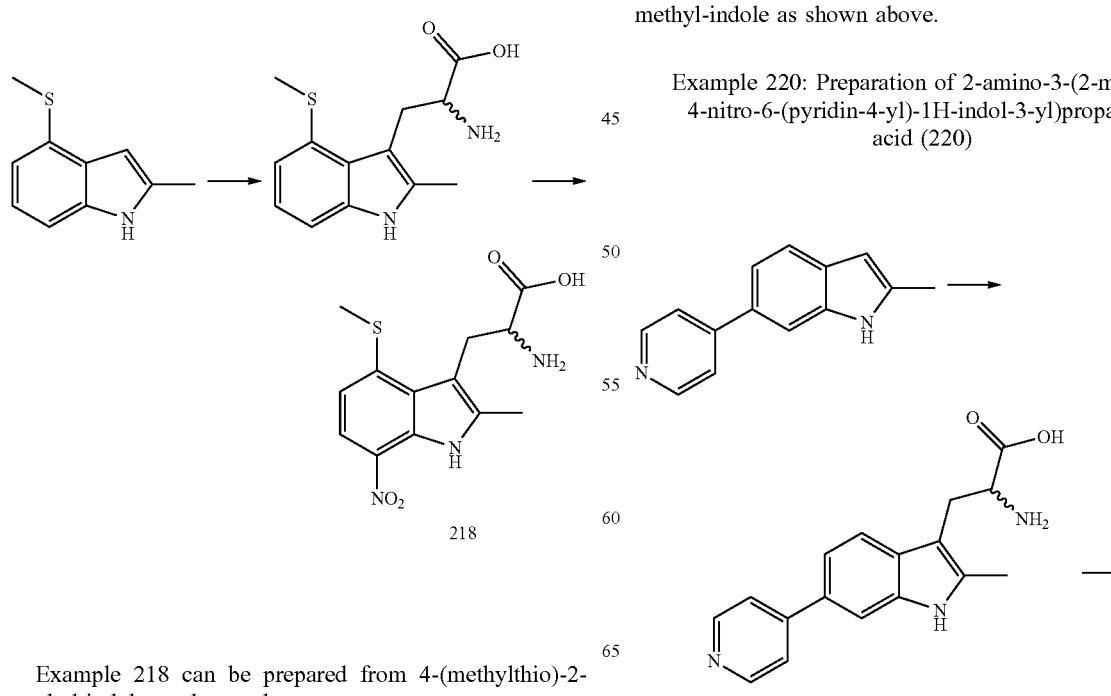

Example 218 can be prepared from 4-(methylthio)-2-methyl-indole as shown above.

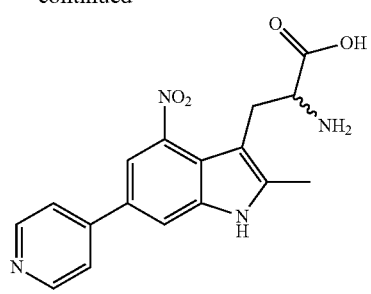

220

Example 220 can be prepared from 6-(pyridin-4-yl)-2-methyl-indole as shown above.

Example 221: Preparation of 2-amino-3-(2-methyl-4-nitro-7-(pyridin-4-yl)-1H-indol-3-yl)propanoic acid (221)

221

Example 221 can be prepared from 7-(pyridin-4-yl)-2-methyl-indole as shown above.

Example 222: Preparation of 2-amino-3-(2-methyl-7-nitro-4-(pyridin-4-yl)-1H-indol-3-yl)propanoic acid (222)

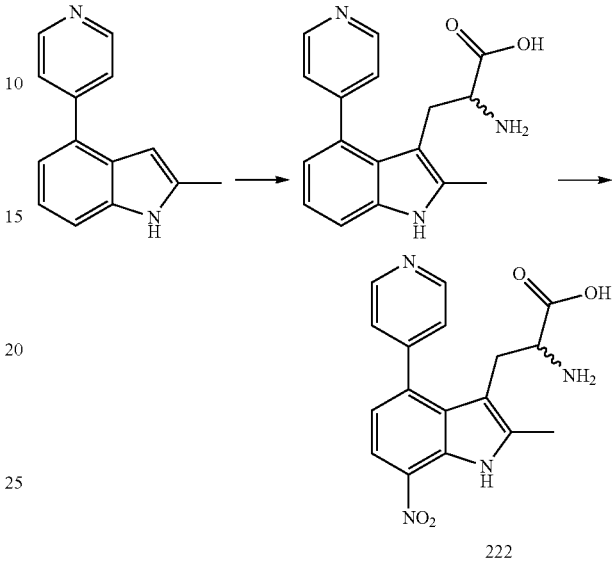

222

Example 222 can be prepared from 4-(pyridin-4-yl)-2-methyl-indole as shown above.

Example 223: Preparation of 2-amino-3-(1,2,5-trimethyl-4-nitro-1H-indol-3-yl)propanoic acid (223)

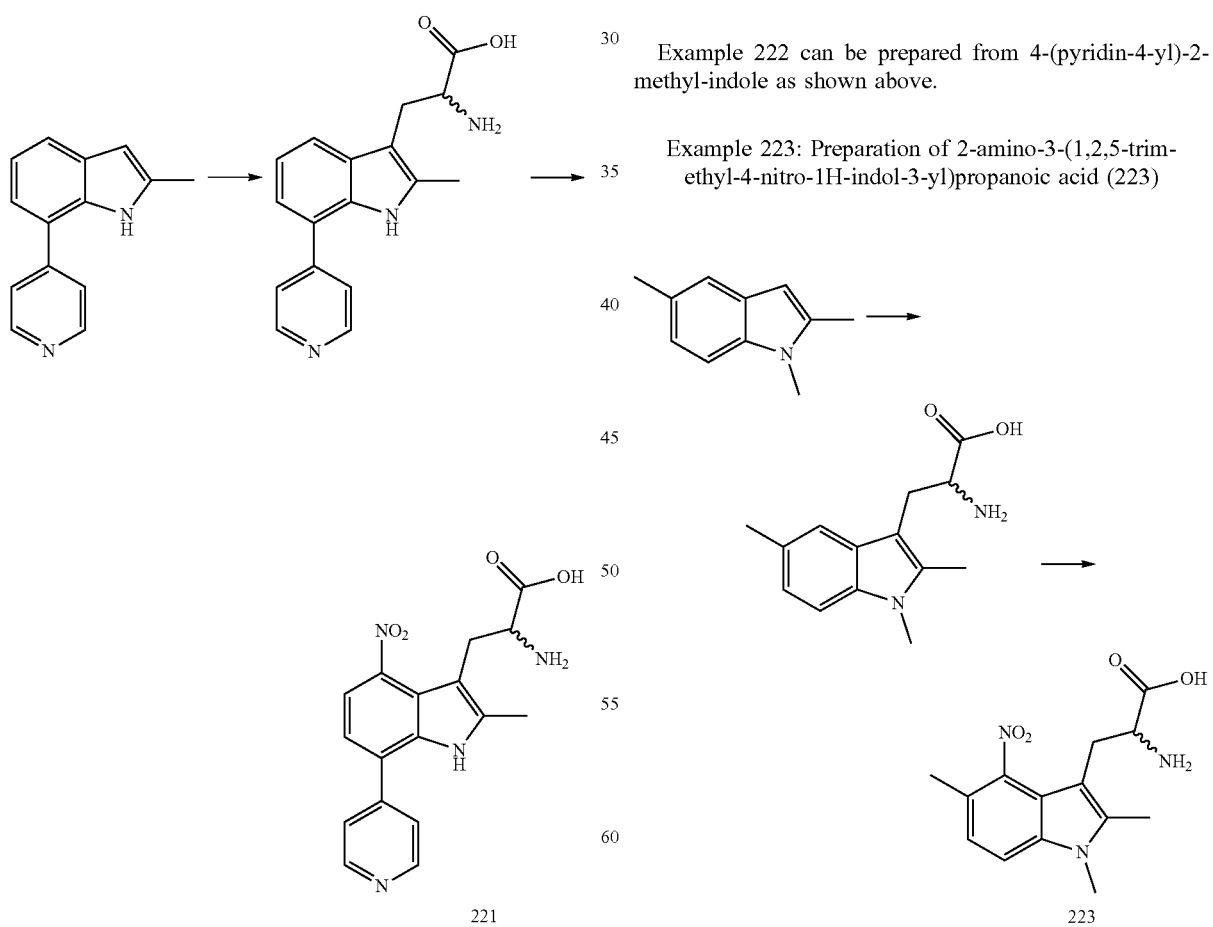

223

Example 223 can be prepared from 1,2,5-trimethyl-1H-indole as shown above.

Example 224: Preparation of 2-amino-3-(1,2,6-trimethyl-4-nitro-1H-indol-3-yl)propanoic acid (224)

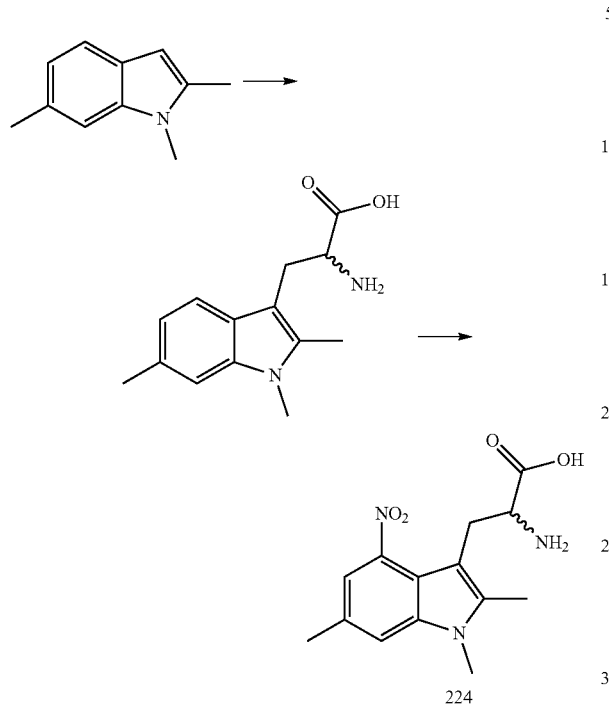

Example 224 can be prepared from 1,2,6-trimethyl-1H-indole as shown above.

Example 225: Preparation of 2-amino-3-(1,2,7-trimethyl-4-nitro-1H-indol-3-yl)propanoic acid (225)

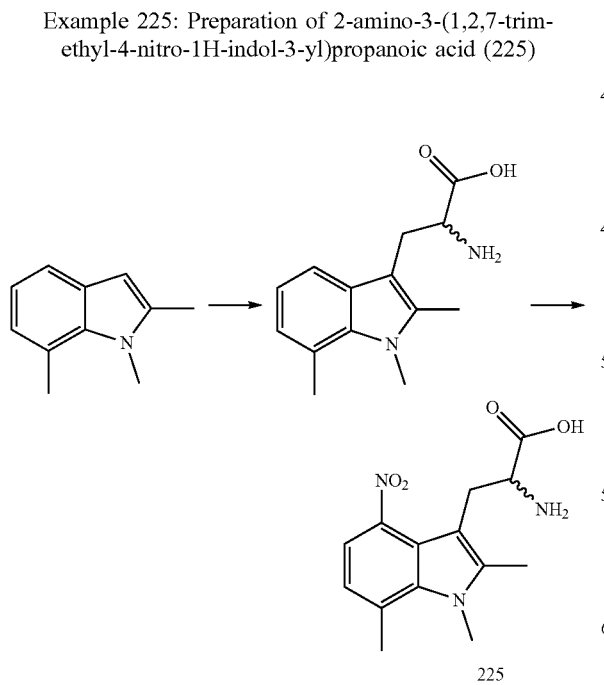

Example 225 can be prepared from 1,2,7-trimethyl-1H-indole as shown above.

Example 226: Preparation of 2-amino-3-(1,2,4-trimethyl-7-nitro-1H-indol-3-yl)propanoic acid (226)

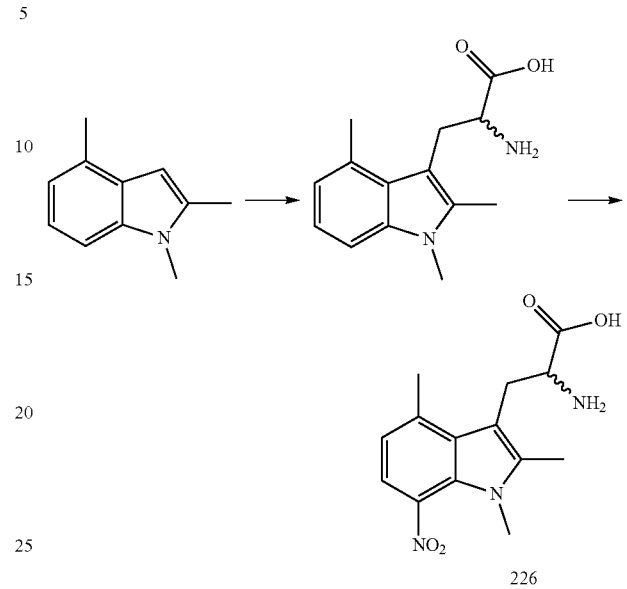

Example 226 can be prepared from 1,2,4-trimethyl-1H-indole as shown above.

Example 227: Preparation of 2-amino-3-(6-fluoro-1,2-dimethyl-4-nitro-1H-indol-3-yl)propanoic acid (227)

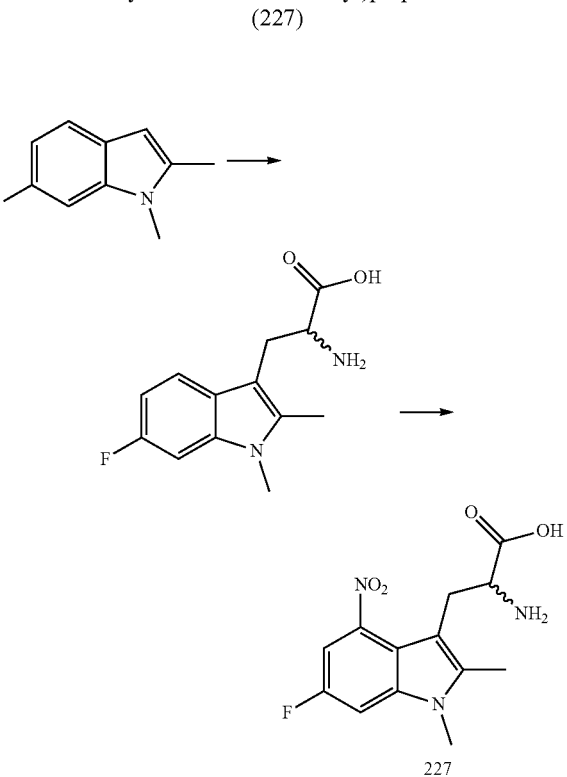

Example 227 can be prepared from 6-fluoro-1,2-dimethyl-1H-indole as shown above.

Example 228: Preparation of 2-amino-3-(7-fluoro-1,2-dimethyl-4-nitro-1H-indol-3-yl)propanoic acid (228)

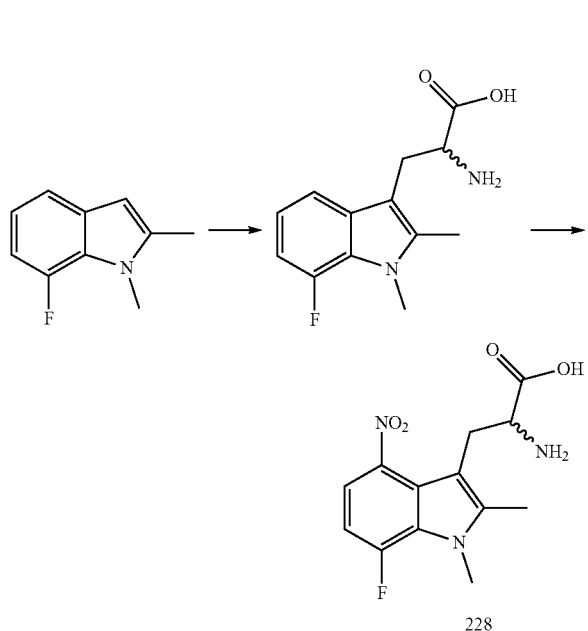

Example 228 can be prepared from 7-fluoro-1,2-dimethyl-indole as shown above.

Example 229: Preparation of 2-amino-3-(4-fluoro-1,2-dimethyl-7-nitro-1H-indol-3-yl)propanoic acid (229)

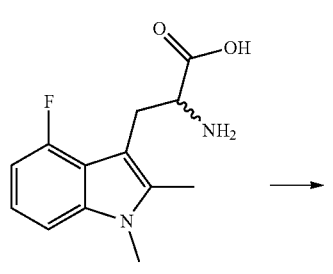

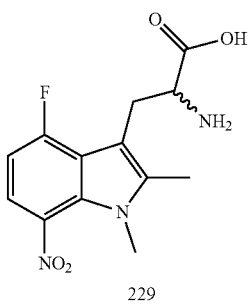

229

Example 229 can be prepared from 4-fluoro-1,2-dimethyl-indole as shown above.

Example 230: Preparation of 2-amino-3-(5-chloro-1,2-dimethyl-4-nitro-1H-indol-3-yl)propanoic acid (230)

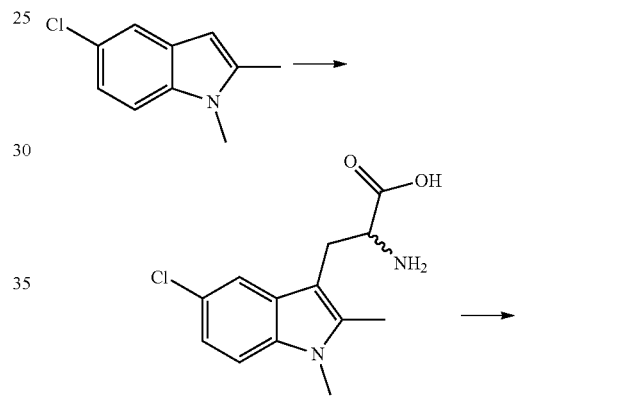

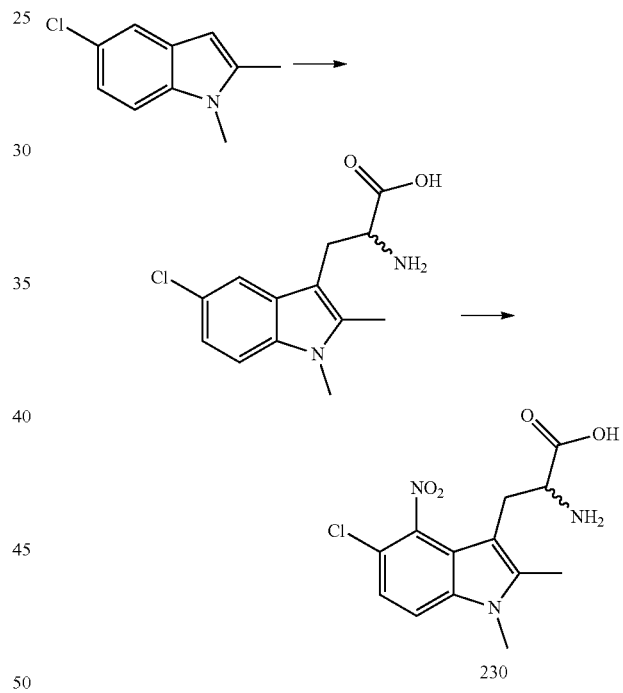

230

Example 230 can be prepared from 5-chloro-1,2-dimethyl-indole as shown above.

Example 231: Preparation of 2-amino-3-(6-chloro-1,2-dimethyl-4-nitro-1H-indol-3-yl)propanoic acid (231)

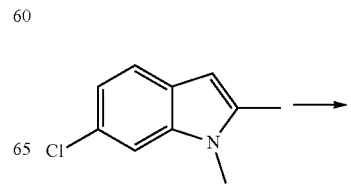

-continued

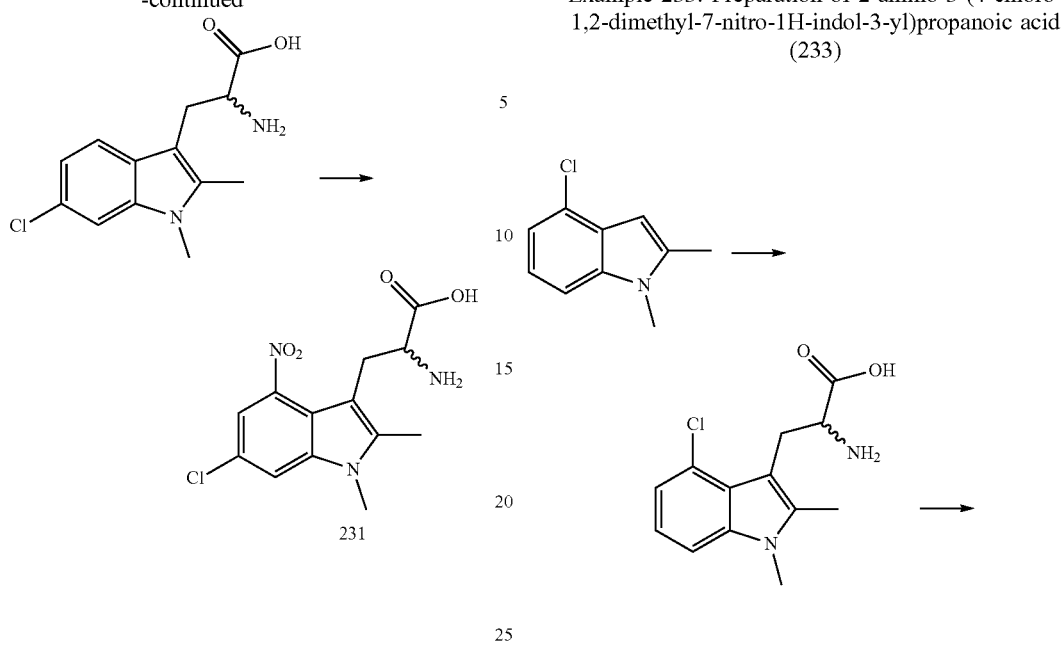

231

Example 231 can be prepared from 6-chloro-1,2-dimethyl-indole as shown above.

Example 232: Preparation of 2-amino-3-(7-chloro-1,2-dimethyl-4-nitro-1H-indol-3-yl)propanoic acid (232)

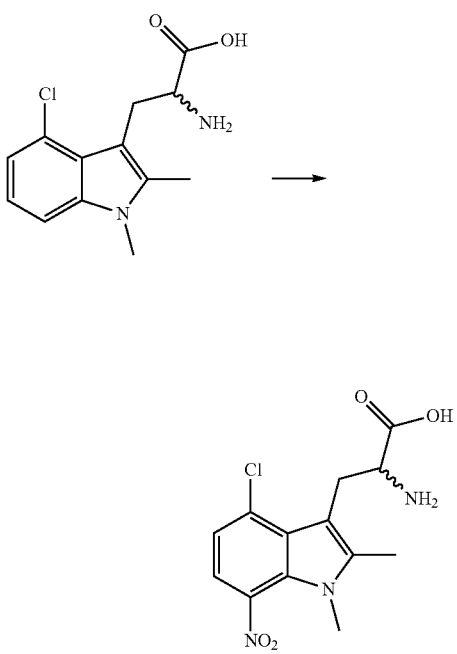

232

Example 232 can be prepared from 7-chloro-1,2-dimethyl-indole as shown above.

Example 233: Preparation of 2-amino-3-(4-chloro-1,2-dimethyl-7-nitro-1H-indol-3-yl)propanoic acid (233)

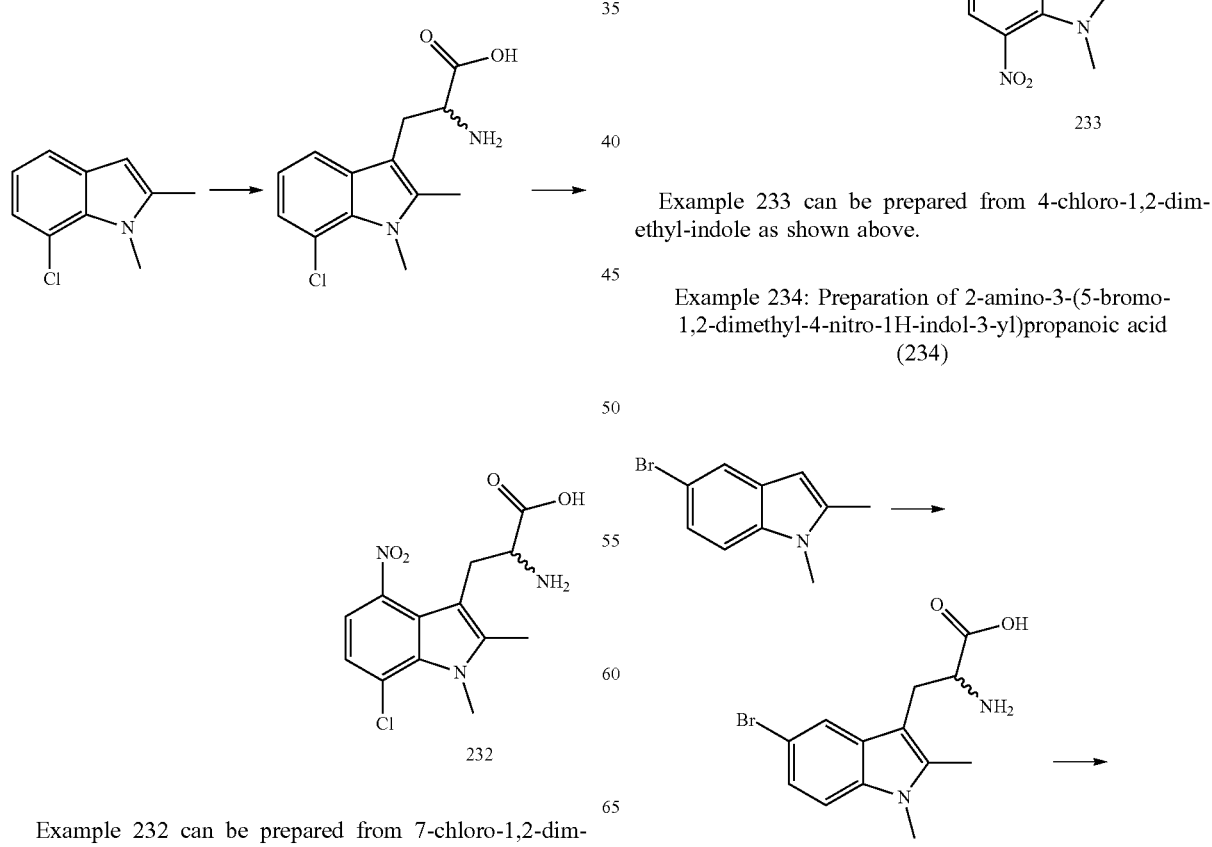

233

Example 233 can be prepared from 4-chloro-1,2-dimethyl-indole as shown above.

Example 234: Preparation of 2-amino-3-(5-bromo-1,2-dimethyl-4-nitro-1H-indol-3-yl)propanoic acid (234)

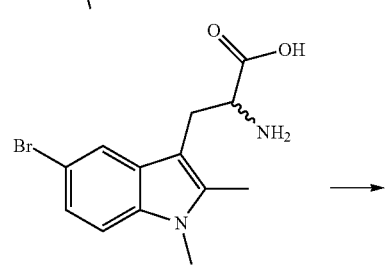

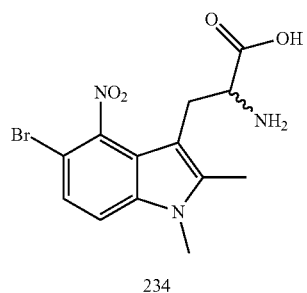

234

Example 234 can be prepared from 5-bromo-1,2-dimethyl-indole as shown above.

Example 235: Preparation of 2-amino-3-(6-bromo-1,2-dimethyl-4-nitro-1H-indol-3-yl)propanoic acid (235)

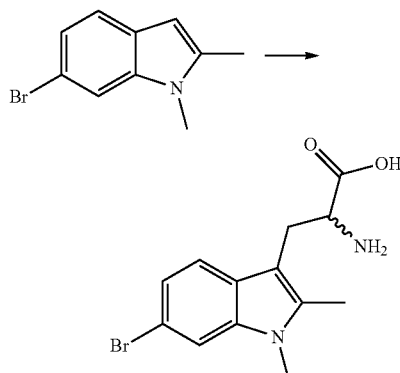

235

Example 235 can be prepared from 6-bromo-1,2-dimethyl-indole as shown above.

Example 236: Preparation of 2-amino-3-(7-bromo-1,2-dimethyl-4-nitro-1H-indol-3-yl)propanoic acid (236)

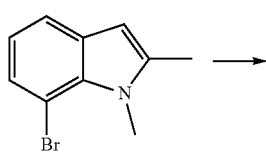

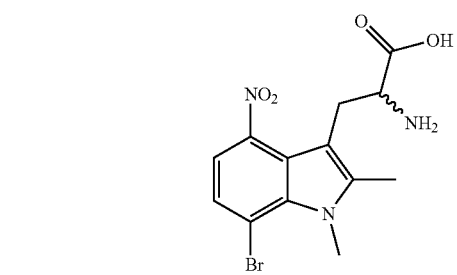

236

Example 236 can be prepared from 7-bromo-1,2-dimethyl-indole as shown above.

Example 237: Preparation of 2-amino-3-(4-bromo-1,2-dimethyl-7-nitro-1H-indol-3-yl)propanoic acid (237)

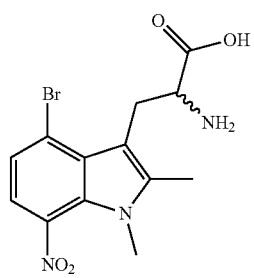

237

Example 237 can be prepared from 4-bromo-1,2-dimethyl-indole as shown above.

Example 238: Preparation of 2-amino-3-(5-methoxy-1,2-dimethyl-4-nitro-1H-indol-3-yl)propanoic acid (238)

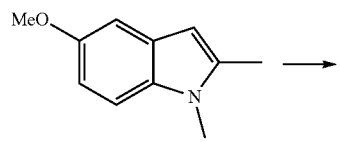

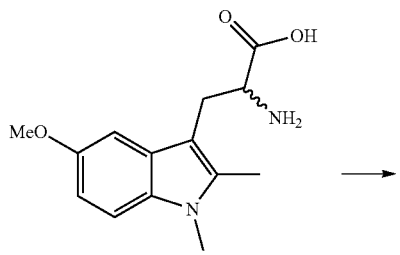

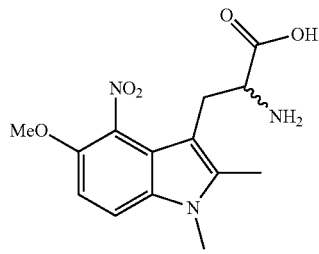

238

Example 238 can be prepared from 5-methoxy-1,2-dimethyl-indole as shown above.

Example 239: Preparation of 2-amino-3-(6-methoxy-1,2-dimethyl-4-nitro-1H-indol-3-yl)propanoic acid (239)

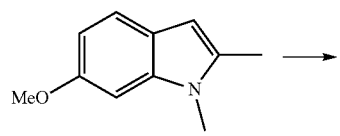

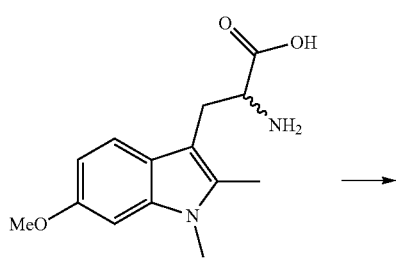

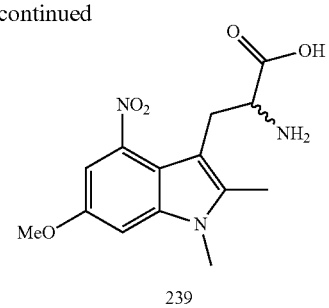

239

Example 239 can be prepared from 6-methoxy-1,2-dimethyl-indole as shown above.

Example 240: Preparation of 2-amino-3-(7-methoxy-1,2-dimethyl-4-nitro-1H-indol-3-yl)propanoic acid (240)

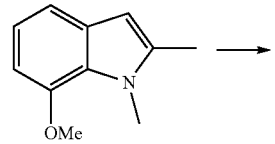

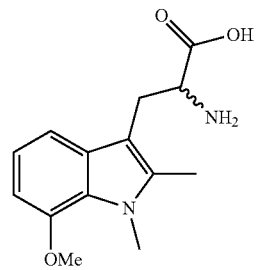

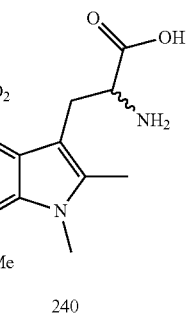

240

Example 240 can be prepared from 7-methoxy-1,2-dimethyl-indole as shown above.

Example 241: Preparation of 2-amino-3-(4-methoxy-1,2-dimethyl-7-nitro-1H-indol-3-yl)propanoic acid (241)

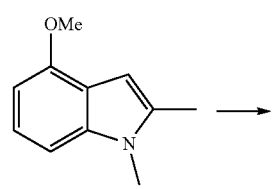

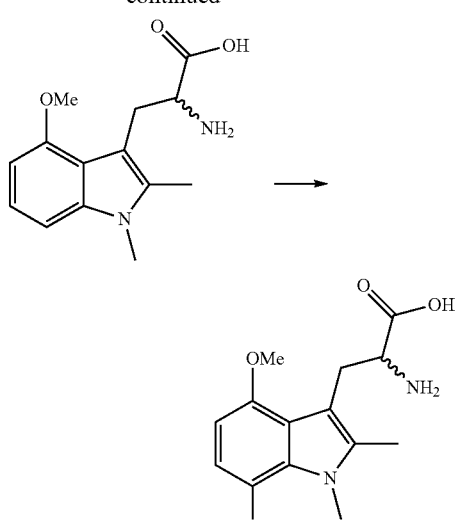

241

Example 241 can be prepared from 4-methoxy-1,2-dimethyl-indole as shown above.

Example 242: Preparation of 2-amino-3-(5-amino-1,2-dimethyl-4-nitro-1H-indol-3-yl)propanoic acid (242)

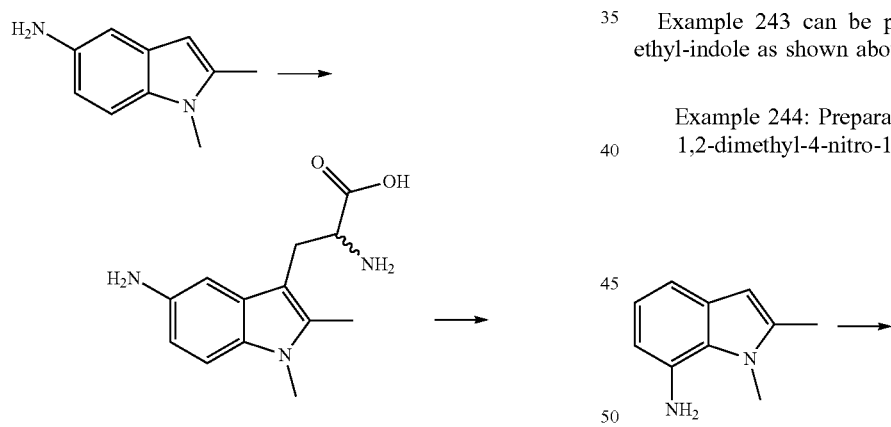

242

Example 242 can be prepared from 5-amino-1,2-dimethyl-indole as shown above.

Example 243: Preparation of 2-amino-3-(6-amino-1,2-dimethyl-4-nitro-1H-indol-3-yl)propanoic acid (243)

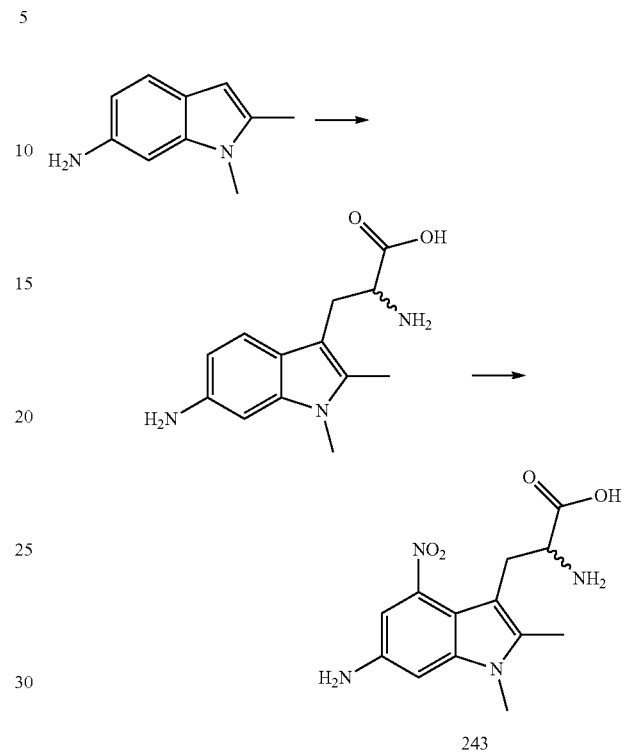

243

Example 243 can be prepared from 6-amino-1,2-dimethyl-indole as shown above.

Example 244: Preparation of 2-amino-3-(7-amino-1,2-dimethyl-4-nitro-1H-indol-3-yl)propanoic acid (244)

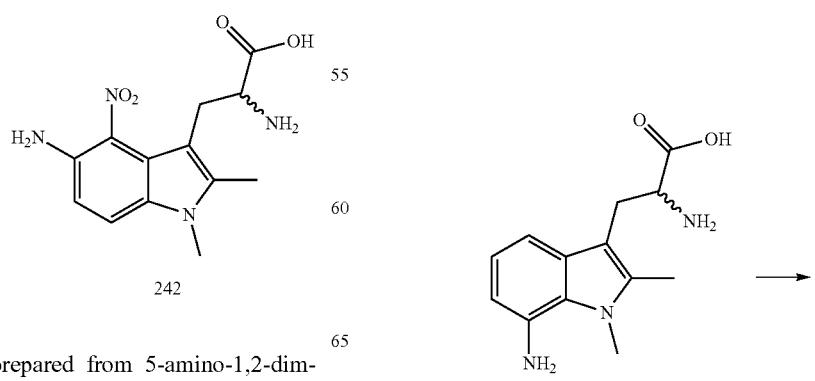

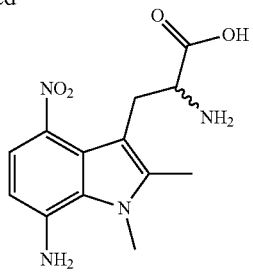

244

Example 244 can be prepared from 7-amino-1,2-dimethyl-indole as shown above.

Example 245: Preparation of 2-amino-3-(4-amino-1,2-dimethyl-7-nitro-1H-indol-3-yl)propanoic acid (245)

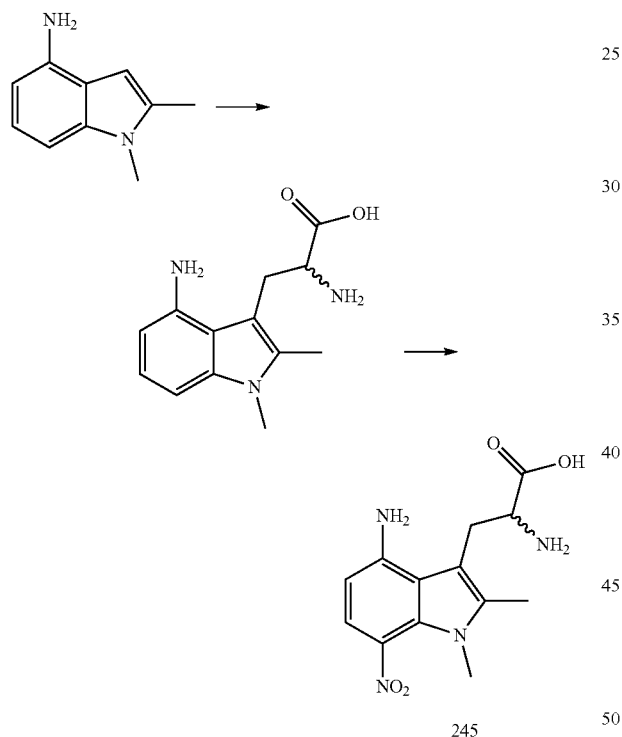

245

Example 245 can be prepared from 4-amino-1,2-dimethyl-indole as shown above.

Example 246: Preparation of 2-amino-3-(5-hydroxy-1,2-dimethyl-4-nitro-1H-indol-3-yl)propanoic acid (246)

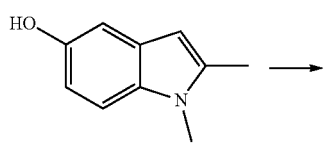

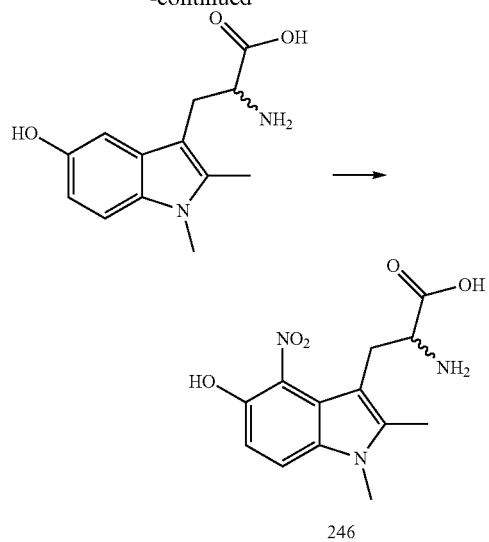

246

Example 246 can be prepared from 5-hydroxy-1,2-dimethyl-indole as shown above.

Example 247: Preparation of 2-amino-3-(6-hydroxy-1,2-dimethyl-4-nitro-1H-indol-3-yl)propanoic acid (247)

247

Example 247 can be prepared from 6-hydroxy-1,2-dimethyl-indole as shown above.

Example 248: Preparation of 2-amino-3-(7-hydroxy-1,2-dimethyl-4-nitro-1H-indol-3-yl)propanoic acid (248)

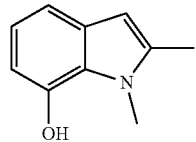

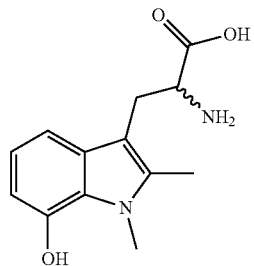

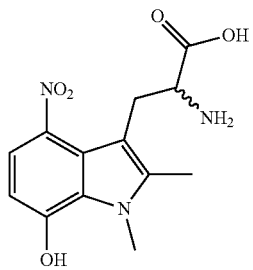

248

Example 248 can be prepared from 7-hydroxy-1,2-dimethyl-indole as shown above.

Example 249: Preparation of 2-amino-3-(4-hydroxy-1,2-dimethyl-7-nitro-1H-indol-3-yl)propanoic acid (249)

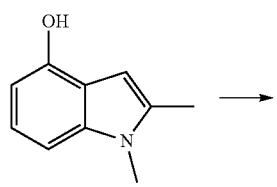

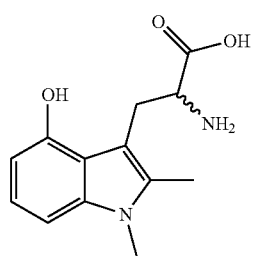

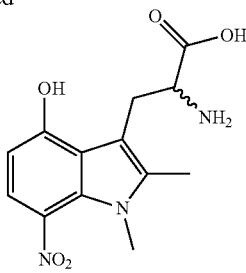

249

Example 249 can be prepared from 4-hydroxy-1,2-dimethyl-indole as shown above.

Example 250: Preparation of 2-amino-3-(1,2-dimethyl-4-nitro-5-phenyl-1H-indol-3-yl)propanoic acid (250)

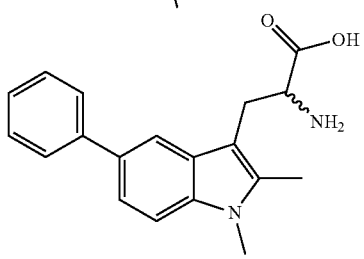

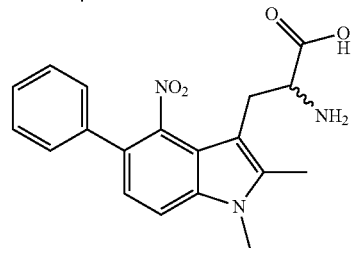

250

Example 250 can be prepared from 5-phenyl-1,2-dimethyl-indole as shown above.

Example 251: Preparation of 2-amino-3-(1,2-dimethyl-4-nitro-6-phenyl-1H-indol-3-yl)propanoic acid (251)

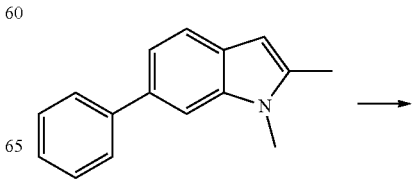

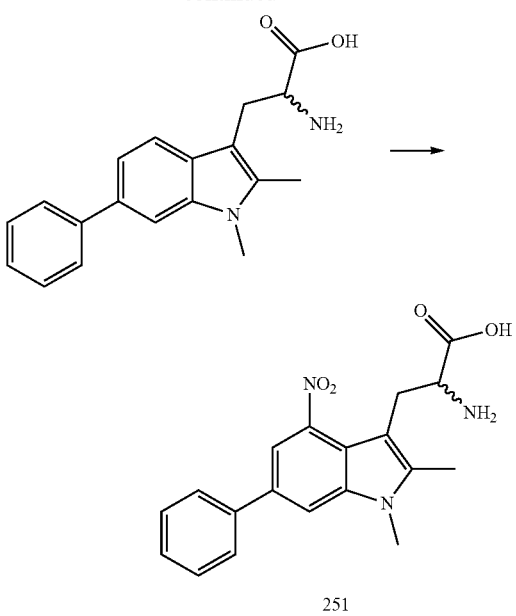
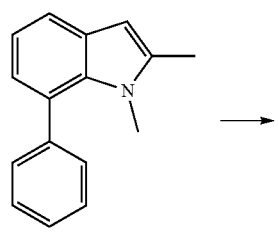
251
Example 251 can be prepared from 6-phenyl-1,2-dimethyl-indole as shown above.
Example 252: Preparation of 2-amino-3-(1,2-dimethyl-4-nitro-7-phenyl-1H-indol-3-yl)propanoic acid (252)
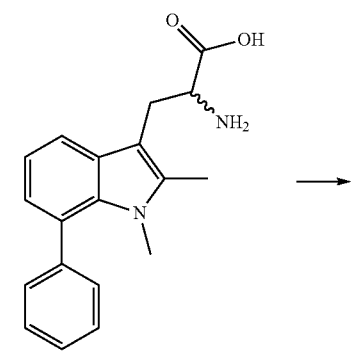
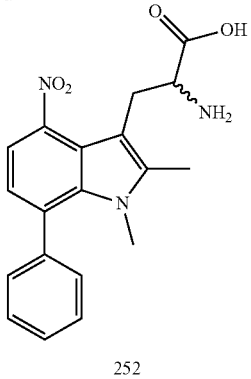
252
Example 252 can be prepared from 7-phenyl-1,2-dimethyl-indole as shown above.
Example 253: Preparation of 2-amino-3-(1,2-dimethyl-7-nitro-4-phenyl-1H-indol-3-yl)propanoic acid (253)
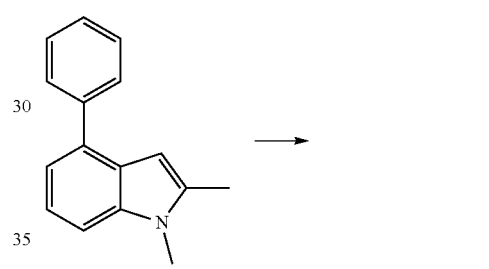
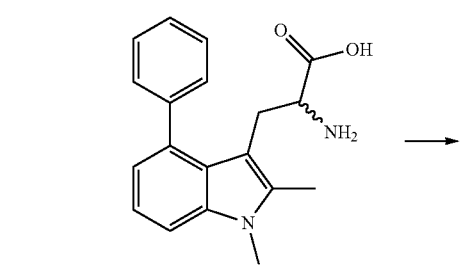
253
Example 253 can be prepared from 4-phenyl-1,2-dimethyl-indole as shown above.

Example 254: Preparation of 2-amino-3-(5-cyclo-propyl-1,2-dimethyl-4-nitro-1H-indol-3-yl)propanoic acid (254)

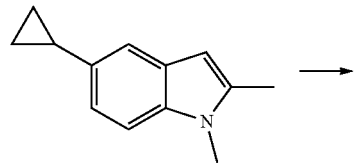

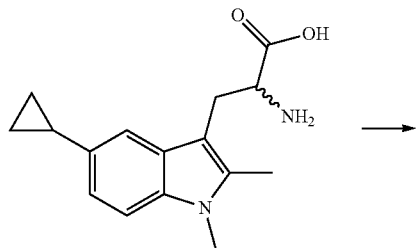

254

Example 254 can be prepared from 5-cyclopropyl-1,2-dimethyl-indole as shown above.

Example 255: Preparation of 2-amino-3-(6-cyclopropyl-1,2-dimethyl-4-nitro-1H-indol-3-yl)propanoic acid (255)

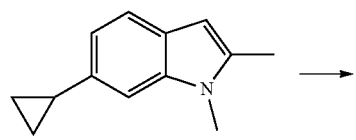

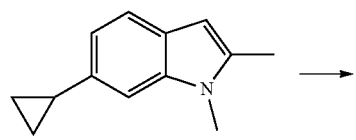

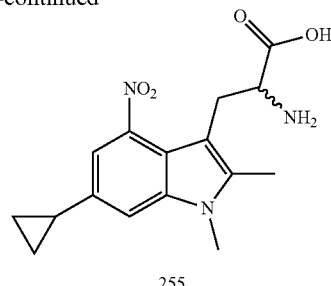

255

Example 255 can be prepared from 6-cyclopropyl-1,2-dimethyl-indole as shown above.

Example 256: Preparation of 2-amino-3-(7-cyclopropyl-1,2-dimethyl-4-nitro-1H-indol-3-yl)propanoic acid (256)

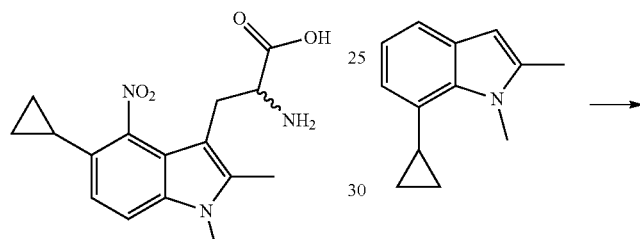

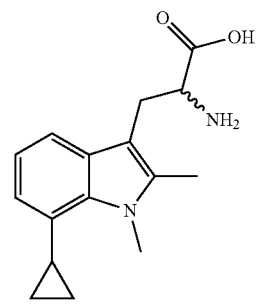

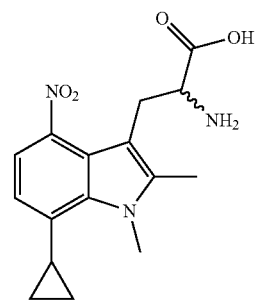

256

Example 256 can be prepared from 7-cyclopropyl-1,2-dimethyl-indole as shown above.

Example 257: Preparation of 2-amino-3-(4-cyclopropyl-1,2-dimethyl-7-nitro-1H-indol-3-yl)propanoic acid (257)

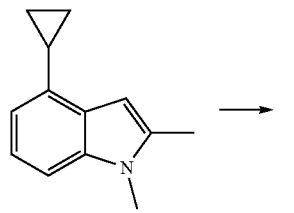

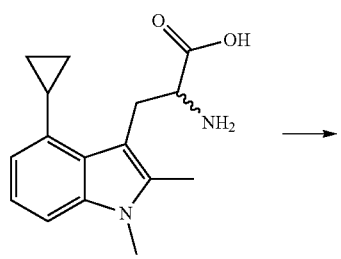

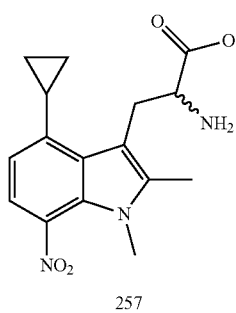

257

Example 257 can be prepared from 4-cyclopropyl-1,2-dimethyl-indole as shown above.

Example 258: Preparation of 2-amino-3-(1,2-dimethyl-4-nitro-5-vinyl-1H-indol-3-yl)propanoic acid (258)

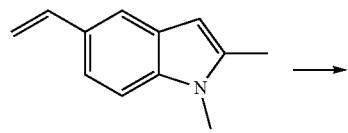

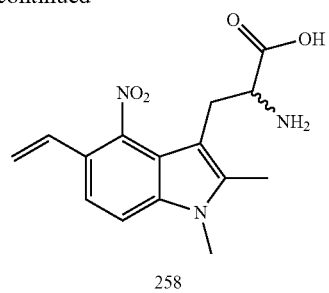

258

Example 258 can be prepared from 5-vinyl-1,2-dimethyl-indole as shown above.

Example 259: Preparation of 2-amino-3-(1,2-dimethyl-4-nitro-6-vinyl-1H-indol-3-yl)propanoic acid (259)

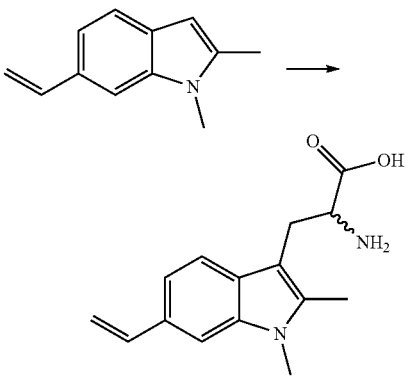

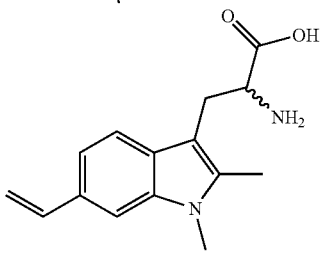

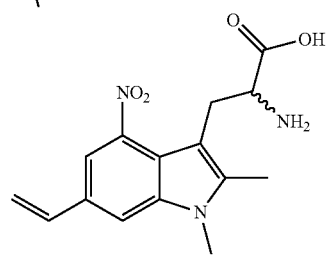

259

Example 259 can be prepared from 6-vinyl-1,2-dimethyl-indole as shown above.

Example 260: Preparation of 2-amino-3-(1,2-dimethyl-4-nitro-7-vinyl-1H-indol-3-yl)propanoic acid (260)

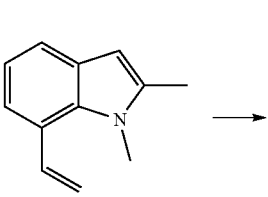

-continued

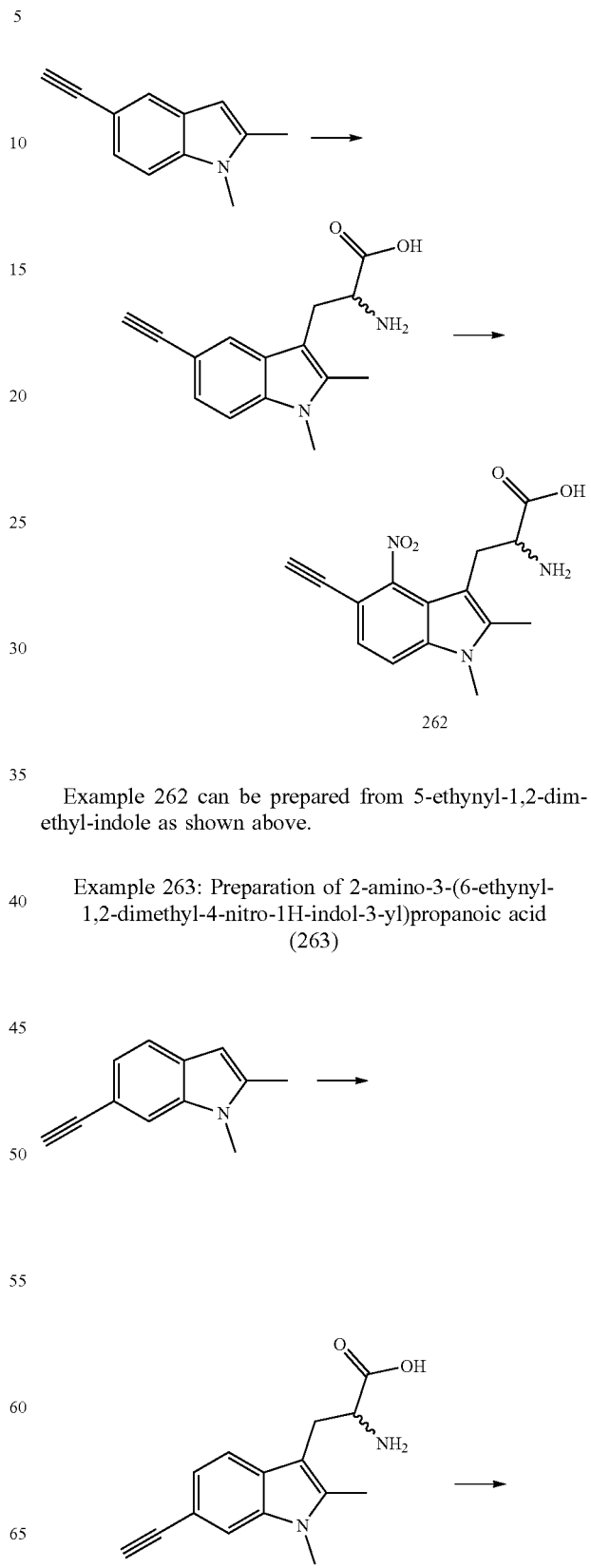

260

Example 260 can be prepared from 7-vinyl-1,2-dimethyl-indole as shown above.

Example 261: Preparation of 2-amino-3-(1,2-dimethyl-7-nitro-4-vinyl-1H-indol-3-yl)propanoic acid (261)

261

Example 261 can be prepared from 4-vinyl-1,2-dimethyl-indole as shown above.

Example 262: Preparation of 2-amino-3-(5-ethynyl-1,2-dimethyl-4-nitro-1H-indol-3-yl)propanoic acid (262)

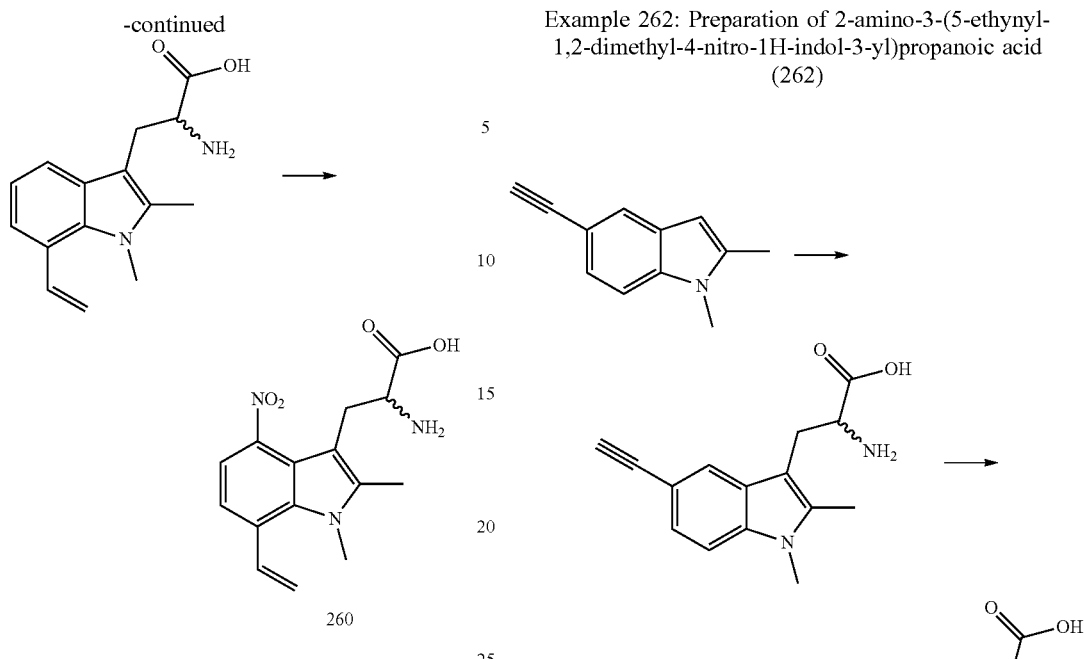

262

Example 262 can be prepared from 5-ethynyl-1,2-dimethyl-indole as shown above.

Example 263: Preparation of 2-amino-3-(6-ethynyl-1,2-dimethyl-4-nitro-1H-indol-3-yl)propanoic acid (263)

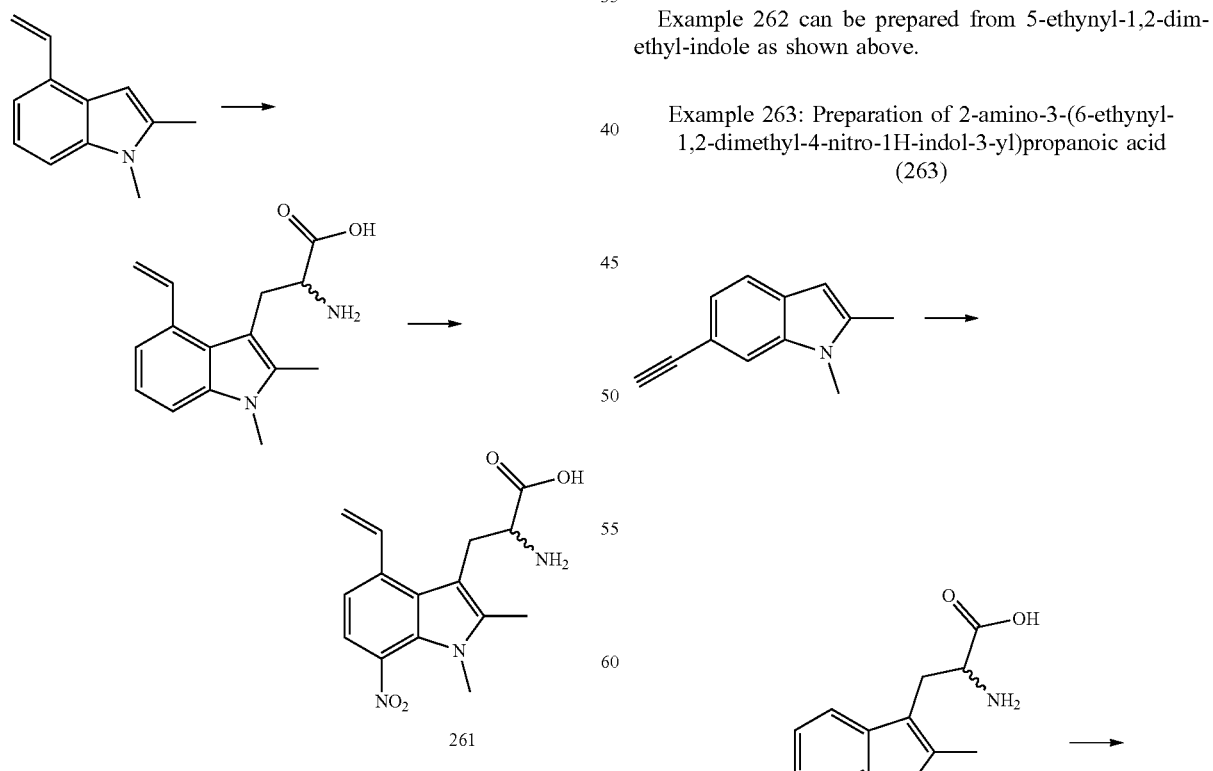

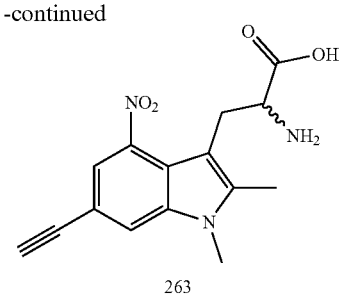

263

Example 263 can be prepared from 6-ethynyl-1,2-dimethyl-indole as shown above.

Example 264: Preparation of 2-amino-3-(7-ethynyl-1,2-dimethyl-4-nitro-1H-indol-3-yl)propanoic acid (264)

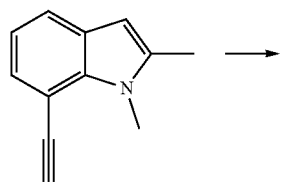

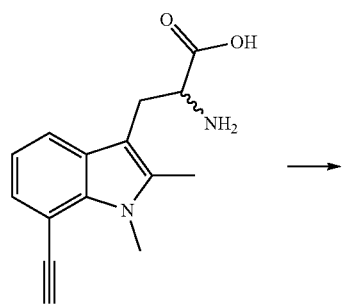

264

Example 264 can be prepared from 7-ethynyl-1,2-dimethyl-indole as shown above.

Example 265: Preparation of 2-amino-3-(4-ethynyl-1,2-dimethyl-7-nitro-1H-indol-3-yl)propanoic acid (265)

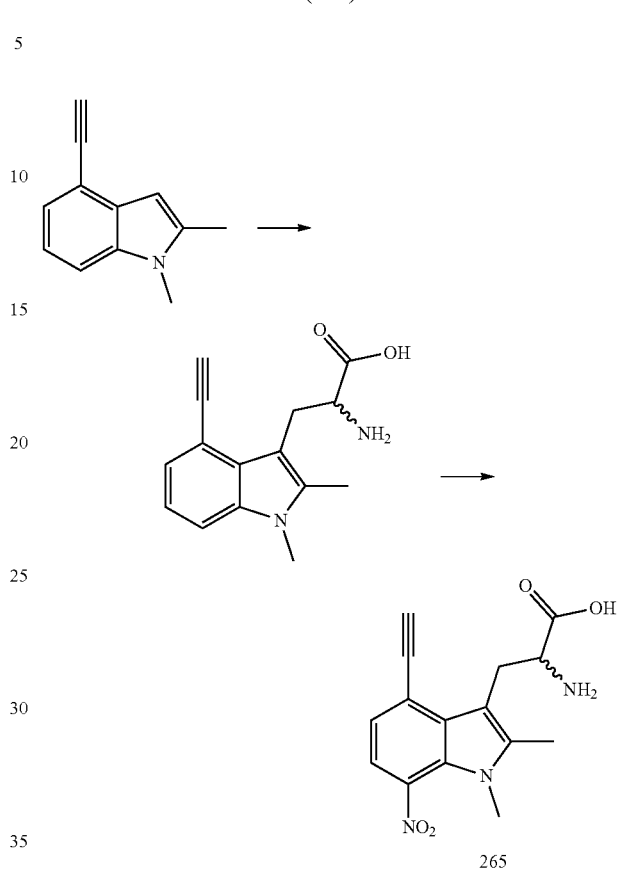

265

Example 265 can be prepared from 4-ethynyl-1,2-dimethyl-indole as shown above.

Example 266: Preparation of 2-amino-3-(1,2-dimethyl-5-morpholino-4-nitro-1H-indol-3-yl)propanoic acid (266)

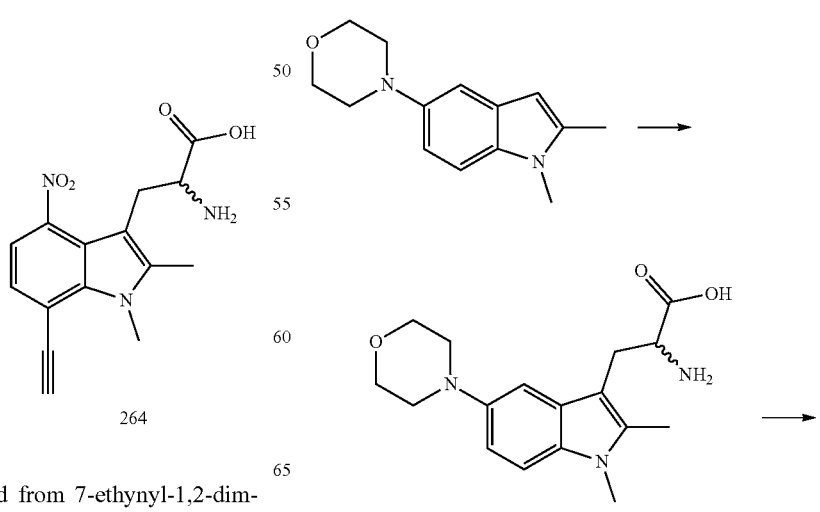

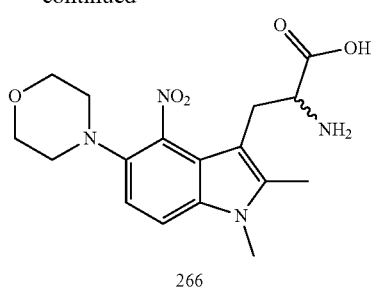

266

Example 266 can be prepared from 5-morpholino-1,2-dimethyl-indole as shown above.

Example 267: Preparation of 2-amino-3-(1,2-dimethyl-6-morpholino-4-nitro-1H-indol-3-yl)propanoic acid (267)

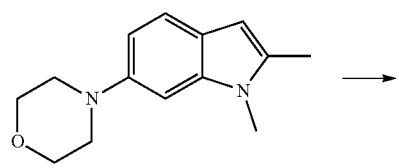

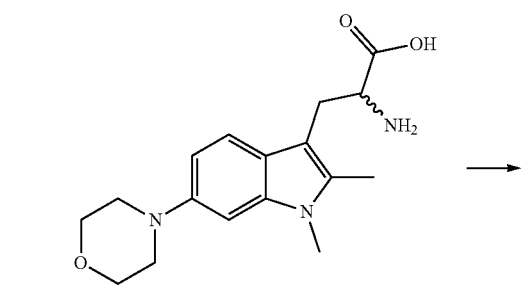

267

Example 267 can be prepared from 6-morpholino-1,2-dimethyl-indole as shown above.

Example 268: Preparation of 2-amino-3-(1,2-dimethyl-7-morpholino-4-nitro-1H-indol-3-yl)propanoic acid (268)

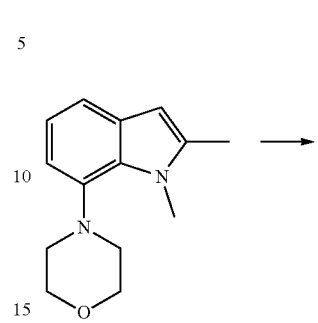

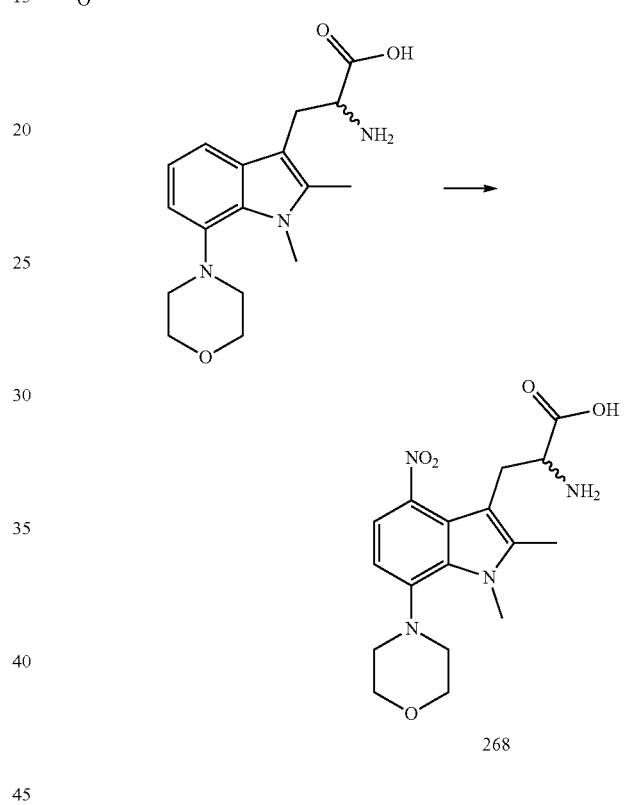

268

Example 268 can be prepared from 7-morpholino-1,2-dimethyl-indole as shown above.

Example 269: Preparation of 2-amino-3-(1,2-dimethyl-4-morpholino-7-nitro-1H-indol-3-yl)propanoic acid (269)

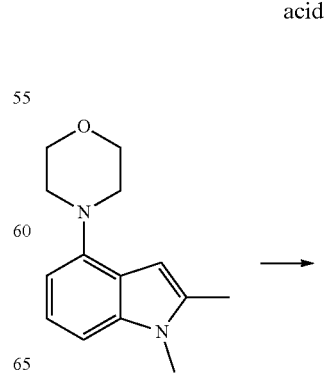

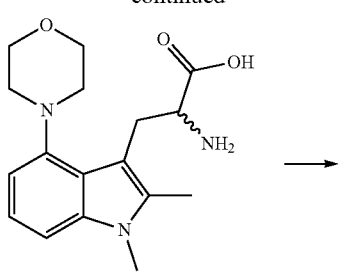

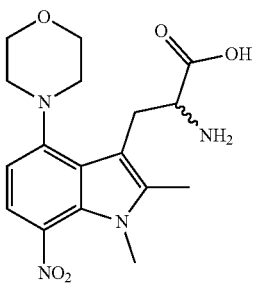

269

Example 269 can be prepared from 4-morpholino-1,2-dimethyl-indole as shown above.

Example 270: Preparation of 2-amino-3-(1,2-dimethyl-5-(methylthio)-4-nitro-1H-indol-3-yl)propanoic acid (270)

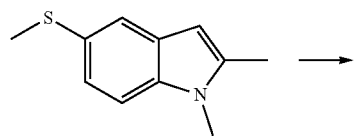

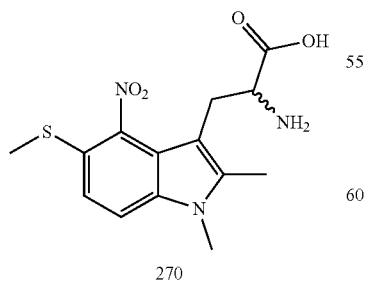

270

Example 270 can be prepared from 5-(methylthio)-1,2-dimethyl-indole as shown above.

Example 271: Preparation of 2-amino-3-(1,2-dimethyl-6-(methylthio)-4-nitro-1H-indol-3-yl)propanoic acid (271)

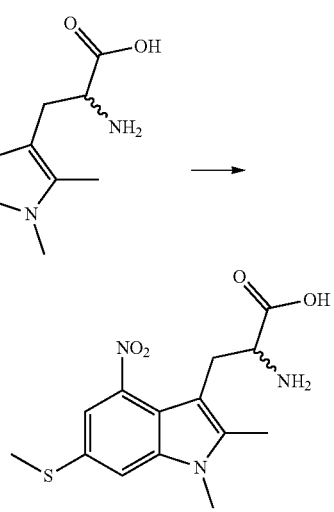

271

Example 271 can be prepared from 6-(methylthio)-1,2-dimethyl-indole as shown above.

Example 272: Preparation of 2-amino-3-(1,2-dimethyl-7-(methylthio)-4-nitro-1H-indol-3-yl)propanoic acid (272)

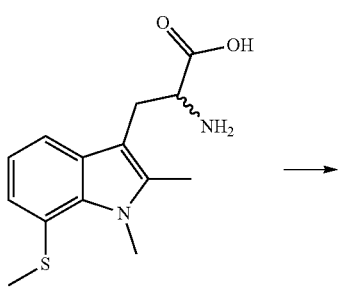

-continued

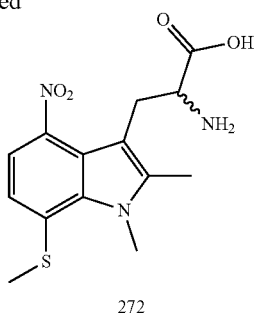
272

Example 272 can be prepared from 7-(methylthio)-1,2-dimethyl-indole as shown above.

Example 273: Preparation of 2-amino-3-(1,2-dimethyl-4-(methylthio)-7-nitro-1H-indol-3-yl)propanoic acid (273)

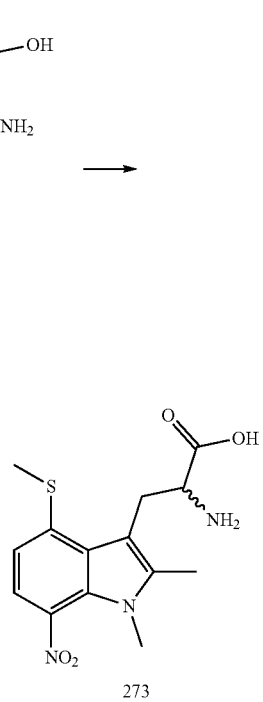
273

Example 273 can be prepared from 4-(methylthio)-1,2-dimethyl-indole as shown above.

Example 274: Preparation of 2-amino-3-(1,2-dimethyl-4-nitro-5-(pyridin-4-yl)-1H-indol-3-yl)propanoic acid (274)

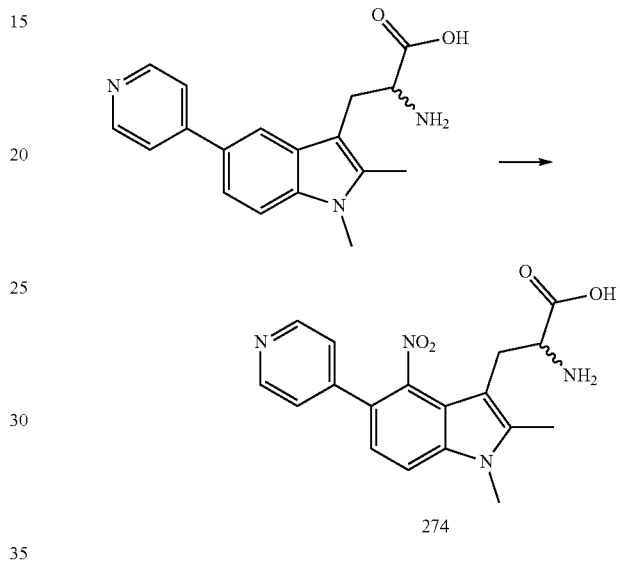
274

Example 274 can be prepared from 5-(pyridin-4-yl)-1,2-dimethyl-indole as shown above.

Example 275: Preparation of 2-amino-3-(1,2-dimethyl-4-nitro-6-(pyridin-4-yl)-1H-indol-3-yl)propanoic acid (275)

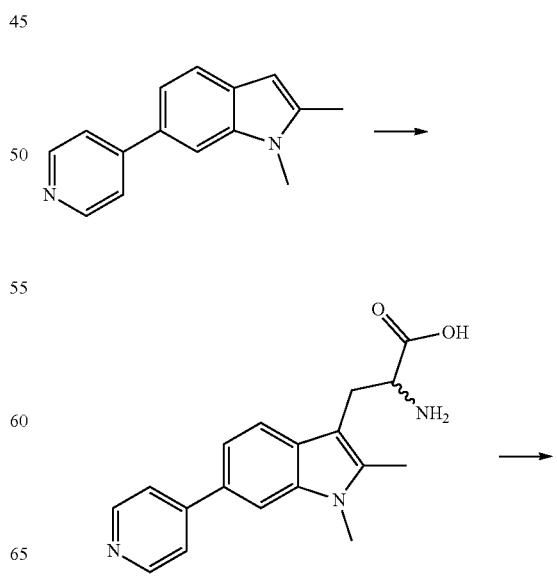

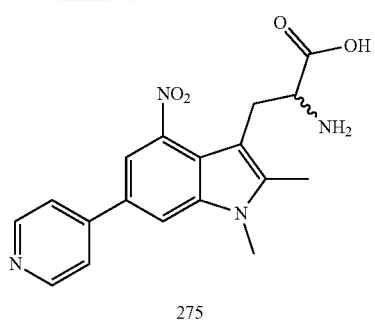

Example 275 can be prepared from 6-(pyridin-4-yl)-1,2-dimethyl-indole as shown above.

Example 276: Preparation of 2-amino-3-(1,2-dimethyl-4-nitro-7-(pyridin-4-yl)-1H-indol-3-yl)propanoic acid (276)

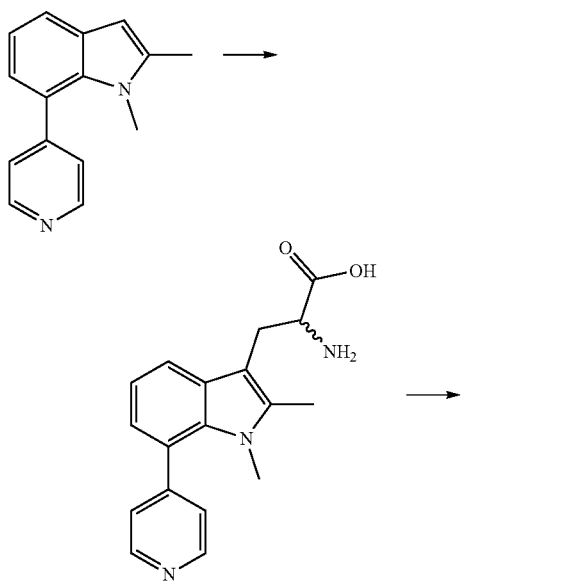

Example 276 can be prepared from 7-(pyridin-4-yl)-1,2-dimethyl-indole as shown above.

Example 277: Preparation of 2-amino-3-(1,2-dimethyl-7-nitro-4-(pyridin-4-yl)-1H-indol-3-yl)propanoic acid (277)

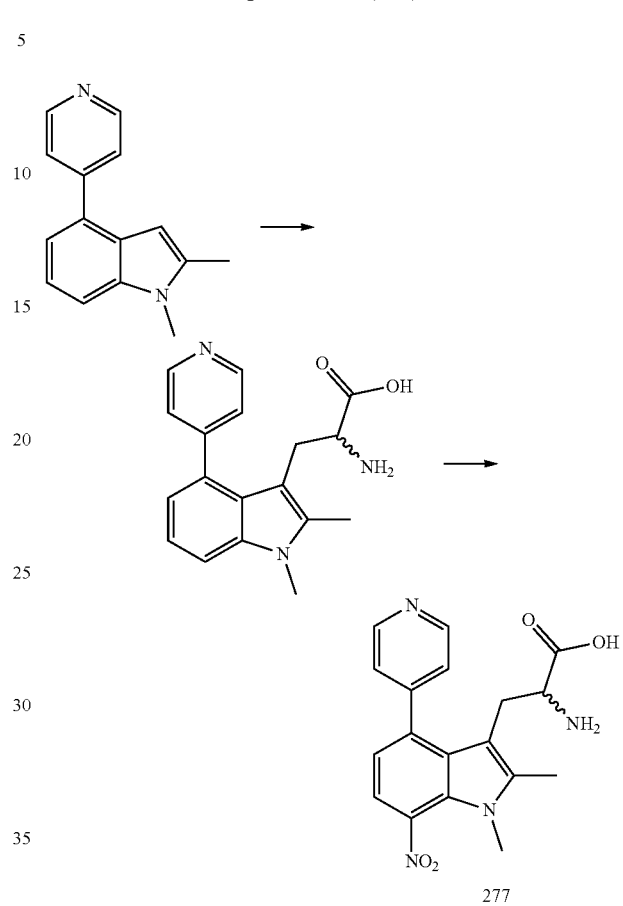

Example 277 can be prepared from 4-(pyridin-4-yl)-1,2-dimethyl-indole as shown above.

Figure 7:
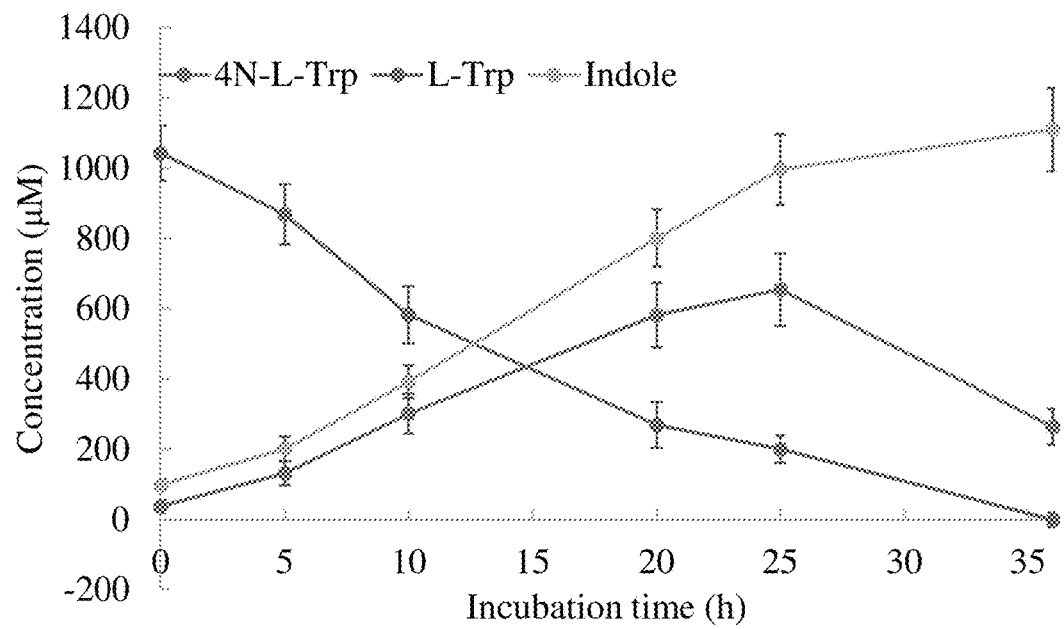
FIG. 7 shows L-Trp, 4-N-L-Trp, and indole concentration as a function of incubation time during a whole cell transformation process.

Example 278: Genetic Engineering of *E. coli* for Further Improving the Productivity In *E. coli*, L-Trp has been observed to be converted into indole, pyruvate and $NH_3$ by tryptophanase TnaA. L-Trp consumption and the formation of $4\text{-}NO_2\text{-}L\text{-}Trp$ and indole was monitored during the whole cell transformation process (FIG. 7). The concentration of L-Trp in the medium was constantly decreased. Concomitantly, the concentration of indole reached as high as 1100 μM after 36 h, while the concentration of $4\text{-}NO_2\text{-}L\text{-}Trp$ was topped at 600 μM at 25 h and then decreased. This result indicated that L-Trp degradation is a strong competitive pathway of $4\text{-}NO_2\text{-}L\text{-}Trp$ synthesis. Therefore, inhibiting the L-Trp degradation pathway, in some embodiments, improves the productivity of $4\text{-}NO_2\text{-}L\text{-}Trp$ in whole cell systems. Accordingly, the tryptophanase encoding gene tnaA was knocked down in the engineered *E. coli* strain by the markerless Red recombination method.

Figure 8:
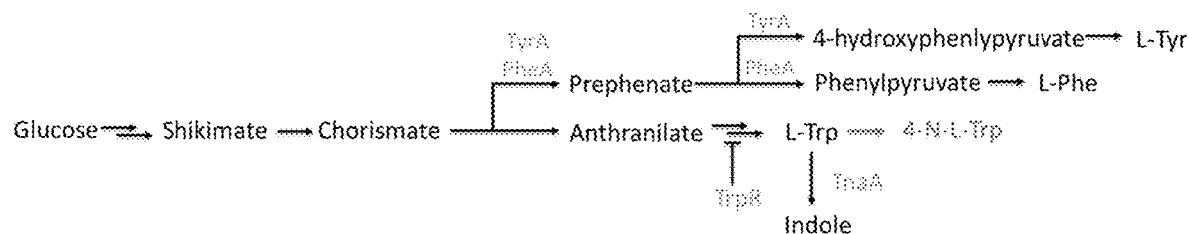
FIG. 8 is a schematic showing biosynthesis pathways of aromatic amino acids and targeted genes (e.g., TyrA, PheA, TrpR, TnaA) in a host engineering study.

During the biological synthesis of L-Trp in *E. coli*, TrpR has been observed to repress the transcription of genes involved in L-Trp synthesis and transport when high concentration of L-Trp are present. In addition, in the biosynthesis pathways of aromatic amino acids, carbon flux from chorismite has been observed to flow to the synthesis of L-Phe, L-Tyr and L-Trp (FIG. 8). In some embodiments, to improve the cellular availability of L-Trp, the negative regulator trpR of L-Trp biosynthesis and tyrA and pheA which catalyze the first two steps of the L-Tyr and L-Phe branch pathways, respectively, are knocked out. A triple knockout E. coli strain (ΔtrpRΔtyrAΔpheA) was produced, and L-Trp concentration in serial fermentation cultures of the mutant is evaluated. The mutant is also transformed with a plasmid combination of pETDUET-GDH-BsNOS and pET28b-TB14 to evaluate the productivity of 4-NO$_2$-L-Trp. Examples of primers used to generate gene knockout of target metabolic genes are shown in Table 2.

TABLE 2

Primers used for the gene knockout.

| | |
|---|---|
| tnaA_fw | ACATCCTTATAGCCACTCTGTAGTATTAATTAAACTTCTTTAAGTT TTGCATTCCGGGGATCCGTCGACC (SEQ ID NO: 27) |
| tnaA_rv | AATATTCACAGGGATCACTGTAATTAAAATAAATGAAGGATTAT GTAATGTGTAGGCTGGAGCTGCTTCG (SEQ ID NO: 28) |
| trpR-FRT_fw | TACAACCGGGGGAGGCATTTTGCTTCCCCCGCTAACAATGGCGA CATATTGTGTAGGCTGGAGCTGCTTC (SEQ ID NO: 29) |
| trpR-FRT_rv | ATTCGGTGCACGATGCCTGATGCGCCACGTCTTATCAGGCCTACA AAACATATGAATATCCTCCTTA (SEQ ID NO: 30) |
| pheA-FRT_fw | GGCCTCCCAAATCGGGGGGCCTTTTTTATTGATAACAAAAAGGC AACACTGTGTAGGCTGGAGCTGCTTC (SEQ ID NO: 31) |
| pheA-FRT_rv | GCCAGTAATAATCCAGTGCCGGATGATTCACATCATCCGGCACCT TTTCACATATGAATATCCTCCTTA (SEQ ID NO: 32) |
| tyrA-FRT_fw | TCAGGATCTGAACGGGCAGCTGACGGCTCGCGTGGCTTAAGAGG TTTATTGTGTAGGCTGGAGCTGCTTC (SEQ ID NO: 33) |
| tyrA-FRT_rv | CAACCTGATGAAAAGGTGCCGGATGATGTGAATCATCCGGCACT GGATTACATATGAATATCCTCCTTA (SEQ ID NO: 34) |

Example 279: Direct Aromatic Nitration System for Synthesis of Nitrotryptophans in *Escherichia coli*

This example describes design of a biosynthetic pathway for nitrotrp production in *E. coli*. The production of Nitrotrp and its derivatives primarily uses complicated, heavily polluting synthetic methods, while biocatalytic nitration processes typically require the use of costly, unstable nitric oxide donors. Native thaxtomin-producing plant pathogenic *Streptomyces* species produce trace amounts of Nitrotrp along with N—CH$_3$-Nitrotrp and the txtB-inactivated mutant accumulates only up to 6 mg/L of Nitrotrp after 5-day fermentation. TxtB is a nonribosomal peptide synthase that utilizes Nitrotrp as substrate to synthesize thaxtomin D. Production of up to 0.22 g/L of thaxtomins within 6 days by heterologously expressing the thaxtomin gene cluster from *S. scabiei* 87.22 in *S. albus* J1074 (*S. albus*-thx2) has been observed. The *S. albus*-thx2 and its mutant carrying only the txtE and txtD genes have been observed to produce up to 80 mg/L of Nitrotrp derivatives, mainly N-acetyl-Nitrotrp, but not Nitrotrp.

Figure 9:
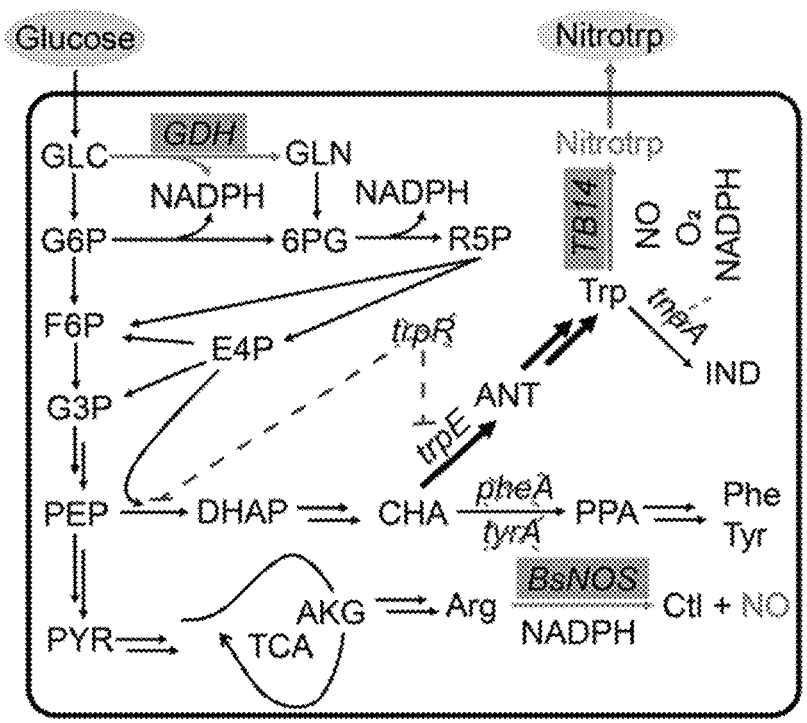
FIG. 9 shows a schematic depicting one embodiment of a Nitrotrp biosynthetic pathway that is integrated with select major metabolic pathways in E. coli. TB14, BsNOS, and GDH genes are shadowed. Cellular Nitrotrp and nitric oxide (NO) are also shown. Inhibition of the shikimate pathway and L-Trp biosynthesis by TrpR is shown in dashed lines. The X symbol indicates gene inactivation. Inactivation of trpR, pheA and tyrA increases synthesis of L-Trp shown as wider arrows. GLC glucose, G6P glucose-6-phosphate, F6P fructose-6-phosphate, G3P glyceraldehyde-3-phosphate, PEP phosphoenolpyruvate, PYR pyruvate, GLN glucono-1,5-lactone, 6PG 6-phosphogluconolactone, R5P ribose-5-phosphate, E4P erythrose-4-phosphate, DAHP 3-deoxy-D-arabino-heptulosonate, CHA chorismate, PPA prephenate, ANT anthranilate, IND indole, TCA tricarboxylic acid cycle, AKG α-ketoglutarate, Ctl L-citrulline, trpE component I of anthranilate synthase, trpR trp operon repressor, tnaA tryptophanase, pheA chorismate mutase/prephenate dehydratase and tyrA chorismate mutase/prephenate dehydrogenase.

A biosynthetic route to Nitrotrp, in some embodiments, comprises TxtE for 1-Trp nitration and one bacterial NOS for the generation of NO from 1-Arg (FIG. 9). Both TxtE and NOS require reducing agent NADPH for their reactions. In *E. coli*, NADPH is primarily produced in the pentose phosphate pathway (FIG. 9), but the predominant reducing equivalent is NADH, which potentially limits the production of Nitrotrp. Instead, a glucose dehydrogenase (GDH), specifically *Bacillus subtilis* GDH, was included in an engineered biosynthetic route to regenerate NADPH from NADP$^+$ via converting glucose into glucono-1,5-lactone (FIG. 9), which is then entered the pentose phosphate pathway. A self-sufficient TxtE variant, TB14, was used to construct this pathway. For the bacterial NOS, TxtD, which is naturally coexpressed with TxtE to produce Nitrotrp, was initially selected for use in several *Streptomyces* strains. However, both wild type and codon-optimized txtD genes from multiple thaxtomin-producing *Streptomyces* strains were either not expressed or formed inclusion body in *E. coli*. Codon-optimized NOS from *Bacillus subtilis* (BsNOS) in *E. coli* was included in the engineered pathway (FIG. 9). Of note, although *E. coli* encodes no NOS, its unspecific redox partners support the reaction of BsNOS.

Figures 10A, 10B, 10C:
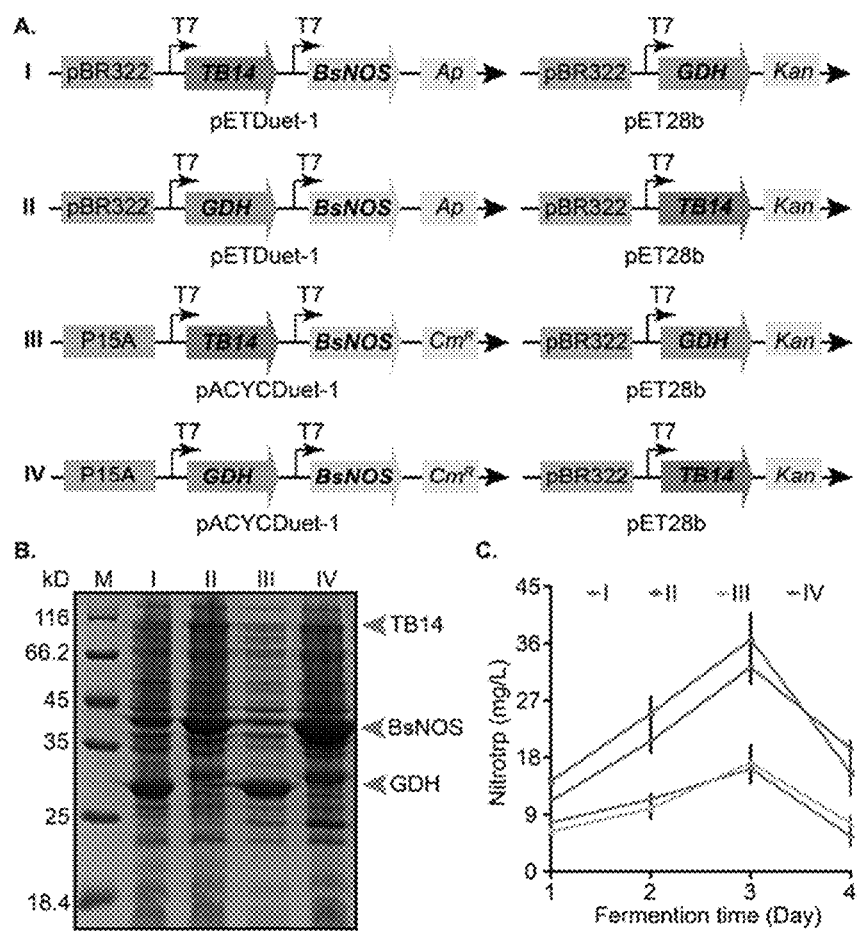
FIGS. 10A-10C show one embodiments of an E. coli-based system to produce Nitrotrp.

TB14 and BsNOS were cloned into the first and second multiple cloning sites (MCS) of pETDuet-1, respectively (FIG. 10A). Each gene is preceded by a T7 promoter/lac operator. The pETDuet-1 vector contains an ampicillin resistant marker (Ap). The GDH gene was expressed under the control of the T7 promoter in pET28b carrying a kanamycin resistant marker (Kan) (FIG. 10A). Both pET vectors have a medium copy number (15 to 60) in *E. coli* BL21 strain. The above two constructs were co-transformed into *E. coli* BL21-GOLD (DE3) (Table 3).

TABLE 3

Bacterial strains

| Name | Function |
|---|---|
| *E. coli* DH5α | Routine molecular biology studies |
| *E. coli* BL21-GOLD (DE3) | Protein expression and production host |
| *E. coli* ΔtnaA | *E. coli* BL21-GOLD (DE3) carrying inactivated tnaA |
| *E. coli* ΔtrpRtyrApheA | *E. coli* BL21-GOLD (DE3) carrying inactivated trpR, tyrA, and pheA |
| *E. coli*-I | *E. coli* BL21-GOLD (DE3) carrying the pathway I |
| *E. coli*-II | *E. coli* BL21-GOLD (DE3) carrying the pathway II |
| *E. coli*-III | *E. coli* BL21-GOLD (DE3) carrying the pathway III |

TABLE 3-continued

Bacterial strains

| Name | Function |
|---|---|
| E. coli-IV | E. coli BL21-GOLD (DE3) carrying the pathway IV |
| E. coli-II-TB14 | E. coli BL21-GOLD (DE3) carrying the pathway II without TB14 |
| E. coli-II-BsNOS | E. coli BL21-GOLD (DE3) carrying the pathway II without BsNOS |
| E. coli-II-GDH | E. coli BL21-GOLD (DE3) carrying the pathway II without GDH |
| E. coli ΔtrpRtyrApheA-II | E. coli ΔtrpRtyrApheA carrying the pathway II |
| E. coli-TB14 | E. coli BL21-GOLD (DE3) carrying only TB14 |

Figure 11:
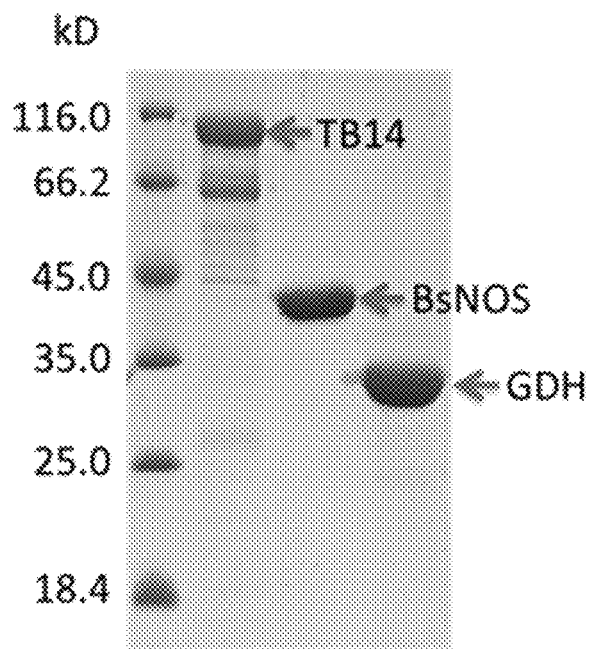
FIG. 11 shows SDS-PAGE analysis of purified recombinant TB14, BsNOS, and GDH. All three proteins showed expected molecular weights, the same as those in E. coli soluble lysates.
Figure 12A:
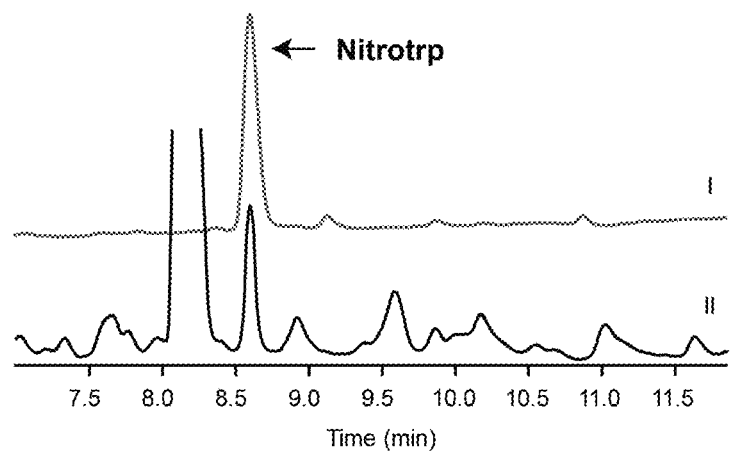
FIGS. 12A-12B show E. coli cells carrying the pathway I produced Nitrotrp.
Figure 12B:
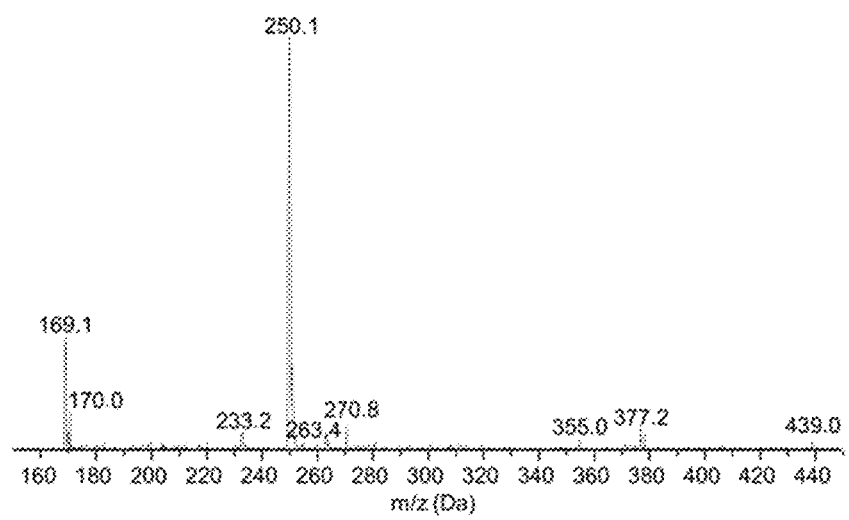
Figure 13:
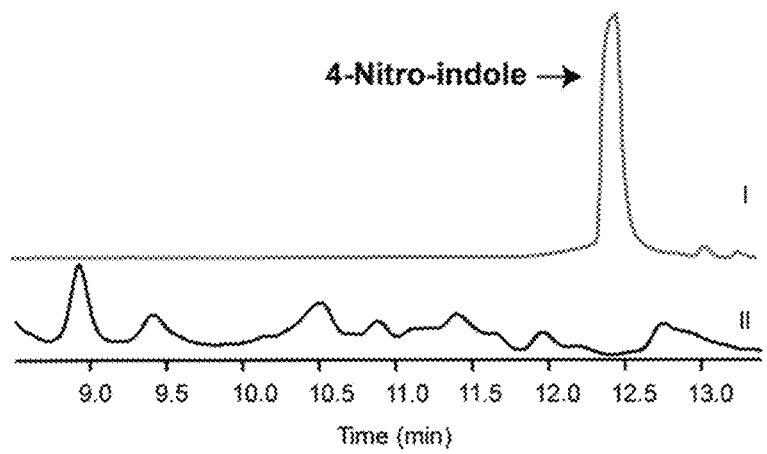
FIG. 13 shows HPLC analysis of authentic 4-nitroindole (I) and clear fermentation medium prepared at day 4 (II) demonstrated no production of 4-nitroindole. The calculated m/z of [M+H]+ is 250.1, identical to determined value.
Figures 14A, 14B:
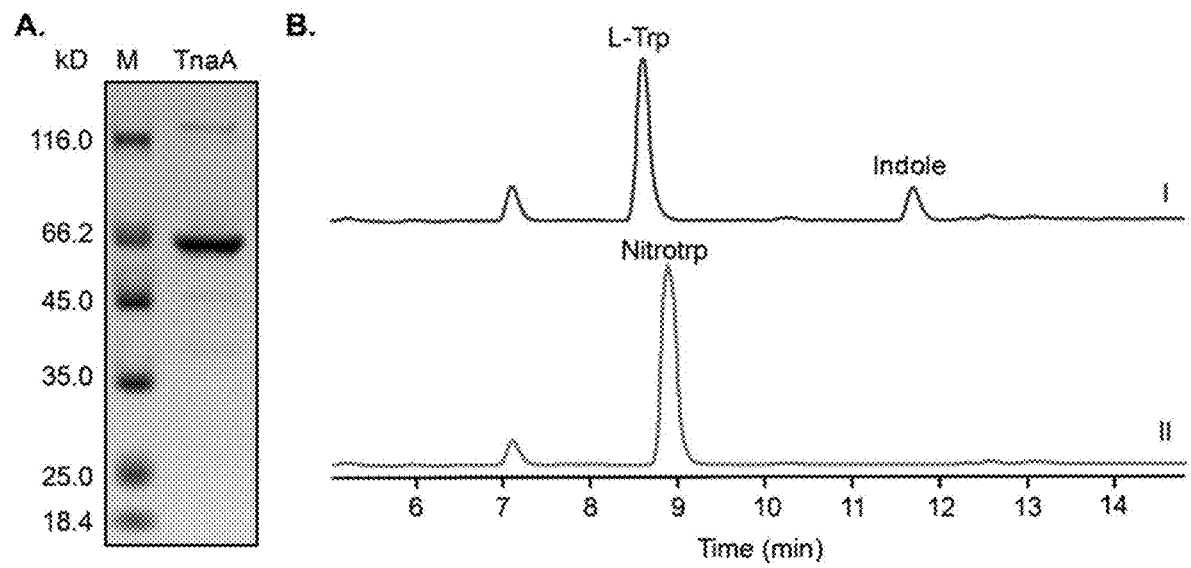
FIGS. 14A-14B show TnaA does not convert Nitrotrp into 4-nitroindole.

After the selection with both ampicillin and kanamycin, one positive colony (E. coli-I) was picked up to express proteins in TB medium induced with 0.5 mM IPTG for 20 h. The SDS-PAGE analysis of the soluble crude extract revealed the successful overexpression of BsNOS (42 kD) and GDH (28 kD) (Lane I, FIG. 10B and FIG. 11). By contrast, TB14 (110 kD) was expressed to a low level, different from the high solubility of TB14 when expressed alone in the same host. This result indicated that the co-expression with BsNOS and/or GDH negatively influenced the expression level of TB14 in E. coli. Nevertheless, E. coli-I was used for the synthesis of Nitrotrp from cellular 1-Trp and 1-Arg in the M9 minimal medium that has been most widely used for the whole cell transformations. After 24 h, HPLC analysis revealed 7.8±0.7 mg/L of Nitrotrp in the fermentation medium (FIG. 10C, FIG. 12A), which was further confirmed in LC-MS analysis (FIG. 12B). The titer of Nitrotrp increased until day 3, reaching 16.2±2.3 mg/L, and then quickly dropped to 5.5±1.5 mg/L on day 4 (FIG. 10C). TnaA is one tryptophanase in E. coli that is known to catalyze the β-elimination of 1-Trp to produce indole (FIG. 9). HPLC analysis of the fermentation medium failed to identify 4-nitro-indole, the potential product of Nitrotrp degradation by TnaA (FIG. 13). The tnaA gene from E. coli was cloned and recombinant enzyme was prepared (FIG. 14A). Recombinant TnaA produced indole from 1-Trp; degraded Nitrotrp was not observed in an in vitro assay (FIG. 14B). On the other hand, E. coli encodes two oxygen-insensitive nitroreductases NsfA and NsfB that are known to reduce nitroaromatics; one or both of these enzymes are involved in the rapid degradation of Nitrotrp in E. coli-I (FIG. 10C). Data described herein indicate a novel cell-based biocatalytic route to Nitrotrp.

Figure 15:
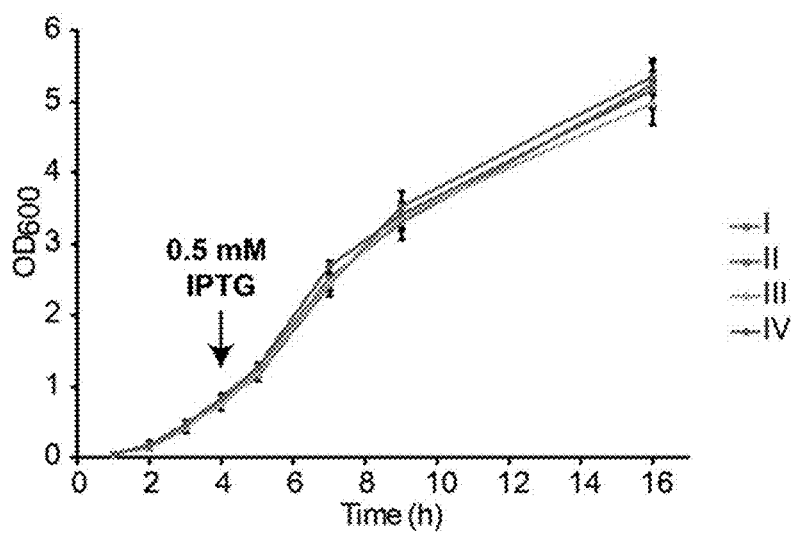
FIG. 15 shows E. coli BL21-GOLD (DE3) transformed with the pathway I-IV showed similar growth rates in TB medium. Cultures were grown at 37° C., 250 rpm for 4 hours and protein expression was induced with 0.5 mM IPTG at 18° C., 250 rpm for 12 hours. OD600 were measured at serial time points. The data represent means±s.d. of at least two independent experiments.

Despite the successful production of Nitrotrp by E. coli-I (I, FIG. 10A), low expression level of TB14 may constrain the nitration process. To address this potential issue, three additional pathways were constructed by varying copy numbers and replicons of plasmid backbones and coexpression of these genes (FIG. 10A). As high expression level is obtained when TB14 is expressed alone, the second design shuffled the TB14 and GDH genes between pETDuet-1 and pET28b (II, FIG. 10A). Furthermore, coexpression of the two genes was investigated in the pACYCDuet-1 backbone that has a low copy number (~10), contains two T7 promoters in two MCSs, carries the P15A replicon, and includes a chloramphenicol resistant marker (CmR) (III-IV, FIG. 10A). These features allowed the assessment of the effects of improved plasmid stability with two different replicons and varied gene dosages on the production of Nitrotrp. The three new Nitrotrp pathways were transformed into E. coli BL21-GOLD (DE3) to generate E. coli-II, —III and —IV as described above (Table 3). All four strains showed similar growth rates when cultured in TB medium and induced with 0.5 mM IPTG (FIG. 15). SDS-PAGE analysis revealed increased levels of TB14 but the decreased levels of GDH in E. coli-II and —IV in comparison to E. coli-I and -III (FIG. 10B). Another finding of the SDS-PAGE analysis was that the co-expression of TB14 and BsNOS on the plasmids of both low and medium copy numbers yielded the same low levels of both enzymes. The three E. coli strains were further fermented along with E. coli-I in the M9 medium for 4 days. HPLC analysis revealed that E. coli-II and —IV, which both carried the separately expressed TB14, produced more Nitrotrp than E. coli-I and -III (FIG. 10C). This data indicates that the low level of GDH in E. coli-II and —IV is sufficient to support the reactions of TB14 and BsNOS (FIG. 10B). The titer of Nitrotrp by all four strains increased until day 3 and then dropped at day 4. The highest titer of Nitrotrp was observed at 36.5±4.0 mg/L with E. coli-II on day 3, the 2.3-fold improvement compared with E. coli-I at day 3 (FIG. 10C). E. coli-II was therefore selected for subsequent studies.

Figure 16A:
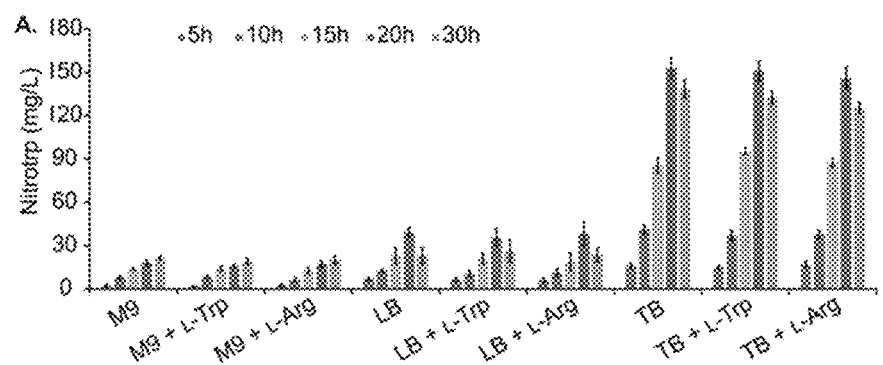
FIGS. 16A-16B show improvement of Nitrotrp production by varying fermentation media and temperature.

The fermentation processes in two commonly used, nutritionally rich media, LB and TB were investigated. As cellular 1-Trp and 1-Arg are consumed to produce Nitrotrp (FIG. 9), the effects of supplemented amino acids (5 mM) in M9, LB and TB media on the production of Nitrotrp by E. coli-II at 20° C. were also examined. HPLC analysis measured the concentration of Nitrotrp in the cell-free media at 5 h, 10 h, 15 h, 20 h, and 30 h (FIG. 16A). E. coli-II reached the highest titer of Nitrotrp in the M9 medium at day 3 (FIG. 10C), but the highest amount appeared after 20 h in both LB and TB, which was then decreased at 30 h. The titer of Nitrotrp was increased from 18.0±2.0 mg/L in M9 to 39.0±3.3 mg/L in LB and 152.8±10.5 mg/L in TB after 20 h, indicating the faster and increased production of Nitrotrp in nutritionally rich media (FIG. 16A). Supplementation of 1-Trp or 1-Arg in all three media resulted in no increase in the production of Nitrotrp.

Figure 16B:
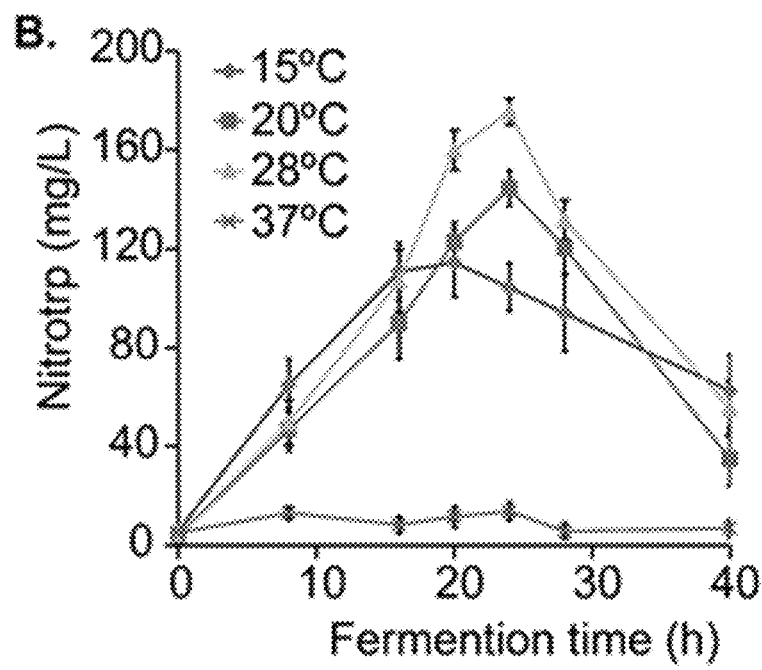

Temperature effects on the whole-cell nitration process were also examined. Fermentation experiments were performed at 20° C., 15° C., 28° C., and 37° C. Crude extracts of fermentation media of E. coli-II cultured at the four temperatures were prepared at 0 h, 8 h, 16 h, 20 h, 24 h, 28 h, and 40 h. HPLC analysis indicated a similar level of Nitrotrp at 8 h and 16 h when E. coli-II was fermented at 15° C., 20° C. and 28° C. (FIG. 16B). At 15° C., the titer of Nitrotrp remained largely unchanged (about 110 mg/L) from 16 h to 24 h and then decreased to about 63 mg/L at 40 h. By contrast, E. coli-II produced the highest amount of Nitrotrp after 24 h at 20° C. and 28° C., and fermentation at 28° C. resulted in production of 175.5±5.3 mg/L Nitrotryp. E. coli-II produced less than 14 mg/L of Nitrotrp at any time point when fermented at 37° C. Data indicate increased production of Nitrotrp in E. coli from 36.5 mg/L for 3 days to 175.5 mg/L for 1 day based upon changes to fermentation media and temperature conditions.

Figure 17:
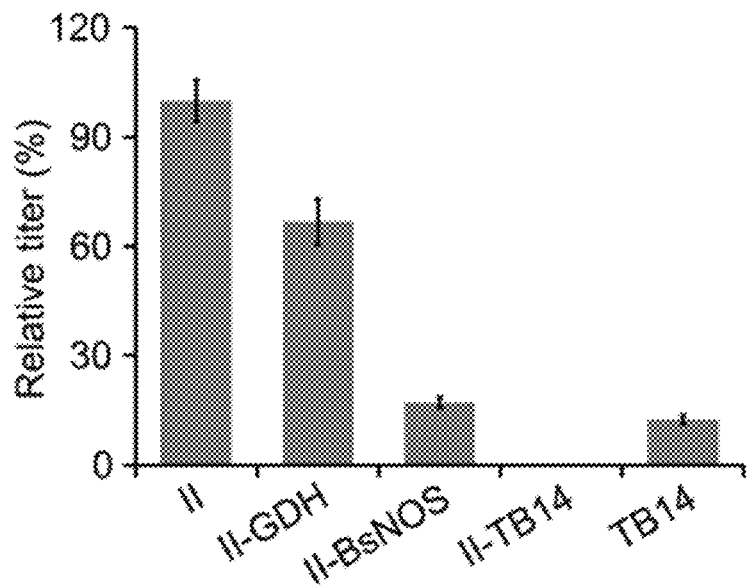
FIG. 17 shows relative titers of Nitrotrp by five E. coli strains. All strains were cultured in TB at 28° C., 250 rpm. Aliquots (0.1 mL) of the fermentation culture were taken after 24 h and the concentration of Nitrotrp in the samples was measured in HPLC analysis. The amount of Nitrotrp by E. coli-II was set as 100% for normalizing the relative titer of other strains. The data represent means±s.d. of at least two independent experiments.

Nitrotrp pathway II comprises TB14, BsNOS, and GDH (FIG. 10A) that together lead to the production of 175 mg/L of Nitrotrp by E. coli-II (FIG. 16B). Removal of each enzyme was investigated. TB14, BsNOS, and GDH genes were removed individually from the pathway II and the three resultants were transformed into E. coli BL21-GOLD (DE3) to generate E. coli-II-TB14, -BsNOS, and -GDH. As the control, pET28b-TB14 was used to create E. coli-TB14 following the same procedure (Table 3). These four new strains along with E. coli-II were cultured in TB at 28° C. for 24 h. HPLC analysis then quantitated the titers of Nitrotrp by all five strains (FIG. 17). *E. coli*-II-TB14 completely lost the ability to produce Nitrotrp. *E. coli*-II-BsNOS retained 17.2±1.5% of the titer of *E. coli*-II, indicating the presence of additional sources of NO for the TB14 reaction (FIG. 17). For example in some embodiments, an indoor atmosphere can supply more than 2 μM of NO for the biotransformation. Similarly, *E. coli*-TB14 also produced a relatively low level of Nitrotrp (12.5±1.2% of the titer of *E. coli*-II). Among the three enzymes in the pathway II, GDH was observed to provide a supporting role to the reactions of TB14 and BsNOS as *E. coli*-II-GDH showed 66.8±6.4% of the titer of *E. coli*-II (FIGS. 9 and 17).

The production of Nitrotrp consumes cellular 1-Trp and 1-Arg of *E. coli* (FIG. 9). The concentrations of 1-Trp in TB were measured at varying time points when fermenting *E. coli*-II; a quick decrease from 260.8±12.0 mg/L at 0 h to 25.3±9.8 mg/L after 24 h was observed (FIG. 18). However, l-Trp supplementation to TB was not observed to have an effect on improving the production of Nitrotrp (FIG. 16A), indicating the increased cellular availability of 1-Trp may be more important to increase Nitrotrp production. Tuning of 1-Trp metabolic pathways in *E. coli* (FIG. 9) was investigated. Of note, l-Arg biosynthesis was not selected as the primary engineering target as the increased 1-Arg may lead, in some embodiments, to the higher production of NO that can be detrimental to *E. coli*. The tnaA gene in *E. coli* BL21-GOLD(DE3) was knocked out by the λ red recombination approach. to prevent the conversion of cellular 1-Trp into indole (FIGS. 9 and 19). Pathway II was then transferred into the *E. coli* ΔtnaA mutant for the production of Nitrotrp (Table 3). Neither recombinant TB14 and BsNOS nor GDH was detectable from soluble protein fraction of *E. coli* ΔtnaA-II by SDS-PAGE analysis (FIG. 20), leading to no observed production of Nitrotrp.

Increasing the metabolic flux to 1-Trp biosynthesis was investigated (FIG. 9). The biosynthetic pathways of 1-Trp, 1-Phe, and 1-Tyr require the same cellular metabolite chorismate that is produced from the shikimate biosynthetic pathway. TyrA and PheA convert chorismate into prephenate for the production of 1-Tyr and 1-Phe, while TrpE produces anthranilate from chorismate to synthesize 1-Trp. The inactivation of both tyrA and pheA genes in *E. coli* BL21-GOLD (DE3), in some embodiments, eliminates the competitive consumption of chorismate for the increased production of 1-Trp in the fermentation stage. TrpR has also been observed to provide a negative feedback regulation on the 1-Trp biosynthesis by acting on 1-Trp biosynthetic gene and the shikimate biosynthetic gene (FIG. 9), and the inactivation of the trpR gene has been observed to overproduce 1-Trp in *E. coli*. These three genes were inactivated in *E. coli* BL21-GOLD (DE3) to create *E. coli* ΔtrpRtyrApheA using the λ red recombination approach (Table 3, FIG. 19). Both wild type *E. coli* and the ΔtrpRtyrApheA mutant were fermented in TB medium under the same conditions for 20 h. HPLC analysis revealed 273±33 mg/L of free 1-Trp in the fermentation medium of the mutant and 142±25 mg/L for the wild type, indicating an increased intracellular supply of 1-Trp in the mutant. *E. coli* ΔtrpRtyrApheA-II was then generated by transforming the designed Nitrotrp pathway II into the mutant. HPLC analysis revealed the concentration of 1-Trp in the culture of *E. coli* ΔtrpRtyrApheA-II was decreasing in the fermentation process but remained higher than *E. coli*-II at the majority of time points (FIG. 18), indicating that the mutant production strain may have a slower rate to consume medium 1-Trp than *E. coli*-II as it synthesizes more cellular 1-Trp. *E. coli* ΔtrpRtyrApheA-II produced a higher level of Nitrotrp than *E. coli*-II at 10 h and 20 h (FIG. 18), and reached the highest titer, 191.8±10.3 mg/L, at 20 h, which was about 10% increased compared with *E. coli*-II at 24 h (FIG. 16B).

Production of Nitrotrp analogs was examined by feeding eight unnatural racemic 1-Trp analogs (except for 5-F-1-Trp) (5 mM) to the fermentation medium of *E. coli*-II (FIGS. 21 and 22A). HPLC analysis revealed that α-Me-Trp, 4-F-Trp, 4-Me-Trp, 5-MeO-Trp, 5-Me-Trp, 5-F-1-Trp, 6-F-Trp and 7-Me-Trp all were nitrated along with 1-Trp to varying extents by *E. coli*-II (FIG. 22B). The 1-amino acid substrate was observed to be nitrated by TB14 in in vitro studies. The strain demonstrated the highest nitration activity toward 5-Me-Trp, followed by 5-F-Trp and 4-Me-Trp, while only about 2.5 mg/L of the nitro product was produced from fed 4-F-Trp (FIG. 21). This data agreed with the observed in vitro catalytic performance of TB14 toward these substrates. The titer of nitro-5-Me-Trp reached 61.5±5.5 mg/L, along with 80.3±10.4 mg/L of Nitrotrp after culturing *E. coli*-II for 24 h (FIG. 21).

Materials and Methods
General Chemicals, DNA Sub-Cloning, and Bacterial Strains

Molecular biology reagents and enzymes were purchased from Fisher Scientific. Primers were ordered from Sigma-Aldrich. Racemic 4-Me-Trp was from MP Biomedical (Santa Ana, CA). Other chemicals and solvents were purchased from Sigma-Aldrich or Fisher Scientific. *Escherichia coli* DH5α (Life Technologies) was used for molecular biology work, while *E. coli* BL21-GOLD (DE3) (Agilent) was used for protein overexpression and the development of the whole cell nitration systems (Table 3). *E. coli* strains were grown in M9, LB or TB. DNA sequencing was performed at Eurofins. A Shimadzu Prominence UHPLC system (Kyoto, Japan) fitted with an Agilent Poroshell 120 EC-C18 column (2.7 μm, 3.0×50 mm), coupled with a PDA detector was used for HPLC analysis.

Creation of Nitrotrp Biosynthetic Pathways

BsNOS, TB14 and GDH genes were amplified from pET15b-BsNOS, pET28b-TB14, and pET21b-GDH, respectively using primers listed in Table 4. PCR amplicons were analyzed by agarose gel and extracted with GeneJET Gel Extraction Kit (Thermo). Purified PCR products, pACYCDuet-1, pETDuet-1, and pET28b were digested with corresponding restriction enzymes, purified and then ligated to create expression constructs. All inserts in the constructs were sequenced to exclude potential errors introduced during PCR amplification and gene manipulation.

Whole-Cell Biotransformation

*E. coli* BL21-GOLD (DE3) competent cells were transformed with the designed pathway I-IV individually (Table 3). Positive colonies of *E. coli*-I, to -IV were selected on LB agar supplemented with 0.1 mg/mL ampicillin and 0.05 mg/mL kanamycin or 0.05 mg/mL chloramphenicol and 0.05 mg/mL kanamycin. One colony of each strain was then grown in LB with proper antibiotics at 37° C., 250 rpm overnight. The seed cultures were used to inoculate 100 mL of TB with proper antibiotics and 1× trace metal solution (1000× stock solution: 50 mM $FeCl_3$, 20 mM $CaCl_2$, 10 mM $MnSO_4$, 10 mM $ZnSO_4$, 2 mM $CoSO_4$, 2 mM $CuCl_2$, 2 mM $NiCl_2$, 2 mM $Na_2MoO_4$, and 2 mM $H_3BO_3$) for culturing at 37° C., 250 rpm until $OD_{600}$ reached 0.6-0.8. We then induced protein expression by 0.5 mM IPTG at 18° C., 250 rpm for 20 h. For the evaluation of protein expression, cell pellets were then collected after centrifugation (5,000 g, 10 min, and 4° C.), and resuspended in the suitable volume of lysis buffer (cell biomass:volume=1:4) [25 mM Tris-HCl, pH 8.0, 100 mM NaCl, 20 mM imidazole, 3 mM β-mercaptoethanol (BME) and 10% glycerol]. Soluble proteins were released by sonication and collected after centrifugation at 35,000×g at 4° C. for 30 min. Clear supernatants (20 µL) was mixed with dye and subject to SDS-PAGE analysis. For the whole cell biotransformation, bacterial cells in TB were harvested after centrifugation (2,000 g at 4° C. for 10 min) and resuspended to $OD_{600}=30$ in fresh test media (M9, LB, or TB with or without 5 mM 1-Trp or 1-Arg). The fermentation was then performed at different temperatures, 250 rpm and aliquots (0.1 mL) of the fermentation culture were taken at various time points. The whole-cell biotransformation in aliquots was quenched by mixing with 0.2 mL of methanol. After centrifugation at 14,000 rpm for 30 minutes, the supernatant was subject to HPLC analysis. All experiments were independently repeated at least twice.

Inactivation of Genes in E. coli

Inactivation of tnaA, trpR, tyrA, and pheA in E. coli BL21-GOLD (DE3) was performed following the λ red recombination protocol (FIG. 19). Specific primers used were included in Table 4.

TnaA Assay

The tnaA gene was amplified from E. coli genomic DNA using primers listed in Table 4. PCR amplicons were analyzed by agarose gel and extracted with GeneJET Gel Extraction Kit (Thermo). Purified PCR products and pET28b were digested with corresponding restriction enzymes, purified and then ligated to create expression constructs. Insert in the construct was sequenced to exclude potential errors introduced during PCR amplification and gene manipulation. Recombinant TnaA was prepared in E. coli BL21-GOLD (DE3). The enzyme assay (0.1 mL) contained 100 mM potassium phosphate buffer (pH 8.3), 0.2 mM pyridoxal 5-phosphate and 0.1 µM purified tnaA. The reaction mixtures were pre-warmed at 37° C. for 5 minutes, and initiated by adding 0.5 mM 1-Trp or Nitrotrp as substrate. After 10 minutes, the reactions were quenched by mixing well with 0.2 mL of methanol. After centrifugation at 14,000 rpm for 30 minutes, the supernatant was subject to HPLC analysis. All experiments were independently repeated at least twice.

HPLC and LC-MS Methods

For HPLC analysis, the $C_{18}$ column was kept at 30° C. and ran first with 5% solvent B (acetonitrile, 0.1% formic acid) for 2 min and then a linear gradient of 5-15% solvent B in 5 min, followed by another linear gradient of 15-95% solvent B in 10 min. The column was further cleaned with 95% solvent B for 3 min and then re-equilibrated with 5% solvent B for 2 min. Solvent A was water with 0.1% formic acid. The flow rate was set as 0.5 mL/min, and the products were detected at 211 nm with a PDA detector. The concentrations of Nitrotrp and/or 1-Trp in the samples were determined on the basis of standard curves of two authentic compounds after HPLC analysis (FIGS. 22A-22B). LC-MS analysis was performed by established protocols.

TABLE 4

| Name | Sequence (5'→3') | Function |
| --- | --- | --- |
| TB14FN | ATACCATGGTGACCGTCCCCTCGCCG (SEQ ID NO: 35) | TB14 cloning |
| TB14RH | ATCAAGCTTCCCAGCCCACACGTCTTTTGC (SEQ ID NO: 36) | TB14 cloning |
| GDHFB | CAGGATCC GATGTATAAAGATCTGGAAGGTAAAGTGGTG (SEQ ID NO: 37) | GDH cloning |
| GDHRH | CAAAGCTTTTAGCCACGACCTGCCTGAAAG (SEQ ID NO: 38) | GDH cloning |
| BsNOSFN | ACTCATATGATGGAAGAAAAAGAAATC (SEQ ID NO: 39) | BsNOS cloning |
| BsNOSRH | ACTAAGCTT CTATTCATACGGTTTGTC (SEQ ID NO: 40) | BsNOS cloning |
| tnaAFB | ACTGGATCCGATGGAAAACTTTAAACATCTCC (SEQ ID NO: 41) | tnaA cloning |
| tnaARE | ACTGAATTCGAAACTTCTTTAAGTTTTGCGGTG (SEQ ID NO: 42) | tnaA cloning |
| trpR-F | TACAACCGGGGGAGGCATTTTGCTTCCCCCGCTAACAATGGCGAC ATATTGTGTAGGCTGGAGCTGCTTC (SEQ ID NO: 43) | trpR knock out |
| trpR-R | ATTCGGTGCACGATGCCTGATGCGCCACGTCTTATCAGGCCTACA AAACATATGAATATCCTCCTTA (SEQ ID NO: 44) | trpR knock out |
| pheA-F | GGCCTCCCAAATCGGGGGGCCTTTTTTATTGATAACAAAAAGGCA ACACTGTGTAGGCTGGAGCTGCTTC (SEQ ID NO: 45) | pheA knock out |
| pheA-R | GCCAGTAATAATCCAGTGCCGGATGATTCACATCATCCGGCACCTT TTCACATATGAATATCCTCCTTA (SEQ ID NO: 46) | pheA knock out |
| tyrA-F | TCAGGATCTGAACGGGCAGCTGACGGCTCGCGTGGCTTAAGAGG TTTATTGTGTAGGCTGGAGCTGCTTC (SEQ ID NO: 47) | tyrA knock out |
| tyrA-R | CAACCTGATGAAAAGGTGCCGGATGATGTGAATCATCCGGCACTG GATTACATATGAATATCCTCCTTA (SEQ ID NO: 48) | tyrA knock out |
| tnaA-F | GGATCACTGTAATTAAAATAAATGAAGGATTATGTAATGGTGTAGGC TGGAGCTGCTTC (SEQ ID NO: 49) | tnaA knock out |
| tnaA-R | GTGGCTAACATCCTTATAGCCACTCTGTAGTATTAATTACATATGAAT ATCCTCCTTA (SEQ ID NO: 50) | tnaA knock out |

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

What is claimed is:

1. A method for producing a nitrated L-tryptophan or nitrated L-tryptophan analogue, the method comprising:
   (i) introducing into a bacterial cell culture comprising a recombinant bacterial cell comprising one or more isolated nucleic acids engineered to express:
      a fusion protein comprising a TxtE enzyme linked to a catalytic domain of a CYP102A1 (P450BM3) reductase enzyme via an amino acid linker sequence that is between 14 and 27 amino acids in length, wherein the fusion protein is a TB14 fusion protein having the sequence set forth in SEQ ID NO: 1;

a nitric oxide synthase (NOS) enzyme; and, optionally a glucose dehydrogenase (GDH) enzyme, one or more L-Trp molecules and/or one or more L-Trp analogue molecules;

(ii) growing the bacterial cell culture under conditions under which the fusion protein catalyzes a nitration reaction which produces one or more nitrated L-Trp molecules and/or one or more nitrated L-Trp analog molecules; and, optionally, (iii) isolating nitrated L-Trp molecules and/or nitrated L-Trp analog molecules.

2. The method of claim 1, wherein the one or more L-Trp analogue molecules are selected from the group consisting of α-Me-Trp, 4-F-Trp, 4-Me-Trp, 5-MeO-Trp, 5-Me-Trp, 5-F-Trp, 6-F-Trp, and 7-Me-Trp.

3. The method of claim 1, wherein the step of growing the bacterial cell culture comprises introducing one or more antibiotic and/or one or more inducer into the bacterial cell culture.

4. The method of claim 3, wherein the one or more antibiotic is selected from ampicillin and kanamycin.

5. The method of claim 3, wherein the one or more inducer is Isopropyl β-D-1-thiogalactopyranoside (IPTG).

6. The method of claim 1, wherein the step of growing the bacterial cell culture is performed at a temperature below 37° C.

7. The method of claim 6, wherein the step of growing the bacterial cell culture is performed at a temperature between 10 to 30° C., optionally at a temperature of 28° C.

8. The method of claim 1, wherein the bacterial cell culture is grown for up to 25 hours.

9. The method of claim 1, wherein the step of isolating the nitrated L-Trp molecules and/or nitrated L-Trp analog molecules comprises lysing the recombinant bacterial cell.

10. The method of claim 9, wherein the step of isolating further comprises performing high-pressure liquid chromatography (HPLC) on the bacterial cell lysate, or performing a liquid extraction method on the bacterial lysate.

11. The method of claim 1, wherein the NOS enzyme is a bacterial NOS enzyme, optionally wherein the NOS enzyme is a *Bacillus subtilis* enzyme or wherein the NOS enzyme is encoded by the sequence set forth in SEQ ID NO: 3.

12. The method of claim 1, wherein the GDH enzyme is a bacterial GDH enzyme, optionally wherein the bacterial GDH enzyme is a *Bacillus megaterium* GDH enzyme.

13. The method of claim 1, wherein an isolated nucleic acid engineered to express the NOS enzyme and an isolated nucleic acid engineered to express the GDH enzyme are located on the same plasmid.

14. The method of claim 13, wherein the isolated nucleic acid engineered to express the fusion protein is located on a plasmid that does not contain an isolated nucleic acid engineered to express the NOS enzyme or an isolated nucleic acid engineered to express the GDH enzyme.

15. The method of claim 1, wherein the bacterial cell is genetically modified to lack expression of one or more of the following genes: traA, trpR, tyrA, and pheA, optionally wherein the bacterial cell comprises the genotype $\Delta$trpR$\Delta$tyrA$\Delta$pheA.

16. The method of claim 1, wherein the bacterial cell is a Gram-negative bacterial cell, optionally wherein the bacterial cell is an *E. coli* cell.

17. The method of claim 1, wherein the one or more nitrated L-Trp analog molecules comprise 4-NO2-L-Trp, 4-NO2-$\alpha$-Me-Trp, 7-NO2-4-F-Trp, 5-NO2-4-Me-Trp, 7-NO2-4-Me-Trp, 4-NO2-5-MeO-Trp, 4-NO2-5-Me-Trp, 4-NO2-5-F-Trp, 4-NO2-6-F-Trp, or 4-NO2-7-Me-Trp.

* * * * *

SEQUENCE LISTING

```
Sequence total quantity: 50
SEQ ID NO: 1              moltype = AA   length = 992
FEATURE                   Location/Qualifiers
REGION                    1..992
                          note = Synthetic Polypeptide
source                    1..992
                          mol_type = protein
                          organism = synthetic construct
SEQUENCE: 1
MTVPSPLADP SIVPDPYPVY ADLAQRRPVH WVERLNAWAV LTYADCAAGL KDPRLTADRG    60
TEVLAAKFPG QPLPPDNIFH RWTKNVVMYT DPPLHDALRR SVRAGFTRAA HQHYDQVLQK   120
VAHDLVASIP AGATEIDAVP ALAAELPVRS AVHAFGVPEE DLGFLIPRVN TIMTYHSGPK   180
DQPVTQEIIL EKLTDLHTYA SELLQGMRGK VLPDTVIARL AAAQDGLTET TPEQTVHQLA   240
LVFIALFAPT TPGSLSSGTL AFARNPRQVE RFLADQACVD NTANEVLRYN ASNQFTWRVA   300
AKDVEMGGVR IEAGQTLALF LGSANRDANM FERPNDFDLD RPNSARHLSF GQGVHACLAA   360
QLISLQLKWF YVALLNRFPG IRTAGEPIWN ENLEFRSLRS LPLSLRELQS AKKVRKKAEN   420
AHNTPLLVLY GSNMGTAEGT ARDLADIAMS KGFAPQVATL DSHAGNLPRE GAVLIVTASY   480
NGHPPDNAKQ FVDWLDQASA DEVKGVRYSV FGCGDKNWAT TYQKVPAFID ETLAAKGAEN   540
IADRGEADAS DDFEGTYEEW REHMWSDVAA YFNLDIENSE DNKSTLSLQF VDSAADMPLA   600
KMHGAFSTNV VASKELQOPG SARSTRHLEI ELPKEASYQE GDHLGVIPRN YEGIVNRVTA   660
RPFGLDASQQI RLEAEEEKLA HLPLAKTVSV EELLQYVELQ DPVTRTQLRA MAAKTVCPPH   720
KVELEALLEK QAYKEQVLAK RLTMLELLEK YPACEMKFSE FIALLPSIRP RYYSISSSPR   780
VDEKQASITV SVVSGEAWSG YGEYKGIASN YLAELQEQDT ITCFISTPQS EFTLPKDPET   840
PLIMVGPGTG VAPFRGFVQA RKQLKEQGQS LGEAHLYFGC RSPHEDYLYQ EELENAQSEG   900
IITLHTAFSR MPNQPKTYVQ HVMEQDGKKL IELLDQGAHF YICGDGSQMA PAVEATLMKS   960
YADVHQVSEA DARLWLQQLE EKGRYAKDVW AG                                 992

SEQ ID NO: 2              moltype = DNA   length = 2985
FEATURE                   Location/Qualifiers
misc_feature              1..2985
                          note = Synthetic Polynucleotide
source                    1..2985
                          mol_type = other DNA
                          organism = synthetic construct
SEQUENCE: 2
atgggcatga ccgtgccgag cccgctggct gatccgagca tcgtgccaga tccgtacccg    60
gtttacgcgg atctggcgca acgtcgcccg gtgcactggg ttgagcgtct gaacgcctgg   120
gcagtgctga cctatgcaga ttgcgcggcg ggtctgaagg accgcgtttt gaccgcggat   180
agaggtaccg aggtgctggc agcgaagttt ccgggtcagc cactgccgcc ggataacatc   240
tttcaccgtt ggaccaagaa tgtggttatg tacaccgatc cgctgcatga tgctcttcg   300
cgtcgcagcg tgcgtgcagg tttcacccgc gcggctcacc aacattatga tcaggtcctg   360
caaaaagtag cccacgatct ggttgcaagc atcccggcgg gtgcaaccga gattgatgct   420
gttccagcac tggcggcgga gctgccggtg cgtagcgcgg tgcatgcatt cggtgttccg   480
gaggaagatt tgggttttct gatcccgcgt gtgaacacga ttatgactta ccactctgga   540
ccgaaggatc agccggttac ccaagagatc attctggaga aactgaccga tctgcacacg   600
tatgcgtcgg agctggttca gggtatgcgt ggtaaggtcc tgccggatac cgtaattgca   660
agactggctg cggcgcaaga tggtctgacc gaaaccaccc cggaacagac ggtccaccaa   720
ctggcgttgg tgttcattgc tctgtttgca ccaaccactc cgggtagcct gagcagcggt   780
accctggcat ttgcaagaaa cccgcgtcag gtggagcgtt ttctggccga tcaagcgtgc   840
gttgataaca ccgcgaatga agtgctgcgt tacaacgcgt ctaatcagtt cacctggcgc   900
gtcgccgcga aggatgtgga gatgggtggt gttcgtattg aagctggtca aaccctggcg   960
ctgttcctgg gtagcgctaa ccgtgatgca aatatgttcg agcgcccgaa cgattttgat  1020
ctggatcgtc cgaacagcgc aagacacctg agcttcggtc agggtgttca tgcgtgtctg  1080
gctgcacagt tgatcagcct gcaactgaaa tggttctatg tggcgctgtt gaaccgtttt  1140
ccgggtattc gcaccgcggg tgaaccgatt tggaatgaga acctggagtt tcgtagcctg  1200
cgtagcctgc cgctgagcct gcgtgagctc cagtctgcta aaaaagtacg caaaaaggca  1260
gaaaacgctc ataatacgcc gctgcttgtg ctatacggtt caaatatggg aacagctgaa  1320
ggaacgcgcg tgatttagc agatattgca atgagcaaag gatttgcacc gcaggtcgca  1380
acgcttgatt cacacgccgg aaatcttccg cgcgaaggag ctgtattaat tgtaacggcg  1440
tcttataacg gtcatccgcc tgataacgca aagcaatttg tcgactggtt agaccaagcg  1500
tctgctgatg aagtaaaagg cgttcgctac tccgtatttg gatgcggcga taaaaactgg  1560
gctactacgt atcaaaaagt gcctgctttt atcgatgaaa cgcttgccgc taaagggcga  1620
gaaaacatcg ctgaccgcgg tgaagcagat gcaagcgacg actttgaagg cacatatgaa  1680
gaatggcgta acatatgtgg gagtgacgta gcagcctact ttaacctcga cattgaaaac  1740
agtgaagata taaatctac tctttcactt caatttgtcg acagcgccgc ggatatgccg  1800
cttgcgaaaa tgcacggtgc gttttcaacg aacgtcgtag caagcaaaga acttcaacag  1860
ccaggcagtg cacgaagcac gcgacatctt gaaattgaac ttccaaaaga agcttcttat  1920
caagaaggag atcatttagg tgttattcct cgcaactatg aaggaatagt aaaccgtgta  1980
acagcaaggt tcggcctaga tgcatcacag caaatccgtc tggaagcaga agaaaaaa   2040
ttagctcatt tgccactcgc taaaacagta tccgtagaag agcttctgca atacgtggag  2100
cttcaagatc ctgttacgcg cacgcagctt cgcgcaatgg ctgctaaaac ggtctgcccg  2160
ccgcataaag tagagcttga agccttgctt gaaaagcaag cctacaaaga acaagtgctg  2220
gcaaaacgtt taacaatgct tgaactgctt gaaaaatacc cggcgtgtga atgaaattc  2280
agcgaattta tcgcccttct gccaagcata cgcccgcgct attactcgat tcttcatca  2340
cctcgtgtcg atgaaaaaca agcaagcatc acggtcagcg ttgtctcagg agaagctgg  2400
agcggatatg gagaatataa aggaattgcg tcgaactatc ttgccgagct gcaagaagga  2460
gatacgatta cgtgctttat ttccacaccg cagtcagaat tacgctgcc aaaagaccct  2520
gaaacgccgc ttatcatggt cggaccggga acaggcgtcg cgccgtttag aggctttgtg  2580
```

```
caggcgcgca aacagctaaa agaacaagga cagtcacttg gagaagcaca tttatacttc  2640
ggctgccgtt cacctcatga agactatctg tatcaagaag agcttgaaaa cgcccaaagc  2700
gaaggcatca ttacgcttca taccgctttt tctcgcatgc caaatcagcc gaaaacatac  2760
gttcagcacg taatgaaaca agacggcaag aaattgattg aacttcttga tcaaggagcg  2820
cacttctata tttgcggaga cggaagccaa atggcacctg ccgttgaagc aacgcttatg  2880
aaaagctatg ctgacgttca ccaagtgagt gaagcagacg ctcgcttatg gctgcagcag  2940
ctagaagaaa aaggccgata cgcaaaagac gtgtgggctg ggtaa              2985

SEQ ID NO: 3              moltype = DNA  length = 1092
FEATURE                   Location/Qualifiers
misc_feature              1..1092
                          note = Synthetic Polynucleotide
source                    1..1092
                          mol_type = other DNA
                          organism = synthetic construct
SEQUENCE: 3
ttggaagaaa aagaaatact ctggaacgaa gcgaaagcgt ttattgccgc atgctatcag  60
gaattgggaa aggaggagga agtgaaagac cgtctcgcgg acattaaaag tgaaattgac  120
ctgaccggaa gctatgtaca tacgaaggaa gagctggagc acggagcgaa aatggcttgg  180
agaaacagca accgctgcat cggcagattg ttctggaatt cgctgaatgt tatcgacaga  240
cgagacgtcc ggacgaagga ggaagtgcgt gatgccctct tcaccatat tgaaaccgcc  300
accaataacg ggaaaatcag accgaccatt acgattttcc ctccggaaga gaagggtgaa  360
aagcaagtcg agatctggaa tcatcagctg atccggtacg ctggatatga gtcagacgga  420
gaaagaatcg gcgacccggc ttcctgttcc ctgacagcag cctgcgaaga gctcggctgg  480
cgcggagagc gaacggattt tgacctgctg ccgctcattt ttcgcatgaa aggggacgag  540
cagcctgtct ggtatgagct gccgcgttca ctttgtgattg aggttccaat cacacatccg  600
gacatcgagg cgttttctga tttgagctg aagtggtacg gcgtgcctat tatttctgat  660
atgaagcttg aggtcgggg cattcattat aatgccgcgc catttaacgg ctggtatatg  720
ggcacggaga tcggagcgag aaacctcgca gatgaaaagc ggtacgacaa gctcaaaaaa  780
gtagcgtccg tgatcggcat cgccgctgat tacaatacgg atttatggaa ggatcaagcg  840
ctagttgaat tgaataaagc tgtgctgcac tcgtataaaa agcagggtgt cagcatcgtt  900
gaccatcata cagcggcaag ccagtttaaa cggtttgaag aacaggagga agaagcgggc  960
agaaagctga cggggactg gacgtggctg attcgccaa tttcacccgc tgccactcat  1020
atcttccacc gctcctatga taactcaatc gttaagccga actattttta tcaagataag  1080
ccttatgagt aa                                                      1092

SEQ ID NO: 4              moltype = DNA  length = 1092
FEATURE                   Location/Qualifiers
misc_feature              1..1092
                          note = Synthetic Polynucleotide
source                    1..1092
                          mol_type = other DNA
                          organism = synthetic construct
SEQUENCE: 4
atggaagaaa aagaaatcct gtggaacgaa gccaaagcat tcatcgcagc gtgctaccaa  60
gaactgggca agaagaaga gtcaaagat cgcctggcgg acattaaaag tgaaatcgat  120
ctgaccggtt cctatgttca tacgaaagaa gaactggagc acggcgcaaa aatggcttgg  180
cgtaacagca atcgctgcat tggtcgtctg ttttggaact ctctgaatgt gatcgatcgt  240
cgcgacgttc gcacgaaaga agaagtccgt gatgcgctgt tcatcacat gaaaccgcc  300
acgaacaatg gtaaaatccg tccgaccatt acgatcttcc cgccggaaga aaaaggcgaa  360
aaacaggttg aaatttggaa ccatcaactg atccgctatg caggctacga aagcgacggc  420
gaacgtattg gtgatccggc tagctgctct ctgaccgcgg cctgtgaaga actgggctgg  480
cgtggtgaac gcacggattt tgacctgctg ccgctgattt tccgcatgaa aggtgatgaa  540
cagccggtgt ggtatgaact gccgcgttct ctggtgattg aagttccgat cacccatccg  600
gacatcgaag cctttagtga tctggaactg aaatggtacg gcgtcccgat tatctccgat  660
atgaaactgg aagtgggcgg tattcactat aaccagctc cgttcaatgg ctggtacatg  720
ggcaccgaaa tcggcgcgcg caatctggcc gacgaaaaac gttacgataa actgaaaaaa  780
gtcgcatcag tgattggtat cgcggccgat acaacacgg acctgtggaa agatcaggca  840
ctggtggaac tgaataaagc tgttctgcac tcatacaaaa aacaaggcgt ttcgattgtg  900
gatcatcaca ccgcagcttc acagtttaaa cgcttcgaag aacaggaaga agaagcgggt  960
cgtaaactga ccggcgattg gacgtggctg attcgccga tctcgccggc agcaacccat  1020
atcttccacc gctcgtatga caatagcatc gtgaaaccga attacttcta ccaggacaaa  1080
ccgtatgaat ag                                                      1092

SEQ ID NO: 5              moltype = AA  length = 363
FEATURE                   Location/Qualifiers
REGION                    1..363
                          note = Synthetic Polypeptide
source                    1..363
                          mol_type = protein
                          organism = synthetic construct
SEQUENCE: 5
MEEKEILWNE AKAFIAACYQ ELGKEEEVKD RLADIKSEID LTGSYVHTKE ELEHGAKMAW   60
RNSNRCIGRL FWNSLNVIDR RDVRTKEEVR DALFHHIETA TNNGKIRPTI TIFPPEEKGE   120
KQVEIWNHQL IRYAGYESDG ERIGDPASCS LTAACEELGW RGERTDFDLL PLIFRMKGDE   180
QPVWYELPRS LVIEVPITHP DIEAFSDLEL KWYGVPIISD MKLEVGGIHY NAAPFNGWYM   240
GTEIGARNLA DEKRYDKLKK VASVIGIAAD YNTDLWKDQA LVELNKAVLH SYKKQGVSIV   300
DHHTAASQFK RFEEQEEEAG RKLTGDWTWL IPPISPAATH IFHRSYDNSI VKPNYFYQDK   360
PYE                                                                 363
```

```
SEQ ID NO: 6              moltype = DNA  length = 786
FEATURE                   Location/Qualifiers
misc_feature              1..786
                          note = Synthetic Polynucleotide
source                    1..786
                          mol_type = other DNA
                          organism = synthetic construct
SEQUENCE: 6
atgtataaag atctggaagg taaagtggtg gtgattaccg gcagcagcac cggtctgggc   60
aaagcaatgg cgattcgttt tgcgaccgaa aaagcgaaag tggtggttaa ctatcgcagc  120
aaagaagaag aagcgaacag cgttctggaa gaaattaaaa aagtgggtgg cgaagcgatt  180
gcggtgaaag gtgatgtgac cgtggaaagc gatgtgatta acctggtgca gagcagcatt  240
aaagaatttg gcaaactgga tgtgatgatt aacaatgcgg gtatggaaaa tccggtgagc  300
agccatgaaa tgagcctgag cgattggaac aaagtgattg ataccaacct gaccggtgcg  360
tttctgggca gccgtgaagc gattaaatac ttcgtggaaa acgatattaa aggcaccgtg  420
attaacatga gcagcgtgca tgaaaaaatt ccgtggccgc tgtttgtgca ttatgcagcg  480
agcaaaggcg gtatgaaact gatgaccgaa accctggctc tggaatatgc accgaaaggc  540
attcgtgtga acaacattgg tccgggtgcg attaacaccc cgattaacgc ggaaaaattt  600
gccgatccgg aacagcgtgc ggatgtgaaa agcatgattc cgatgggcta tattggcgaa  660
ccggaagaaa ttgcagcggt ggcagcgtgg ctggcaagca gcgaagcgag ctatgtgacc  720
ggcattaccc tgtttgcgga tggcggtatg acccagtatc cgagctttca ggcaggtcgt  780
ggctaa                                                             786

SEQ ID NO: 7              moltype = AA  length = 261
FEATURE                   Location/Qualifiers
REGION                    1..261
                          note = Synthetic Polypeptide
source                    1..261
                          mol_type = protein
                          organism = synthetic construct
SEQUENCE: 7
MYKDLEGKVV VITGSSTGLG KAMAIRFATE KAKVVVNYRS KEEEANSVLE EIKKVGGEAI   60
AVKGDVTVES DVINLVQSSI KEFGKLDVMI NNAGMENPVS SHEMSLSDWN KVIDTNLTGA  120
FLGSREAIKY FVENDIKGTV INMSSVHEKI PWPLFVHYAA SKGGMKLMTE TLALEYAPKG  180
IRVNNIGPGA INTPINAEKF ADPEQRADVE SMIPMGYIGE PEEIAAVAAW LASSEASYVT  240
GITLFADGGM TQYPSFQAGR G                                            261

SEQ ID NO: 8              moltype = DNA  length = 8215
FEATURE                   Location/Qualifiers
misc_feature              1..8215
                          note = Synthetic Polynucleotide
source                    1..8215
                          mol_type = other DNA
                          organism = synthetic construct
SEQUENCE: 8
atccggatat agttcctcct ttcagcaaaa aaccccctca agacccgttta gaggccccaa   60
gggttatgc tagttattgc tcagcggtgg cagcagccaa ctcagcttcc tttcgggctt   120
tgttagcagc cggatctcag tggtggtggt ggtggtgctc gagcccagcc cacacgtctt   180
ttgcgtatcg gccttttttct tctagctgct gcagccataa gcgagcgtct gcttcactca   240
cttggtgaac gtcagcatag cttttcataa gcgttgcttc aacggcaggt gccatttggc   300
ttccgtctcc gcaaatatag aagtgcgctc cttgatcaag aagttcaatc aatttcttgc   360
cgtcttgttc cattacgtgc tgaacgtatg ttttcggctg atttggcatg cgagaaaaag   420
cggtatgaag cgtaatgatg ccttcgcttt gggcgttttc aagctcttct tgatacagat   480
agtcttcatg aggtgaacgg cagccgaagt ataaatgact ttctccaagt gactgtcctt   540
gttcttttag ctgtttgcgc gcctgcacaa agcctctaaa cggcgcgacg cctgttcccg   600
gtccgaccat gataagcggc gtttcagggt cttttggcag cgtaaattct gactgcggtg   660
tggaaataaa gcacgtaatc gtatctcctt cttgcagctc ggcaagatag ttcgacgcaa   720
ttcctttata ttctccatat ccgctccacg ctttctcctg gacaacgctg accgtgatgc   780
ttgcttgttt ttcatcgaca cgaggtgatg aagaaatcga gtaatacgc gggcgtatgc   840
ttggcagaag ggcgataaat tcgctgaatt tcatttcaca cgccgggtat ttttcaagca   900
gttcaagcat tgttaaacgt tttgccagca cttgttcttt gtaggcttgc ttttcaagca   960
aggcttcaag ctctactttta tgcggcgggc agaccgtttt agcagccatt gcgcgaagct  1020
gcgtgcgcgt aacaggatct tgaagctcca cgtattgcag aagctcttct acggatactg  1080
ttttagcgag tggcaaatga gctaatttttt cttcttctgc ttccagacgg atttgctgtg  1140
atgcatctag gccgaacctt gctgttacac ggtttactat tccttcatag ttgcgaggaa  1200
taacacctaa atgatctcct tcttgataag aagcttcttt tggaagttca atttcaagat  1260
gtcgcgtgct tcgtgcactg cctggctgtt gaagttcttt gcttgctacg acgttcgttg  1320
aaaacgcacc gtgcattttc gcaagcggca tccgcggca aattgaagtg  1380
aaagagtaga tttattatct tcactgtttt caatgtcgag gttaaagtag gctgctacgt  1440
cactccacat atgttcacgc cattcttcat atgtgccttc aaagtcgtcg cttgcatctg  1500
cttccacgcg gtcagcgatg ttttctgccc ctttagcggc aagcgtttca tcgataaaag  1560
caggcacttt ttgatacgta gtagcccagt ttttatcgcc gcatccaaat acggagtagc  1620
gaacgcctct tacttcatca gcagacgctt ggtctaacca gtcgacaaat tgctttgcgt  1680
tatcaggcgc atgaccgtta taagacgccg ttacaattaa tacagctcct tcgcgcggaa  1740
gattccggc gtgtgaatca agcgttcgaa cctgcggtgc aaatcctttg ctcattgcaa  1800
tatctgctaa atcacgcgcc gttccttcag ctgttcccat atttgaaccg tatagcacaa  1860
gcagcggcgt attatgagcg ttttctgcct ttttgcgtac ttttttagca gactggagct  1920
cacgcaggct cagcggcagg ctacgcaggc tacgaaactc aggttctcca ttccaaatcg  1980
```

```
gttcacccgc ggtgcgaata cccggaaaac ggttcaacag cgccacatag aaccatttca 2040
gttgcaggct gatcaactgt gcagccagac acgcatgaac accctgaccg aagctcaggt 2100
gtcttcgcgt gttcggacga tccagatcaa aatcgttcgg gcgctcgaac atatttgcat 2160
cacgttagc gctacccagg aacagcgcca gggtttgacc agcttcaata cgaacaccac 2220
ccatctccac atccttgcg gcgacgcgcc aggtgaactg attagacgcg ttgtaacgca 2280
gcacttcatt cgcggtgtta tcaacgcacg cttgatcggc cagaaaacgc tccacctgac 2340
gcgggtttct tgcaaatgcc agggtaccgc tgctcaggct acccggggtg gttggtgcaa 2400
acagagcaat gaacaccaac gccagttggt ggaccgtctg ttccggggtg gtttcggtca 2460
gaccatcttg cgccgcagcc agtcttgcaa ttacggtatc cggcaggacc ttaccacgca 2520
taccctgcaa cagctccgac gcatacgtgt gcagatcggt cagtttctcc agaatgatct 2580
cttgggtaac cggctgatcc ttcggaccag agtggtaagt cataatcgtg ttcacacgcg 2640
ggatcagaaa acccaaatct tcctccggaa caccgaatgc atgcaccgcg ctacgcaccg 2700
gcagctccgc cgccagtgct ggaacagcat caatctcggt tgcacccgcc gggatgcttg 2760
caaccagatc gtgggctact ttttgcagga cctgatcata atgttggtga gccgcgcggc 2820
tgaaacctgc acgcacgctg cgacgcaaag catcatgcag cggcggatcg gtgtacataa 2880
ccacattctt ggtccaacgg tgaaagatgt tatccggcgg cagtggctga cccggaaact 2940
tcgctgccag cacctcggta cctctatccg cggtcaaacg cgggtccttc agacccgccg 3000
cgcaatctgc ataggtcagc actgcccagg cgttcagacg ctcaacccag tgcaccgggc 3060
gacgttgcgc cagatccgcg taaacccggg acggatctgc cacgatgctc ggatcagcca 3120
gcgggctcgg cacggtcatc gccatggtat atctccttct taaagttaaa caaaattatt 3180
tctagagggg aattgttatc cgctcacaat tcccctatag tgagtcgtat taatttcgcg 3240
ggatcgagat ctcgatcctc tacgccgac gcatcgtgg cgcatcacc ggccacag 3300
gtgcggttgc tggcgcctat atcgccgaca tcaccgatgg ggaagatcgg gctcgccact 3360
tcgggctcat gagcgcttgt ttcggcgtgg gtatggtggc aggccccgtg gccggggggac 3420
tgttgggcgc catctccttg catgcaccat tccttgcggc ggcggtgctc aacggcctca 3480
acctactact gggctgcttc ctaatgcagg agtcgcataa gggagagcgt cgagatcccg 3540
gacaccatcg aatggcgcaa aacctttcgc ggtatggcat gatagcgccc ggaagagagt 3600
caattcaggg tggtgaatgt gaaaccagta acgttatacg atgtcgcaga gtatgccggt 3660
gtctcttatc agaccgtttc ccgcgtggtg aaccaggcca gccacgtttc tgcgaaaacg 3720
cgggaaaaag tggaagcggc gatggcggag ctgaattaca ttcccaaccg cgtggcacaa 3780
caactggcgg gcaaacagtc gttgctgatt ggcgttgcca cctccagtct ggccctgcac 3840
gcgccgtcgc aaattgtcgc ggcgattaaa tctcgcgccg atcaactggg tgccagcgtg 3900
gtggtgtcga tggtagaacg aagcggcgtc gaagcctgta aagcggcggt gcacaatctt 3960
ctcgcgcaac gcgtcagtgg gctgatcatt aactatccgc tggatgacca ggatgccatt 4020
gctgtggaag ctgcctgcac taatgttccg gcgttatttc ttgatgtctc tgaccagaca 4080
cccatcaaca gtattatttt ctcccatgaa gacggtacgc gactgggcgt ggagcatctg 4140
gtcgcattgg gtcaccagca aatcgcgctg ttagcgggcc cattaagttc tgtctcggcg 4200
cgtctgcgtc tggctggctg gcataaatat ctcactcgca atcaaattca gccgatagc 4260
gaacggatcg ggactggag tgccatgtcc ggttttcaac aaaccatgca aatgctgaat 4320
gagggcatcg ttcccactgc gatgctggtt gccaacgatc agatggcgct gggcgcaatg 4380
cgcgccatta ccgagtccgg gctgcgcgtt ggtgcggata tctcggtagt gggatacgac 4440
gataccgaag acagctcatg ttatatcccg ccgttaacca ccatcaaaca ggattttcgc 4500
ctgctggggc aaaccagcgt ggaccgcttg ctgcaactct ctcagggcca ggcggtgaag 4560
ggcaatcagc tgttgcccgt ctcactggtg aaaagaaaaa ccaccctggc gcccaatacg 4620
caaaccgcct ctccccgcgc gttggccgat tcattaatgc agctggcacg acaggtttcc 4680
cgactggaaa gcgggcagtg agcgcaacgc aattaatgta agttagctca ctcattaggc 4740
accggatct cgaccgatgc ccttgagagc cttcaaccca gtcagctcct tccggtgggc 4800
gcggggcatg actatcgtcg ccgcacttat gactgtcttc tttatcatgc aactcgtagg 4860
acaggtgccg gcagcgctct gggtcatttt cggcgaggac cgctttcgct ggagcgcgac 4920
gatgatcggc ctgtcgcttg cggtattcgg aatcttcac gccctcgctc aagccttcgt 4980
cactggtccc gccaccaaac gtttcggcga agcaggcca attatcgccg gcatgggcgc 5040
cccacgggtg cgcatgatcg tgctcctgtc gttgaggacc cggctaggct gcgggggttg 5100
ccttactggt tagcagaatg aataccgat acgcgagcga acgtgaagcg actgctgctg 5160
caaaacgtct gcgacctgag caacaacatg aatggtcttc ggtttccgtg tttcgtaaag 5220
tctggaaacg cggaagtcag cgccctgcac cattatgttc cggatctgca tcgcaggatg 5280
ctgctggcta ccctgtggaa cacctacatc tgtattaacg aagcgctgg attgaccctg 5340
agtgattttt ctctggtccc gccgcatcca taccgccagt tgtttaccct cacaacgttc 5400
cagtaaccgg gcatgttcat catcagtaac ccgtatcgtg agcatcctct ctcgtttcat 5460
cggtatcatt accccatga acagaaatcc ccttacacg gaggcatcag tgaccaaaca 5520
ggaaaaaacc gcccttaaca tggcccgctt tatcagaagc cagacattaa cgcttctgga 5580
gaaactcaac gagctggacg cggatgaaca ggcagacatc tgtgaatcgc ttcacgacca 5640
cgctgatgag ctttaccgca gctgcctcgc gcgtttcggt gatgacggtg aaaacctctg 5700
acacatgcag ctcccggaga cggtcacagc ttgtctgtaa gcggatgccg ggagcagaca 5760
agcccgtcag ggcgcgtcag cgggtgttgg cgggtgtcgg ggcgcagcca tgacccagtc 5820
acgtagcgat agcggagtgt atactggctt aactatgcgg catcagagca gattgtactg 5880
agagtgcacc atatatgcgg tgtgaaatac cgcacagatg cgtaaggaga aaataccgca 5940
tcaggcgctc ttccgcttcc tcgctcactg actcgctgcg ctcggtcgtt cggctgcggc 6000
gagcggtatc agctcactca aaggcggtaa tacggttatc cacagaatca ggggataacg 6060
caggaaagaa catgtgagca aaaggccag aaaaggccag gaaccgtaaa aaggccgcgt 6120
tgctggcgtt tttccatagg ctccgccccc ctgacgagca tcacaaaaat cgacgctcaa 6180
gtcagaggtg gcgaaacccg acaggactat aaagatacca ggcgtttccc cctggaagct 6240
ccctcgtgcg ctctcctgtt ccgacccctg ccgcttaccg gatacctgtcc gcctttctcc 6300
cttcgggaag cgtggcgctt tctcatagct cacgctgtag gtatctcagt tcggtgtagg 6360
tcgttcgctc caagctgggc tgtgtgcacg aaccccccgt tcagcccgac cgctgcgcct 6420
tatccggtaa ctatcgtctt gagtccaacc cggtaagaca cgacttatcg ccactggcag 6480
cagccactgg taacaggatt agcagagcga ggtatgtagg cggtgctaca gagttcttga 6540
agtggtggcc taactacggc tacactagaa ggacagtatt tggtatctgc gctctgctga 6600
agccagttac cttcggaaaa agagttggta gctcttgatc cggcaaacaa accaccgctg 6660
gtagcggtgg tttttttgtt tgcaagcagc agattacgcg cagaaaaaaa ggatctcaag 6720
```

```
aagatccttt gatcttttct acggggtctg acgctcagtg gaacgaaaac tcacgttaag  6780
ggattttggt catgaacaat aaaactgtct gcttacataa acagtaatac aagggggtgtt  6840
atgagccata ttcaacggga aacgtcttgc tctaggccgc gattaaattc caacatggat  6900
gctgattat atgggtataa atgggctcgc gataatgtcg ggcaatcagg tgcgacaatc  6960
tatcgattgt atgggaagcc cgatgcgcca gagttgtttc tgaaacatgg caaaggtagc  7020
gttgccaatg atgttacaga tgagatggtc agactaaact ggctgacgga atttatgcct  7080
cttccgacca tcaagcattt tatccgtact cctgatgatg catggttact caccactgcg  7140
atccccggga aaacagcatt ccaggtatta agaagatatc ctgattcagg tgaaaatatt  7200
gttgatgcgc tggcagtgtt cctgcgccgg ttgcattcga ttcctgtttg taattgtcct  7260
tttaacagcg atcgcgtatt tcgtctcgct caggcgcaat cacgaatgaa taacggtttg  7320
gttgatgcga gtgattttga tgacgagcgt aatggctggc ctgttgaaca agtctggaaa  7380
gaaatgcata aacttttgcc attctcaccg gattcagtcg tcactcatgg tgatttctca  7440
cttgataacc ttatttttga cgaggggaaa ttaataggtt gtattgatgt tggacgagtc  7500
ggaatcgcag accgatacca ggatcttgcc atcctatgga actgcctcgg tgagttttct  7560
ccttcattac agaaacggct ttttcaaaaa tatggtattg ataatcctga tatgaataaa  7620
ttgcagtttc atttgatgct cgatgagttt ttctaagaat taattcatga gcggatacat  7680
atttgaatgt atttagaaaa ataaacaaat aggggttccg cgcacatttc cccgaaaagt  7740
gccacctgaa attgtaaacg ttaatatttt gttaaaattc gcgttaaatt tttgttaaat  7800
cagctcattt tttaaccaat aggccgaaat cggcaaaatc ccttataaat caaaagaata  7860
gaccgagata gggttgagtg ttgttccagt ttggaacaag agtccactat taaagaacgt  7920
ggactccaac gtcaaagggc gaaaaaccgt ctatcagggc gatggcccac tacgtgaacc  7980
atcaccctaa tcaagttttt tggggtcgag gtgccgtaaa gcactaaatc ggaacctaa  8040
agggagcccc cgatttagag cttgacgggg aaagccggcg aacgtggcga aaaggaagg  8100
gaagaaagcg aaaggagcgg gcgctagggc gctggcaagt gtagcggtca cgctgcgcgt  8160
aaccaccaca cccgccgcgc ttaatgcgcc gctacagggc gcgtcccatt cgcca  8215

SEQ ID NO: 9             moltype = DNA   length = 6135
FEATURE                  Location/Qualifiers
misc_feature             1..6135
                         note = Synthetic Polynucleotide
source                   1..6135
                         mol_type = other DNA
                         organism = synthetic construct
SEQUENCE: 9
atccggatat agttcctcct ttcagcaaaa accccctcaa gacccgttta gaggccccaa  60
ggggttatgc tagttattgc tcagcggtgg cagcagccaa ctcagcttcc tttcgggctt  120
tgttagcagc cggatctcag tggtggtggt ggtggtgctc gagtgcggcc gcaagctttt  180
agccacgacc tgcctgaaag ctcggatact gggtcatacc gccatccgca aacagggtaa  240
tgccgtcac atagctcgct tcgctgcttg ccagccagcc tgccaccgct gcaatttctt  300
ccggttcgcc aatatagccc atcggaatca tgctttccac atccgcacgc tgttccggat  360
cggcaaattt ttccgcgtta atcgggtgt taatcgcacc cggaccaatg ttgttcacac  420
gaatgccttt cggtgcatat tccagggcca gggtttcggt catcagtttc ataccgcctt  480
tgctcgctgc ataatgcaca aacagcggcc acggaatttt ttcatgcacg ctgctcatgt  540
taatcacggt gcctttaata tcgttttcca cgaagtattt aatcgcttca cggctgccca  600
gaaacgcacc ggtcaggttg gtatcaatca ctttgttcca atcgctcagg ctcatttcat  660
ggctgctcac cggattttcc ataccgcat tgttaatcat cacatccagt ttgccaaatt  720
ctttaatgct gctctgcacc aggttaatca catcgtcttc acggtcaca tcacctttca  780
ccgcaatcgc ttcgccaccc actttttaa tttcttccag aacgctgttc gcttcttctt  840
ctttgctgcg atagttaacc accactttcg cttttttcggt cgcaaaacga atcgccattg  900
ctttgcccag accggtgctg ctgccggtaa tcaccaccac tttaccttcc agatctttat  960
acatggatcc cgacccattt gctgtccacc agtcatgcca gccatatggc tgccgcgcgg  1020
caccaggccg ctgctgtgat gatgatgatg atggctgctg cccatggtat atctcctct  1080
taaagttaaa caaaattatt tctagagggg aattgttatc cgctcacaat tcccctatag  1140
tgagtcgtat taatttcgcg ggatcgagat tcgatcctc tacgccggac gcatcgtggc  1200
cggcatcacc ggcgccacag gtgcggttgc tggcggcctat atgccgaca tcaccgatgg  1260
ggaagatcgg gctcgccact tcgggctcat gagcgcttgt ttcggcgtgg gtatggtggc  1320
aggccccgtg gccggggac tgttgggcgc catctccttg catgcaccat tccttgcggc  1380
ggcggtgctc aacggcctca acctactact gggctgcttc ctaatgcagg agtcgcataa  1440
gggagagcgt cgagatccg gacaccatcg aatggcgcaa aacctttcgc ggtatggcat  1500
gatagcgccc ggaagagagt caattcaggg tggtgaatgt gaaaccagta acgttatacg  1560
atgtcgcaga gtatgccggt gtctcttatc agaccgtttc ccgcgtggtg aaccaggcca  1620
gccacgtttc tgcgaaaacg cgggaaaaag tggaagcggc gatggcggag ctgaattaca  1680
ttcccaaccg cgtggcacaa caactggcgg gcaaacagtc gttgctgatt ggcgttgcca  1740
cctccagtct ggccctgcac gcgccgtcgc aaattgtcgc ggcgattaaa tctcgcgccg  1800
atcaactggg tgccagcgtg gtggtgtcga tggtagaacg aagcggcgtc gaagcctgta  1860
aagcggcggt gcacaatctt ctcgcgcaac gcgtcagtgg gctgatcatt aactatccgc  1920
tggatgacca ggatgccatt gctgtggaag ctgcctgcac taatgttccg gcgttatttc  1980
ttgatgtctc tgaccagaca cccatcaaca gtattatttt ctcccatgaa gacggtacgc  2040
gactgggcgt ggagcatctg gtcgcattgg gtcaccagca aatcgcgctg ttagcgggcc  2100
cattaagttc tgtctcggcg cgtctgcgtc tggctggctg cataaatat ctcactcgca  2160
atcaaattca gccgatagcg gaacgggaag gcgactggag tgccatgtcc ggttttcaac  2220
aaaccatgca aatgctgaat gagggcatcg ttcccactgc gatgctggtt gccaacgatc  2280
agatggcgct gggcgcaatg cgcgccatta ccgagtccgg gctgcgcgtt ggtgcggata  2340
tctcggtagt gggatacgac gataccgaag acagctcatg ttatatcccg ccgttaacca  2400
ccatcaaaca ggattttcgc ctgctggggc aaaccagcgt ggaccgcttg ctgcaactct  2460
ctcagggcca ggcggtgaag ggcaatcagc tgttgcccgt ctcactggtg aaaagaaaaa  2520
ccaccctggc gcccaatacg caaaccgcct ctccccgcgc gttggccgat tcattaatgc  2580
agctggcacg acaggtttcc cgactggaaa gcgggcagtg agcgcaacgc aattaatgta  2640
agttagctca ctcattaggc accgggatct cgaccgatgc ccttgagagc cttcaaccca  2700
```

```
gtcagctcct tccggtgggc gcggggcatg actatcgtcg ccgcacttat gactgtcttc   2760
tttatcatgc aactcgtagg acaggtgccg gcagcgctct gggtcatttt cggcgaggac   2820
cgctttcgct ggagcgcgac gatgatcggc ctgtcgcttg cggtattcgg aatcttgcac   2880
gccctcgctc aagccttcgt cactggtccc gccaccaaac gtttcggcga aagcaggcc    2940
attatcgccg gcatggcggc cccacgggtg cgcatgatcg tgctcctgtc gttgaggacc   3000
cggctaggct ggcggggttg ccttactggt tagcagaatg aatcaccgat acgcgagcga   3060
acgtgaagcg actgctgctg caaaacgtct gcgacctgag caacaacatg aatggtcttc   3120
ggtttccgtg tttcgtaaag tctggaaacg cggaagtcag cgccctgcac cattatgttc   3180
cggatctgca tcgcaggatg ctgctggcta ccctgtggaa cacctacatc tgtattaacg   3240
aagcgctggc attgaccctg agtgatttt ctctggtccc gccgcatcca taccgccagt    3300
tgtttaccct cacaacgttc cagtaaccgg gcatgttcat catcagtaac ccgtatcgtg   3360
agcatcctct ctcgtttcat cggtatcatt accccccatga acagaaatcc cccttacacg   3420
gaggcatcag tgaccaaaca ggaaaaaacc gcccttaaca tggcccgctt tatcagaagc   3480
cagacattaa cgcttctgga gaaactcaac gagctgaacg cggatgaaca ggcagacatc   3540
tgtgaatcgc ttcacgacca cgctgatgag ctttaccgca gctgcctcgc gcgtttcggt   3600
gatgacggtg aaaacctctg acacatgcag ctcccggaga cggtcacagc ttgtctgtaa   3660
gcggatgccg ggagcagaca agcccgtcag ggcgcgtcag cgggtgttgg cgggtgtcgg   3720
ggcgcagcca tgacccagtc aactgtagcgat agcgaagtgt atactggctt aactatgcgg   3780
catcagagca gattgtactg agagtgcacc atatatgcgg tgtgaaatac cgcacagatg   3840
cgtaaggaga aaataccgca tcaggcgctc ttccgcttcc tcgctcactg actcgctgcg   3900
ctcggtcgtt cggctgcggc gagcggtatc agctcactca aaggcggtaa tacgttatc    3960
cacagaatca ggggataacg caggaaagaa catgtgagca aaaggccagc aaaaggccag   4020
gaaccgtaaa aaggccgcgt tgctggcgtt tttccatagg ctccgccccc ctgacgagca   4080
tcacaaaaat cgacgctcaa gtcagaggtg gcgaaacccg acaggactat aaagatacca   4140
ggcgtttccc cctggaagct ccctcgtgcg ctctcctgtt ccgaccctgc cgcttaccgg   4200
atacctgtcc gcctttctcc cttcgggaag cgtggcgctt tctcatagct cacgctgtag   4260
gtatctcagt tcggtgtagg tcgttcgctc caagctgggc tgtgtgcacg aaccccccgt   4320
tcagcccgac cgctgcgcct tatccggtaa ctatcgtctt gagtccaacc cggtaagaca   4380
cgacttatcg ccactggcag cagccactgg taacaggatt agcagagcga ggtatgtagg   4440
cggtgctaca gagttcttga agtggtggcc taactacgcg tacactagaa ggacagtatt   4500
tggtatctgc gctctgctga agccagttac cttcggaaaa agagttggta gctcttgatc   4560
cggcaaacaa accaccgctg gtagcggtgg tttttttgtt tgcaagcagc agattacgcg   4620
cagaaaaaaa ggatctcaag aagatccttt gatcttttct acggggtctg acgctcagtg   4680
gaacgaaaac tcacgttaag ggattttggt catgaacaat aaaactgtct gcttacataa   4740
acagtaatac aagggggtgtt atgagccata ttcaacggga aacgtcttgc tctaggccgc   4800
gattaaattc caacatggat gctgatttat atgggtataa atgggctcgc gataatgtcg   4860
ggcaatcagg tgcgacaatc tatcgattgt atgggaagcc cgatgcgcca gagttgtttc   4920
tgaaacatgg caaaggtagc gttgccaatg atgttacaga tgagatggtc agactaaact   4980
ggctgacgga atttatgcct cttccgacca tcaagcattt tatccgtact cctgatgatg   5040
catggttact caccactgcg atccccggga aaacagcatt ccaggtatta gaagaatatc   5100
ctgattcagg tgaaaatatt gttgatgcgc tggcagtgtt cctgcgccgg ttgcattcga   5160
ttcctgtttg taattgtcct tttaacagcg atcgcgtatt tcgtctcgct caggcgcaat   5220
cacgaatgaa taacggtttg gttgatgcga gtgattttga tgacgagcgt aatggctggc   5280
ctgttgaaca agtctggaaa gaaatgcata actttgcc attctcaccg gattcagtcg     5340
tcactcatgg tgatttctca cttgataacc ttatttttga cgaggggaaa ttaataggtt   5400
gtattgatgt tggacgagtc ggaatcgcag accgatacca ggatcttgcc atcctatgga   5460
actgcctcgg tgagttttct ccttcattac agaaacggct ttttcaaaaa tatggtattg   5520
ataatcctga tatgaataaa ttgcagtttc atttgatgct cgatgagttt ttctaagaat   5580
taattcatga gcggatacat atttgaatgt atttagaaaa ataaacaaat aggggttccg   5640
cgcacatttc cccgaaaagt gccacctgaa attgtaaacg ttaatatttt gttaaaattc   5700
gcgttaaatt tttgttaaat cagctcattt tttaaccaat aggccgaaat cggcaaaatc   5760
ccttataaat caaagaata gaccgagata gggttgagtg ttgttccagt ttggaacaag   5820
agtccactat taaagaacgt ggactccaac gtcaagggc gaaaaccgt ctatcagggc     5880
gatgcccac tacgtgaacc atcacctaa tcaagttttt tggggtcgag gtgccgtaaa     5940
gcactaaatc ggaaccctaa agggagcccc cgatttagag cttgacgggg aaagccgggc   6000
aacgtggcga aaaggaagg gaagaaagcg aaaggagcgg cgcgtaggc gctggcaagt     6060
gtagcggtca cgctgcgcgt aaccaccaca cccgccgcgc ttaatgcgcc gctacagggc   6120
gcgtcccatt cgcca                                                    6135
SEQ ID NO: 10           moltype = DNA  length = 9371
FEATURE                 Location/Qualifiers
misc_feature            1..9371
                        note = Synthetic Polynucleotide
source                  1..9371
                        mol_type = other DNA
                        organism = synthetic construct
SEQUENCE: 10
ggggaattgt gagcggataa caattcccct ctagaaataa ttttgtttaa ctttaagaag   60
gagatatacc atgggcatga ccgtgccgag cccgctggct gatccgagca tcgtgccaga   120
tccgtacccg gtttacgcgg atctggcgca acgtcgcccg gtgcactggg ttgagcgtct   180
gaacgcctgg gcagtgctga cctatgcaga ttgcgcggcg gtctgaagg acccgcgttt    240
gaccgcggat agaggtaccg aggtgctggc agcgaagttt ccgggtcagc cactgccgcc   300
ggataacatc tttcaccgtt ggaccaagaa tgtggttatg tacaccgatc cgccgctgca   360
tgatgctttg cgtcgcagcg tgcgtgcagg ttttcaccgc ggctcacc aacattatga    420
tcaggtcctg caaaaagtag cccacgatcg gttgcaagc atcccggcgg gtgcaaccga    480
gattgatgct gttccagcac tggcggcgga gctgccggtg cgtagcgcgg tgcatgcatt   540
cggtgttccg gaggaagatt tgggttttct gatcccgcgt gtgaacacga ttatgactta   600
ccactctggt ccgaaggatc agccggttac ccaagagatc attctggaga aactgaccga   660
tctgcacacg tatgcgtcgg agctgttgca gggtatgcgt ggtaaggtcc tgccggatac   720
```

```
cgtaattgca agactggctg cggcgcaaga tggtctgacc gaaaccaccc cggaacagac  780
ggtccaccaa ctggcgttgg tgttcattgc tctgtttgca ccaaccaccc cgggtagcct  840
gagcagcggt accctggcat ttgcaagaaa cccgcgtcag gtggagcgtt ttctggccga  900
tcaagcgtgc gttgataaca ccgcgaatga agtgctgcgt tacaacgcgt ctaatcagtt  960
cacctggcgc gtcgccgcga aggatgtgga gatgggtggt gttcgtattg aagctggtca 1020
aaccctggcg ctgttcctgg gtagcgctaa ccgtgatgca aatatgttcg agcgcccgaa 1080
cgattttgat ctggatcgtc cgaacagcgc aagacacctg agcttcgtc  agggtgttca 1140
tgcgtgtctg gctgcacagt tgatcagcct gcaactgaaa tggttctatg tggcgctgtt 1200
gaaccgtttt ccgggtattc gcaccgcggg tgaaccgatt tggaatgaga acctggagtt 1260
tcgtagcctg cgtagcctgc cgctgagcct gcgtgagctc cagtctgcta aaaaagtacg 1320
caaaaaggca gaaaacgctc ataatacgcc gctgcttgtg ctatacggtt caaatatggg 1380
aacagctgaa ggaacggcgc gtgatttagc agatattgca atgagcaaag gatttgcacc 1440
gcaggtcgca acgcttgatt cacacgccgg aaatcttccg cgcgaaggag ctgtattaat 1500
tgtaacggcg tcttataacg gtcatccgcc tgataacgca aagcaattg tcgactggtt 1560
agaccaagcg tctgctgatg aagtaaaagg cgttcgctac tccgtatttg gatgcggcga 1620
taaaaactgg gctactacgt atcaaaaagt gcctgctttt atcgatgaaa cgcttgccgc 1680
taaaggggca gaaaacatcg ctgaccgcgg tgaagcagat gcaagcgacg actttgaagg 1740
cacatatgaa gaatgcgtg  aacatatgtg gagtgacgta gcagcctact ttaacctcga 1800
cattgaaaac agtgaagata taaatctac  tcttcactt  caatttgtcg acagcgccgc 1860
ggatatgccg cttgcgaaaa tgcacggtgc gttttcaacg aacgtcgtag caagcaaaga 1920
acttcaacag ccaggcagtg cacgaagcac gcgacatctt gaaattgaac ttccaaaaga 1980
agcttcttat caagaaggag atcatttagg tgttattcct gcaactatg aaggaatagt 2040
aaaccgtgta acagcaaggt tcggcctaga tgcatcacag caaatccgtc tggaagcaga 2100
agaagaaaaa ttagctcatt tgccactcgc taaaacagta tccgtagaag agcttctgca 2160
atacgtggag cttcaagatc ctgttacgcg cacgcagctt cgcgcaatgg ctgctaaaac 2220
ggtctgcccg ccgcataaag tagagcttga agccttgctt gaaaagcaag cctacaaaga 2280
acaagtgctg gcaaaacgtt taacaatgct tgaactgctt gaaaaatacc ggcgtgtga  2340
aatgaaattc agcgaattta tcgcccttct gccaagcata cgcccgcgct attactcgat 2400
ttcttcatca cctcgtgtcg atgaaaaaca agcaagcatc acggtcagcg ttgtctcagg 2460
agaagcgtgg agcggatatg gagaatataa aggaattgcg tcgaactact ttgccgacct 2520
gcaagaagga gatacgatta cgtgctttat ttccacaccg cagtcagaat ttacgctgcc 2580
aaaagaccct gaaacgccgc ttatcatggt cggaccggga acaggcgtcg cgccgtttag 2640
aggctttgtg caggcgcgca aacagctaaa agaacaagga cagtcacttg gagaagcaca 2700
tttatacttc ggctgccgtt cacctcatga agactatctg tatcaagaag agcttgaaaa 2760
cgcccaaagc gaaggcatca ttaccgcttca taccgctttt tctcgcatgc caaatcagcc 2820
gaaaacatac gttcagcacg taatggaaca agacggcaag aaattgattg aacttcttga 2880
tcaaggagcg cacttctata tttgcggaga cggaagccaa atggcacctg ccgttgaagc 2940
aacgcttatg aaaagctatg ctgacgttca ccaagtgagt gaagcagacg ctcgcttatg 3000
gctgcagcag ctagaagaaa aaggccgata cgcaaaagac gtgtgggctg ggtaaaagct 3060
tgcggccgca taatgcttaa gtcgaacaga aagtaatcgt attgtacacg gccgcataat 3120
cgaaattaat acgactcact ataggggaat tgtgagcgga taacaattcc catcttagt  3180
atattagtta agtataagaa ggagatatac atatggaaga aaaagaaatc ctgtggaacg 3240
aagccaaagc attcatcgca gcgtgctacc aagaactggg caaagaagaa gaagtcaaag 3300
atcgcctggc ggacattaaa agtgaaatcg atctgaccgg ttcctatgtt catacgaaag 3360
aagaactgga cacgcgcgca aaaatggctt ggcgtaacag caatcgctgc attggtcgtc 3420
tgttttggaa ctctctgaat gtgatcgatc gtcgcgacgt tcgcacgaaa gaagaagtcc 3480
gtgatgcgct gtttcatcac attgaaaccg ccacgaacaa tggtaaaatc cgtccgacca 3540
ttacgatctt cccgccggaa gaaaaggcg  aaaaacaggt tgaaatttgg aaccatcaac 3600
tgatccgcta tgcaggctac gaaagcgacg gcaacgtat  tggtgatccg gctagctgct 3660
ctctgaccgg ggcctgtgaa gaactgggct ggcgtggtga acgcacggat tttgacctgc 3720
tgccgctgat tttccgcatg aaaggtgatg aacagccggt gtggtatgaa ctgccgcgtt 3780
ctctggtgat tgaagttccg atcacccatc cggacatcga agcctttagt gatctggaac 3840
tgaaatggta cggcgtcccg attatctccg atatgaaact ggaagtgggc ggtattcact 3900
ataacgcagc tccgttcaat ggctggtaca tgggcaccga atcggcgcg  cgcaatctgg 3960
ccgacgaaaa acgttacgat aaactgaaaa agtcgcatc  agtgattggt atcgcggccg 4020
attacaacac ggaccgtgtg aaagatcagg cactgctggt aactgaataaa gctgttctgc 4080
actcataaa  aaaacaaggc gtttcgattg tggatcatca caccgcagct tcacagttta 4140
aacgcttcga agaacaggaa gaagaagcgg gtcgtaaact gaccggcgat tggacgtggc 4200
tgattccgcc gatctcgccg gcagcaaccc atatcttcca ccgtcgtat  gacaatagca 4260
tcgtgaaacc gaattacttc taccaggaca aaccgtatga atagctcgag tctggtaaag 4320
aaaccgctgc tgcgaaattt gaacgccagc acatggactc gtctactagc gcagcttaat 4380
taacctaggc tgctgccacc gctgagcaat aactagcata ccccttggg  gcctctaaac 4440
gggtcttgag gggtttttg  ctgaaaggag gaactatatc cggattggcg aatgggacgc 4500
gccctgtagc ggcgcattaa gcgcggcggg tgtggtggtt acgcgcagcg tgaccgctac 4560
acttgccagc gccctagcgc ccgctccttt cgctttcttc ccttcctttc tcgccacgtt 4620
cgccggcttt cccgtcaag  ctctaaatcg ggggctccct ttagggttcc gatttagtgc 4680
tttacggcac ctcgacccca aaaaacttga ttagggtgat ggttcacgta gtgggccatc 4740
gccctgatag acggtttttc gccctttgac gttggagtcc acgttcttta atagtggact 4800
cttgttccaa actggaacaa cactcaaccc tatctgtttg atttttataagg 4860
gattttgccg atttcggcct attggttaaa aaatgagctg atttaacaaa atttaacgc  4920
gaatttaac  aaaatattaa cgtttacaat ttctggcggc acgatggcat gagattatca 4980
aaaggatct  tcacctagat ccttttaaat taaaatgaa  gttttaaatc aatctaaagt 5040
atatatgagt aaacttggtc tgacagttac caatgcttaa tcagtgaggc acctatctca 5100
gcgatctgtc tatttcgttc atccatagtt gcctgactcc ccgtcgtgta gataactacg 5160
atacgggagg gcttaccatc tggccccagt gctgcaatga taccgcgaga cccacgctca 5220
ccggctccag atttatcagc aataaaccag ccagccggaa gggccgagcg cagaagtggt 5280
cctgcaactt tatccgcctc catccagtct attaattgtt gccgggaagc tagagtaagt 5340
agttcgccag ttaatagttt gcgcaacgtt gttgccattg ctacaggcat cgtggtgtca 5400
cgctcgtcgt ttggtatggc ttcattcagc tccggttccc aacgatcaag gcgagttaca 5460
```

```
tgatccccca tgttgtgcaa aaaagcggtt agctccttcg gtcctccgat cgttgtcaga    5520
agtaagttgg ccgcagtgtt atcactcatg gttatggcag cactgcataa ttctcttact    5580
gtcatgccat ccgtaagatg cttttctgtg actggtgagt actcaaccaa gtcattctga    5640
gaatagtgta tgcggcgacc gagttgctct tgcccggcgt caatacggga taataccgcg    5700
ccacatagca gaactttaaa agtgctcatc atttggaaaa cgttcttcgg gcgaaaactc    5760
tcaaggatct taccgctgtt gagatccagt tcgatgtaac ccactcgtgc acccaactga    5820
tcttcagcat cttttacttt caccagcgtt tctgggtgag caaaaacagg aaggcaaaat    5880
gccgcaaaaa agggaataag ggcgacacgg aaatgttgaa tactcatact cttccttttt    5940
caatcatgat tgaagcattt atcagggtta ttgtctcatg agcggataca tatttgaatg    6000
tatttagaaa aataaacaaa taggtcatga ccaaaatccc ttaacgtgag ttttcgttcc    6060
actgagcgtc agaccccgta gaaaagatca aaggatcttc ttgagatcct ttttttctgc    6120
gcgtaatctg ctgcttgcaa acaaaaaaac caccgctacc agcggtggtt tgtttgccgg    6180
atcaagagct accaactctt tttccgaagg taactggctt cagcagagcg cagataccaa    6240
atactgtcct tctagtgtag ccgtagttag gccaccactt caagaactct gtagcaccgc    6300
ctacatacct cgctctgcta atcctgttac cagtggctgc tgccagtggc gataagtcgt    6360
gtcttaccgg gttggactca agacgatagt taccggataa ggcgcagcgg tcgggctgaa    6420
cggggggttc gtgcacacag cccagcttgg agcgaacgac ctacaccgaa ctgagatacc    6480
tacagcgtga gctatgagaa agcgccacgc ttcccgaagg gagaaaggcg gacaggtatc    6540
cggtaagcgg cagggtcgga acaggagagc gcacgaggga gcttccaggg ggaaacgcct    6600
ggtatcttta tagtcctgtc gggtttcgcc acctctgact tgagcgtcga tttttgtgat    6660
gctcgtcagg gggcggagc ctatggaaaa acgccagcaa cgcggccttt ttacggttcc    6720
tggccttttg ctggccttttt gctcacatgt tctttcctgc gttatcccct gattctgtgg    6780
ataaccgtat taccgccttt gagtgagctg ataccgctcg ccgcagccga acgaccgagc    6840
gcagcgagtc agtgagcgag gaagcggaag agcgcctgat gcggtatttt ctccttacgc    6900
atctgtgcgg tatttcacac cgcatatatg gtgcactctc agtacaatct gctctgatgc    6960
cgcatagtta agccagtata cactccgcta tcgctacgtg actgggtcat ggctgcgccc    7020
cgacacccgc caacacccgc tgacgcgccc tgacgggctt gtctgctccc ggcatccgct    7080
tacagacaag ctgtgaccgt ctccgggagc tgcatgtgtc agaggttttc accgtcatca    7140
ccgaaacgcg cgaggcagct gcggtaaagc tcatcagcgt ggtcgtgaag cgattcacag    7200
atgtctgcct gttcatccgc gtccagctcg ttgagtttct ccagaagcgt taatgtctgg    7260
cttctgataa agcgggccat gttaagggcg gttttttcct gtttggtcac tgatgcctcc    7320
gtgtaagggg gatttctgtt catggggta atgataccga tgaaacgaga gaggatgctc    7380
acgatacggg ttactgatga tgaacatgcc cggttactgg aacgttgtga gggtaaacaa    7440
ctggcggtat ggatgcggcg ggaccagaga aaaatcactc agggtcaatg ccagcgcttc    7500
gttaatacag atgtaggtgt tccacagggt agccagcagc atcctgcgat gcagatccgg    7560
aacataatgg tgcagggcgc tgacttccgc gtttccagac tttacgaaac acggaaaccg    7620
aagaccattc atgttgttgc tcaggtcgca gacgttttgc agcagcagtc gcttcacgtt    7680
cgctcgcgta tcggtgattc attctgctaa ccagtaaggc aaccccgcca gcctagccgg    7740
gtcctcaacg acaggagcac gatcatgcta gtcatgccga aggagctg    7800
actgggttga aggctctcaa gggcatcggt cgagatcccg gtgcctaatg agtgagctaa    7860
cttacattaa ttgcgttgcg ctcactgccc gctttccagt cgggaaacct gtcgtgccag    7920
ctgcattaat gaatcggcca acgcgcgggg agaggcggtt tgcgtattgg gcgccaggt    7980
ggtttttctt ttcaccagtg agacgggcaa cagctgattg cccttcaccg cctggccctg    8040
agagagttgc agcaagcggt ccacgctggt ttgccccagc aggcgaaaat cctgtttgat    8100
ggtggttaac ggcgggatat aacatgagct gtcttcggta tcgtcgtatc ccactaccga    8160
gatgtccgca ccaacgcgca gcccggactc ggtaatggcg cgcattgcgc ccagcgccat    8220
ctgatcgttg gcaaccagca tcgcagtggg aacgatgccc tcattcagca tttgcatggt    8280
ttgttgaaaa ccggacatgg cactccagtc gccttcccgt tccgctatcg gctgaatttg    8340
attgcgagtg agatatttat gccagccagc cagacgcaga cgcgccgaga cagaacttaa    8400
tgggcccgct aacagcgcga tttgctggtg acccaatgcg accagatgct ccacgcccag    8460
tcgcgtaccg tcttcatggg agaaaataat actgttgatg ggtgtctggt cagagacatc    8520
aagaaataac gccggaacat tagtgcaggc agcttccaca gcaatggcat cctggtcatc    8580
cagcggatag ttaatgatca gcccactgac gcgttgcgcg agaagattgt gcaccgccgc    8640
tttacaggct tcgacgccgc ttcgttctac catcgacacc accacgctgg cacccagttg    8700
atcggcgcga gatttaatcg ccgcgacaat ttgcgacggc gcgtgcaggg ccagactgga    8760
ggtggcaacg ccaatcagca acgactgttt gcccgccagt tgttgtgcca cgcggttggg    8820
aatgtaattc agctccgcca tcgccgcttc cactttttcc cgcgttttcg cagaaacgtg    8880
gctggcctgg ttcaccacgc gggaaacggt ctgataagag acaccggcat actctgcgac    8940
atcgtataac gttactggtt tcacattcac caccctgaat tgactctctt ccgggcgcta    9000
tcatgccata ccgcgaaagg ttttgcgcca ttcgatggtg tccgggatct cgacgctctc    9060
ccttatgcga ctcctgcatt aggaagcagc ccagtagtag gttgaggccg ttgagcaccg    9120
ccgccgcaag gaatggtgca tgcaaggaga tggcgcccaa cagtccccg gccacggggc    9180
ctgccaccat acccacgccg aaacaagcgc tcatgagccc gaagtggcga gcccgatctt    9240
ccccatcggt gatgtcggcg atataggcgc cagcaaccgc acctgtggcg ccggtgatgc    9300
cggccacgat gcgtccggcg tagaggatcg agatcgatct cgatcccgcg aaattaatac    9360
gactcactat a                                                         9371
```

SEQ ID NO: 11      moltype = DNA  length = 7214
FEATURE            Location/Qualifiers
misc_feature       1..7214
                   note = Synthetic Polynucleotide
source             1..7214
                   mol_type = other DNA
                   organism = synthetic construct
SEQUENCE: 11
```
ggggaattgt gagcggataa caattcccct ctagaaataa ttttgtttaa ctttaagaag     60
gagatatacc atgggcagca gccatcacca tcatcaccac agccaggatc cgatgtataa    120
agatctggaa ggtaaagtgg tggtgattac cggcagcagc accggtctgg gcaaagcaat    180
ggcgattcgt tttgcgaccg aaaaagcgaa agtggtggtt aactatcgca gcaaagaaga    240
```

```
agaagcgaac agcgttctgg aagaaattaa aaaagtgggt ggcgaagcga ttgcggtgaa  300
aggtgatgtg accgtggaaa gcgatgtgat taacctggtg cagagcagca ttaaagaatt  360
tggcaaactg gatgtgatga ttaacaatgc gggtatggaa atccggtgaa gcagccatga  420
aatgagcctg agcgattgga acaaagtgat tgataccaac ctgaccggtg cgtttctggg  480
cagccgtgaa gcgattaaat acttcgtgga aaacgatatt aaaggcaccg tgattaacat  540
gagcagcgtg catgaaaaaa ttccgtggca gctgtttgtg cattatgcag cgagcaaagg  600
cggtatgaaa ctgatgaccg aaaccctggc cctggaatat gcaccgaaag cattcgtgt  660
gaacaacatt ggtccgggtg cgattaacac cccgattaac gcggaaaaat ttgccgatcc  720
ggaacagcgt gcggatgtgg aaagcatgat tccgatgggc tatattggcg aaccggaaga  780
aattgcagcg gtggcagcgt ggctggcaag cagcgaagcg agctatgtga ccggcattac  840
cctgtttgcg gatggcggta tgacccagta tccgagcctt caggcaggtc gtggctaaaa  900
gcttgcggcc gcataatgct taagtcgaac agaaagtaat cgtattgtac acggccgcat  960
aatcgaaatt aatacgactc actataggg  aattgtgagc ggataacaat tccccatctt  1020
agtatattag ttaagtataa gaaggagata tacatatgga agaaaaagaa atcctgtgga  1080
acgaagccaa agcattcatc gcagcgtgct accaagaact gggcaaagaa gaagaagtca  1140
aagatcgcct ggcggacatt aaaagtgaaa tcgatctgac cggttcctat gttcatacga  1200
aagaagaact ggaacacggc gcaaaaatgg cttggcgtaa cagcaatcgc tgcattggtc  1260
gtctgttttg gaactctctg aatgtgatcg atcgtcgcga cgttcgcacg aaagaagaag  1320
tccgtgatgc gctgtttcat cacattgaaa ccgccacgua caatggtaaa atccgtccga  1380
ccattacgat cttcccgccg gaagaaaaag gcgaaaaaca ggttgaaatt tggaaccatc  1440
aactgatccg ctatgcaggc tacgaaagcg acggcgaacg tattggtgat ccggctagct  1500
gctctctgac cgcggcctgt gaagaactgg gctggcgtgg tgaacgcacg gattttgacc  1560
tgctgccgct gattttccgc atgaaaggtg atgaacagcc ggtgtggtat gaactgccgc  1620
gttctctggt gattgaagtt ccgatcaccc atccggacat cgaagccttt agtgatctgg  1680
aactgaaatg gtacgcgtc  ccgattatct ccgatatgaa actggaagtg gcgcggtattc  1740
actataacgc agctccgttc aaatggctgg catatggcac acgaaatcggc gcgcgcaatc  1800
tggccgacga aaaacgttac gataaactga aaaaagtcgc atcagtgatt ggtatcgcgg  1860
ccgattacaa cacggacctg tggaaagatc aggcactggt ggaactgaat aaagctgttc  1920
tgcactcata caaaaaacaa ggcgtttcga ttgtggatca tcacaccgca gcttcacagt  1980
ttaaacgctt cgaagaacag gaagaagaag cgggtcgtaa actgaccggc gattggacgt  2040
ggctgattcc gccgatctcg ccggcagaag cccatatctt ccaccgctcg tatgacaata  2100
gcatcgtgaa accgaattac ttctaccagg acaaaccgta tgaatagctc gagtctggta  2160
aagaaaccgc tgctgcgaaa tttgaacgcc agcacatgga ctcgtctact agcgcagctt  2220
aattaaccta ggctgctgcc accgctgagc aataactagc ataaccccctt ggggcctcta  2280
aacgggtctt gaggggttt  ttgctgaaag gaggaactat atccggattg gcgaatggga  2340
cgcgccctgt agcggcgcat taagcgcggc gggtgtggtg gttacgcgca gcgtgaccgc  2400
tacacttgcc agcgccctag cgcccgctcc tttcgctttc ttcccttcct ttctcgccac  2460
gttcgccggc tttccccgtc aagctctaaa tcggggggctc cctttagggt tccgatttag  2520
tgctttacgg cacctcgacc ccaaaaaact tgattaggggt gatggttcac gtagtgggcc  2580
atcgccctga tagacggttt ttcgcccttt gacgttggag tccacgttct taatagtagt  2640
actcttgttc caaactggaa caacactcaa ccctatctcg gtctattctt ttgatttata  2700
agggattttg ccgatttcgg cctattggtt aaaaaatgag ctgatttaac aaaaatttaa  2760
cgcgaattt  aacaaaatat taactgttac aatttctggc ggcacgatgg catgagatta  2820
tcaaaaagga tcttcaccta gatccttta  aattaaaaat gaagttttaa atcaatctaa  2880
agtatatatg agtaaacttg gtctgacagt taccaatgct taatcagtga ggcacctatc  2940
tcagcgatct gtctatttcg ttcatccata gttgcctgac tccccgtcgt gtagataact  3000
acgatacggg agggcttacc atctggcccc agtgctgcaa tgataccgcg agacccacgc  3060
tcaccggctc cagatttatc agcaataaac cagccagccg aagggccgga gcgcagaagt  3120
ggtcctgcaa ctttatccgc ctccatccag tctattaatt gttgccggga agctagtga  3180
agtagttcgc cagttaatag tttgcgcaac gttgttgcca ttgctacagg catcgtggtg  3240
tcacgctcgt cgtttggtat ggcttcattc agctccggtt cccaacgatc aaggcgagtt  3300
acatgatccc ccatgttgtg caaaaaagcg gttagctcct tcggtcctcc gatcgttgtc  3360
agaagtaagt tggccgcagt gttatcactc atggttatgg cagcactgca taattctctt  3420
actgtcatgc catccgtaag atgcttttct gtgactggtg agtactcaac caagtcattc  3480
tgagaatagt gtatgcggcg accgagttgc tcttgcccgg cgtcaatacg ggataataccc 3540
gcgccacata gcagaacttt aaaagtgctc atcattggaa aacgttcttc ggggcgaaaa  3600
ctctcaagga tcttaccgct gttgagatcc agttcgatgt aacccactcg tgcacccaac  3660
tgatcttcag catcttttac tttcaccagc gtttctgggt gagcaaaaac aggaaggcaa  3720
aatgccgcaa aaaagggaat aagggcgaca cggaaatgtt gaatactcat actcttcctt  3780
tttcaatcat gattgaagca tttatcaggg ttattgtctc atgagcggat acatatttga  3840
atgtatttag aaaataaaac aaataggtca tgaccaaaat cccttaacgt gagttttcgt  3900
tccactgagc gtcagacccc gtagaaaaga tcaaaggatc ttcttgagat cctttttttc  3960
tgcgcgtaat ctgctgcttg caaacaaaaa aaccaccgct accagcggtg gtttgtttgc  4020
cggatcaaga gctaccaact cttttttccga aggtaactgg cttcagcaga gcgcagatac  4080
caaatactgt ccttctagtg tagccgtagt taggccacca cttcaagaac tctgtagcac  4140
cgcctacata cctcgctctg ctaatcctgt taccagtggc tgctgccagt ggcgataagt  4200
cgtgtcttac cgggttggac tcaagacgat agttaccgga taaggcgcag cggtcgggct  4260
gaacgggggg ttcgtgcaca cagcccagct tggagcgaac gacctacacc gaactgagat  4320
acctacagcg tgagctatga gaaagcgcca cgcttcccga agggagaaag gcggacaggt  4380
atccggtaag cggcagggtc ggaacaggag agcgcacgag ggagcttcca ggggaaacg  4440
cctggtatct ttatagtcct gtcgggtttc gccacctctg acttgagcgt cgatttttgt  4500
gatgctcgtc agggggcgg  agcctatgga aaaacgccag caacgcggcc ttttacggt  4560
tcctggcctt ttgctggcct tttgctcaca tgttctttcc tgcgttatcc cctgattctg  4620
tggataaccg tattaccgcc tttgagtgag ctgcgcacc gcaacgacg  4680
agcgcagcga gtcagtgagc gaggaagcgg aagagcgcct gatgcggtat tttctcctta  4740
cgcatctgtg cggtatttca caccgcatat atggtgcact ctcagtacaa tctgctctga  4800
tgccgcatag ttaagccagt atacactccg ctatcgctac gtgactgggt catggctgcg  4860
ccccgacacc cgccaacacc cgctgacgcg ccctgacggg cttgtctgct cccggcatcc  4920
gcttacagac aagctgtgac cgtctccggg agctgcatgt gtcagaggtt ttcaccgtca  4980
```

```
tcaccgaaac gcgcgaggca gctgcggtaa agctcatcag cgtggtcgtg aagcgattca   5040
cagatgtctg cctgttcatc cgcgtccagc tcgttgagtt tctccagaag cgttaatgtc   5100
tggcttctga taaagcgggc catgttaagg gcggttttt cctgtttggt cactgatgcc    5160
tccgtgtaag ggggatttct gttcatgggg gtaatgatac cgatgaaacg agagaggatg   5220
ctcacgatac gggttactga tgatgaacat gcccggttgc tggaacgttg tgagggtaaa   5280
caactggcgg tatggatgcg gcgggaccag agaaaaatca ctcagggtca atgccagcgc   5340
ttcgttaata cagatgtagg tgttccacag ggtagccagc agcatcctgc gatgcagatc   5400
cggaacataa tggtgcaggg cgctgacttc cgcgtttcca gactttacga aacacggaaa   5460
ccgaagacca ttcatgttgt tgctcaggtc gcagacgttt tgcagcagca gtcgcttcca   5520
gttcgctcgc gtatcggtga ttcattctgc taaccagtaa ggcaaccccg ccagcctagc   5580
cgggtcctca acgacaggag cacgatcatg ctagtcatgc cccgcgccca ccggaaggag   5640
ctgactgggt tgaaggctct caagggcatc ggtcgagatc ccggtgccta atgagtgagc   5700
taacttacat taattgcgtt gcgctcactg cccgctttcc agtcgggaaa cctgtcgtgc   5760
cagctgcatt aatgaatcgg ccaacgcgcg gggagaggcg gtttgcgtat tgggcgccag   5820
ggtggttttt cttttcacca gtgagacggg caacagctga ttgcccttca ccgcctggcc   5880
ctgagagagt tgcagcaagc ggtccacgct ggttgccc agcaggcgaa atcctgttt     5940
gatggtggtt aacggcggga tataacatga gctgtcttcg gtatcgtcgt atcccactac   6000
cgagatgtcc gcaccaacgc gcagcccgga ctcggtaatg gcccgcattg cgcccagcgc   6060
catctgatcg ttggcaacca gcatcgcagt gggaacgatg ccctcattca gcatttgcat   6120
ggtttgttga aaaccggaca tggcactcca gtcgccttcc cgttccgcta tcggctgaat   6180
ttgattgcga gtgagatatt tatgccagcc agccagacgc agacgcgccg agacagaact   6240
taatgggccc gctaacgcg cgatttgctg gtgacccaat gcgaccagat gctccacgcc     6300
cagtcgcgta ccgtcttcat gggagaaaat aatactgttg atgggtgtct ggtcagagac   6360
atcaagaaat aacgccggaa cattagtgca ggcagcttcc acagcaatgg catcctggtc   6420
atccagcgga tagttaatga tcagcccact gacgcgttgc gcgagaagat tgtgcaccgc   6480
cgctttacag gcttcgacgc cgcttcgttc taccatcgac accaccagc tggcacccag   6540
ttgatcggcg cgagatttaa tcgccgcgac aatttgcgac ggcgcgtgca gggccagact   6600
ggaggtggca acgccaatca gcaacgactg tttgcccgcc agttgttgtg ccacgcggtt   6660
gggaatgtaa ttcagctccg ccatcgccgc ttccacttt tcccgcgttt cgcagaaac   6720
gtggctggcc tggttcacca cgcggggaaac ggtctgataa gagacaccgg catactctgg   6780
gacatcgtat aacgttactg gtttcacatt caccaccctg aattgactct cttccgggga    6840
ctatcatgcc ataccgcgaa aggttttgcg ccattcgatg gtgtccggga tctcgacgct   6900
ctcccttatg cgactcctgc attaggaagc agcccagtag taggttgagg ccgttgagca   6960
ccgccgccgc aaggaatggt gcatgcaagg agatggcgag caacagtccc ccggcccacg   7020
ggcctgccac catacccacg ccgaaacaag cgctcatgag cccgaagtgg cgagcccgat   7080
cttccccatc ggtgatgtcg gcgatatagg cgccagcaac cgcacctgtg gcgccggtga   7140
tgccggccac gatgcgtccg gcgtagagga tcgagatcga tctcgatccc gcgaaattaa   7200
tacgactcac tata                                                      7214

SEQ ID NO: 12           moltype = DNA   length = 7959
FEATURE                 Location/Qualifiers
misc_feature            1..7959
                        note = Synthetic Polynucleotide
source                  1..7959
                        mol_type = other DNA
                        organism = synthetic construct
SEQUENCE: 12
ggggaattgt gagcggataa caattcccct gtagaaataa ttttgtttaa ctttaataag    60
gagatatacc atgggcatga ccgtgccgag cccgctggct gatccgagca tcgtgccaga   120
tccgtacccg gttacgcgg atctggcgca acgtcgcccg gtgcactggg ttgagcgtct   180
gaacgcctgg gcagtgctga cctatgcaga ttgcgcgacg ggtctgaagg acccgcgttt   240
gaccgcggat agaggtaccg aggtgctggc agcgaagttt ccgggtcagc cactgccgcc   300
ggataacatc tttcaccgtt ggaccaagaa tgtggttatg tacaccgatc cgccgctgca   360
tgatgctttg cgtcgcagcg tgcgtgcagg tttcacccgc gcggctcacc aacattatga   420
tcaggtcctg caaaaagtag cccacgatct ggttgcaagc atcccggcgg gtgcaaccga   480
gattgatgct gttccagcac tggcggcgga gctgccggtg cgtagcgcgg tgcatgcatt   540
cggtgttccg gaggaagatt tgggttttct gatcccgcgt gtgaacacga ttatgactta   600
ccactctggt ccgaaggatc agccggttac ccaagagatc attctggaga aactgaccga   660
tctcacacg tatgcgtcgg agctgttgca gggtatgcgt ggtaaggtcc tgcggatac    720
cgtaattgca agactggctg cggcgcaaga tggtctgacc gaaaccaccc ggaacagac    780
ggtccaccaa ctggcgttgg tgttcattgc tctgtttgca ccaaccaccc cgggtagcct   840
gagcagcggt accctggcat ttgcaagaaa cccgcgtcag gtggagcgtt ttctggccga   900
tcaagcgtgc gttgataaca ccgcgaatga agtgctgcgt tacaacgcgt ctaatcagtt   960
cacctggccg gtcgccgcga aggatgtgga gttcgtattg aagctggtca                  1020
aaccctggcg ctgttcctgg gtagcgctaa ccgtgatgca aatatgttcg agcgcccgaa   1080
cgattttgat ctggatcgtc gaacagcgc aagacacctg agcttcggtc agggtgttca   1140
tgcgtgtctg gctgcacagt tgatcagcct gcaactgaaa tggttctatg tggcgctgtt   1200
gaaccgtttt ccgggtattc gcaccgcggg tgaatcgatt tggaatgaga acctggagtt   1260
tcgtagcctg cgtagccgc cgctgagcct gcgtagccgc cagtctgcta aaaaagtacg   1320
caaaaaggca gaaaacgctc ataatacgcc gctgcttgtg ctatacggtt caaatatggg   1380
aacagctgaa ggaacggcgc gtgatttagc agatattgca atgagcaaag gatttgcacc   1440
gcaggtcgca acgcttgatt cacacgcggg aaatcttccg cgcgaaggag ctgtattaat   1500
tgtaacggcg tcttataacg gtcatccgcc tgataacgaa aagcaatttg tcgactggtt   1560
agaccaagcg ttgctgatg aagtaaaagg cttcgctac tccgtatttg gatgcggcga     1620
taaaaactgg gctactacgt atcaaaaagt gcctgctttt atcgatgaaa cgcttggccgc   1680
taaaggggca gaaaacatcg ctgaccgcgg tgaagcagat gcaagcgacg actttgaagg   1740
cacatatgaa gaatggcgtg aacatatgtg gagtgacgta gcagcctact ttaacctcga   1800
cattgaaaac agtgaagata taaaatctac tctttcactt caatttgtcg acagcgccgc   1860
ggatatgccg cttgcgaaaa tgcacggtgc gttttcaacg aacgtcgtag caagcaaaga   1920
```

```
acttcaacag ccaggcagtg cacgaagcac gcgacatctt gaaattgaac ttccaaaaga  1980
agcttcttat caagaaggag atcatttagg tgttattcct cgcaactatg aaggaatagt  2040
aaaccgtgta acagcaaggt tcggcctaga tgcatcacag caaatccgtc tggaagcaga  2100
agaagaaaaa ttagctcatt tgccactcgc taaaacagta tccgtagaag agcttctgca  2160
atacgtggag cttcaagatc ctgttacgcg cacgcagctt cgcgcaatgg ctgctaaaac  2220
ggtctgcccg ccgcataaag tagagcttga agccttgctt gaaaagcaag cctacaaaga  2280
acaagtgctg gcaaaacgtt taacaatgct tgaactgctt gaaaaatacc cggcgtgtga  2340
aatgaaattc agcgaattta tcgcccttct gccaagcata cgcccgcgct attactcgat  2400
ttcttcatca cctcgtgtcg atgaaaaaca agcaagcatc acggtcagcg ttgtctcagg  2460
agaagcgtgg agcggatatg gagaatataa aggaattgcg tcgaactatc ttgccgagct  2520
gcaagaagga gatacgatta cgtgctttat ttccacaccg cagtcagaat ttacgctgcc  2580
aaaagaccct gaaacgccgc ttatcatggt cggaccggga acaggcgtcg cgccgtttag  2640
aggctttgtg caggcgcgca aacagctaaa agaacaagga cagtcacttg gagaagcaca  2700
tttatacttc ggctgccgtt cacctcatga agactatctg tatcaagaag agcttgaaaa  2760
cgcccaaagc gaaggcatca ttacgcttca taccgctttt tctcgcatgc caaatcagcc  2820
gaaaacatac gttcagcacg taatggaaca agacggcaag aaattgattg aacttcttga  2880
tcaaggagcg cacttctata tttgcggaga cggaagccaa atggcacctg ccgttgaagc  2940
aacgcttatg aaaagctatg ctgacgttca ccaagtgagt gaagcagacg ctcgcttatg  3000
gctgcagcag ctagaagaaa aaggccgata cgcaaaagac gtgacgggctg ggtaaaagct  3060
tgcggccgca taatgcttaa gtcgaacaga aagtaatcgt attgtacacg gccgcataat  3120
cgaaattaat acgactcact ataggggaat tgtgagcgga taacaattcc ccatcttagt  3180
atattagtta agtataagaa ggagatatac atatggaaga aaaagaaatc ctgtggaacg  3240
aagccaaagc attcatcgca gcgtgctacc aagaactggg caaagaagaa gaagtcaaag  3300
atcgcctggc ggacattaaa agtgaaatcg atctgaccgg ttcctatgtt catacgaaag  3360
aagaactgga acacgcgcaa aaatggcttg gcgtaacag caatcgctgc attggtcgtc  3420
tgttttggaa ctctctgaat gtgatcgatc gtcgcacgaa tcgcacgaaa gaagaagtcc  3480
gtgatgcgct gtttcatcac attgaaaccg ccacgaacaa tggtaaaatc cgtccgacca  3540
ttacgatctt cccgccggaa gaaaaaggcg aaaaacaggt tgaaatttgg aaccatcaac  3600
tgatccgcta tgcaggctac gaaagcgacg gcgaacgtat tggtgatccg gctagctgct  3660
ctctgaccgc ggcctgtgaa gaactgggct ggcgtggtga ggcacggat tttgacctgc  3720
tgccgctgat tttccgcatg aaaggtgatg aacagccggt gtggtatgaa ctgccgcgtt  3780
ctctggtgat tgaagttccg atcacccatc cggacatcga agcctttagt gatctggaac  3840
tgaaatggta cggcgtcccg attatctccg atatgaaact ggaagtgggc ggtattcact  3900
ataacgcagc tccgttcaat ggctggtaca tgggcaccga aatcggcgcg cgcaatctgg  3960
ccgacgaaaa acgttacgat aaactgaaaa aagtcgcatc agtcgattggt atcgcggccg  4020
attacaacac ggacctgtgg aaagatcagg cactggtgga actgaataaa gctgttctgc  4080
actcataca aaaacaaggc gtttcgattg tggatcatca caccgcagct tcacagttta  4140
aacgcttcga agaacaggaa gaagaagcgg tcgtaaact gaccggcgat tggacgtggc  4200
tgattccgcc gatctcgccg gcagcaaccc atatcttcca ccgctcgtat gacaatagca  4260
tcgtgaaacc gaattacttc taccaggaca aaccgtatga atagctcgag tctggtaaag  4320
aaaccgctgc tgcgaaattt gaacgccagc acatggactc gtctactagc gcagcttaat  4380
taacctaggc tgctgccacc gctgagcaat aactagcata ccccttggg gcctctaaac  4440
gggtcttgag gggttttttg ctgaaacctc aggcatttga gaagcacacg gtcacactgc  4500
ttccggtagt caataaaccg gtaaaccagc aatagacata gcggctatt taacgaccct  4560
gccctgaacc gacgaccggg tcgaatttgc tttgaattt ctgccattca tccgcttatt  4620
atcacttatt caggcgtagc accaggcgtt taagggcacc aataactgcc ttaaaaaaat  4680
tacgccccgc cctgccactc cattcgcagtac tgttgtaatt cattaagcat tctgccgaca  4740
tggaagccat cacagacggc atgatgaacc tgaatcgcca gcggcatcag caccttgtcg  4800
ccttgcgtat aatatttgcc catagtgaaa acggggcga agaagttgtc catattggcc  4860
acgttaaat caaaactggt gaaactcacc cagggattgg ctgagacgaa aaacatattc  4920
tcaataaacc ctttagggaa ataggccagg ttttcaccgt aacacgccac atcttgcgaa  4980
tatatgtgta gaaactgccg gaaatcgtcg tggtattcac tccagagcga tgaaaacgtt  5040
tcagtttgct catggaaaac ggtgtaacaa gggtgaacac tatcccatat caccagctca  5100
ccgtctttca ttgccatacg gaactccgga tgagcattca tcaggcgggc aagaatgtga  5160
ataaaggccg gataaaactt gtgcttattt ttctttaaaa tcttaaaaa ggccgtaata  5220
tccagctgaa cggtctggtt ataggtacat tgagcaactg actgaaatgc ctcaaaatgt  5280
tctttacgat gccattggga tatatcaacg gtggtatatc cagtgatttt ttctccatt  5340
ttagcttcct tagctcctga aaatctcgat aactcaaaaa atacgcccgg tagtgatctt  5400
atttcattat ggtgaaagtt ggaacctctt acgtgccgat cactgtctca ttttcgccaa  5460
aagttggccc agggcttccc ggtatcaaca gggacaccag gatttattta ttctgcgaag  5520
tgatcttccg tcacaggtat ttattcggcg caaagtgcgt cgggtgatgc tgccaactta  5580
ctgatttagt gtatgatggt gttttttgagg tgctccagtg cttctgtttt ctatcagctg  5640
tccctcctgt tcagctactg acggggtggt gcgtaacggc aaaagcaccg ccggacatca  5700
gcgctagccg agtgtatact ggcttactat gttggcactg atgagggtgt cagtgaagtg  5760
cttcatgtgg caggagaaaa aaggctgcac cggtgcgtca gcagaatatg tgatacagga  5820
tatattccgc ttcctcgctc actgactcgc tacgctcggt cgttcgactg cggcgagcgg  5880
aaatggctta cgaacgggc ggagatttcc tggaagatgc caggaagata cttaacaggg  5940
aagtgagagg gccgcggcaa agccgttttt ccataggctc cgccccctg acaagcatca  6000
cgaaatctga cgctcaaatc agtggtggcg aaacccgaca ggactataaa gataccaggc  6060
gtttccctg gcggctccct cgtgcgctct cctgttcctg cctttcggtt taccggtgtc  6120
attccgctgt tatggccgcg tttgtctcat tccacgcctg acactcagtt ccgggtaggc  6180
agttcgctcc aagctggact gtatgcacga accccccgtt cagtccgacc gctgcgcctt  6240
atccggtaac tatcgtcttg agtccaaccc ggaaagacat gcaaaagcac cactggcagc  6300
agccactggt aattgattta gaggagttag tcttgaagtc atgcgccggt taaggctaaa  6360
ctgaaaggac aagttttggt gactgcgctc ctccaagcca gttacctcgg ttcaaagagt  6420
tggtagctca gagaaccttc gaaaaaccgc cctgcaaggc ggttttttcg ttttcagagc  6480
aagagattac gcgcagacca aaacgatctc aagaagatca tcttattaat cagataaaat  6540
atttctagat ttcagtgcaa tttatctctt caaatgtagc acctgaagtc agccccatac  6600
gatataagtt gtaattctca tgttagtcat gccccgcgcc caccggaagg agctgactgg  6660
```

```
gttgaaggct ctcaagggca tcggtcgaga tcccggtgcc taatgagtga gctaacttac  6720
attaattgcg ttgcgctcac tgcccgcttt ccagtcggga aacctgtcgt gccagctgca  6780
ttaatgaatc ggccaacgcg cggggagagg cggtttgcgt attgggcgcc agggtggttt  6840
ttcttttcac cagtgagacg ggcaacagct gattgcccct caccgcctgg ccctgagaga  6900
gttgcagcaa gcggtccacg ctggtttgcc ccagcaggcg aaaatcctgt ttgatggtgg  6960
ttaacggcgg gatataacat gagctgtctt cggtatcgtc gtatcccact accgagatgt  7020
ccgcaccaac gcgcagcccg gactcggtaa tggcgcgcat tgcgcccagc gccatctgat  7080
cgttggcaac cagcatcgca gtgggaacga tgccctcatt cagcatttgc atggtttgtt  7140
gaaaaccgga catggcactc cagtcgcctt cccgttccgc tatcggctga atttgattgc  7200
gagtgagata tttatgccag ccagccagac gcagacgcgc cgagacagaa cttaatgggc  7260
ccgctaacag cgcgatttgc tggtgaccca atgcgaccag atgctccacg cccagtcgcg  7320
taccgtcttc atgggagaaa ataatactgt tgatgggtgt ctggtcagag acatcaagaa  7380
ataacgccgg aacattagtg caggcagctt ccacagcaat ggcatcctgg tcatccagcg  7440
gatagttaat gatcagccca ctgacgcgtt gcgcgagaag attgtgcacc gccgctttac  7500
aggcttcgac gccgcttcgt tctaccatcg acaccaccac gctggcaccc agttgatcgg  7560
cgcgagattt aatcgccgcg acaatttgcg acggcgcgtg cagggccaga ctggaggtgg  7620
caacgccaat cagcaacgac tgtttgcccg ccagttgttg tgccacgcgg ttgggaatgt  7680
aattcagctc cgccatcgcc gcttccactt tttcccgcgt tttcgcagaa acgtggctgg  7740
cctggttcac cacgcgggaa acggtctgat aagagacacc ggcatactct gcgacatcgt  7800
ataacgttac tggtttcaca ttcaccaccc tgaattgact ctcttccggg cgctatcatg  7860
ccataccgcg aaaggttttg cgccattcga tggtgtccgg gatctcgacg ctctccctta  7920
tgcgactcct gcattaggaa attaatacga ctcactata                         7959

SEQ ID NO: 13           moltype = DNA   length = 5802
FEATURE                 Location/Qualifiers
misc_feature            1..5802
                        note = Synthetic Polynucleotide
source                  1..5802
                        mol_type = other DNA
                        organism = synthetic construct
SEQUENCE: 13
ggggaattgt gagcggataa caattcccct gtagaaataa ttttgtttaa ctttaataag  60
gagatatacc atgggcagca gccatcacca tcatcaccac agccaggatc cgatgtataa  120
agatctggaa ggtaaagtgg tggtgattac cggcagcagc accggtctgg gcaaagcaat  180
ggcgattcgt tttgcgaccg aaaaagcgaa agtggtggtt aactatcgca gcaaagaaga  240
agaagcgaac agcgttctgg aagaaattaa aaaagtgggt ggcgaagcga ttgcggtgaa  300
aggtgatgtg accgtggaaa gcgatgtgat taacctggtg cagagcagca ttaaagaatt  360
tggcaaactg gatgtgatga ttaacaatgc gggtatggaa aatccggtga gcagccatga  420
aatgagcctg agcgattgga caaaagtgat tgataccaac ctgaccggtg cgtttctggt  480
cagccgtgaa gcgattaaat acttcgtgga aaacgatatt aaaggcaccg tgattaacat  540
gagcagcgtg catgaaaaaa ttccgtggcc gctgtttgtg cattatgcag cgagcaaagg  600
cggtatgaaa ctgatgaccg aaaccctggc cctggaatat gcaccgaaag cattcgtgt  660
gaacaacatt ggtccgggtg cgattaacac cccgattaac gcggaaaaat ttgccgatcc  720
ggaacagcgt gcggatgtgg aaagcatgat tccgatgggc tatattgcg aaccggaaga  780
aattgcagcg gtggcagcgt ggctggcaag cagcgaagcg agctatgtga ccggcattac  840
cctgtttgcg gatggcggta tgacccagta tccgagcttt caggcaggtc gtggctaaaa  900
gcttcgggcc gcataatgct taagtcgaac agaaagtaat cgtattgtac acggccgcat  960
aatcgaaatt aatacgactc actatagggg aattgtgagc ggataacaat tcccatctt  1020
agtatattag ttaagtataa gaaggagata tacatatgga agaaaagaa atcctgtgga  1080
acgaagccaa agcattcatc gcagcgtgct accaagaact gggcaaagaa gaagaagtca  1140
aagatcgcct ggcggacatt aaaagtgaaa tcgatctgac cggttcctat gttcatacga  1200
aagaagaact ggaacacggc gcaaaaatgg cttggcgtaa cagcaatcgc tgcattggtc  1260
gtctgttttg gaactctctg aatgtgatcg atcgtcgcga cgttcgcacg aaagaagaag  1320
tccgtgatgc gctgtttcat cacattgaaa ccgccacgaa caatggtaaa atccgtccga  1380
ccattacgat cttcccgccg gaagaaaaag gcgaaaaaca gttgaaatt tggaaccatc  1440
aactgatccg ctatgcaggc tacgaaagcc acgcgaacg tattggtgat ccggctagct  1500
gctctctgac cgcggcctgt gaagaactgg gctggcgtgg taacgcacg gattttgacc  1560
tgctgccgct gattttccgc atgaaggtg atgaacagcc ggtgtggtat gaactgccgc  1620
gttctctggt gattgaagtt ccgatcaccc atccggacat gcaagccttt agtgatctgg  1680
aactgaaatg gtacggcgtc ccgattatct ccgatatgaa actgaagtg ggcggtattc  1740
actataacgc agctccgttc aatggctggt acatgggcac cgaaatcggc gcgcgcaatc  1800
tggccgacga aaaacgttac gataaactga aaaaagtcgc atcagtgatt ggtatcgcgg  1860
ccgattacaa cacggacctg tggaaagatc aggcactggt ggaactgaat aaagctgttc  1920
tgcactcata caaaaaacaa ggcgtttcga tgtggatca tcacaccgca gcttcacagt  1980
ttaaacgctt cgaagaacag gaagaagaag cgggtcgtaa actgaccggc gattgacgt  2040
ggctgattcc gccgatctcg ccggcagcaa cccatatctt ccaccgctcg tatgacaata  2100
gcatcgtgaa accgaattac ttctaccagg acaaaccgta tgaatagctc gagtctggta  2160
aagaaaccgc tgctgcgaaa tttgaacgc agcacatgaa ctcgtctact agcgcagctt  2220
aattaaccta ggctgctgcc accgctgagc aataactagc ataaccccct ggggcctcta  2280
aacgggtctt gaggggtttt ttgctgaaac ctcaggcatt tgagaagcac acggtcacac  2340
tgcttccggt agtcaataaa ccggtaaacc agcaatagac ataagcggct atttaacgac  2400
cctgccctga accgacgacc gggtcgaatt tgctttcgaa tttctgccat tcatccgctt  2460
attatcactt attcaggcgt agcaccaggc gtttaagggc accaataact gccttaaaaa  2520
aattacgccc cgccctgcca ctcatcgcag tactgttgta attcattaag cattctgccg  2580
acatggaagc catcacagac ggcatgatga acctgaatcg ccagcggcat cagcaccttg  2640
tcgccttgcg tataatattt gcccatagtg aaaacggggg cgaagaagtt gtccatattg  2700
gccacgttta aatcaaaact ggtgaaactc acccagggat tggctgagac gaaaaacata  2760
ttctcaataa acccttaggg aaataggcc aggttttcac cgtaacacgc cacatcttgc  2820
gaatatatgt gtagaaactg ccggaaatcg tcgtggtatt cactccagag cgatgaaaac  2880
```

```
gtttcagttt gctcatggaa acggtgtaa caagggtgaa cactatccca tatcaccagc  2940
tcaccgtctt tcattgccat acggaactcc ggatgagcat tcatcaggcg ggcaagaatg  3000
tgaataaagg ccggataaaa cttgtgctta tttttcttta cggtctttaa aaaggccgta  3060
atatccagct gaacggtctg gttataggta cattgagcaa ctgactgaaa tgcctcaaaa  3120
tgttctttac gatgccattg gatatatca acggtggtat atccagtgat ttttttctcc  3180
attttagctt ccttagctcc tgaaaatctc gataactcaa aaaatacgcc cggtagtgat  3240
cttatttcat tatggtgaaa gttggaacct cttacgtgcc gatcaacgtc tcattttcgc  3300
caaaagttgg cccagggctt cccggtatca acagggacac caggatttat ttattctgcg  3360
aagtgatctt ccgtcacagg tatttattcg gcgcaaagtg cgtcggtgtg tgctgccaac  3420
ttactgattt agtgtatgat ggtgtttttg aggtgtccca gtggctttctg tttctatcag  3480
ctgtccctcc tgttcagcta ctgacggggt ggtgcgtaac ggcaaaagca ccgccggaca  3540
tcagcgctag cggagtgtat actggcttac tatgttggca ctgatgaggg tgtcagtgaa  3600
gtgcttcatg tggcaggaga aaaaaggctg caccggtgcg tcagcagaat atgtgataca  3660
ggatatattc cgcttcctcg ctcactgact cgctacgctc ggtcgttcga ctgcggcggt  3720
cggaaatggc ttacgaacgg ggcggagatt tcctggaaga tgccaggaag atacttaaca  3780
gggaagtgag agggccgcgg caaagccgtt tttccatagg ctccgccccc ctgacaagca  3840
tcacgaaatc tgacgctcaa atcagtggtg gcgaaacccg acaggactat aaagatacca  3900
ggcgtttccc ctggcggctc cctcgtgcgc tctcctgttc ctgcctttcg gtttaccggt  3960
gtcattccgc tgttatggcc gcgtttgtct cattccacgc ctgacactca gttccggta   4020
ggcagttcgc tccaagctgg actgtatgca cgaaccccc gttcagtccg accgctgcgc   4080
cttatccggt aactatcgtc ttgagtccaa cccggaaaga catgcaaaag caccactggc   4140
agcagccact ggtaattgat ttagaggagt tagtcttgaa gtcatgcgcc ggttaaggct   4200
aaactgaaag gacaagtttt ggtgactgcg ctcctccaag ccagttacct cggttcaaag   4260
agttggtagc tcagagaacc ttcgaaaaac cgccctgcaa ggcggttttt tcgttttcag   4320
agcaagagat tacgcgcaga ccaaaacgat ctcaagaaga tcatcttatt aatcagataa   4380
aatattccta gatttcagtg caatttatct cttcaaatgt agcacctgaa gtcagcccca   4440
tacgatataa gttgtaattc tcatgttagt catgccccgc gcccaccgga aggagctgac   4500
tgggttgaag gctctcaagg gcatcggtcg atatcccggt gcctaatgag tgagctaact   4560
tacattaatt gcgttgcgct cactgcccgc tttccagtcg ggaaacctgt cgtgccagct   4620
gcattaatga atcggccaac gcgcggggag aggcggtttg cgtattgggc gccagggtgg   4680
tttttctttt caccagtgag acgggcaaca gctgattgcc cttcaccgcc tggccctagc   4740
agagttgcag caagcggtcc acgctggttt gccccagcag gcgaaaatcc tgtttgatgg   4800
tggttaacgc cgggatataa catgagctgt cttcggtatc gtcgtatccc actaccgaga   4860
tgtccgcacc aacgcgcagc ccggactcgg taatggcgcg cattgcgccc agcgccatct   4920
gatcgttggc aaccagcatc gcagtgggaa cgatgccctc attcagcatt tgcatggttt   4980
gttgaaaacc ggacatggca ctccagtcgc cttcccgttc cgctatcggc tgaatttgat   5040
tgcgagtgag atatttatgc cagccagcca gacgcagacg cgccgagaca gaacttaatg   5100
ggcccgctaa cagcgcgatt tgctggtgac ccaatgcgac cagatgctcc acgcccagtc   5160
gcgtaccgtc ttcatgggag aaaataatac tgttgatggg tgtctggtca gagacatcaa   5220
gaaataacgc cggaacatta gtgcaggcag cttccacagc aatggcatcc tggtcatcca   5280
gcggatagtt aatgatcagc ccactgacgc gttgcgcgag aagattgtgc accgccgctt   5340
tacaggcttc gacgccgctt cgttctacca tcgacaccac cacgctggca cccagttgat   5400
cggcgcgaga tttaatgcc gcgacaattt gcgacggcgc gtgcagggcc agactggagg   5460
tggcaacgcc aatcagcaac gactgtttgc ccgccagttg ttgtgccacg cggttgggaa   5520
tgtaattcag ctccgccatc gccgcttcca cttttttccg cgttttcgca gaaacgtggc   5580
tggcctggtt caccacgcgg gaaacggtct gataagagac accggcatac tctgcgacat   5640
cgtataacgt tactggtttc acattcacca ccctgaattg actctcttcc gggcgctatc   5700
atgccatacc gcgaaaggtt ttgcgccatt cgatgtgtc cgggatctcg acgctctccc   5760
ttatgcgact cctgcattag gaaattaata cgactcacta ta                    5802

SEQ ID NO: 14           moltype = AA  length = 406
FEATURE                 Location/Qualifiers
REGION                  1..406
                        note = Synthetic Polypeptide
source                  1..406
                        mol_type = protein
                        organism = synthetic construct
SEQUENCE: 14
MTVPSPLADP SIVPDPYPVY ADLAQRRPVH WVERLNAWAV LTYADCAAGL KDPRLTADRG   60
TEVLAAKFPG QPLPPDNIFH RWTKNVVMYT DPPLHDALRR SVRAGFTRAA HQHYDQVLQK  120
VAHDLVASIP AGATEIDAVP ALAAELPVRS AVHAFGVPEE DLGFLIPRVN TIMTYHSGPK  180
DQPVTQEIIL EKLTDLHTYA SELLQGMRGK VLPDTVIARL AAAQDGLTET TPEQTVHQLA  240
LVFIALFAPT TPGSLSSGTL AFARNPRQVE RFLADQACVD ASNQFTWRVA  300
AKDVEMGGVR IEAGQTLALF LGSANRDANM FERPNDFDLD RPNSARHLSF GQGVHACLAA  360
QLISLQLKWF YVALLNRFPG IRTAGEPIWN ENLEFRSLRS LPLSLR                406

SEQ ID NO: 15           moltype = AA  length = 572
FEATURE                 Location/Qualifiers
REGION                  1..572
                        note = Synthetic Polypeptide
source                  1..572
                        mol_type = protein
                        organism = synthetic construct
SEQUENCE: 15
AHNTPLLVLY GSNMGTAEGT ARDLADIAMS KGFAPQVATL DSHAGNLPRE GAVLIVTASY   60
NGHPPDNAKQ FVDWLDQASA DEVKGVRYSV FGCGDKNWAT TYQKVPAFID ETLAAKGAEN  120
IADRGEADAS DDFEGTYEEW REHMWSDVAA YFNLDIENSE DNKSTLSLQF VDSAADMPLA  180
KMHGAFSTNV VASKELQQPG SARSTRHLEI ELPKEASYQE GDHLGVIPRN YEGIVNRVTA  240
RFGLDASQQI RLEAEEEKLA HLPLAKTVSV EELLQYVELQ DPVTRTQLRA MAAKTVCPPH  300
```

```
KVELEALLEK QAYKEQVLAK RLTMLELLEK YPACEMKFSE FIALLPSIRP RYYSISSSPR    360
VDEKQASITV SVVSGEAWSG YGEYKGIASN YLAELQEGDT ITCFISTPQS EFTLPKDPET    420
PLIMVGPGTG VAPFRGFVQA RKQLKEQGQS LGEAHLYFGC RSPHEDYLYQ EELENAQSEG    480
IITLHTAFSR MPNQPKTYVQ HVMEQDGKKL IELLDQGAHF YICGDGSQMA PAVEATLMKS    540
YADVHQVSEA DARLWLQQLE EKGRYAKDVW AG                                  572

SEQ ID NO: 16         moltype = AA   length = 25
FEATURE               Location/Qualifiers
REGION                1..25
                      note = Synthetic Polypeptide
source                1..25
                      mol_type = protein
                      organism = synthetic construct
SEQUENCE: 16
KIPLGGIPSP STEQSAKKVR KKAEN                                          25

SEQ ID NO: 17         moltype = DNA   length = 26
FEATURE               Location/Qualifiers
misc_feature          1..26
                      note = Synthetic Polynucleotide
source                1..26
                      mol_type = other DNA
                      organism = synthetic construct
SEQUENCE: 17
ataccatggt gaccgtcccc tcgccg                                         26

SEQ ID NO: 18         moltype = DNA   length = 30
FEATURE               Location/Qualifiers
misc_feature          1..30
                      note = Synthetic Polynucleotide
source                1..30
                      mol_type = other DNA
                      organism = synthetic construct
SEQUENCE: 18
atcaagcttc ccagcccaca cgtcttttgc                                     30

SEQ ID NO: 19         moltype = DNA   length = 39
FEATURE               Location/Qualifiers
misc_feature          1..39
                      note = Synthetic Polynucleotide
source                1..39
                      mol_type = other DNA
                      organism = synthetic construct
SEQUENCE: 19
caggatccga tgtataaaga tctggaaggt aaagtggtg                           39

SEQ ID NO: 20         moltype = DNA   length = 30
FEATURE               Location/Qualifiers
misc_feature          1..30
                      note = Synthetic Polynucleotide
source                1..30
                      mol_type = other DNA
                      organism = synthetic construct
SEQUENCE: 20
caaagctttt agccacgacc tgcctgaaag                                     30

SEQ ID NO: 21         moltype = DNA   length = 27
FEATURE               Location/Qualifiers
misc_feature          1..27
                      note = Synthetic Polynucleotide
source                1..27
                      mol_type = other DNA
                      organism = synthetic construct
SEQUENCE: 21
actcatatga tggaagaaaa agaaatc                                        27

SEQ ID NO: 22         moltype = DNA   length = 27
FEATURE               Location/Qualifiers
misc_feature          1..27
                      note = Synthetic Polynucleotide
source                1..27
                      mol_type = other DNA
                      organism = synthetic construct
SEQUENCE: 22
actaagcttc tattcatacg gtttgtc                                        27

SEQ ID NO: 23         moltype = DNA   length = 26
FEATURE               Location/Qualifiers
misc_feature          1..26
```

```
                       note = Synthetic Polynucleotide
source                 1..26
                       mol_type = other DNA
                       organism = synthetic construct
SEQUENCE: 23
ctacatatgg tgactttcga agtcgc                                           26

SEQ ID NO: 24          moltype = DNA   length = 28
FEATURE                Location/Qualifiers
misc_feature           1..28
                       note = Synthetic Polynucleotide
source                 1..28
                       mol_type = other DNA
                       organism = synthetic construct
SEQUENCE: 24
ctcaagcttc tgatgagggt aaaagttg                                         28

SEQ ID NO: 25          moltype = DNA   length = 30
FEATURE                Location/Qualifiers
misc_feature           1..30
                       note = Synthetic Polynucleotide
source                 1..30
                       mol_type = other DNA
                       organism = synthetic construct
SEQUENCE: 25
actcatatgg tgactttcga agtcgccctg                                       30

SEQ ID NO: 26          moltype = DNA   length = 31
FEATURE                Location/Qualifiers
misc_feature           1..31
                       note = Synthetic Polynucleotide
source                 1..31
                       mol_type = other DNA
                       organism = synthetic construct
SEQUENCE: 26
actaagcttc tgatgagggt aaaagttggg g                                     31

SEQ ID NO: 27          moltype = DNA   length = 70
FEATURE                Location/Qualifiers
misc_feature           1..70
                       note = Synthetic Polynucleotide
source                 1..70
                       mol_type = other DNA
                       organism = synthetic construct
SEQUENCE: 27
acatccttat agccactctg tagtattaat taaacttctt taagttttgc attccgggga      60
tccgtcgacc                                                             70

SEQ ID NO: 28          moltype = DNA   length = 70
FEATURE                Location/Qualifiers
misc_feature           1..70
                       note = Synthetic Polynucleotide
source                 1..70
                       mol_type = other DNA
                       organism = synthetic construct
SEQUENCE: 28
aatattcaca gggatcactg taattaaaat aaatgaagga ttatgtaatg tgtaggctgg      60
agctgcttcg                                                             70

SEQ ID NO: 29          moltype = DNA   length = 70
FEATURE                Location/Qualifiers
misc_feature           1..70
                       note = Synthetic Polynucleotide
source                 1..70
                       mol_type = other DNA
                       organism = synthetic construct
SEQUENCE: 29
tacaaccggg ggaggcattt tgcttccccc gctaacaatg gcgacatatt gtgtaggctg      60
gagctgcttc                                                             70

SEQ ID NO: 30          moltype = DNA   length = 67
FEATURE                Location/Qualifiers
misc_feature           1..67
                       note = Synthetic Polynucleotide
source                 1..67
                       mol_type = other DNA
                       organism = synthetic construct
SEQUENCE: 30
attcggtgca cgatgcctga tgcgccacgt cttatcaggc ctacaaaaca tatgaatatc      60
```

```
SEQ ID NO: 31          moltype = DNA   length = 70
FEATURE                Location/Qualifiers
misc_feature           1..70
                       note = Synthetic Polynucleotide
source                 1..70
                       mol_type = other DNA
                       organism = synthetic construct
SEQUENCE: 31
ggcctcccaa atcgggggc cttttttatt gataacaaaa aggcaacact gtgtaggctg    60
gagctgcttc                                                          70

SEQ ID NO: 32          moltype = DNA   length = 69
FEATURE                Location/Qualifiers
misc_feature           1..69
                       note = Synthetic Polynucleotide
source                 1..69
                       mol_type = other DNA
                       organism = synthetic construct
SEQUENCE: 32
gccagtaata atccagtgcc ggatgattca catcatccgg cacctttca catatgaata    60
tcctcctta                                                           69

SEQ ID NO: 33          moltype = DNA   length = 70
FEATURE                Location/Qualifiers
misc_feature           1..70
                       note = Synthetic Polynucleotide
source                 1..70
                       mol_type = other DNA
                       organism = synthetic construct
SEQUENCE: 33
tcaggatctg aacgggcagc tgacggctcg cgtggcttaa gaggtttatt gtgtaggctg    60
gagctgcttc                                                          70

SEQ ID NO: 34          moltype = DNA   length = 69
FEATURE                Location/Qualifiers
misc_feature           1..69
                       note = Synthetic Polynucleotide
source                 1..69
                       mol_type = other DNA
                       organism = synthetic construct
SEQUENCE: 34
caacctgatg aaaaggtgcc ggatgatgtg aatcatccgg cactggatta catatgaata    60
tcctcctta                                                           69

SEQ ID NO: 35          moltype = DNA   length = 26
FEATURE                Location/Qualifiers
misc_feature           1..26
                       note = Synthetic Polynucleotide
source                 1..26
                       mol_type = other DNA
                       organism = synthetic construct
SEQUENCE: 35
ataccatggt gaccgtcccc tcgccg                                         26

SEQ ID NO: 36          moltype = DNA   length = 30
FEATURE                Location/Qualifiers
misc_feature           1..30
                       note = Synthetic Polynucleotide
source                 1..30
                       mol_type = other DNA
                       organism = synthetic construct
SEQUENCE: 36
atcaagcttc ccagcccaca cgtctttgc                                      30

SEQ ID NO: 37          moltype = DNA   length = 39
FEATURE                Location/Qualifiers
misc_feature           1..39
                       note = Synthetic Polynucleotide
source                 1..39
                       mol_type = other DNA
                       organism = synthetic construct
SEQUENCE: 37
caggatccga tgtataaaga tctggaaggt aaagtggtg                           39

SEQ ID NO: 38          moltype = DNA   length = 30
FEATURE                Location/Qualifiers
misc_feature           1..30
```

```
                    note = Synthetic Polynucleotide
source              1..30
                    mol_type = other DNA
                    organism = synthetic construct
SEQUENCE: 38
caaagctttt agccacgacc tgcctgaaag                                       30

SEQ ID NO: 39       moltype = DNA   length = 27
FEATURE             Location/Qualifiers
misc_feature        1..27
                    note = Synthetic Polynucleotide
source              1..27
                    mol_type = other DNA
                    organism = synthetic construct
SEQUENCE: 39
actcatatga tggaagaaaa agaaatc                                          27

SEQ ID NO: 40       moltype = DNA   length = 27
FEATURE             Location/Qualifiers
misc_feature        1..27
                    note = Synthetic Polynucleotide
source              1..27
                    mol_type = other DNA
                    organism = synthetic construct
SEQUENCE: 40
actaagcttc tattcatacg gtttgtc                                          27

SEQ ID NO: 41       moltype = DNA   length = 32
FEATURE             Location/Qualifiers
misc_feature        1..32
                    note = Synthetic Polynucleotide
source              1..32
                    mol_type = other DNA
                    organism = synthetic construct
SEQUENCE: 41
actggatccg atggaaaact ttaaacatct cc                                    32

SEQ ID NO: 42       moltype = DNA   length = 33
FEATURE             Location/Qualifiers
misc_feature        1..33
                    note = Synthetic Polynucleotide
source              1..33
                    mol_type = other DNA
                    organism = synthetic construct
SEQUENCE: 42
actgaattcg aaacttcttt aagttttgcg gtg                                   33

SEQ ID NO: 43       moltype = DNA   length = 70
FEATURE             Location/Qualifiers
misc_feature        1..70
                    note = Synthetic Polynucleotide
source              1..70
                    mol_type = other DNA
                    organism = synthetic construct
SEQUENCE: 43
tacaaccggg ggaggcattt tgcttccccc gctaacaatg gcgacatatt gtgtaggctg      60
gagctgcttc                                                             70

SEQ ID NO: 44       moltype = DNA   length = 67
FEATURE             Location/Qualifiers
misc_feature        1..67
                    note = Synthetic Polynucleotide
source              1..67
                    mol_type = other DNA
                    organism = synthetic construct
SEQUENCE: 44
attcggtgca cgatgcctga tgcgccacgt cttatcaggc ctacaaaaca tatgaatatc      60
ctcctta                                                                67

SEQ ID NO: 45       moltype = DNA   length = 70
FEATURE             Location/Qualifiers
misc_feature        1..70
                    note = Synthetic Polynucleotide
source              1..70
                    mol_type = other DNA
                    organism = synthetic construct
SEQUENCE: 45
ggcctcccaa atcgggggc cttttttatt gataacaaaa aggcaacact gtgtaggctg       60
gagctgcttc                                                             70
```

```
SEQ ID NO: 46          moltype = DNA  length = 69
FEATURE                Location/Qualifiers
misc_feature           1..69
                       note = Synthetic Polynucleotide
source                 1..69
                       mol_type = other DNA
                       organism = synthetic construct
SEQUENCE: 46
gccagtaata atccagtgcc ggatgattca catcatccgg caccttttca catatgaata   60
tcctcctta                                                           69

SEQ ID NO: 47          moltype = DNA  length = 70
FEATURE                Location/Qualifiers
misc_feature           1..70
                       note = Synthetic Polynucleotide
source                 1..70
                       mol_type = other DNA
                       organism = synthetic construct
SEQUENCE: 47
tcaggatctg aacgggcagc tgacggctcg cgtggcttaa gaggtttatt gtgtaggctg   60
gagctgcttc                                                          70

SEQ ID NO: 48          moltype = DNA  length = 69
FEATURE                Location/Qualifiers
misc_feature           1..69
                       note = Synthetic Polynucleotide
source                 1..69
                       mol_type = other DNA
                       organism = synthetic construct
SEQUENCE: 48
caacctgatg aaaaggtgcc ggatgatgtg aatcatccgg cactggatta catatgaata   60
tcctcctta                                                           69

SEQ ID NO: 49          moltype = DNA  length = 59
FEATURE                Location/Qualifiers
misc_feature           1..59
                       note = Synthetic Polynucleotide
source                 1..59
                       mol_type = other DNA
                       organism = synthetic construct
SEQUENCE: 49
ggatcactgt aattaaaata aatgaaggat tatgtaatgg tgtaggctgg agctgcttc    59

SEQ ID NO: 50          moltype = DNA  length = 58
FEATURE                Location/Qualifiers
misc_feature           1..58
                       note = Synthetic Polynucleotide
source                 1..58
                       mol_type = other DNA
                       organism = synthetic construct
SEQUENCE: 50
gtggctaaca tccttatagc cactctgtag tattaattac atatgaatat cctcctta     58
```